(12) United States Patent
Grenning et al.

(10) Patent No.: US 11,912,704 B2
(45) Date of Patent: Feb. 27, 2024

(54) METHODS AND COMPOSITIONS FOR SUBSTITUTED ARYLCYCLOHEPTANE ANALOGS

(71) Applicant: UNIVERSITY OF FLORIDA RESEARCH FOUNDATION, Gainesville, FL (US)

(72) Inventors: Alexander James Grenning, Gainesville, FL (US); Ehsan Fereyduni, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 375 days.

(21) Appl. No.: 17/262,107

(22) PCT Filed: Aug. 7, 2019

(86) PCT No.: PCT/US2019/045535
§ 371 (c)(1),
(2) Date: Jan. 21, 2021

(87) PCT Pub. No.: WO2020/033567
PCT Pub. Date: Feb. 13, 2020

(65) Prior Publication Data
US 2021/0300928 A1    Sep. 30, 2021

Related U.S. Application Data

(60) Provisional application No. 62/715,495, filed on Aug. 7, 2018.

(51) Int. Cl.
*C07D 471/08* (2006.01)
*C07C 255/31* (2006.01)
*C07C 255/34* (2006.01)
*C07D 317/72* (2006.01)

(52) U.S. Cl.
CPC .......... *C07D 471/08* (2013.01); *C07C 255/31* (2013.01); *C07C 255/34* (2013.01); *C07D 317/72* (2013.01)

(58) Field of Classification Search
None
See application file for complete search history.

(56) References Cited

U.S. PATENT DOCUMENTS

2007/0259056 A1    11/2007  Bowen et al.
2019/0270700 A1 *  9/2019   Grenning .............. C07C 255/31

FOREIGN PATENT DOCUMENTS

WO              199802182 A1       1/1998
WO           2018053322 A1         3/2018
WO     WO-2018053322 A1 *    3/2018    ............ C07B 37/02

OTHER PUBLICATIONS

International Search Report dated Oct. 22, 2019 for PCT/US2019/045535.
Pubchem CID 89390677, pp. 1-5, Create Date: Feb. 13, 2015; p. 2.
Mastracchio, A et al., Direct and enantioselective alpha-allylation of ketones via singly occupied molecular orbital (SOMO) catalysis, Proceedings of the National Academy of Sciences of the United States of America vol. 107, No. 48, pp. 20648-20651, 2010; p. 20650, table 1, see compound 12.
Fereyduni, E et al., Transient (3,3) Cope rearrangement of 3,3-dicyano-1,5-dienes: computational analysis and 2-step synthesis of arylcycloheptanes, Chemical Science 9, pp. 8760-8764, Published online Sep. 21, 2018; p. 8761, scheme 2, compounds 5a-5c, 5h-5k, 6a-6c & 6h-6k.

* cited by examiner

*Primary Examiner* — Joseph R Kosack
(74) *Attorney, Agent, or Firm* — Thomas Horstemeyer, LLP

(57) ABSTRACT

In one aspect, the disclosure relates to methods for preparation of intermediates useful for the preparation of aryl-cycloheptene scaffolds. In a further aspect, the disclosed methods pertain to the preparation of compounds comprising an aryl-cycloheptene structure. The disclosed methods utilize abundant starting materials and simple reaction sequences that can be used to modularly and scalably assemble common such cores. In various aspects, the present disclosure pertains to compounds prepared using the disclosed methods. This abstract is intended as a scanning tool for purposes of searching in the particular art and is not intended to be limiting of the present disclosure.

18 Claims, 57 Drawing Sheets

PMP = p-methoxyphenyl

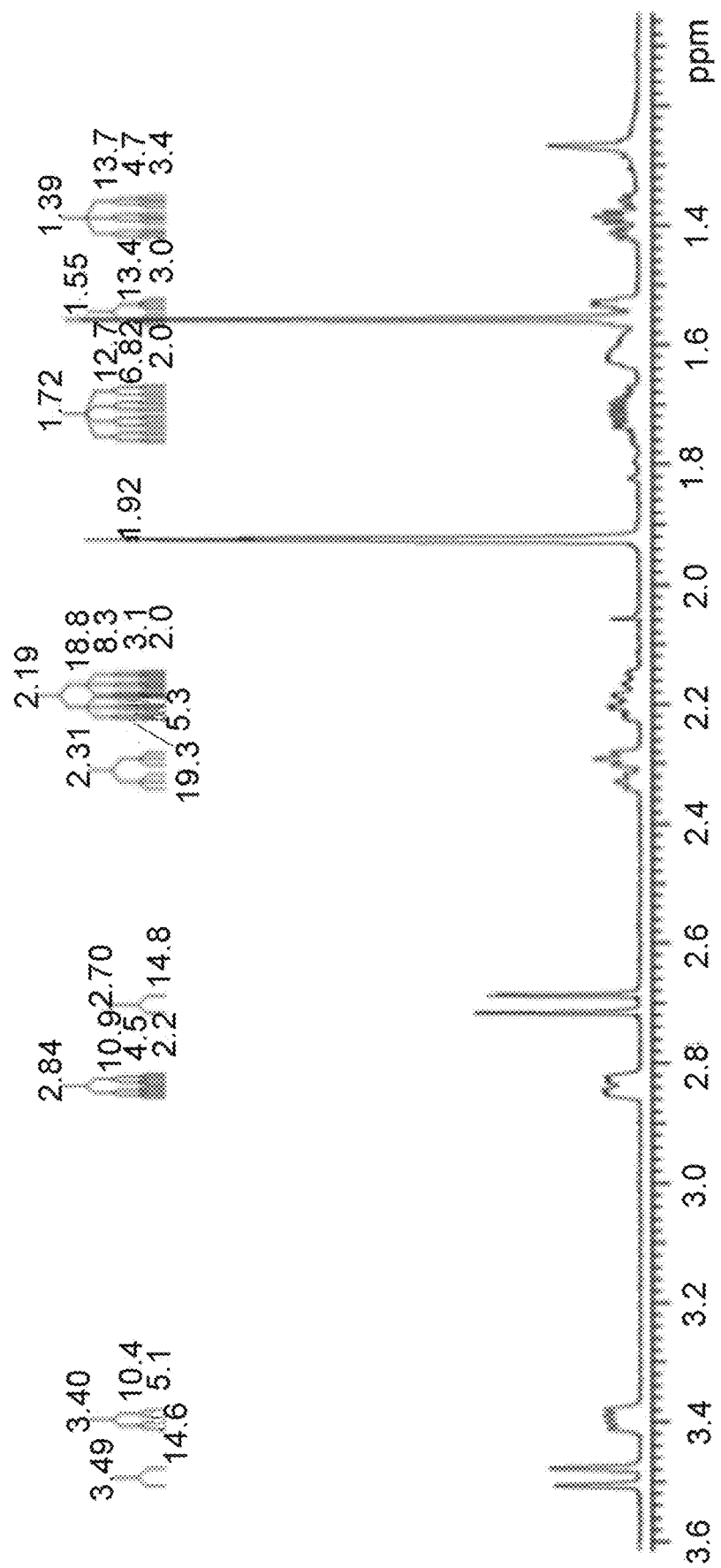

METHODS AND COMPOSITIONS FOR SUBSTITUTED ARYLCYCLOHEPTANE ANALOGS

CROSS-REFERENCE TO RELATED APPLICATIONS

This Application claims the benefit of U.S. Provisional Application No. 62/715,495, filed on Aug. 7, 2018, which is incorporated herein by reference in its entirety.

BACKGROUND

Structurally complex natural products are promising leads for treating diseases and are commonly acquired by isolation and semi-synthesis. De novo synthesis of complex bioactive molecules and their analogs is a modern synthetic challenge. The most successful examples address synthetic ideality: efficiency, practicality, and scalability. From a drug discovery perspective, modularity is a critical synthetic challenge that remains to be well addressed, including practical synthetic routes to polycyclic architectures that are simple and efficient from abundant starting material classes. If there were synthetic methods that were simple and efficient available, then it would be possible to more easily advance drug discovery efforts directed to target and target-analog synthesis based on therapeutically interesting bioactive aryl-cycloheptanes or aryl-cycloheptenes, such as exemplary compounds shown in FIG. 1 that include terpenes (the frondosins, liphagal, pharbinilic acid), resveratrol-derivatives (vitisinol C, ampelopsin A) and cyclohepta[b]indoles, such as ambiguine, actinophyllic acid, and the drug Irosustat.

Despite advances in research directed towards preparation of natural product inspired aryl-cycloheptene scaffolds, there remain a scarcity of methods for preparation of aryl-cycloheptene scaffolds that utilize abundant starting materials and simple reaction sequences that can be used to modularly and scalably assemble common aryl-cycloheptene scaffolds. Moreover, in view of the limitations of current methods, there are limited compounds comprising such cores that can be easily derivatized for biological evaluation. These needs and other needs are satisfied by the present disclosure.

SUMMARY

In accordance with the purpose(s) of the disclosure, as embodied and broadly described herein, the disclosure, in one aspect, relates to methods for preparation of intermediates useful for the preparation of aryl-cycloheptene scaffolds. In a further aspect, the disclosed methods pertain to the preparation of compounds comprising an aryl-cycloheptene structure. The disclosed methods utilize abundant starting materials and simple reaction sequences that can be used to modularly and scalably assemble common such cores. In various aspects, the present disclosure pertains to compounds prepared using the disclosed methods.

Disclosed are compounds having a formula represented by a structure:

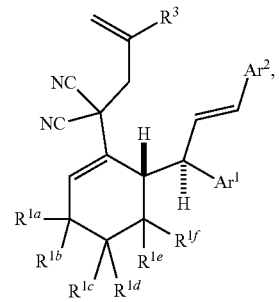

wherein each of $R^{1a}$, $R^{1b}$, $R^{1c}$, $R^{1d}$, $R^{1e}$, $R^{1f}$ and $R^3$ is independently selected from hydrogen, halogen, and C1-C8 alkyl; or wherein each of $R^{1a}$, $R^{1b}$, $R^{1e}$, $R^{1f}$ and $R^3$ is independently selected from hydrogen and C1-C8 alkyl, and wherein $R^{1c}$ and $R^{1d}$ are combined and form a $C_3$ to $C_8$ cycloalkyl, $C_3$ to $C_8$ cycloalkenyl, or 5-atom or 6-atom heterocycle containing one or more oxygens; wherein $Ar^1$ is a phenyl group optionally independently substituted with 1, 2, or 3 groups that are electron-withdrawing or electron-donating; and wherein $Ar^2$ is a phenyl group optionally independently substituted with 1, 2, or 3 groups that are electron-withdrawing or electron-donating.

Also disclosed herein are compounds having a formula represented by a structure:

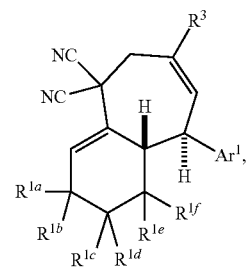

wherein each of $R^{1a}$, $R^{1b}$, $R^{1c}$, $R^{1d}$, $R^{1e}$, $R^{1f}$ and $R^3$ is independently selected from hydrogen, halogen, and C1-C8 alkyl; or wherein each of $R^{1a}$, $R^{1b}$, $R^{1e}$, $R^{1f}$ and $R^3$ is independently selected from hydrogen and C1-C8 alkyl, and wherein $R^{1c}$ and $R^{1d}$ are combined and form a $C_3$ to $C_8$ cycloalkyl, $C_3$ to $C_8$ cycloalkenyl, or 5-atom or 6-atom heterocycle containing one or more oxygens; and wherein $Ar^1$ is a phenyl group optionally independently substituted with 1, 2, or 3 groups that are electron-withdrawing or electron-donating.

Also disclosed herein are methods of synthesizing a bis-allylated compound, the method comprising: reacting a Knoevenagel adduct and chalcone-derived electrophile in the presence of a palladium catalyst and base at a first reaction temperature for a first reaction time; wherein the Knoevenagel adduct has a formula represented by a structure:

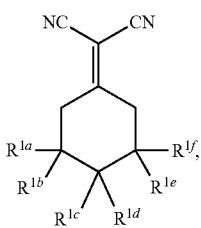

wherein each of $R^{1a}$, $R^{1b}$, $R^{1c}$, $R^{1d}$, $R^{1e}$ and $R^{1f}$ is independently selected from hydrogen, halogen, and C1-C8 alkyl; or wherein each of $R^{1a}$, $R^{1b}$, $R^{1e}$ and $R^{1f}$ is independently selected from hydrogen and C1-C8 alkyl, and wherein $R^{1c}$ and $R^{1d}$ are combined and form a $C_3$ to $C_8$ cycloalkyl, $C_3$ to $C_8$ cycloalkenyl, or 5-atom or 6-atom heterocycle containing one or more oxygens; wherein the chalcone-derived electrophile has a formula represented by a structure:

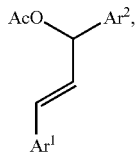

wherein $Ar^1$ is a phenyl group optionally independently substituted with 1, 2, or 3 groups that are electron-withdrawing or electron-donating; and wherein $Ar^2$ is a phenyl group optionally independently substituted with 1, 2, or 3 groups that are electron-withdrawing or electron-donating; after completion of the first reaction time, adding to the reaction an allylic electrophile and continuing the reaction at second reaction temperature for a second reaction time, wherein the allylic electrophile has a formula represented by a structure:

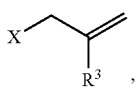

wherein X is a halogen; and wherein $R^3$ is selected from hydrogen and C1-C8 alkyl; thereby synthesizing the bis-allylated compound, wherein the bis-allylated compound has a formula represented by a structure:

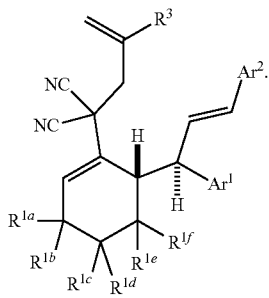

and wherein the base can be potassium carbonate, sodium carbonate, potassium hydroxide, sodium hydroxide, potassium bicarbonate, sodium bicarbonate, or a combination thereof. In one aspect, the base is potassium carbonate. In another aspect, the first reaction temperature and the second reaction temperature are, independently, from 0 to 50° C., or is about 0, 5, 10, 15, 20, 25, 30, 35, 40, 45, or about 50° C. In one aspect, the first reaction temperature is from 20 to 30° C.

Also disclosed herein are methods of synthesizing an aryl-cycloheptene compound, the method comprising: reacting a bis-allylated compound in the presence of a Grubbs catalyst, and wherein the bis-allylated compound has a formula represented by a structure:

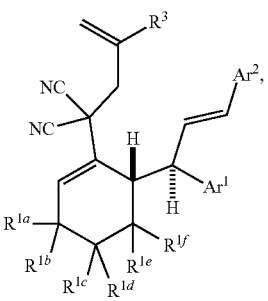

wherein each of $R^{1a}$, $R^{1b}$, $R^{1c}$, $R^{1d}$, $R^{1e}$, $R^{1f}$ and $R^3$ is independently selected from hydrogen, halogen, and C1-C8 alkyl; or wherein each of $R^{1a}$, $R^{1b}$, $R^{1e}$, $R^{1f}$ and $R^3$ is independently selected from hydrogen and C1-C8 alkyl, and wherein $R^{1c}$ and $R^{1d}$ are combined and form a $C_3$ to $C_8$ cycloalkyl, $C_3$ to $C_8$ cycloalkenyl, or 5-atom or 6-atom heterocycle containing one or more oxygens; wherein $Ar^1$ is a phenyl group optionally independently substituted with 1, 2, or 3 groups that are electron-withdrawing or electron-donating; and wherein $Ar^2$ is a phenyl group optionally independently substituted with 1, 2, or 3 groups that are electron-withdrawing or electron-donating; thereby synthesizing an aryl-cycloheptene compound having a formula represented by a structure:

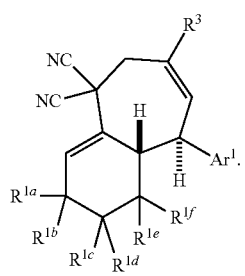

In a further aspect, also disclosed herein are compounds comprising one or more product of a disclosed synthetic methods described herein.

In a further aspect, also disclosed herein are compounds produced by a disclosed synthetic method described herein.

In a further aspect, also disclosed herein are pharmaceutical compositions comprising a therapeutically effective amount of the product of the disclosed methods and a pharmaceutically acceptable carrier.

In a further aspect, also disclosed herein are methods for manufacturing a medicament comprising combining at least one compound of any of disclosed compounds or at least one product of the disclosed methods with a pharmaceutically acceptable carrier or diluent.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the disclosure.

FIG. 2A shows a general scheme for a Cope rearrangement and a ring-closing metathesis. FIG. 2B shows a scheme including intermediate steps using starting materials and products disclosed herein. FIG. 2C shows one synthetic route from compounds 1a-1f disclosed herein to final products 6a-6o disclosed herein.

FIG. 4A shows a representative synthetic scheme for three-component bis-allylation of Knoevenagel adducts using symmetric chalcone-derived electrophiles. In FIG. 4A, standard conditions are: 0.6 mmol 1, 0.5 mmol 2, 1 mol % Pd(PPh$_3$)$_4$, 3 equivalents of K$_2$CO$_3$, CH$_2$Cl$_2$, room temperature. 4 is added after 2 is consumed based on TLC. FIG. 4B shows a representative synthetic scheme for access to aryl-6-7 scaffolds by ring-closing metathesis of the compounds shown in FIG. 4A per the reaction conditions as given therein and further described herein below.

FIG. 6A shows a representative synthetic scheme for three-component bis-allylation of Knoevenagel adducts using non-symmetric chalcone-derived electrophiles per the reaction conditions as given therein and further described herein below. FIG. 6B shows a representative synthetic scheme for access to aryl-6-7 scaffolds by ring-closing metathesis of the compounds shown in FIG. 6A per the reaction conditions as given therein and further described herein below.

FIG. 9A shows a $^1$H NMR spectrum of compound 3a. FIG. 9B shows a $^{13}$C NMR spectrum of compound 3a.

FIG. 11B shows a $^{13}$C NMR spectrum of compound 5a.

FIG. 26B shows a $^{13}$C NMR spectrum of compound 6a.

FIG. 37A-I show characterization of 7-methyl-9-phenyl-1,2,3,6,9,9a-hexahydro-5H-benzo[7]annulene-5,5-dicarbonitrile (compound 6n). FIG. 37A shows the structure of compound 6n with $^1$H and $^{13}$C NMR chemical shifts assigned to their respective hydrogen and carbon atoms. FIG. 37B shows a $^1$H NMR spectrum of compound 6n. FIG. 37C shows an expanded view of the $^1$H NMR spectrum of FIG. 37B from 3.6 to 1.2 ppm. FIG. 37D shows an expanded view of the $^1$H NMR spectrum of FIG. 37B from 7.4 to 5.6 ppm. FIG. 37E shows a gHMBC spectrum of compound 6n. FIG. 37F shows a portion of an HSQC spectrum of compound 6n. FIG. 37G shows a different portion of the HSQC spectrum of compound 6n. FIG. 37H shows a NOESY spectrum of compound 6n. FIG. 37I shows a different portion of the NOESY spectrum of compound 6n.

FIG. 39B shows a $^{13}$C NMR spectrum of compound 9a.

FIG. 43B shows a $^{13}$C NMR spectrum of compound 10a.

Figure 1:
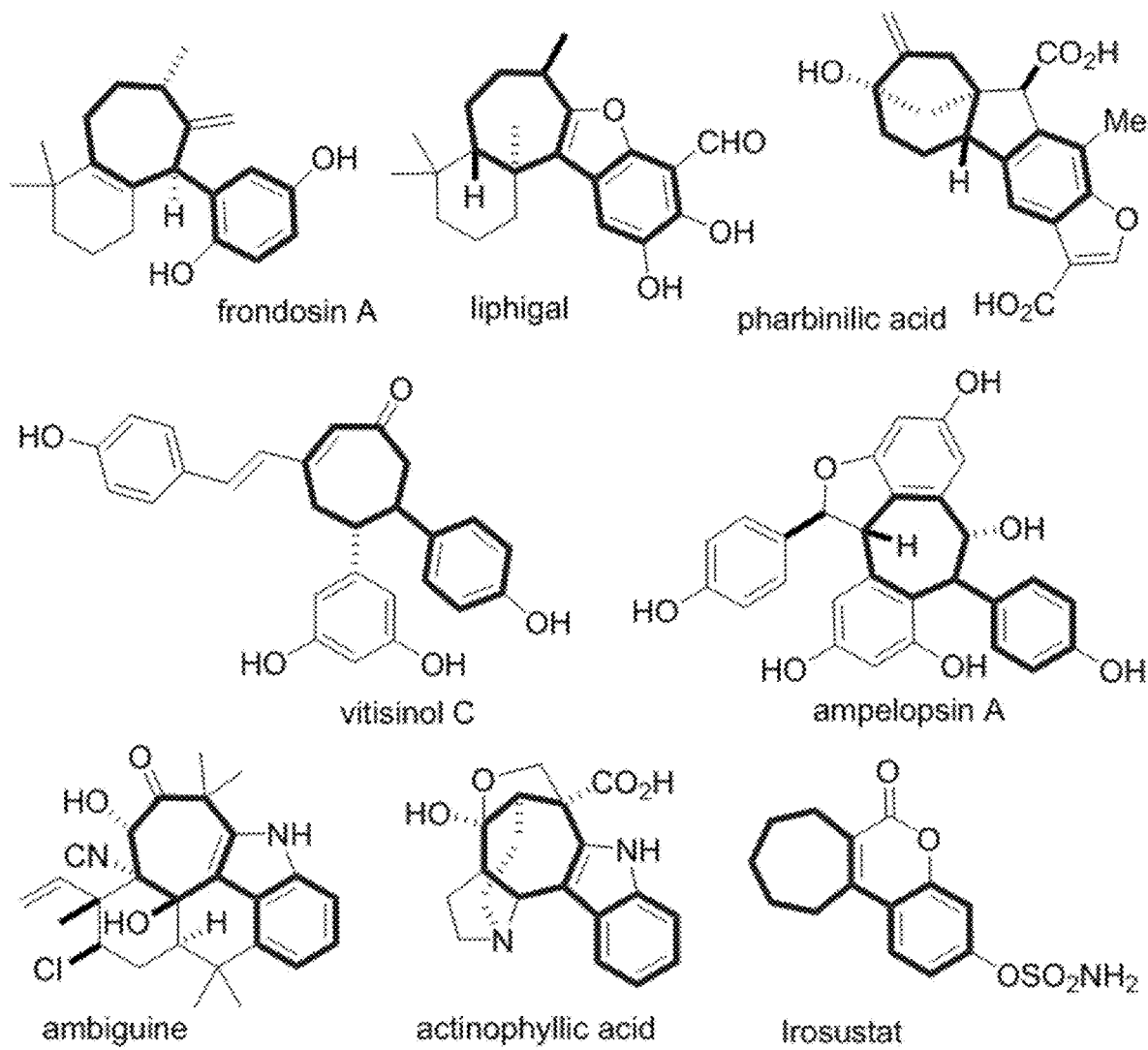
FIG. 1 shows representative therapeutically interesting aryl-cycloheptene scaffolds.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of".

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

A weight percent (wt. %) of a component, unless specifically stated to the contrary, is based on the total weight of the formulation or composition in which the component is included.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

Unless otherwise specified, temperatures referred to herein are based on atmospheric pressure (i.e. one atmosphere).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "electron-withdrawing group" is recognized in the art, and denotes the tendency of a substituent to withdraw electron density from neighboring atoms or bonds, i.e., the substituent is electronegative with respect to neighboring atoms and tend to stabilize anions or electron rich structures. A quantification of the level of electron-withdrawing capability is given by the Hammett sigma (a) constant. This well-known constant is described in many references, for instance, J. March, Advanced Organic Chemistry, McGraw Hill Book Company, New York, (1977 edition) pp. 251-259. The Hammett constant values are generally positive for electron withdrawing groups (e.g., $\sigma[P]=0.78$ for a nitro group, where $\sigma[P]$ indicating para substitution). Exemplary electron-withdrawing groups include nitro, carbonyl containing groups such as aldehyde and ketone containing groups, acyl, formyl, sulfonyl, trifluoromethyl, cyano, halogen, and the like.

The term "electron-donating group" is recognized in the art, and denotes the tendency of a substituent to add electron density to neighboring atoms or bonds, i.e., the substituent is electropositive with respect to neighboring atoms and tend to stabilize anions or electron rich structures. The Hammett constant values are generally negative for electron donating groups (e.g., $\sigma[P]=-0.66$ for $NH_2$, where $\sigma[P]$ indicating para substitution). Exemplary electron-donating groups include amino, alkoxy, ester, phenyl, alkyl, alkenyl, and the like.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "carboxylic acid" as used herein is represented by the formula —C(O)OH or —(C=O)OH.

The term "ester" as used herein is represented by the formula —OC(O)$A^1$, —C(O)O$A^1$, or —(C=O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$ or -($A^1$O(O)C-$A^2$-OC(O))$_a$, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]

pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The term "nitrile" or "cyano" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

"R$^1$," "R$^2$," "R$^3$," . . . "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ$$_2$; —(CH$_2$)$_{0-4}$S(O)R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —P(O)$_2$R$^\circ$; —P(O)R$^\circ$$_2$; —OP(O)R$^\circ$$_2$; —OP(O)(OR$^\circ$)$_2$; SiR$^\circ$$_3$; —(C$_{1-4}$ straight or branched alkylene)O—N(R$^\circ$)$_2$; or —(C$_{1-4}$ straight or branched alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R*, -(haloR*), —OH, —OR*, —O(haloR*), —CN, —C(O)OH, —C(O)OR*, —NH$_2$, —NHR*, —NR*$_2$, or —NO$_2$, wherein each R* is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R*, -(haloR*), —OH, —OR*, —O(haloR*), —CN, —C(O)OH, —C(O)OR*, —NH$_2$, —NHR*, —NR*$_2$, or —NO$_2$, wherein each R* is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

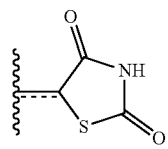

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present disclosure unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein can contain one or more double bonds and, thus, potentially give rise to cis/trans (E/Z) isomers, as well as other conformational isomers. Unless stated to the contrary, the disclosure includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present disclosure includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the disclosure include isotopes of hydrogen, carbon, nitrogen, oxygen, sulfur, fluorine and chlorine, such as $^2$H, $^3$H, $^{13}$C, $^{14}$C $^{15}$N, $^{18}$O, $^{17}$O $^{35}$S, $^{18}$F, and $^{36}$Cl, respectively. Compounds further comprise prodrugs thereof and pharmaceutically acceptable salts of said compounds or of said prodrugs which contain the aforementioned isotopes and/or other isotopes of other atoms are within the scope of this disclosure. Certain isotopically-labeled compounds of the present disclosure, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present disclosure and prodrugs thereof can generally be prepared by carrying out the procedures below, by substituting a readily available isotopically labeled reagent for a non-isotopically labeled reagent.

The compounds described in the disclosure can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the disclosure to form solvates and hydrates. Unless stated to the contrary, the disclosure includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the disclosure can be present in different polymorphic forms, with it being possible for particular modifications to be metastable. Unless stated to the contrary, the disclosure includes all such possible polymorphic forms.

In some aspects, a structure of a compound can be represented by a formula:

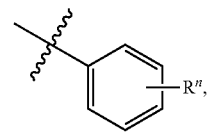

which is understood to be equivalent to a formula:

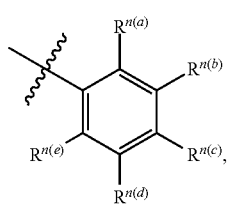

wherein n is typically an integer. That is, $R^n$ is understood to represent five independent substituents, $R^{n(a)}$, $R^{n(b)}$, $R^{n(c)}$, $R^{n(d)}$, and $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific embodiment or combination of embodiments of the methods of the disclosure.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Disclosed Compounds

In one aspect, the present disclosure relates to compounds that can be used as intermediates useful for the preparation of preparation of aryl-cycloheptene scaffolds. In a further aspect, the disclosed methods pertain to the preparation of compounds comprising an aryl-cycloheptene structure. The disclosed methods utilize abundant starting materials and simple reaction sequences that can be used to modularly and scalably assemble common such cores. In various aspects, the present disclosure pertains to compounds prepared using the disclosed methods.

In various aspects, disclosed herein are Knoevenagel adduct compounds having a formula represented by a structure:

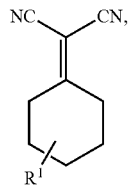

which is understood to be equivalent to a formula:

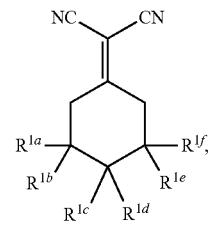

wherein each of $R^{1a}$, $R^{1b}$, $R^{1c}$, $R^{1d}$, $R^{1e}$, $R^{1f}$ and $R^3$ is independently selected from hydrogen, halogen, and C1-C8 alkyl; or wherein each of $R^{1a}$, $R^{1b}$, $R^{1e}$, $R^{1f}$ and $R^3$ is independently selected from hydrogen and C1-C8 alkyl, and wherein $R^{1c}$ and $R^{1d}$ are combined and form a $C_3$ to $C_8$ cycloalkyl, $C_3$ to $C_8$ cycloalkenyl, or 5-atom or 6-atom heterocycle containing one or more oxygens. In one aspect, $R^{1c}$ and $R^{1d}$ are independent selected from fluoro, chloro, bromo, and iodo groups.

In various aspects, disclosed herein are Knoevenagel adduct compounds having a formula represented by a structure:

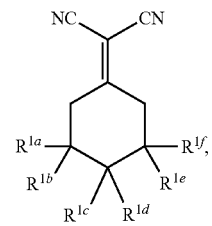

wherein each of $R^{1a}$, $R^{1b}$, $R^{1c}$, $R^{1d}$, $R^{1e}$ and $R^{1f}$ is independently selected from hydrogen and C1-C8 alkyl; or wherein each of $R^{1a}$, $R^{1b}$, $R^{1e}$ and $R^{1f}$ is independently selected from hydrogen and C1-C8 alkyl, and wherein $R^{1c}$ and $R^{1d}$ are combined and form a $C_3$ to $C_8$ cycloalkyl, $C_3$ to $C_8$ cycloalkenyl, or 5-atom or 6-atom heterocycle containing one or more oxygens. In one aspect, $R^{1c}$ and $R^{1d}$ are independent selected from fluoro, chloro, bromo, and iodo groups.

In a further aspect, a Knoevenagel adduct compound can be present as:

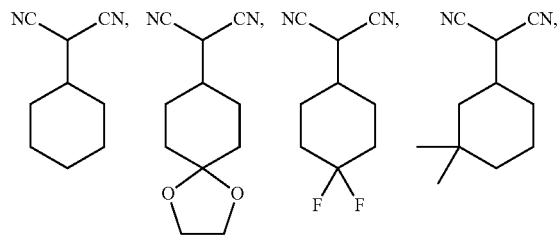

or a subgroup thereof.

In a further aspect, a Knoevenagel adduct compound can be present as:

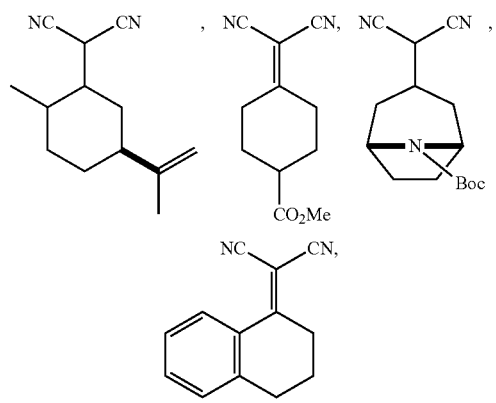

or a subgroup thereof.

In various aspects, disclosed herein are chalcone-derived electrophile compounds has a formula represented by a structure:

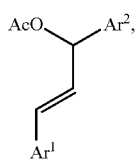

wherein Ar¹ is a phenyl group optionally independently substituted with 1, 2, or 3 groups that are electron-withdrawing or electron-donating; and wherein Ar² is a phenyl group optionally independently substituted with 1, 2, or 3 groups that are electron-withdrawing or electron-donating.

In a further aspect, a chalcone-derived electrophile compound can be present as:

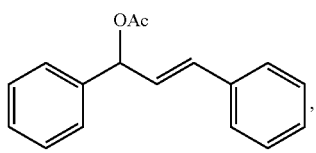

-continued

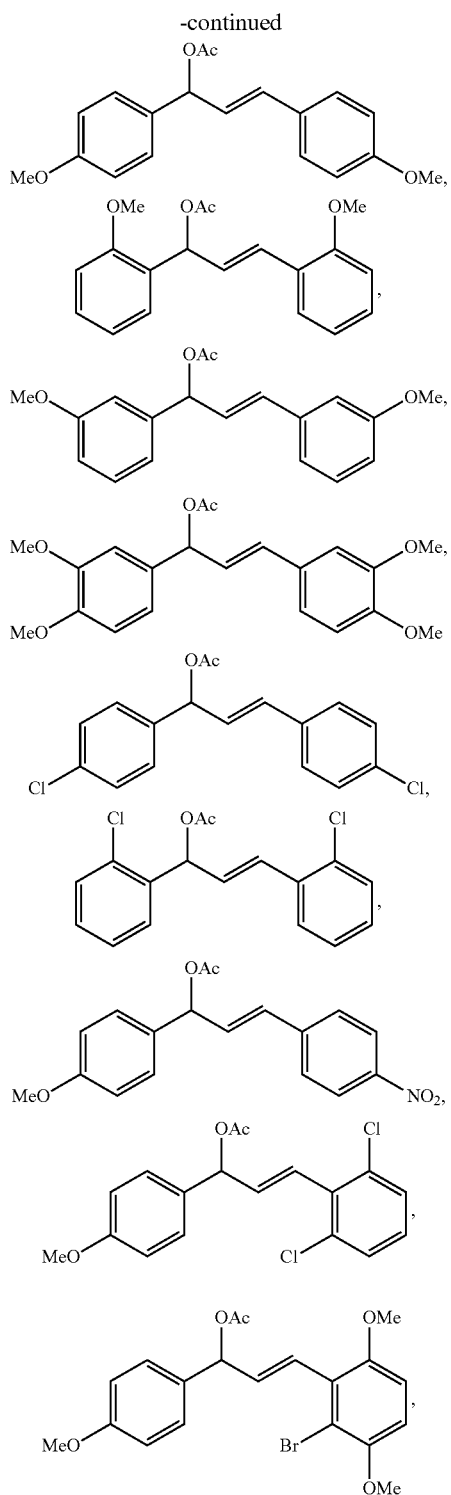

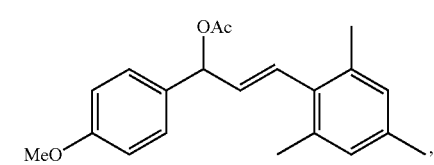

or a subgroup thereof.

In various aspects, disclosed herein are allylic electrophile compounds having a formula represented by a structure:

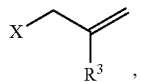

wherein X is a halogen; and wherein $R^3$ is selected from hydrogen and C1-C8 alkyl;

In a further aspect, an allylic electrophile compound can be present as:

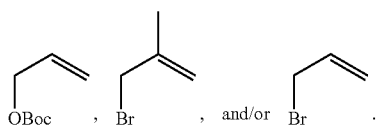

In various aspects, disclosed herein are bis-allylated compounds having a formula represented by a structure:

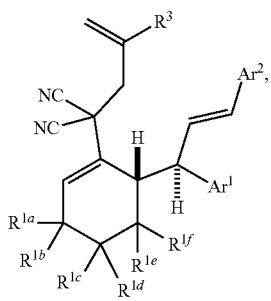

wherein each of $R^{1a}$, $R^{1b}$, $R^{1c}$, $R^{1d}$, $R^{1e}$, $R^{1f}$ and $R^3$ is independently selected from hydrogen and C1-C8 alkyl; or wherein each of $R^{1a}$, $R^{1b}$, $R^{1e}$, $R^{1f}$ and $R^3$ is independently selected from hydrogen and C1-C8 alkyl, and wherein $R^{1c}$ and $R^{1d}$ are combined and form a $C_3$ to $C_8$ cycloalkyl, $C_3$ to $C_8$ cycloalkenyl, or 5-atom or 6-atom heterocycle containing one or more oxygens; wherein $Ar^1$ is a phenyl group optionally independently substituted with 1, 2, or 3 groups that are electron-withdrawing or electron-donating; and wherein $Ar^2$ is a phenyl group optionally independently substituted with 1, 2, or 3 groups that are electron-withdrawing or electron-donating. In one aspect, $Ar^1$ and $Ar^2$ are, independently, 2-methoxyphenyl, 3-methoxyphenyl, 4-methoxyphenyl, 3,4-dimethoxyphenyl, 2,5-dimethoxyphenyl, 4-chlorophenyl, and combinations thereof. In one aspect, $R^{1c}$ and $R^{1d}$ are independent selected from fluoro, chloro, bromo, and iodo groups.

In various aspects, disclosed herein are bis-allylated compounds having a formula represented by a structure:

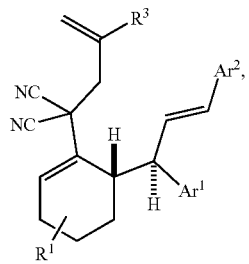

which is understood to be equivalent to a formula:

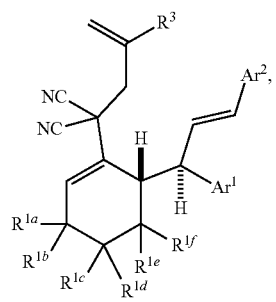

wherein each of $R^{1c}$, $R^{1b}$, $R^{1c}$, $R^{1d}$, $R^{1e}$, $R^{1f}$ and $R^3$ is independently selected from hydrogen and C1-C8 alkyl; or wherein each of $R^{1a}$, $R^{1b}$, $R^{1e}$, $R^{1f}$ and $R^3$ is independently selected from hydrogen and C1-C8 alkyl, and wherein $R^{1c}$ and $R^{1d}$ can be combined to form a $C_3$ to $C_8$ cycloalkyl, $C_3$ to $C_8$ cycloalkenyl, or 5-atom or 6-atom heterocycle containing one or more oxygens; wherein $Ar^1$ is a phenyl group optionally independently substituted with 1, 2, or 3 groups that are electron-withdrawing or electron-donating; and wherein $Ar^2$ is a phenyl group optionally independently substituted with 1, 2, or 3 groups that are electron-withdrawing or electron-donating. In one aspect, $R^{1c}$ and $R^{1d}$ are independent selected from fluoro, chloro, bromo, and iodo groups.

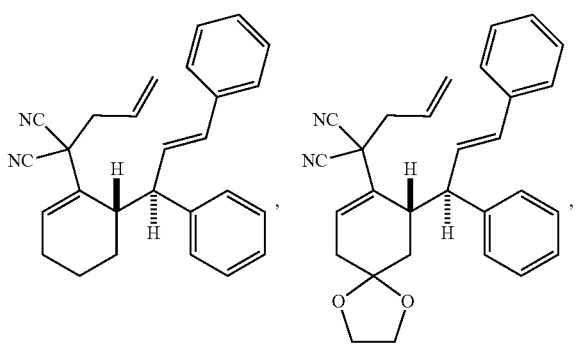

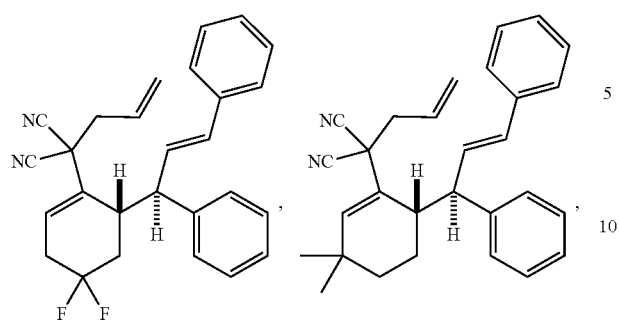
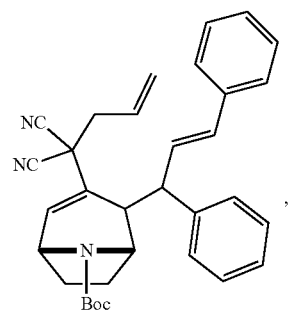
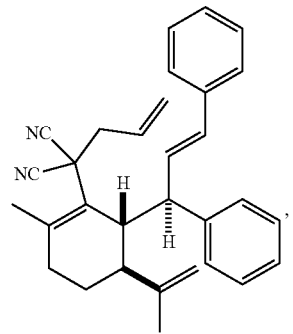
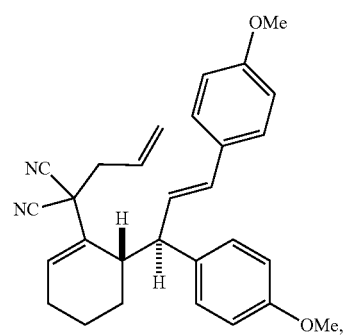
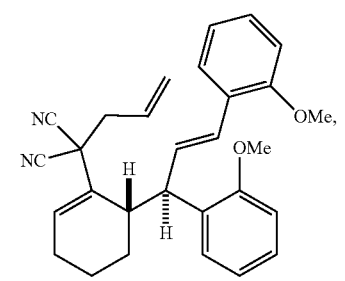
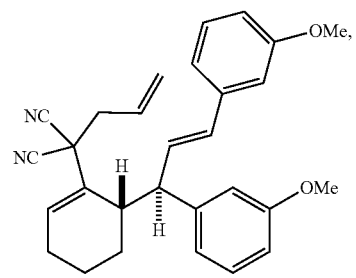
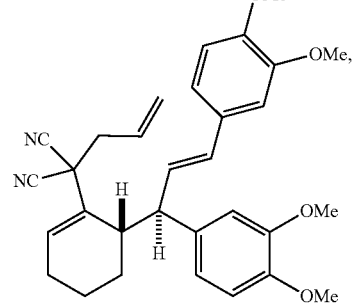
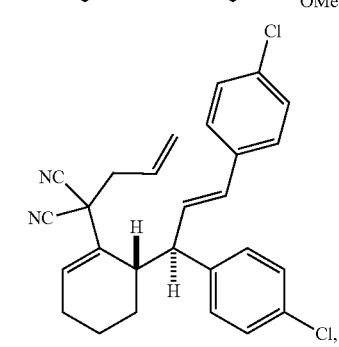
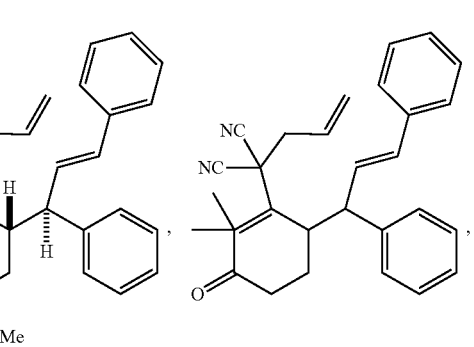
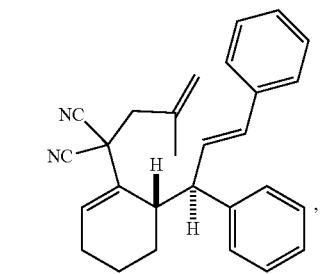

-continued

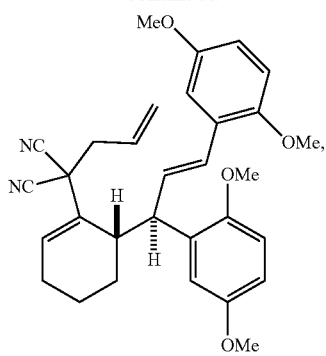

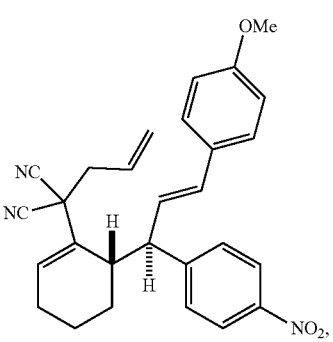

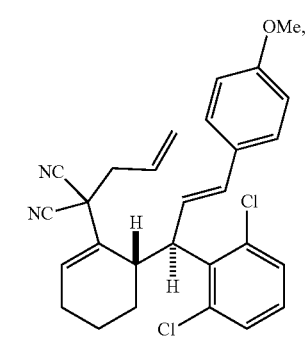

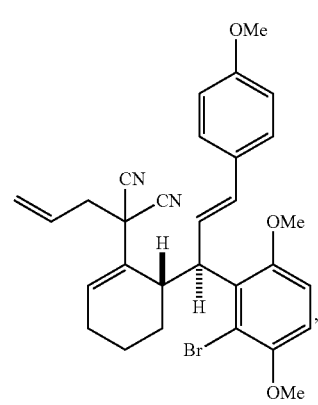

-continued

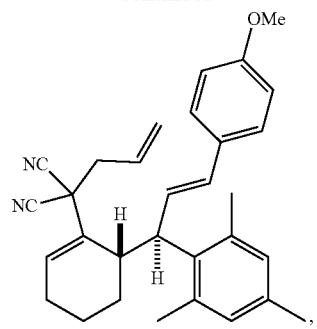 [SMILES: C=CCC(C#N)(C#N)C1=CCCC[C@H]1[C@@H](/C=C/c1ccc(OC)cc1)c1c(C)cc(C)cc1C]

or a subgroup thereof.

In various aspects, disclosed herein are aryl-cycloheptene compounds having a formula represented by a structure:

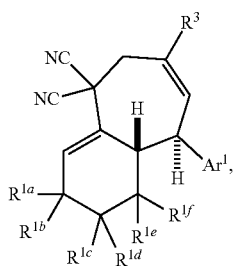

wherein each of $R^{1a}$, $R^{1b}$, $R^{1c}$, $R^{1d}$, $R^{1e}$, $R^{1f}$ and $R^3$ is independently selected from hydrogen and C1-C8 alkyl; or wherein each of $R^{1a}$, $R^{1b}$, $R^{1e}$, $R^{1f}$ and $R^3$ is independently selected from hydrogen and C1-C8 alkyl, and wherein $R^{1c}$ and $R^{1d}$ are combined and form a $C_3$ to $C_8$ cycloalkyl, $C_3$ to $C_8$ cycloalkenyl, or 5-atom or 6-atom heterocycle containing one or more oxygens; and wherein $Ar^1$ is a phenyl group optionally independently substituted with 1, 2, or 3 groups that are electron-withdrawing or electron-donating. In a further aspect, $Ar^1$ can be 2-methoxyphenyl, 3-methoxyphenyl, 4-methoxyphenyl, 3,4-dimethoxyphenyl, 2,5-dimethoxyphenyl, or 4-chlorophenyl. In one aspect, $R^{1c}$ and $R^{1d}$ are independent selected from fluoro, chloro, bromo, and iodo groups.

In various aspects, disclosed herein are aryl-cycloheptene compounds having a formula represented by a structure:

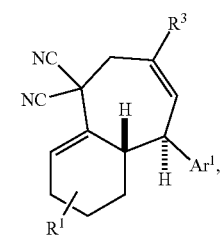

which is understood to be equivalent to a formula:

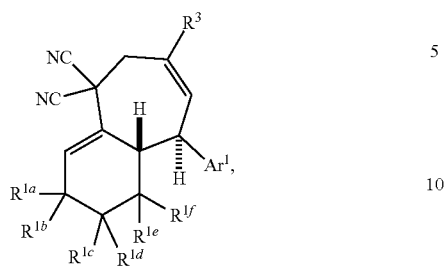

wherein each of $R^{1a}$, $R^{1b}$, $R^{1c}$, $R^{1d}$, $R^{1e}$, $R^{1f}$ and $R^3$ is independently selected from hydrogen and C1-C8 alkyl; or wherein each of $R^{1a}$, $R^{1b}$, $R^{1e}$, $R^{1f}$ and $R^3$ is independently selected from hydrogen and C1-C8 alkyl, and wherein $R^{1c}$ and $R^{1d}$ are combined and form a $C_3$ to $C_8$ cycloalkyl, $C_3$ to $C_8$ cycloalkenyl, or 5-atom or 6-atom heterocycle containing one or more oxygens; and wherein $Ar^1$ is a phenyl group optionally independently substituted with 1, 2, or 3 groups that are electron-withdrawing or electron-donating. In a further aspect, $Ar^1$ can be 2-methoxyphenyl, 3-methoxyphenyl, 4-methoxyphenyl, 3,4-dimethoxyphenyl, 2,5-dimethoxyphenyl, or 4-chlorophenyl. In one aspect, $R^{1c}$ and $R^{1d}$ are independent selected from fluoro, chloro, bromo, and iodo groups.

In a further aspect, an aryl-cycloheptene compound can be present as:

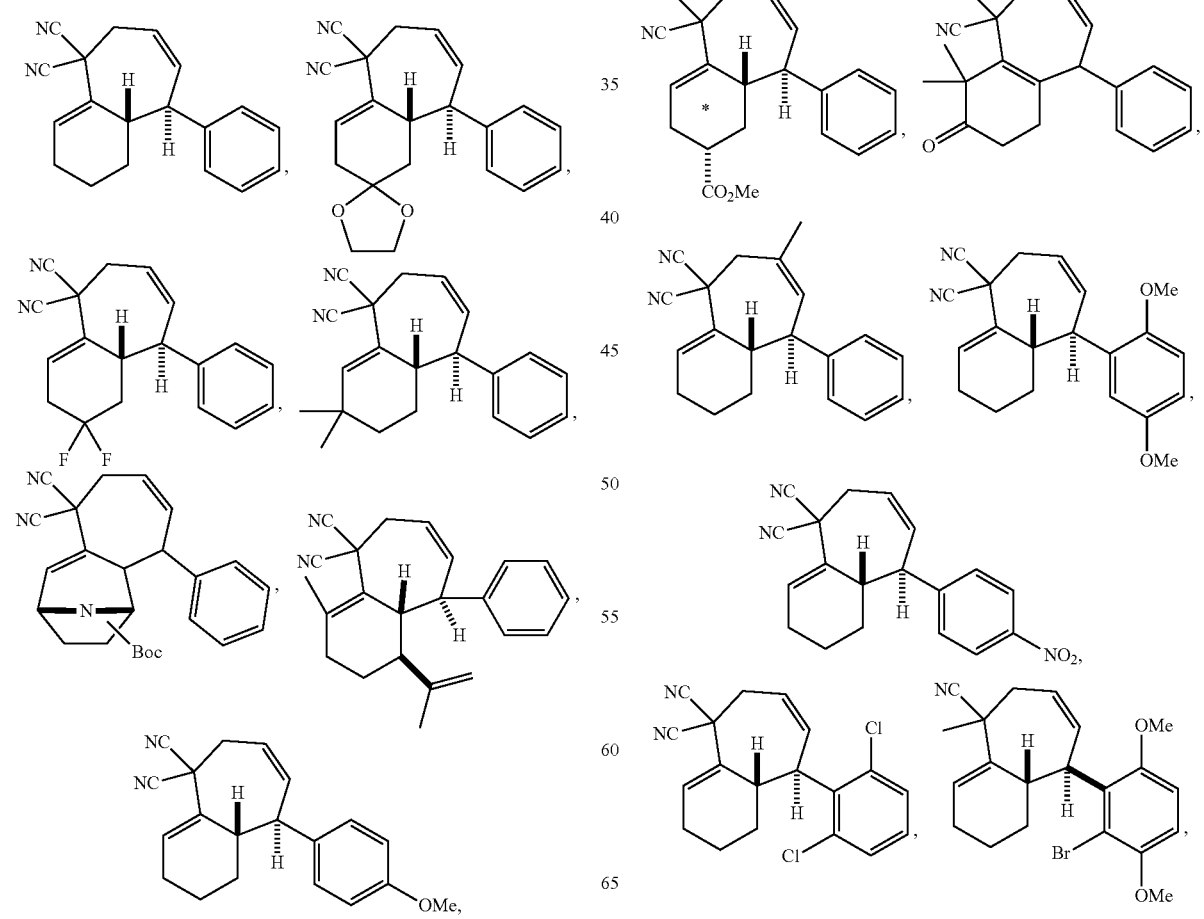

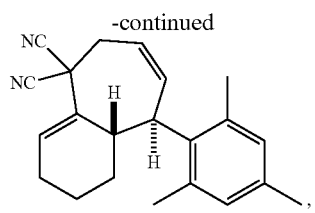

or a subgroup thereof.

In a further aspect, $Ar^1$ is a phenyl group optionally independently substituted with 1 or 2 groups that are electron-withdrawing or electron-donating. In a still further aspect, $Ar^1$ is a phenyl group optionally monosubstituted at an ortho, meta, or para position that is electron-withdrawing or electron-donating. In a still further aspect, $Ar^1$ is a phenyl group optionally independently disubstituted with groups that are electron-withdrawing or electron-donating.

Methods of Making the Disclosed Compounds

In one aspect, the present disclosure relates to methods of making compounds useful in the preparation of intermediates for synthesis of for preparation of aryl-cycloheptene compounds and intermediates useful for the preparation of same. In one aspect, the disclosure relates to the disclosed synthetic manipulations.

The compounds of this disclosure can be prepared by employing reactions as shown in the disclosed schemes, in addition to other standard manipulations that are known in the literature, exemplified in the experimental sections or clear to one skilled in the art. The following examples are provided so that the disclosure might be more fully understood, are illustrative only, and should not be construed as limiting. For clarity, examples having a fewer substituent can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the disclosure. It is understood that a disclosed method can be used to provide the disclosed compounds. It is also understood that the products of the disclosed methods can be employed in the disclosed compositions, kits, and uses.

In one aspect, the disclosed methods utilized mild reaction conditions, and as such the disclosed methods allow syntheses to be carried out that previously had not been possible.

In one aspect, the aryl-cycloheptene compounds of the present disclosure can be prepared generically by the synthetic scheme as shown below. Compounds are represented in generic form, with substituents as noted in compound descriptions elsewhere herein.

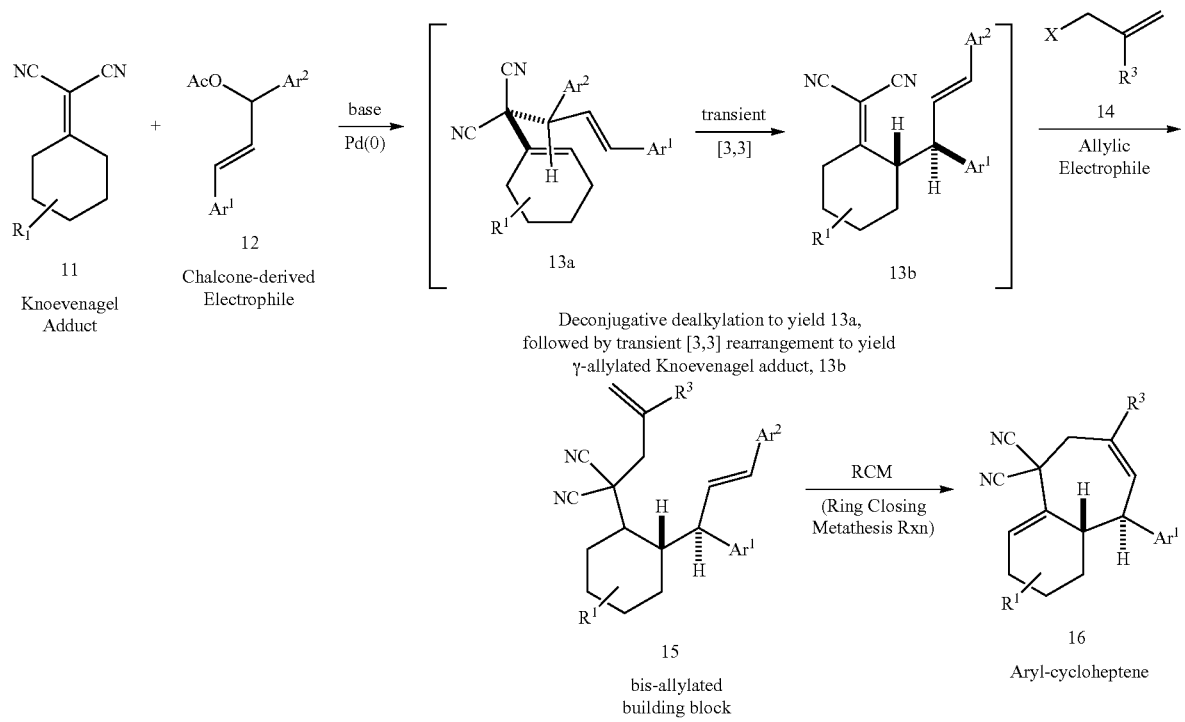

In the foregoing synthesis scheme, the reaction of a compound of formula 11 and 12 is carried out in the presence of palladium and a base. The based can be any suitable base, e.g., an alkali or alkaline earth salt of carbonate such as $K_2CO_3$.

In one aspect, compounds having formula 11 can be synthesized by published methods (e.g., see Knoevenagel, E. Condensation von Malonsäure mit aromatischen Aldehyden durch Ammoniak und Amine Chem. Ber. 1898, 31, 2596-2619; and Jones, G. Knoevenagel Condensation. Org. React. 1967, 15, 204-599).

In one aspect, compounds having formula 12 can be synthesized by published methods (e.g., see Yuan, F.-Q.; Gao, L.-X.; Han, F.-S., Chemical Communications 2011, 47, 5289-5291; Lea, D.; Peng, C.; Jian, L. Acta Chimica Sinica 2013, 71, 1239-1242; and Chan, C.-K.; Tsai, Y.-L.; Chang, M.-Y., Tetrahedron 2017, 73, 3368-3376). In a further aspect, the following synthetic scheme is useful for synthesizing compounds having formula 12, where the general $Ar^1$ can be any group that satisfies the description of $Ar^1$ and/or $Ar^2$:

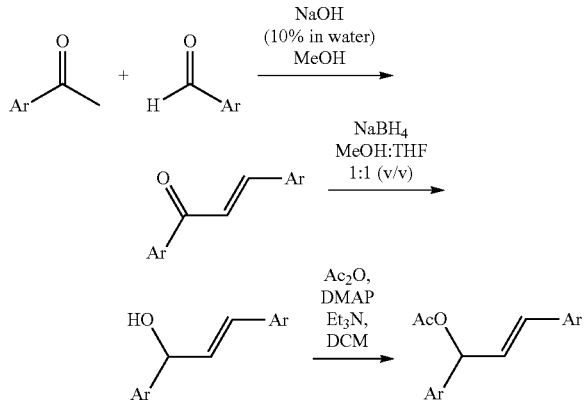

In one aspect, the disclosed methods comprise a method of synthesizing a bis-allylated compound, the method comprising: reacting a Knoevenagel adduct and chalcone-derived electrophile in the presence of a palladium catalyst and base at a first reaction temperature for a first reaction time; wherein the Knoevenagel adduct has a formula represented by a structure:

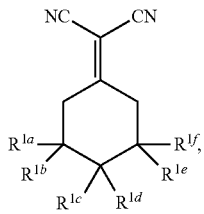

wherein each of $R^{1a}$, $R^{1b}$, $R^{1c}$, $R^{1d}$, $R^{1e}$ and $R^{1f}$ is independently selected from hydrogen, halogens, and C1-C8 alkyl; or wherein each of $R^{1a}$, $R^{1b}$, $R^{1e}$ and $R^{1f}$ is independently selected from hydrogen and C1-C8 alkyl, and wherein $R^{1c}$ and $R^{1d}$ are optionally combined and form a $C_3$ to $C_8$ cycloalkyl, $C_3$ to $C_8$ cycloalkenyl, or 5-atom or 6-atom heterocycle containing one or more oxygens; wherein the chalcone-derived electrophile has a formula represented by a structure:

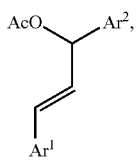

wherein $Ar^1$ is a phenyl group optionally independently substituted with 1, 2, or 3 groups that are electron-withdrawing or electron-donating; and wherein $Ar^2$ is a phenyl group optionally independently substituted with 1, 2, or 3 groups that are electron-withdrawing or electron-donating; after completion of the first reaction time, adding to the reaction an allylic electrophile and continuing the reaction at second reaction temperature for a second reaction time, wherein the allylic electrophile has a formula represented by a structure:

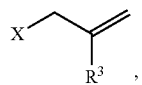

wherein X is a halogen; and wherein $R^3$ is selected from hydrogen and C1-C8 alkyl; thereby synthesizing the bis-allylated compound, wherein the bis-allylated compound has a formula represented by a structure:

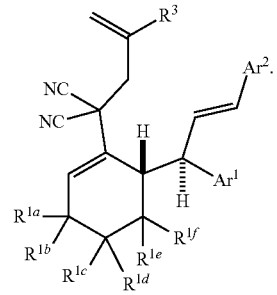

In various aspects, the first reaction temperature is a temperature of less than about 50° C., or from about 0° C. to about 50° C., or at about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., or a combination of any of the foregoing values, or a range encompassing any of the foregoing values. In a further aspect, the first reaction temperature can be room temperature or at about 20° C. to about 30° C.

In various aspects, the second reaction temperature is a temperature of less than about 50° C., or from about 0° C. to about 50° C., or at about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., or a combination of any of the foregoing values, or a range encompassing any of the foregoing values. In a further aspect, the second reaction temperature can be room temperature or at about 20° C. to about 30° C.

In a further aspect, $R^{1c}$ and $R^{1d}$ are fluoro, chloro, bromo, or iodo groups. In a still further aspect, $R^{1c}$ and $R^{1d}$ are combined to form a 5-atom heterocycle with two oxygen atoms. In a yet further aspect, $Ar^1$ and $Ar^2$ are phenyl and $R^{1c}$ and $R^{1d}$ are combined to form a 5-atom heterocycle with two oxygen atoms.

In one aspect, the disclosed methods comprise a method of synthesizing an aryl-cycloheptene compound, the method comprising: reacting a bis-allylated compound in the presence of a Grubbs catalyst, and wherein the bis-allylated compound has a formula represented by a structure:

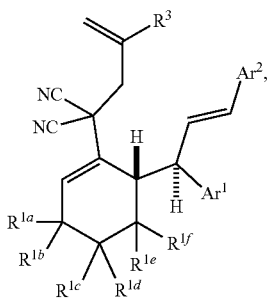

wherein each of $R^{1a}$, $R^{1b}$, $R^{1c}$, $R^{1d}$, $R^{1e}$, $R^{1f}$ and $R^3$ is independently selected from hydrogen, halogen, and C1-C8 alkyl; or wherein each of $R^{1a}$, $R^{1b}$, $R^{1e}$, $R^{1f}$ and $R^3$ is independently selected from hydrogen and C1-C8 alkyl, and wherein $R^{1a}$ and $R^{1d}$ are optionally combined to form a $C_3$ to $C_8$ cycloalkyl, $C_3$ to $C_8$ cycloalkenyl, or 5-atom or 6-atom heterocycle containing one or more oxygens; wherein $Ar^1$ is a phenyl group optionally independently substituted with 1, 2, or 3 groups that are electron-withdrawing or electron-donating; and wherein $Ar^2$ is a phenyl group optionally independently substituted with 1, 2, or 3 groups that are electron-withdrawing or electron-donating; thereby synthesizing an aryl-cycloheptene compound having a formula represented by a structure:

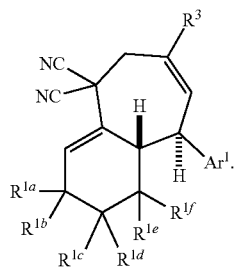

In a further aspect, $Ar^1$ and $Ar^2$ are, independently, selected from 2-methoxyphenyl, 3-methoxyphenyl, 4-methoxyphenyl, 3,4-dimethoxyphenyl, 2,5-dimethoxyphenyl, and 4-chlorophenyl. In a still further aspect, $R^{1c}$ and $R^{1d}$ are fluoro, chloro, bromo, or iodo groups. In an even further aspect, $R^{1c}$ and $R^{1d}$ are combined to form a C3 cycloalkyl group with two oxygen atoms. In a yet further aspect, $Ar^1$ and $Ar^2$ are phenyl and $R^{1c}$ and $R^{1d}$ are combined to form a C3 cycloalkyl group with two oxygen atoms.

Synthetic Flexibility

In one aspect, because the reaction conditions disclosed herein are mild, syntheses that have previously not been possible can be accomplished using the processes disclosed herein. In one aspect, the reactions described herein can be carried out at a temperature of less than about 120° C., or from about 15° C. to about 120° C., or at about 15, 20, 25, 30, 35, 40, 45, 50, 55, 60, 65, 70, 75, 80, 85, 90, 95, 100, 105, 110, 115, or about 120° C., or a combination of any of the foregoing values, or a range encompassing any of the foregoing values. In one aspect, the reactions described herein can be carried out at room temperature or at about 22° C.

In a further aspect, Meldrum's acid moieties are excellent handles for functional group interconversion but Meldrum's acid derivatives decompose to ketene, carbon dioxide, and acetone (i.e., at about 120° C.) at temperatures lower than those previously required for the Cope rearrangement (typically 250° C.). In a further aspect, the methods disclosed herein are useful for preparation of cycloheptene scaffolds bearing an embedded Meldrum's moiety in lieu of the gem-dinitrile shown herein. In a similar aspect, the methods disclosed herein can be adapted to incorporate other temperature-sensitive functional groups into the disclosed scaffolding.

Pharmaceutical Compositions

In various aspects, the present disclosure relates to pharmaceutical compositions comprising a therapeutically effective amount of at least one disclosed compound, at least one product of a disclosed method, or a pharmaceutically acceptable salt thereof. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed compound, at least one product of a disclosed method, or a pharmaceutically acceptable salt thereof as an active ingredient, a pharmaceutically acceptable carrier, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitonealy, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, a therapeutically effective amount of a disclosed compound, a product of a disclosed method of making, a pharmaceutically acceptable salt, a hydrate thereof, a solvate thereof, a polymorph thereof, or a stereochemically isomeric form thereof. In a further aspect, a disclosed compound, a product of a disclosed method of making, a pharmaceutically acceptable salt, a hydrate thereof, a solvate thereof, a polymorph thereof, or a stereochemically isomeric form thereof, or any subgroup or combination thereof may be formulated into various pharmaceutical forms for administration purposes.

Pharmaceutically acceptable salts can be prepared from pharmaceutically acceptable non-toxic bases or acids. For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed compound comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N,N'-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed compound comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with a basic reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids which can be used to prepare the pharmaceutically acceptable acid-addition salts of the base compounds are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the compounds of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentaerythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example *arachis* oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik und angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure suitable injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present invention may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices. These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present invention include a single-layer or multilayer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-in-adhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present invention include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising the topical composition of the invention formulated in a pharmaceutically acceptable carrier may also be prepared, placed in an appropriate container, and labeled for treatment of an indicated condition.

Another patch system configuration which can be used by the present invention is a reservoir transdermal system design which is characterized by the inclusion of a liquid compartment containing a drug solution or suspension separated from the release liner by a semi-permeable membrane and adhesive. The adhesive component of this patch system can either be incorporated as a continuous layer between the membrane and the release liner or in a concentric configuration around the membrane. Yet another patch system configuration which can be utilized by the present invention is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions, an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The disclosed pharmaceutical compositions can further comprise other therapeutically active compounds, which are usually applied in the treatment of the above mentioned pathological or clinical conditions.

It is understood that the disclosed compositions can be prepared from the disclosed compounds. It is also understood that the disclosed compositions can be employed in the disclosed methods of using.

As already mentioned, the present disclosure relates to a pharmaceutical composition comprising a therapeutically effective amount of a disclosed compound, a product of a disclosed method of making, a pharmaceutically acceptable salt, a hydrate thereof, a solvate thereof, a polymorph thereof, and a pharmaceutically acceptable carrier. Additionally, the present disclosure relates to a process for preparing such a pharmaceutical composition, characterized in that a pharmaceutically acceptable carrier is intimately mixed with a therapeutically effective amount of a compound according to the present disclosure.

As already mentioned, the present disclosure also relates to a pharmaceutical composition comprising a disclosed compound, a product of a disclosed method of making, a pharmaceutically acceptable salt, a hydrate thereof, a solvate thereof, a polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present disclosure also relates to a combination of disclosed compound, a product of a disclosed method of making, a pharmaceutically acceptable salt, a hydrate thereof, a solvate thereof, a polymorph thereof, and an additional therapeutic agent. The present disclosure also relates to such a combination for use as a medicine. The present disclosure also relates to a product comprising (a) disclosed compound, a product of a disclosed method of making, a pharmaceutically acceptable salt, a hydrate thereof, a solvate thereof, a polymorph thereof, and (b) an additional therapeutic agent, as a combined preparation for simultaneous, separate or sequential use in the treatment or prevention of a condition in a mammal, including a human, the treatment or prevention of which is affected or facilitated by the modulatory effect of the disclosed compound and the additional therapeutic agent. The different drugs of such a combination or product may be combined in a single preparation together with pharmaceutically acceptable carriers or diluents, or they may each be present in a separate preparation together with pharmaceutically acceptable carriers or diluents. In one aspect, the condition can be selected from cystic fibrosis, gingivitis, psoriasis, obesity, diabetes, inflammatory bowel disease, arthritis, sepsis, gastritis, asthma, atherosclerosis, macular degeneration, Alzheimer's disease, hypertension, bacterial infection, fungal infection, another condition associated with inflammation, or cancer including, but not limited to, colon cancer, glioblastoma, nasopharyngeal cancer, breast cancer, endometrial cancer, prostate cancer, or another cancer.

Before proceeding to the Examples, it is to be understood that this disclosure is not limited to particular aspects described, and as such may, of course, vary. Other systems, methods, features, and advantages of foam compositions and components thereof will be or become apparent to one with skill in the art upon examination of the following drawings and detailed description. It is intended that all such additional systems, methods, features, and advantages be included within this description, be within the scope of the present disclosure, and be protected by the accompanying claims. It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: General Experimental Details

All commercial materials were used without further purification. $^1$H NMR and $^{13}$C NMR spectra were recorded in either chloroform-d, acetone-d6 or dimethyl sulfoxide-d6 using a 500 MHz or 300 MHz spectrometer. All $^{13}$C NMR spectra were recorded with complete proton decoupling. HRMS data were recorded on Agilent Time of Flight 6200 spectrometer. Reaction progress was monitored by thin-layer chromatography (TLC) and visualized by UV light, phosphomolybdic acid stain, and $KMnO_4$ stain. All reactions were carried out using anhydrous solvents obtained dried by passing through activated alumina columns. According to the reported synthetic processes, chalcones were easily synthesized in nearly quantitative yields by NaOH-mediated aldol condensation of acetophenones and arylaldehydes in ethanol. Without further purification, the chalcone derivatives was treated with 1.0 equiv. of $NaBH_4$ in in the co-solvent of THF and MeOH (v/v: 1/1) at 0° C. for 10 min., followed by acetylation of the resulting the allylic alcohols in an excellent yield. Allyl tert-butyl carbonate (4a) was prepared from prop-2-en-1-ol according to the previously reported procedure. All spectroscopic data for these three electrophiles were consistent with those reported in the literature. The allylated malononitrile (11a) was synthesized using the know procedure in the literature and all the analytical data were identical to the cited reference. All other synthetic protocols were as outlined below.

Figure 2A:
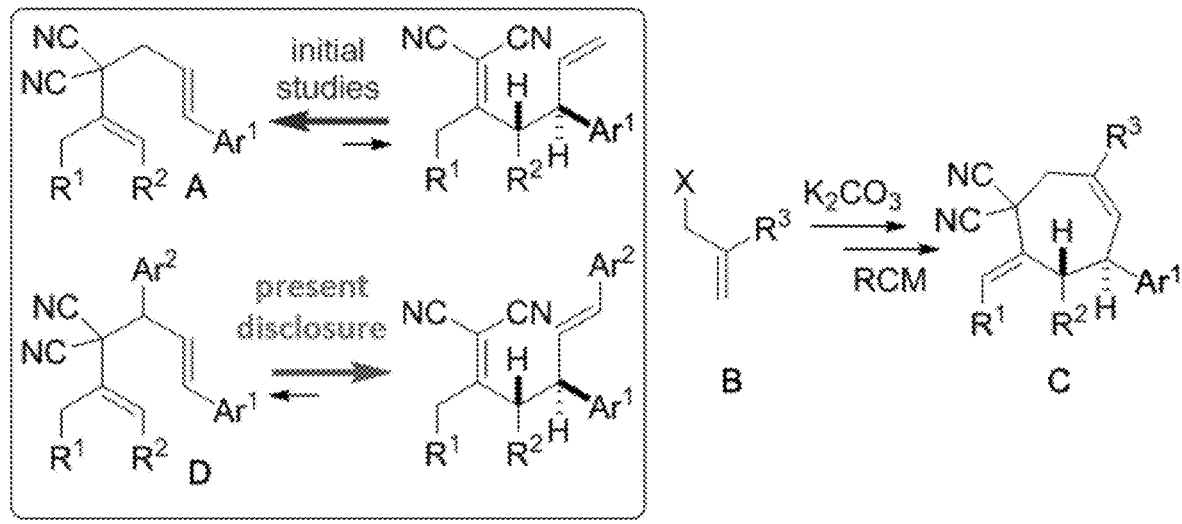
FIGS. 2A-2C show representative disclosed synthetic methods using a Cope rearrangement-centered route to prepare aryl-cycloheptene scaffolds.

Example 2: General Procedures A, A1, and B: Pd-Catalyzed Diallylation of Knoevenagel Adducts (One-Pot) and Ring Closing Metathesis It was hypothesized that 1,5-dienes A and an allylic electrophile B, could be converted to the aryl-cycloheptane scaffold C over, in theory, a simple procedure involving Cope rearrangement, deconjugative allylation, and ring-closing metathesis (RCM) (FIG. 2A). Notably, 1,5-dienes of type A are conventionally prepared by a simple and convergent two-step protocol from ketones, malononitrile and cinnamyl electrophiles; all abundant starting material classes. Unfortunately, initial studies demonstrated that the Cope rearrangement was not thermodynamically favorable due to styrene-deconjugation.

Figure 2B:
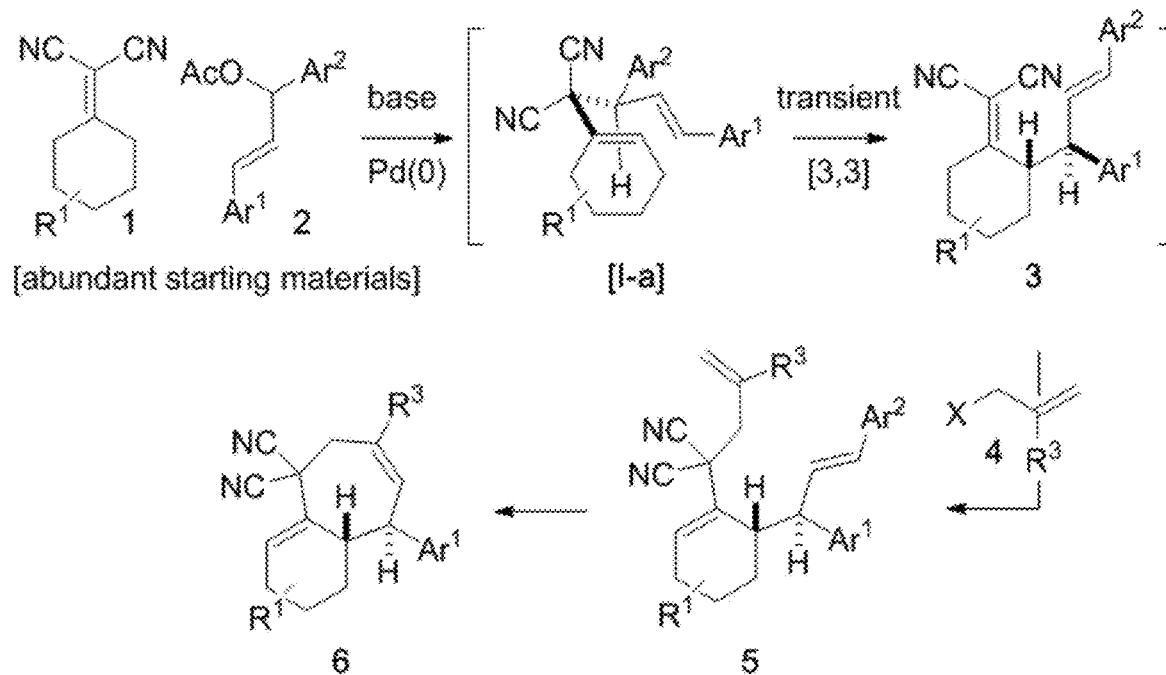
Figure 2C:
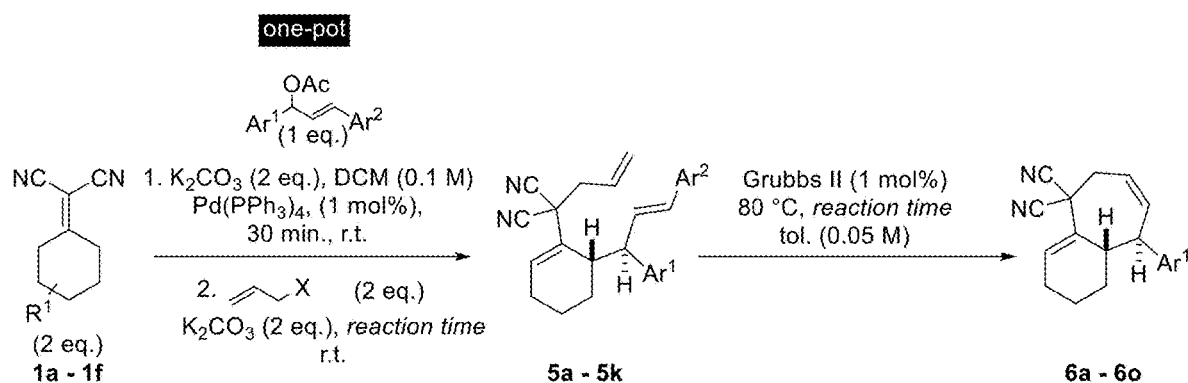

To combat the poor conversions observed with 1,5-dienes A, it was further hypothesized that that the 4,6-diaryl-1,5-dienes D would be more reactive toward thermal rearrangement as styrene deconjugation is offset (FIG. 2B). Thus, the exact same products C can be accessed as the [3,3]-promoting aryl group ($Ar^2$) is removed in the ring-closing metathesis step. Surprisingly, in the present disclosure, it was found that Knoevenagel adducts 1 and chalcone-derived electrophiles 2 undergo deconjugative alkylation to [I-a] followed by a transient [3,3] rearrangement (unexpectedly occurring at room-temperature with a calculated barrier of 19.5 kcal/mol) to yield the γ-allylated Knoevenagel adduct 3. Deconjugative alkylation with allylic electrophiles 4 yields the bis-allylated building blocks 5 in one-step from 1 and 2 which undergo facile RCM to aryl-cycloheptenes 6 (see FIG. 2B)

Figure 3:
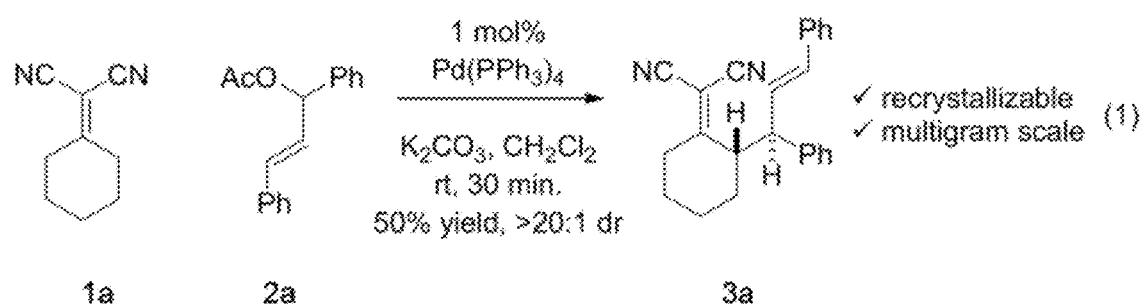
FIG. 3 shows a representative synthetic scheme for the preparation of a representative disclosed compound.
Figure 4A:
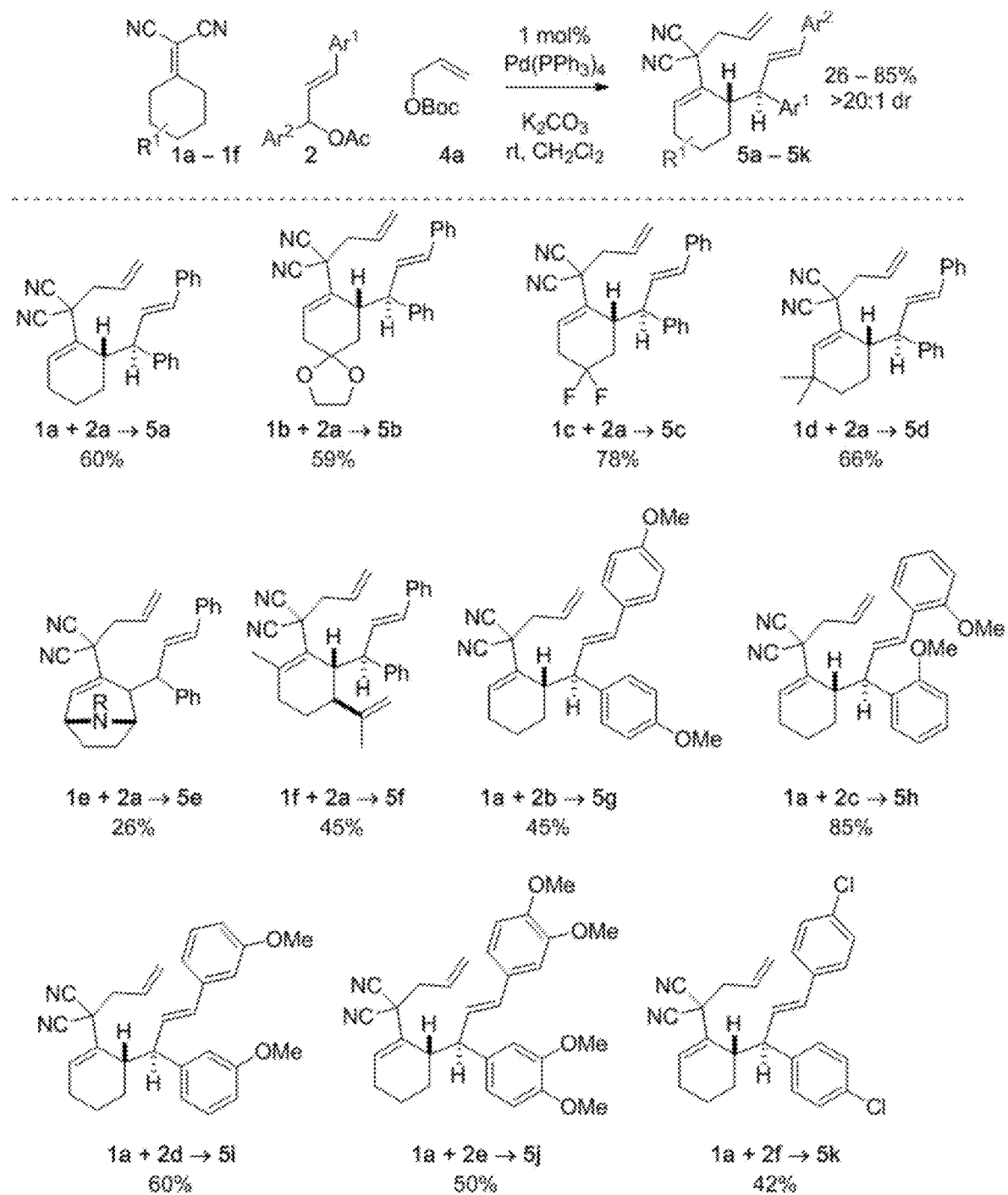
FIGS. 4A-4B show representative synthetic schemes for the preparation of a representative disclosed compounds.
Figure 4B:
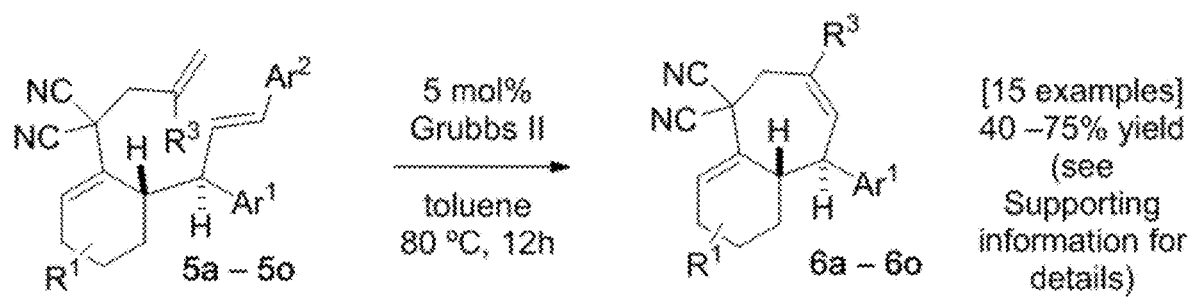

The reaction was examined using a model Knoevenagel adduct 1a and chalcone-derived electrophile 2a, using Pd(0)-catalysis, and it was surprisingly found that the molecules couple yielding the γ-allylated scaffold 3a (FIG. 3). The reaction was determined to be efficient, diastereoselective, and scalable. Moreover, the product can be recrystallized. The regioselectivity was also unexpected as alkyl electrophiles (e.g. alkyl halides and allyl acetates/carbonates) tend to yield deconjugative alkylation products). Thus, this result raises the question as to whether 3 is accessed by a [3,3] rearrangement as originally proposed or by a direct γ-allylation mechanism. This connectivity is nonetheless welcomed as the high acidity of the Knoevenagel adduct remains unchanged allowing for three-component coupling directly to bis-allylated scaffolds 5a-5k (FIGS. 4A and 4B). This transformation tolerated a wide array of cyclic Knoevenagel adducts 1a-1f and symmetric chalcone-derived electrophiles 2a-2f (FIGS. 4A and 4B).

Figure 5:
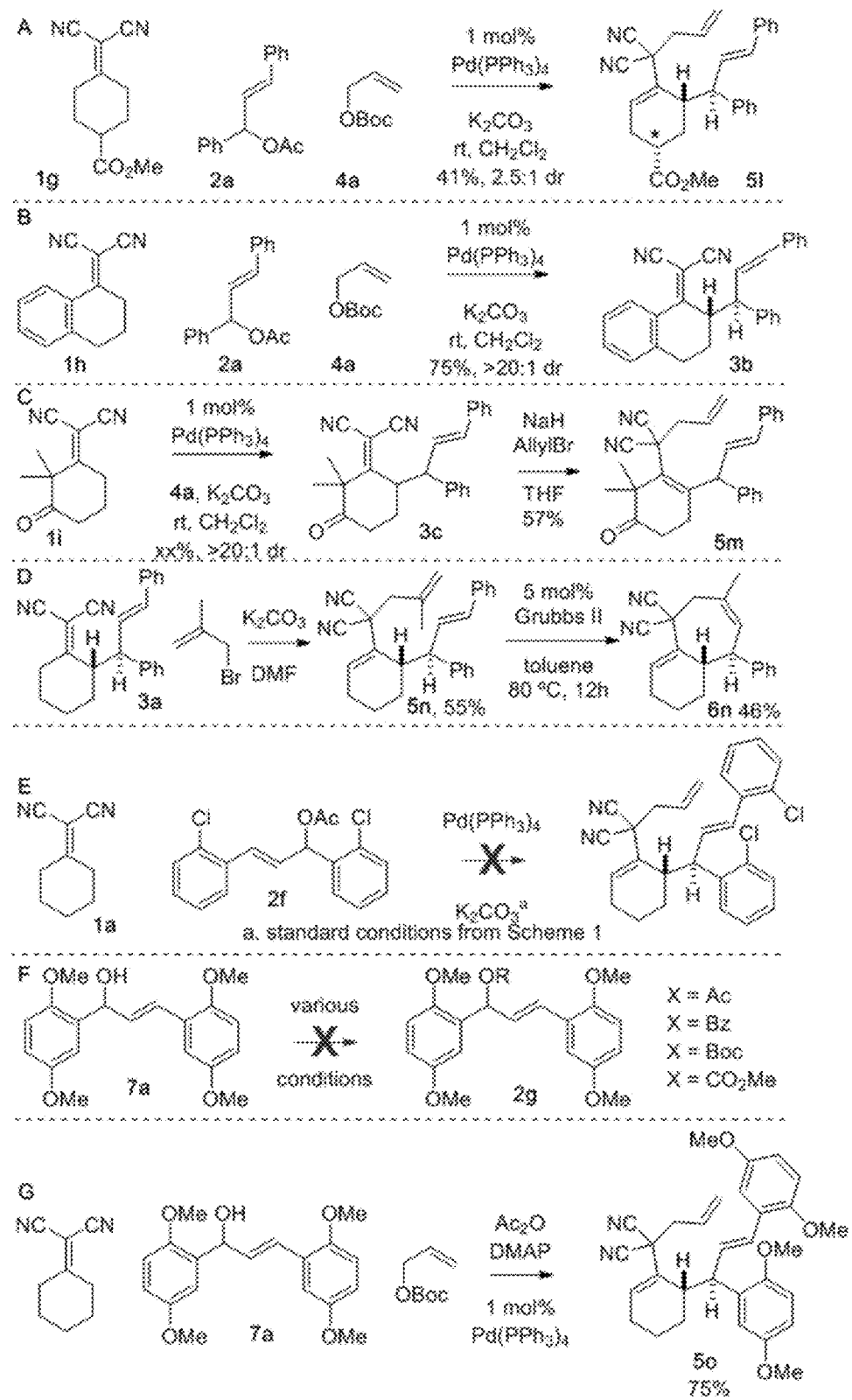
FIG. 5 shows a representative synthetic schemes related to the Knoevenagel adduct bis-allylation protocol per the reaction conditions as given therein and further described herein below.

There were several other notable findings related to the scope of the Knoevenagel adduct bis-allylation protocol (FIG. 5). Pro-chiral Knoevenagel adducts with a remote stereocenter (e.g. 1g) gave rise to diastereomeric mixtures (FIG. 5, Scheme A). Also, when examining the tetralone-derived Knoevenagel adduct 1h for three-component bis-alkylation reactivity, only two-component coupling was observed to 3b (FIG. 5, Scheme B). Similarly, this was observed with Knoevenagel adduct 1i. However, deprotonation of sterically encumbered γ-C-H's can be achieved with NaH as the base (5m; FIG. 5, Scheme C). The sequence can also be performed with 2-substituted allylic electrophiles ultimately yielding trisubstituted olefins by RCM (FIG. 5, Scheme D). Next, the electron-deficient chalcone-derivative 2g did not react under the standard conditions (0% conversion), likely due to challenges associated with the oxidative addition step (FIG. 5, Scheme E). Attempts to make the activated chalcone-derived electrophile 2h were unsuccessful (FIG. 5, Scheme F). Without wishing to be bound by a particular theory, it is possible that the issue might be that acylation is occurring, but the acetate/carbonate is prone to hydrolysis back to the alcohol under standard work-up conditions (extraction conditions, silica gel, etc.). In agreement with this, successful coupling was achieved directly from the alcohol 7a using an in-situ acylation strategy (FIG. 5, Scheme G).

Figure 6A:
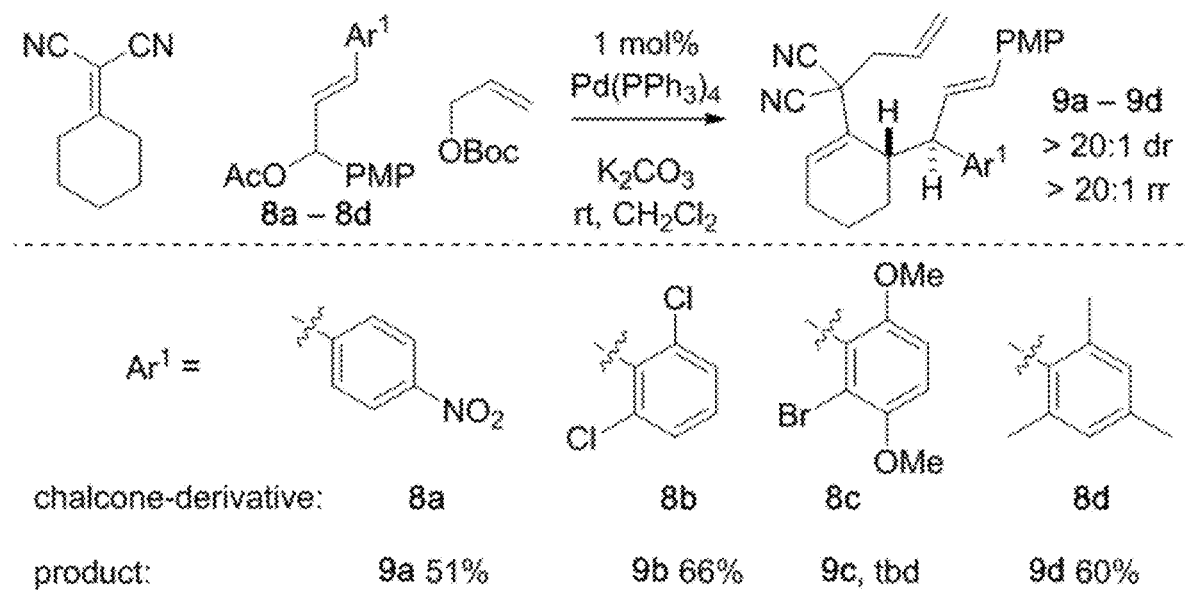
FIGS. 6A-6B show representative synthetic schemes for the preparation of a representative disclosed compounds.
Figure 6B:
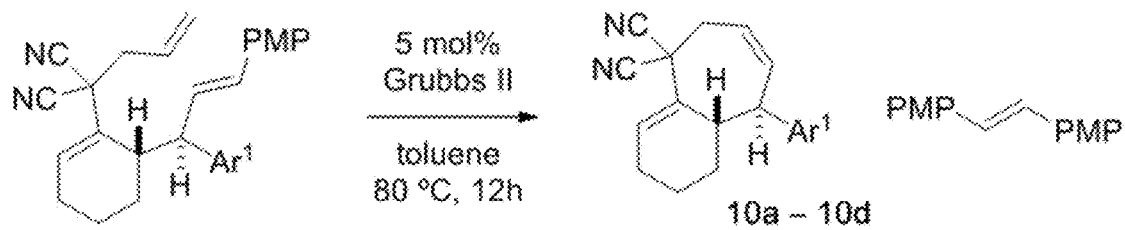

In the course of examining non-symmetric chalcone-derived electrophiles 8a-8d with Knoevenagel adduct 1a, it was determined that diastereo- and regioselective transformation to the bis-allylated products 9a-9d could be achieved (FIGS. 6A-6B). The electrophiles bore a p-methoxyphenyl (PMP) and a variable-arene (p-nitrophenyl (8a), 2,6-dichloro (8b), 2-bromo-3,6-dimethoxyphenyl (8c), and 2,4,6,-trimethylphenyl (8d)). In all cases, the variable arene was installed at the allylic position. Thus, upon ring-closing metathesis, the PMP-group was removed and the variable-aryl-cycloheptenes 10a-10d were prepared (FIG. 6B).

Figure 7A:
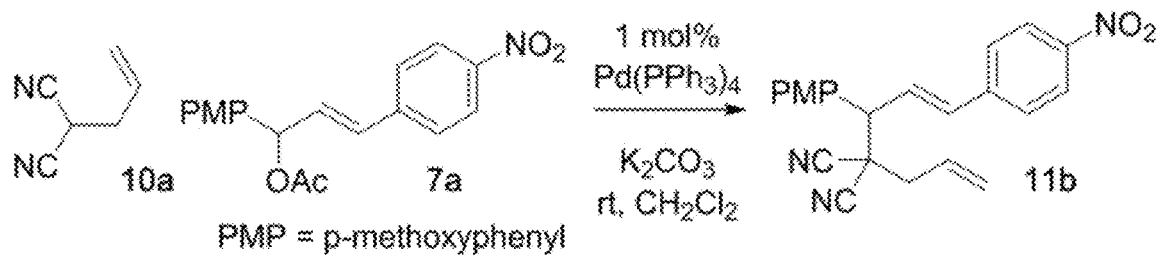
FIG. 7A shows one reaction scheme demonstrating that γ-allylation occurs via a transient Cope rearrangement reaction.
Figure 7B:
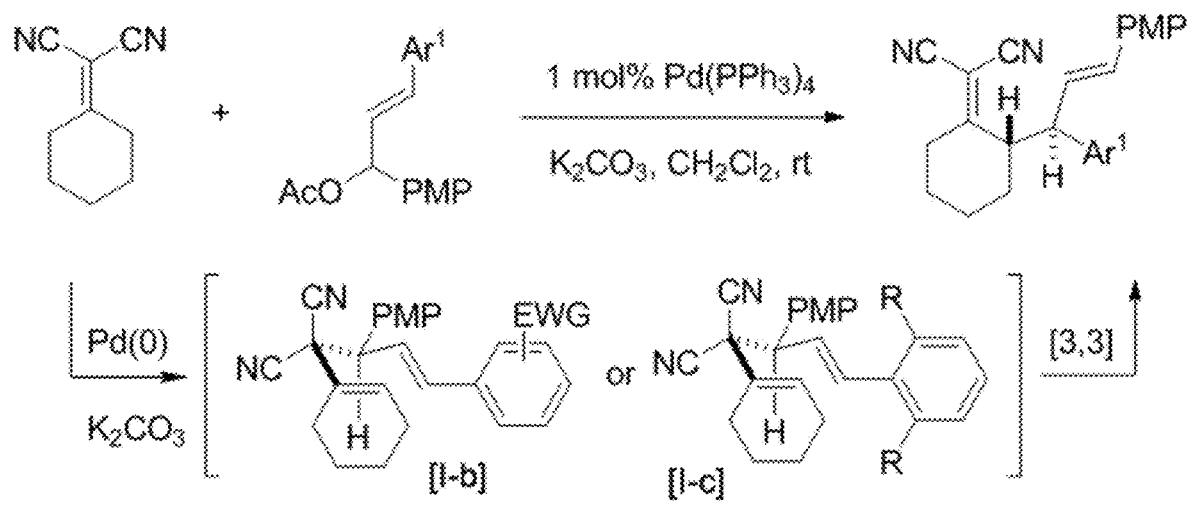
FIG. 7B shows a second reaction scheme demonstrating that γ-allylation occurs via a transient Cope rearrangement reaction.

In order to better understand the mechanism of the initial coupling between the Knoevenagel adduct and the chalcone-derived allylic electrophile occurs by the originally conceived deconjugative alkylation/transient [3,3] rearrangement sequence or by a direct γ-allylation mechanism further experiments were carried out (FIGS. 7A-7B). The regioselectivity in FIGS. 6A-6B, and discussed above, suggests that the reaction is proceeding by low-barrier Cope rearrangement (occurring at room-temperature). This is surprising as related 3,3-dicyano-1,5-dienes do not undergo rearrangement until heated >120° C. Furthermore, Cope rearrangements occurring at room temperature usually bear a strain element or are "oxy-Cope" substrates. Consider the following data: (a) allyl malononitrile 10a reacts with 7a to yield product 11b where the PMP group, not the p-nitrophenyl group, is at the allylic position (FIG. 7A). This result is opposite to the connectivity in 9a (FIGS. 6A-6B); and (b) regioselectivity of allylation with 8b-8d is such that the sterically bulky arene is at the allylic position on the bis-allylated building blocks 9b-9d. As shown in FIG. 7B, the deconjugative alkylation occurs first yielding the 1,5-dienes [I-a/b]. This transformation is either electronically [I-b] or sterically [I-c] driven (or both). Cope rearrangement then yields the γ-allylated product with connectivity that matches the products from bis-allylation (FIGS. 6A-6B).

General Procedure A: Pd-Catalyzed Diallylation of Knoevenagel Adducts (One-Pot)

All reactions were performed under nitrogen atmosphere in flame-dried round bottom flasks. Chalcone derivatives were added at room temperature to a solution of tetrakis(triphenylphosphine)palladium(0) (1 mol %), the Knoevenagel adduct (1 equiv.) and $K_2CO_3$ (2 equiv.) in DCM (0.1 M). The mixture was stirred at room temperature for 30 minutes. Then, 2 equivalents of the allyl tert-butyl carbonate or allyl bromide was added via syringe. After completion, toluene was removed in vacuo, and the resulting residue was purified by flash column chromatography on silica gel and the crude products were purified by column chromatography (hexanes-ethyl acetate).

General Procedure A1: Pd-Catalyzed Diallylation of Knoevenagel Adducts (One-Pot)

All reactions were performed under nitrogen atmosphere in flame-dried round bottom flasks. Chalcone derivatives were added at room temperature to a solution of tetrakis(triphenylphosphine)palladium(0) (1 mol %), the Knoevenagel adduct (1 equiv.) and K2CO3 (2 equiv.) in DCM (0.1 M). The mixture was stirred at room temperature for 30 minutes. After completion, DCM was removed in vacuo, and the resulting residue was purified by flash column chromatography on silica gel and the crude products were purified by column chromatography (hexanes-ethyl acetate).

General Procedure B: Ring Closing Metathesis

All reactions were performed under nitrogen atmosphere in flame-dried round bottom flasks. The γ,α-diallylated Knoevenagel adduct 5a-5k was taken in anhydrous degassed toluene (0.05 M). Then, Grubbs Catalyst $2^{nd}$ generation (1 mol %) was added to it and the solution was stirred at 80° C. for the time shown for each compound. After completion of the reaction, it was cooled to room temperature and passed through a short silica gel bed and washed with ethyl acetate. Then the solution was evaporated under reduced pressure. The residue was then purified by silica gel chromatography (EtOAc/hexane) to afford the final product. Note: Stereochemistry of the final products was assigned based on 6n and those reported in the previous work.

Example 3: Preparation of Knoevenagel Adducts (1a-1i)

Knoevenagel adducts 1a-1i were synthesized according to previously reported procedures and had spectroscopic data consistent with those reported in the literature. Structures of compounds 1a-1f are found in Table 1 below.

TABLE 1

| Knoevenagel Adducts 1a-1f | |
|---|---|
| Compound Identification No. | Structure |
| 1a | NC CN (cyclohexyl) |
| 1b | NC CN (spiro dioxolane cyclohexyl) |
| 1c | NC CN (4,4-difluorocyclohexyl) |

TABLE 1-continued

Knoevenagel Adducts 1a-1f

| Compound Identification No. | Structure |
| --- | --- |
| 1d | NC-CH(CN)-(3,3-dimethylcyclohexyl) |
| 1e | NC-CH(CN)-(N-Boc-azabicyclic) |
| 1f | NC-CH(CN)-(2-methyl-5-isopropenylcyclohexyl) |

Example 4: Preparation of Chalcone Derivatives (2a-2g)

Synthesis of chalcone derivatives (2a-2g and 7a) was carried out according to previously published synthetic methods according to the reaction scheme below.

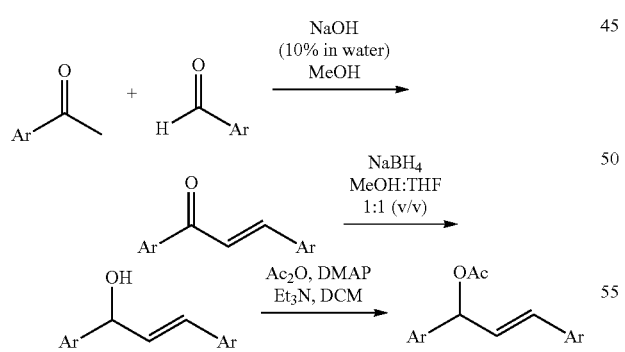

The first and third steps of the foregoing reaction were carried out as previously described by Yuan, F.-Q., Gao, L.-X., and Han, F.-S. Chemical Communications 2011, 47, 5289-5291, and the second step carried out as previously described by Chan, C.-K.; Tsai, Y.-L.; Chang, M.-Y., Tetrahedron 2017, 73, 3368-3376. The spectroscopic data for the products were consistent with those reported in the literature. Further information is provided in Table 2 below.

TABLE 2

Chalcone Derivatives 2a-2g and 7a

| Compound Identification No. | Structure |
| --- | --- |
| 2a | 1,3-diphenyl-1-OAc-propene |
| 2b | bis(4-methoxyphenyl)-1-OAc-propene |
| 2c | bis(2-methoxyphenyl)-1-OAc-propene |
| 2d | bis(3-methoxyphenyl)-1-OAc-propene |
| 2e | bis(3,4-dimethoxyphenyl)-1-OAc-propene |
| 2f | bis(4-chlorophenyl)-1-OAc-propene |
| 2g | bis(2-chlorophenyl)-1-OAc-propene |
| 7a | 1-(4-methoxyphenyl)-3-(4-nitrophenyl)-1-OAc-propene |

Example 5: Preparation of γ-Allylated Knoevenagel Adducts (3a-3b)

Example 5.1: (E)-2-(2-(1,3-diphenylallyl)cyclohexylidene)malononitrile (3a)

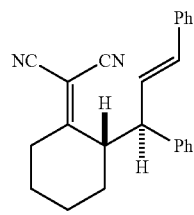 [SMILES: N#CC(C#N)=C1CCCC[C@H]1[C@@H](/C=C/c1ccccc1)c1ccccc1]

Figure 9A:
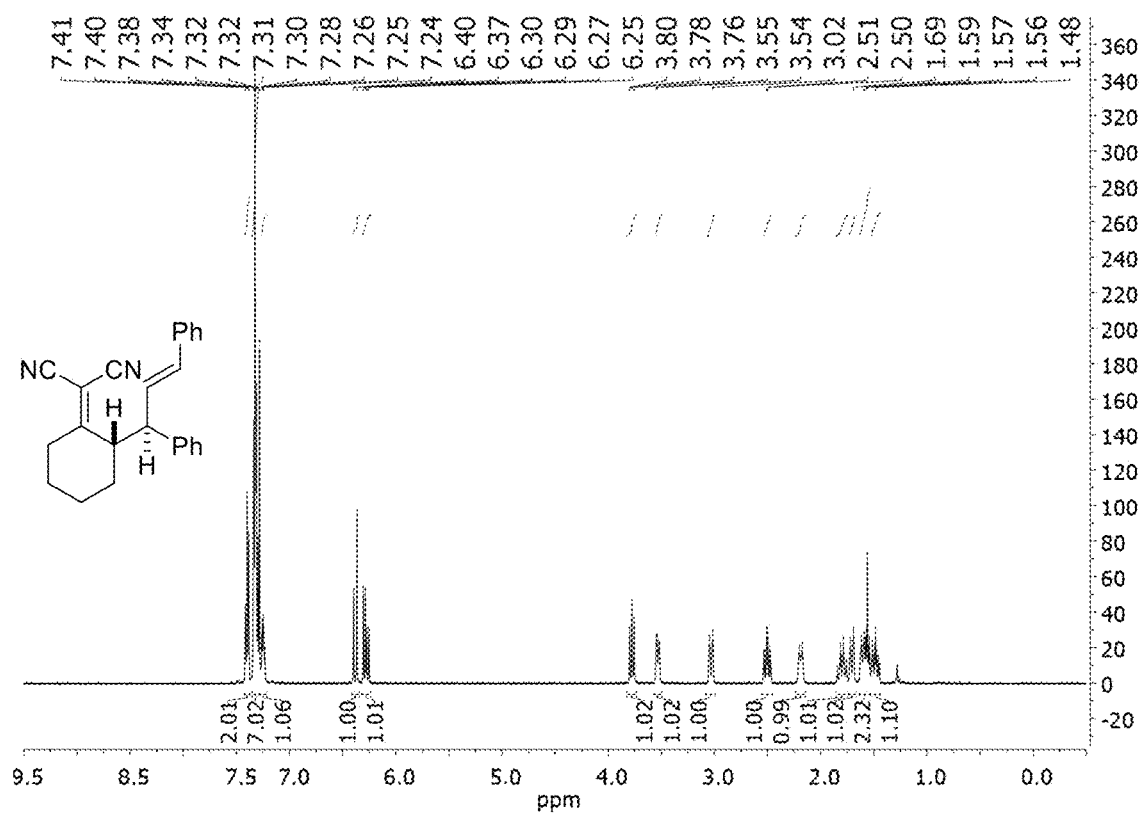
Figure 9B:
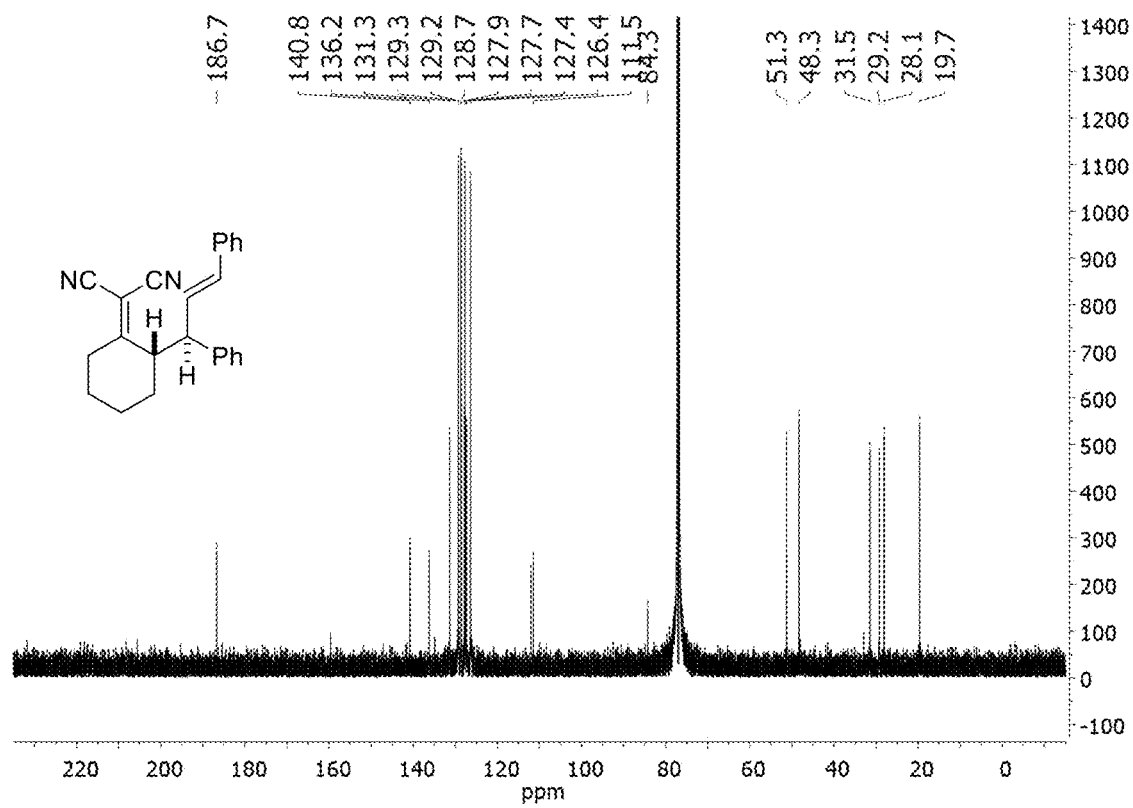

Prepared by general procedure A1 with a reaction time of 30 min. Isolated: 5 g. Yield: 50% (>20:1 dr). Physical state: white solid. TLC: $R_f$=0.59 (20% EtOAc in hexanes); Purified using recrystallization (ethanol). $^1$H NMR (500 MHz, CDCl$_3$) major diastereomer: δ 7.40 (t, J=7.5 Hz, 2H), 7.31 (dt, J=12.9, 5.5 Hz, 7H), 7.27-7.22 (m, 1H), 6.38 (d, J=15.6 Hz, 1H), 6.28 (dd, J=15.6, 9.4 Hz, 1H), 3.82-3.74 (m, 1H), 3.53 (dd, J=11.2, 4.3 Hz, 1H), 3.03 (d, J=14.3 Hz, 1H), 2.50 (td, J=13.8, 5.5 Hz, 1H), 2.19 (d, J=12.9 Hz, 1H), 1.86-1.74 (m, 1H), 1.71 (d, J=14.0 Hz, 1H), 1.64-1.53 (m, 2H), 1.48 (ddd, J=18.7, 9.5, 4.5 Hz, 1H). $^{13}$C NMR (126 MHz, CDCl$_3$): δ 186.7, 140.8, 136.2, 131.3, 129.3, 129.2, 128.7, 127.9, 127.7, 127.4, 126.4, 112.0, 111.5, 84.3, 51.3, 48.3, 31.5, 29.2, 28.1, 19.7. Representative NMR spectra can be seen in FIGS. 9A-9B.

Example 5.2: (E)-2-(2-(1,3-diphenylallyl)-3,4-dihydro naphthalen-1(2H)-ylidene)malononitrile (3b)

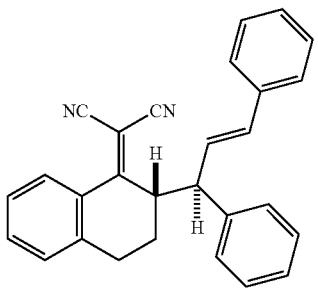 [SMILES: N#CC(C#N)=C1c2ccccc2CC[C@H]1[C@@H](/C=C/c1ccccc1)c1ccccc1]

Figure 10A:
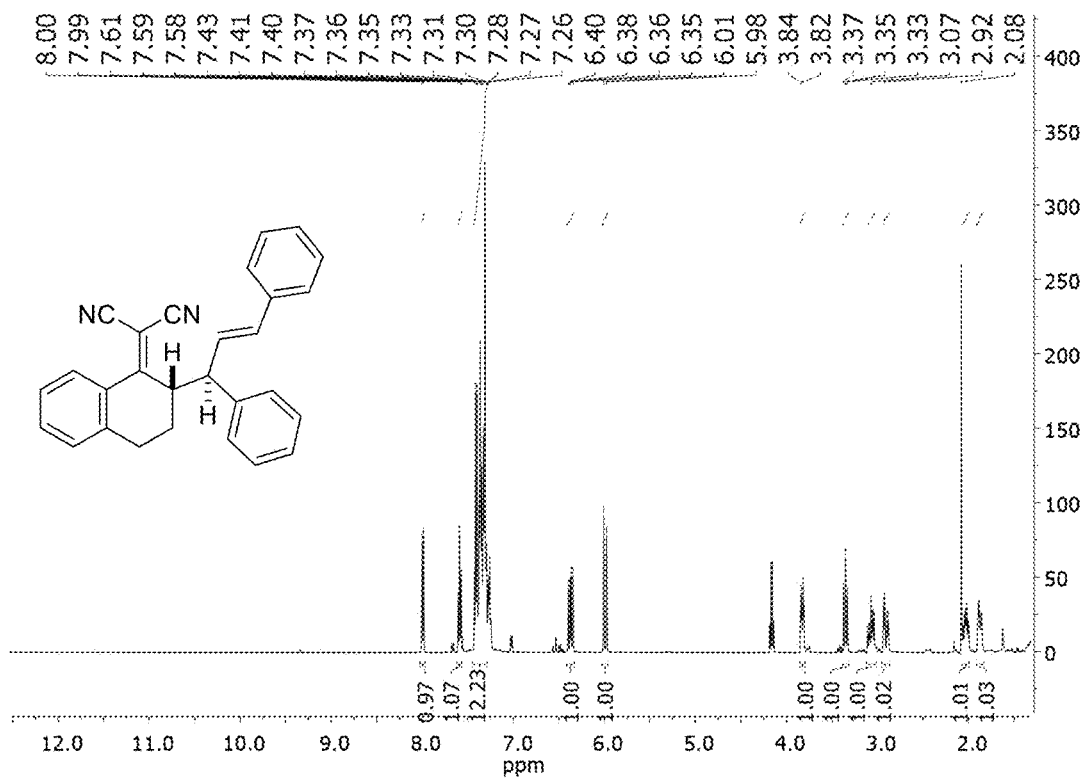
FIG. 10A shows a $^1$H NMR spectrum of (E)-2-(2-(1,3-diphenylallyl)-3,4-dihydronaphthalen-1(2H)-ylidene)malononitrile (compound 3b).
Figure 10B:
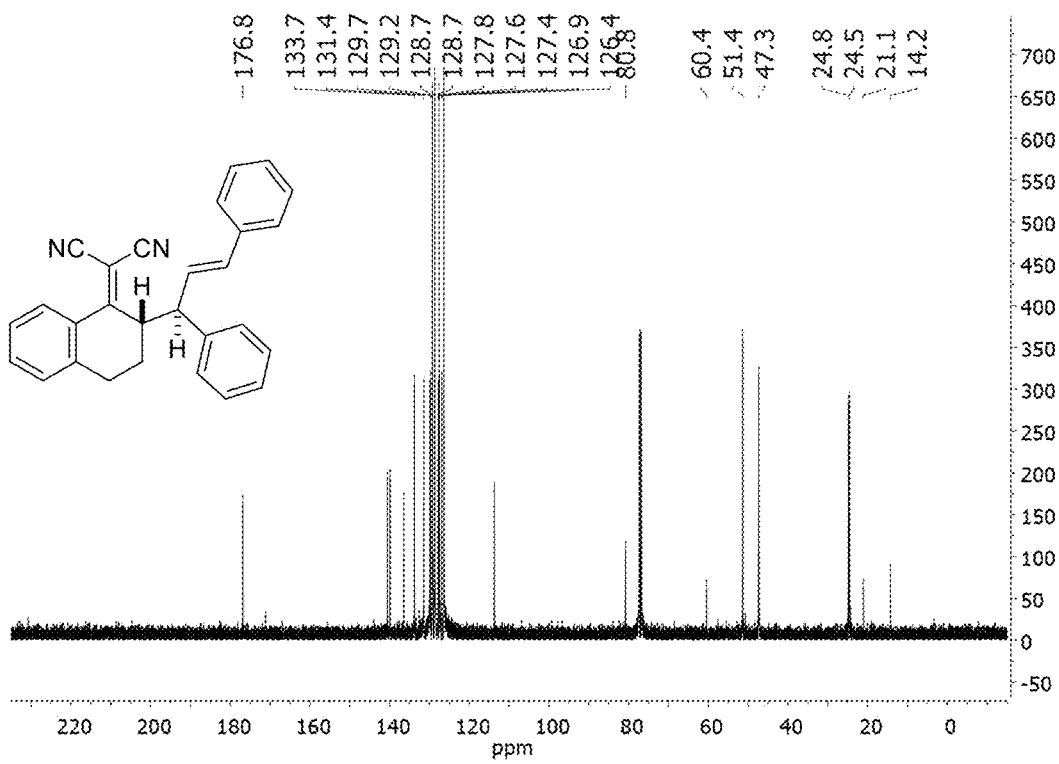
FIG. 10B shows a $^{13}$C NMR spectrum of compound 3b.

Prepared by general procedure A1 using a reaction time of 30 min. Isolated: 0.7 g. Yield: 75% (>20:1 dr). Physical state: colorless oil. TLC: $R_f$=0.53 (20% EtOAc in hexanes); Purified using 10% EtOAc in hexane. $^1$H NMR (500 MHz, CDCl$_3$) major diastereomer: δ 7.99 (d, J=7.9 Hz, 1H), 7.59 (t, J=7.6 Hz, 1H), 7.45-7.29 (m, 12H), 6.37 (dd, J=15.6, 9.6 Hz, 1H), 5.99 (d, J=15.6 Hz, 1H), 3.83 (dt, J=11.1, 3.4 Hz, 1H), 3.35 (t, J=10.3 Hz, 1H), 3.07 (ddd, J=17.8, 11.1, 6.4 Hz, 1H), 2.91 (dd, J=18.1, 6.4 Hz, 1H), 2.07-1.99 (m, 1H), 1.92-1.84 (m, 1H). $^{13}$C NMR (126 MHz, CDCl$_3$): δ 176.8, 140.6, 139.9, 136.4, 133.7, 131.4, 129.9, 129.7, 129.2, 128.7, 128.7, 128.0, 127.8, 127.6, 127.4, 126.9, 113.7, 113.7, 80.8, 60.4, 51.4, 47.3, 24.8, 24.6, 21.1, 14.2. Representative NMR spectra can be seen in FIGS. 10A-10B.

Example 6: Preparation of Bis-Allylated Building Blocks (5a-5o)

Example 6.1: (E)-2-allyl-2-(6-(1,3-diphenylallyl)cyclohex-1-en-1-yl)malononitrile (5a)

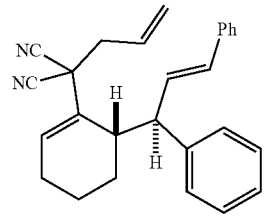 [SMILES: C=CCC(C#N)(C#N)C1=CCCC[C@H]1[C@@H](/C=C/c1ccccc1)c1ccccc1]

Figure 11A:
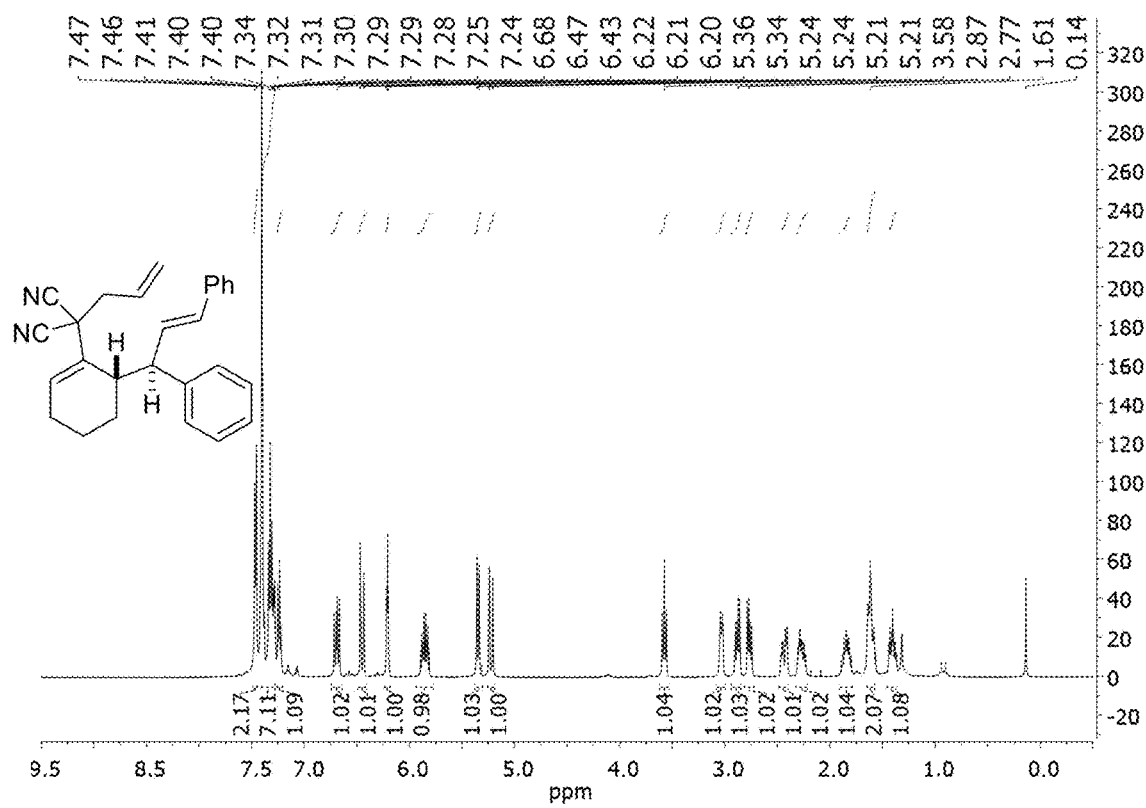
FIG. 11A shows a $^1$H NMR spectrum of (E)-2-allyl-2-(6-(1,3-diphenylallyl)cyclohex-1-3n-1-yl)malononitrile (compound 5a).
Figure 11B:
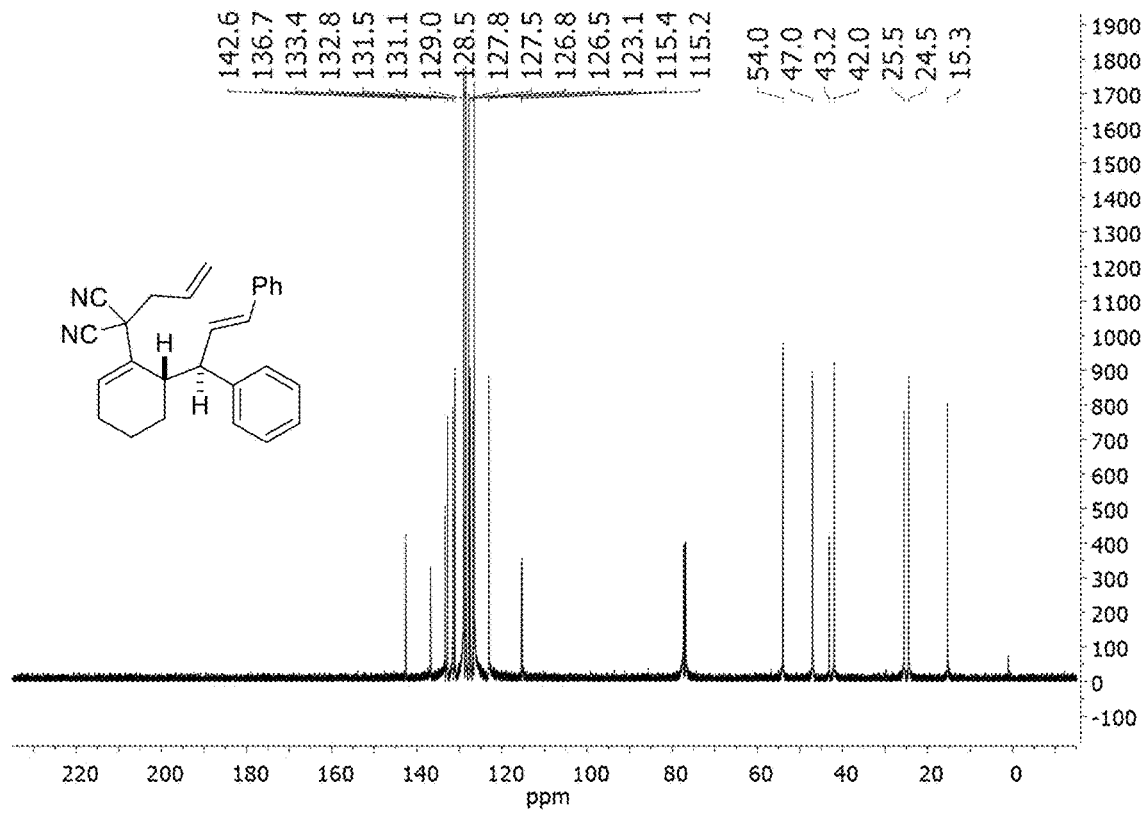

Prepared by general procedure using a reaction time of 2 hours. Isolated: 156 mg. Yield: 60% (>20:1 dr). Physical state: colorless oil. TLC: $R_f$=0.52 (20% EtOAc in hexanes); Purified using 8% EtOAc in hexane. $^1$H NMR (500 MHz, CDCl$_3$) major diastereomer: δ 7.46 (d, J=7.5 Hz, 2H), 7.41-7.28 (m, 7H), 7.24 (t, J=7.3 Hz, 1H), 6.69 (dd, J=15.7, 9.6 Hz, 1H), 6.45 (d, J=15.7 Hz, 1H), 6.21 (t, J=3.9 Hz, 1H), 5.93-5.77 (m, 1H), 5.34 (t, J=10.8 Hz, 1H), 5.22 (dd, J=16.9, 1.0 Hz, 1H), 3.58 (t, J=9.8 Hz, 1H), 3.03 (d, J=9.5 Hz, 1H), 2.88 (dd, J=13.6, 7.4 Hz, 1H), 2.76 (dd, J=13.6, 7.1 Hz, 1H), 2.49-2.39 (m, 1H), 2.27 (tdd, J=12.9, 8.6, 4.6 Hz, 1H), 1.91-1.79 (m, 1H), 1.65-1.57 (m, 2H), 1.41 (ddd, J=14.0, 9.0, 4.3 Hz, 1H). $^{13}$C NMR (126 MHz, CDCl$_3$): δ 142.6, 136.7, 133.4, 132.8, 131.5, 131.1, 129.0, 128.5, 127.8, 127.5, 126.8, 126.5, 123.1, 115.5, 115.2, 54.0, 47.0, 43.2, 42.0, 25.5, 24.5, 15.3. Representative NMR spectra can be seen in FIGS. 11A-11B.

Example 6.2: (E)-2-allyl-2-(9-(1,3-diphenylallyl)-1,4-dioxaspiro[4.5]dec-7-en-8-yl)malononitrile (5b)

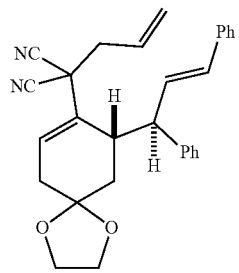 [SMILES: C=CCC(C#N)(C#N)C1=CCC2(C[C@H]1[C@@H](/C=C/c1ccccc1)c1ccccc1)OCCO2]

Figure 12A:
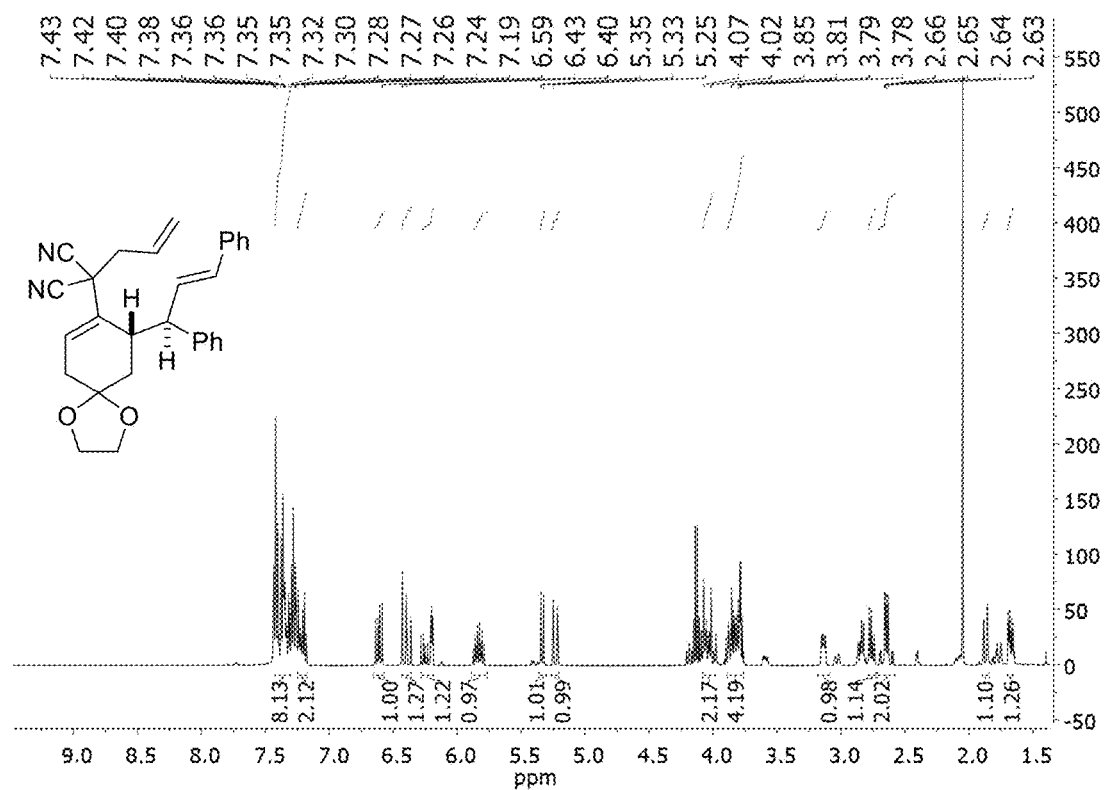
FIG. 12A shows a $^1$H NMR spectrum of (E)-2-allyl-2-(9-(1,3-diphenylallyl)-1,4-dioxaspiro[4.5]dec-7-en-8-yl) malononitrile (compound 5b).
Figure 12B:
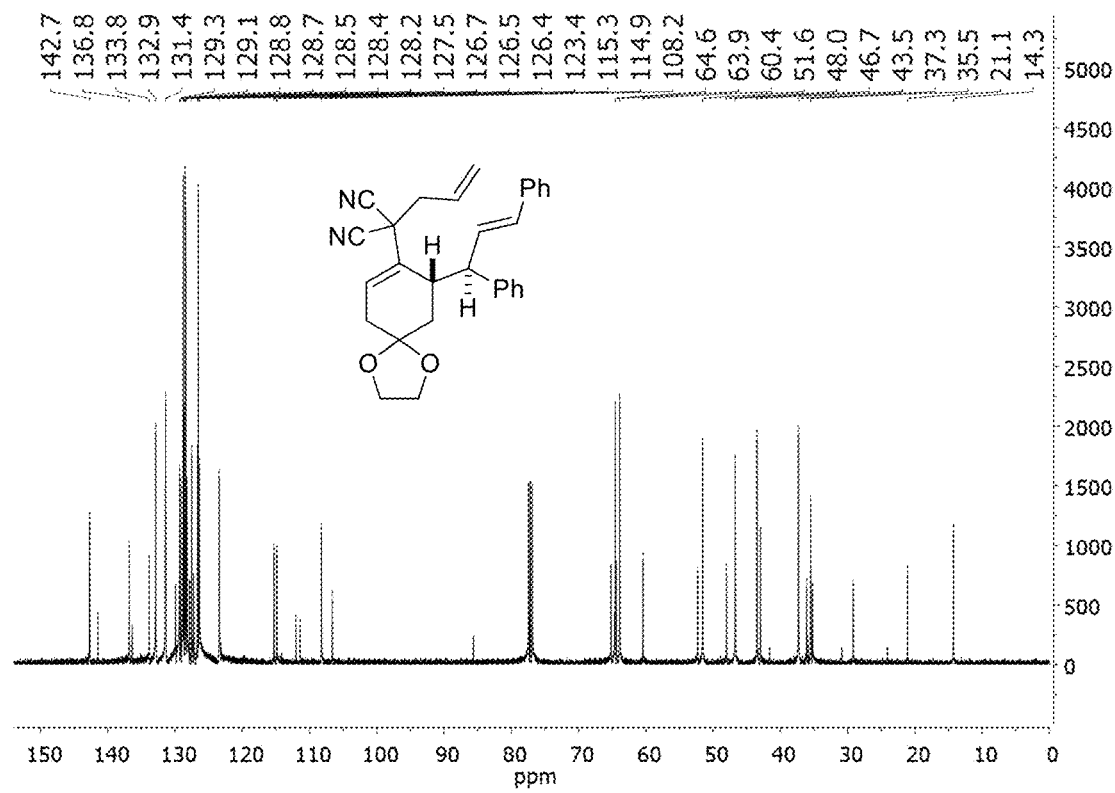
FIG. 12B shows a $^{13}$C NMR spectrum of compound 5b.

Prepared by general procedure A using a reaction time of 1 hour. Isolated: 124 mg. Yield: 59% (>20:1 dr). Physical state: colorless oil. TLC: $R_f$=0.23 (20% EtOAc in hexanes); Purified using 10% EtOAc in hexane. $^1$H NMR (500 MHz, CDCl$_3$) major diastereomer: δ 7.42-7.30 (m, 8H), 7.25-7.18 (m, 2H), 6.61 (dd, J=15.7, 9.8 Hz, 1H), 6.40 (dd, J=18.6, 15.8 Hz, 1H), 6.28-6.19 (m, 1H), 5.83 (ddt, J=17.3, 10.1, 7.2 Hz, 1H), 5.34 (d, J=10.2 Hz, 1H), 5.23 (d, J=16.9 Hz, 1H), 4.08-3.98 (m, 2H), 3.89-3.76 (m, 4H), 3.18-3.09 (m, 1H), 2.76 (dd, J=13.8, 7.2 Hz, 1H), 2.65 (dd, J=9.8, 4.4 Hz, 2H), 1.87 (dd, J=14.0, 2.5 Hz, 1H), 1.70-1.65 (m, 1H). $^{13}$C NMR (126 MHz, CDCl$_3$): δ 142.7, 136.8, 133.8, 132.9, 131.4, 129.3, 129.1, 128.8, 128.7, 128.5, 128.4, 128.2, 127.5, 126.7, 126.5, 126.4, 123.4, 115.3, 114.9, 112.0, 111.4, 108.2, 106.6, 64.6, 63.9, 60.4, 52.3, 51.6, 48.0, 46.7, 43.5, 37.3, 36.1, 35.9, 35.5, 29.2, 21.1, 14.3. Representative NMR spectra can be seen in FIGS. 12A-12B.

Example 6.3: (E)-2-allyl-2-(6-(1,3-diphenylallyl)-4,4-difluorocyclohex-1-en-1-yl)malononitrile (5c)

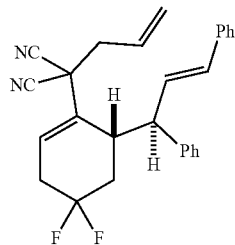 [SMILES: C=CCC(C#N)(C#N)C1=CCC(F)(F)C[C@H]1[C@@H](/C=C/c1ccccc1)c1ccccc1]

Figure 13A:
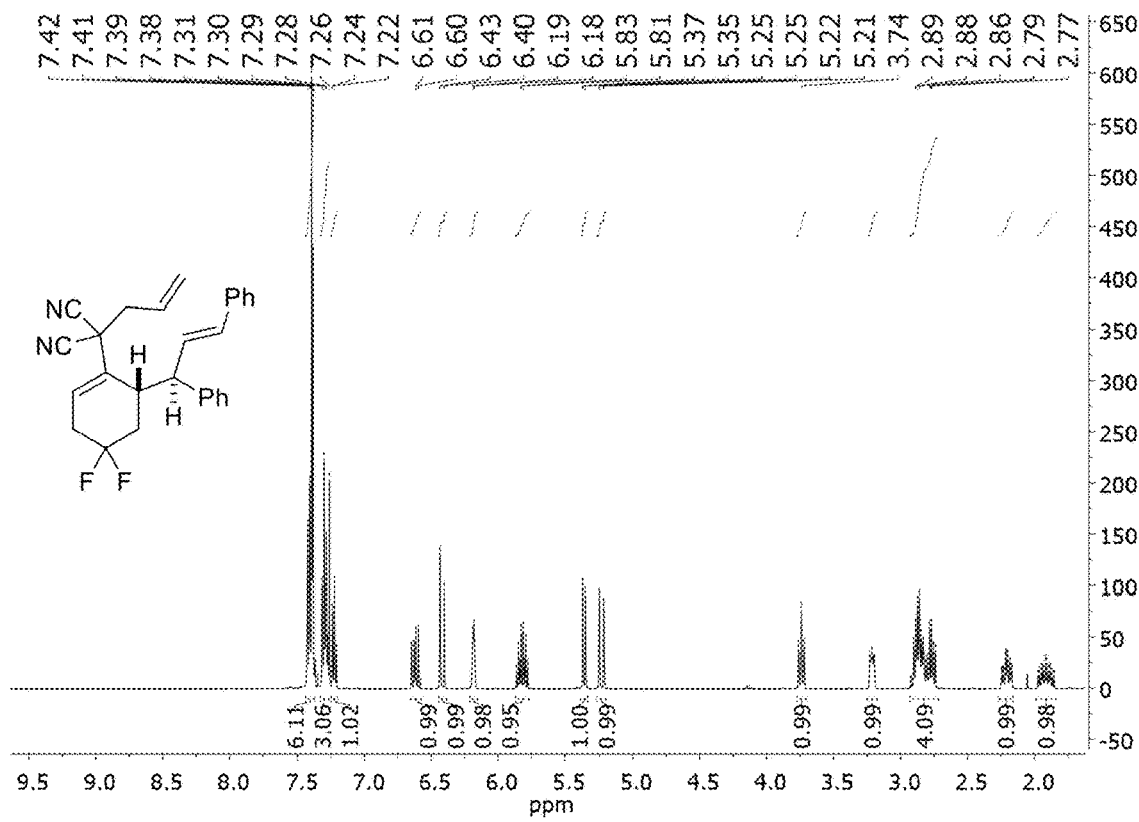
FIG. 13A shows a $^1$H NMR spectrum of (E)-2-allyl-(6-(1,3-diphenylallyl)-4,4-difluorocyclohex-1-en-1-yl)malononitrile (compound 5c).
Figure 13B:
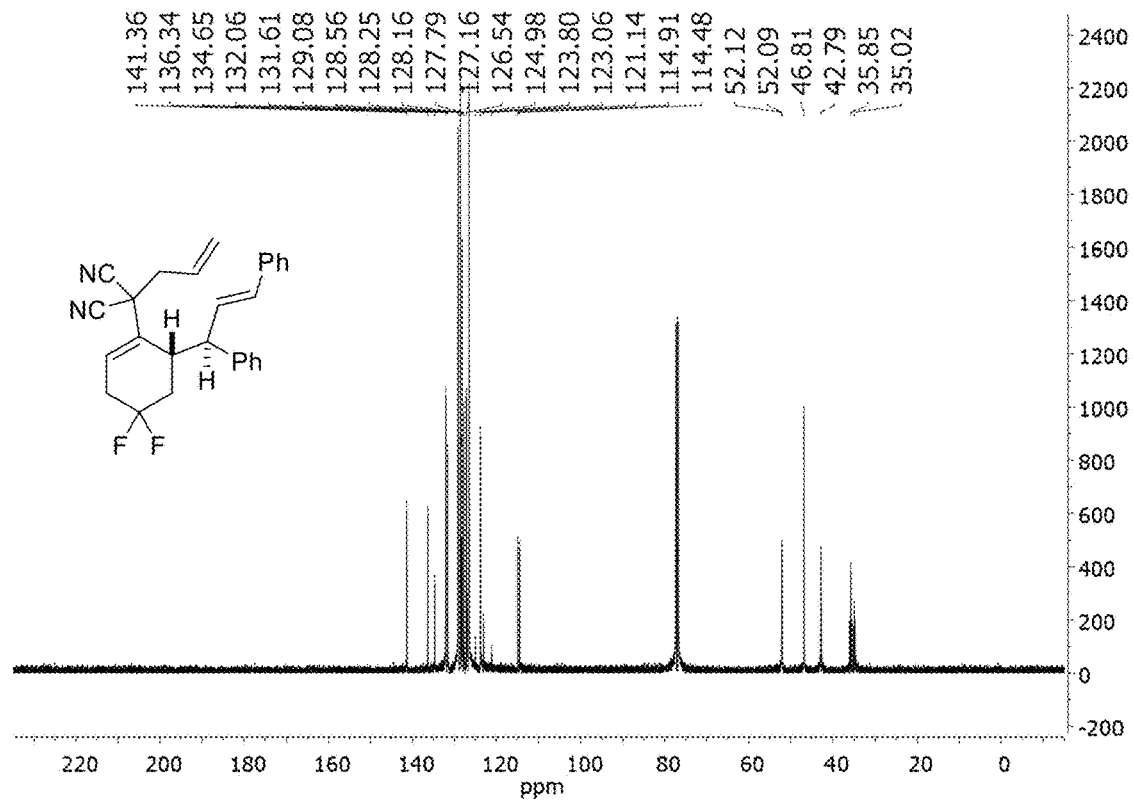
FIG. 13B shows a $^{13}$C NMR spectrum of compound 5c.

Prepared by general procedure A using a reaction time of 1 hour. Isolated: 178 mg. Yield: 78% (>20:1 dr). Physical state: yellow oil. TLC: $R_f$=0.48 (20% EtOAc in hexanes); Purified using 5% EtOAc in hexane. $^1$H NMR (500 MHz, CDCl$_3$) major diastereomer: δ 7.44-7.37 (m, 6H), 7.29 (dt, J=9.9, 5.9 Hz, 3H), 7.22 (t, J=7.3 Hz, 1H), 6.62 (ddd, J=15.7, 9.6, 1.0 Hz, 1H), 6.42 (d, J=15.7 Hz, 1H), 6.21-6.15 (m, 1H), 5.82 (ddt, J=17.4, 10.1, 7.3 Hz, 1H), 5.36 (d, J=9.7 Hz, 1H), 5.23 (dd, J=16.9, 1.1 Hz, 1H), 3.74 (t, J=10.0 Hz, 1H), 3.21 (dd, J=11.4, 4.6 Hz, 1H), 2.93-2.72 (m, 4H), 2.21 (tdd, J=15.1, 6.9, 2.1 Hz, 1H), 1.99-1.84 (m, 1H). $^{13}$C NMR (126 MHz, CDCl$_3$): δ 141.4, 136.3, 134.7, 132.1, 131.6, 129.1, 128.6, 128.2, 127.8, 127.2, 126.5, 125.0, 123.8, 123.1, 121.1, 114.9, 114.5, 52.1, 52.1, 46.8, 42.8, 35.9, 35.0. Representative NMR spectra can be seen in FIGS. 13A-13B.

Example 6.4: (E)-2-allyl-2-(60(1,3-diphenylallyl)-3,3-dimethylcyclohex-1-en-1-yl)malononitrile (5d)

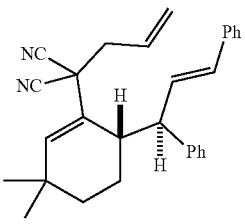 [SMILES: C=CCC(C#N)(C#N)C1=CC(C)(C)CC[C@H]1[C@@H](/C=C/c1ccccc1)c1ccccc1]

Figure 14A:
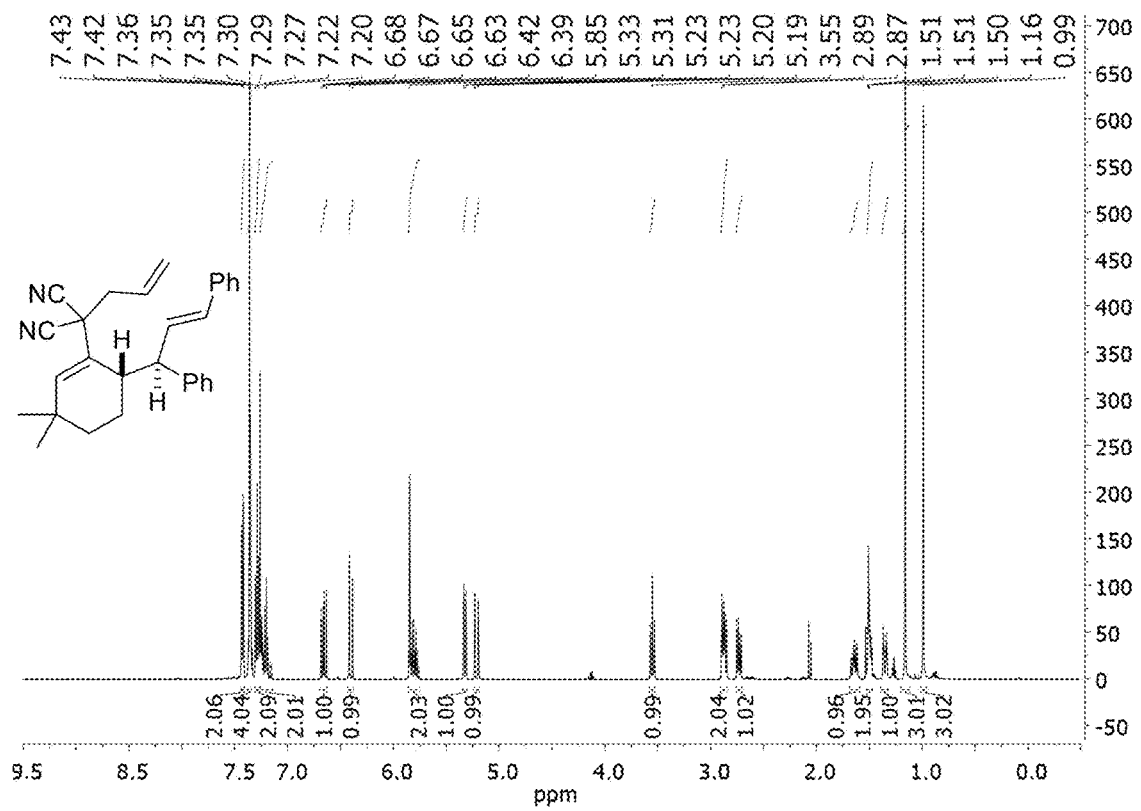
FIG. 14A shows a $^1$H NMR spectrum of (E)-2-allyl-2-(6-(1,3-diphenylallyl)-3,3-dimethylcyclohex-1-en-1-yl)malononitrile (compound 5d).
Figure 14B:
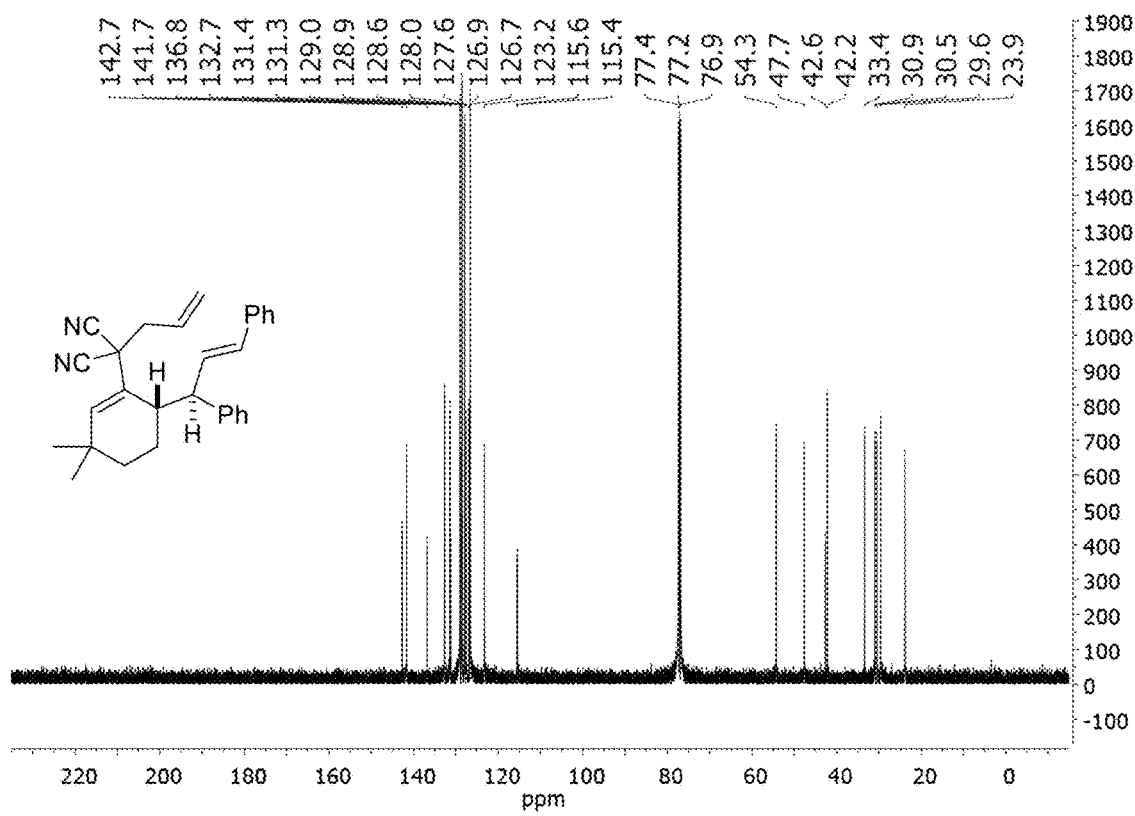
FIG. 14B shows a $^{13}$C NMR spectrum of compound 5d.

Prepared by general procedure A using a reaction time of 1 hour. Isolated: 176 mg. Yield: 66% (>20:1 dr). Physical state: colorless oil. TLC: $R_f$=0.65 (20% EtOAc in hexanes); Purified using 5% EtOAc in hexane. $^1$H NMR (500 MHz, CDCl$_3$) major diastereomer: δ 7.43 (d, J=7.4 Hz, 4H), 7.38-7.35 (m, 2H), 7.29 (t, J=7.6 Hz, 2H), 7.26-7.15 (m, 2H), 6.66 (dd, J=15.7, 9.5 Hz, 1H), 6.40 (d, J=15.7 Hz, 1H), 5.86-5.75 (m, 2H), 5.32 (d, J=10.1 Hz, 1H), 5.21 (dd, J=16.9, 1.1 Hz, 1H), 3.55 (t, J=9.5 Hz, 1H), 2.91-2.84 (m, 2H), 2.73 (dd, J=13.6, 7.3 Hz, 1H), 1.64 (tt, J=13.6, 6.8 Hz, 1H), 1.50 (dt, J=7.4, 3.5 Hz, 2H), 1.35 (dt, J=13.9, 3.0 Hz, 1H), 1.16 (s, 3H), 0.99 (s, 3H). $^{13}$C NMR (126 MHz, CDCl$_3$): δ 142.7, 141.7, 136.8, 132.7, 131.4, 131.3, 129.0, 128.9, 128.6, 128.0, 127.6, 126.9, 126.7, 123.2, 115.6, 115.4, 54.3, 47.7, 42.6, 42.2, 33.4, 31.0, 30.5, 29.6, 23.9. Representative NMR spectra can be seen in FIGS. 14A-14B.

Example 6.5: tert-butyl(1S,5R)-3-(1,1-dicyanobut-3-en-1-yl)-4-((E)-1,3-diphenylallyl)-8-Azabicyclo[3.2.1]oct-2-ene-8-carboxylate (5e)

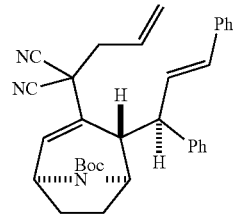 [SMILES: C=CCC(C#N)(C#N)C1=C[C@@H]2CC[C@H]([C@H]1[C@@H](/C=C/c1ccccc1)c1ccccc1)N2C(=O)OC(C)(C)C]

Figure 15A:
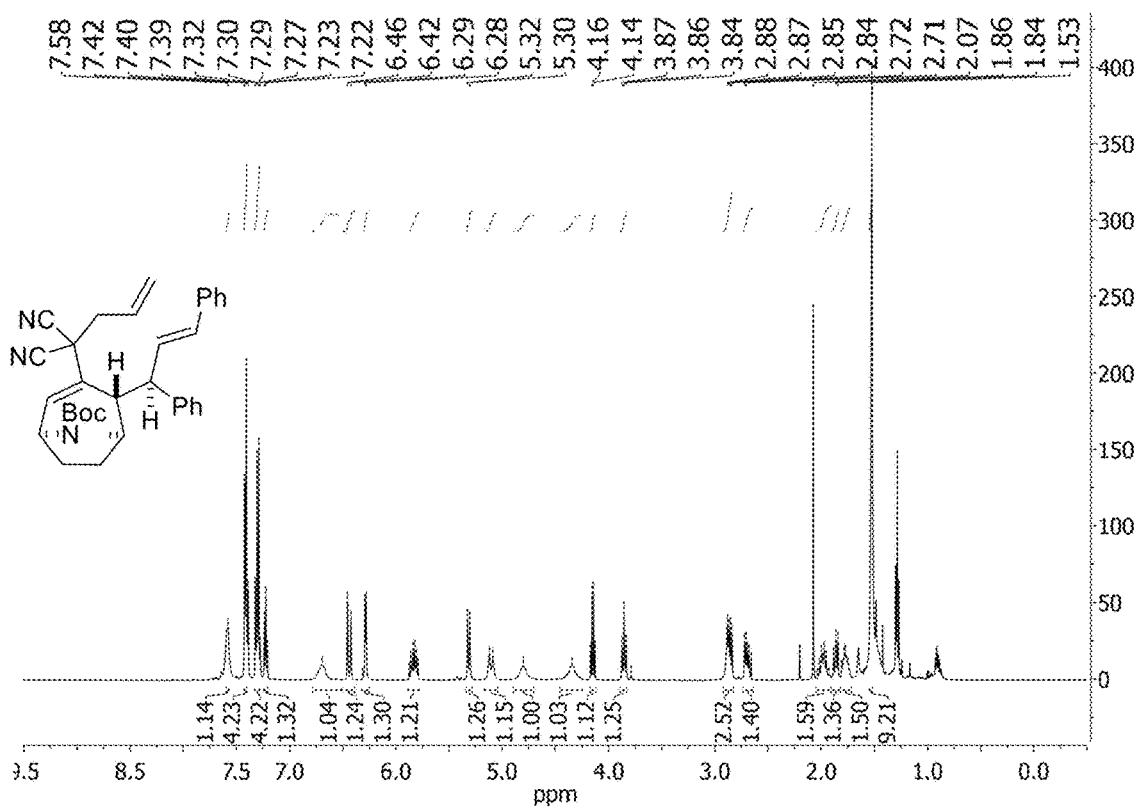
FIG. 15A shows a $^1$H NMR spectrum of tert-butyl(1S,5R)-3-(1,1-dicyanobut-3-en-1-yl)-4-((E)-1,3-diphenylallyl)-8-azabicyclo[3.2.1]oct-2-ene-8-carboxylate (compound 5e).
Figure 15B:
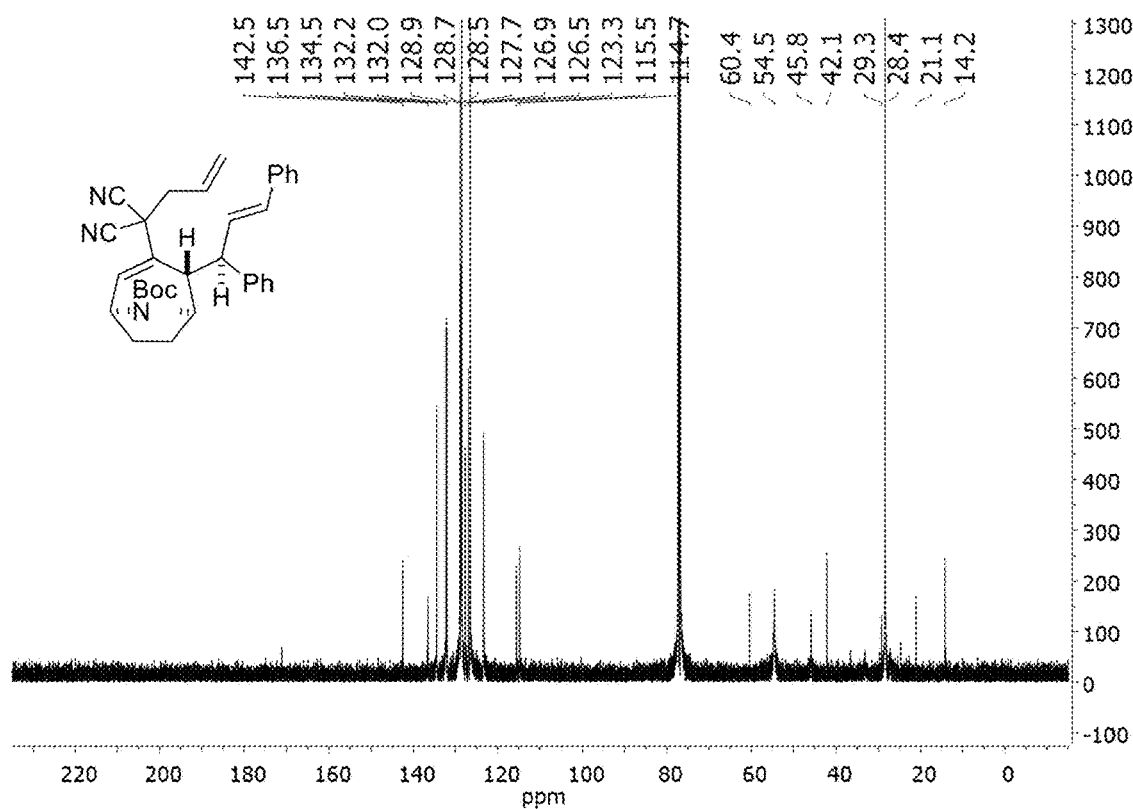
FIG. 15B shows a $^{13}$C NMR spectrum of compound 5e.

Prepared by general procedure A using a reaction time of 3 hours. Isolated: 48 mg. Yield: 26% (>20:1 dr). Physical state: colorless oil. TLC: $R_f$=0.5 (20% EtOAc in hexanes); Purified using 5% EtOAc in hexane. $^1$H NMR (500 MHz, CDCl$_3$) major diastereomer: δ 7.58 (s, 1H), 7.41 (d, J=7.7 Hz, 3H), 7.32-7.28 (m, 3H), 7.22 (t, J=7.3 Hz, 1H), 6.70 (s, 1H), 6.44 (d, J=15.7 Hz, 1H), 6.30 (t, J=8.0 Hz, 1H), 5.83 (td, J=17.1, 7.2 Hz, 1H), 5.31 (d, J=10.2 Hz, 1H), 5.10 (d, J=16.7 Hz, 1H), 4.80 (s, 1H), 4.35 (s, 1H), 4.15 (q, J=7.1 Hz, 1H), 3.86 (t, J=9.6 Hz, 1H), 2.86 (dd, J=13.9, 7.5 Hz, 2H), 2.74-2.64 (m, 1H), 2.04-1.90 (m, 1H), 1.90-1.82 (m, 1H), 1.82-1.72 (m, 1H), 1.53 (s, 7H). $^{13}$C NMR (126 MHz, CDCl$_3$): δ 142.5, 136.6, 134.5, 132.2, 132.0, 128.9, 128.7, 128.6, 127.7, 126.9, 126.5, 123.3, 115.5, 114.8, 60.4, 54.5, 45.8, 42.1, 29.3, 28.4, 21.1, 14.2. Representative NMR spectra can be seen in FIGS. 15A-15B.

Example 6.6: 2-allyl-2((5S)-6-((E)-1,3-diphenylallyl)-2-methyl-5-(prop-1-3n-2-yl)cyclohex-1-en-1-yl)malononitrile (5f)

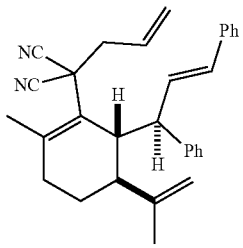 [SMILES: C=CCC(C#N)(C#N)C1=C(C)CC[C@H](C(=C)C)[C@H]1[C@@H](/C=C/c1ccccc1)c1ccccc1]

Figure 16A:
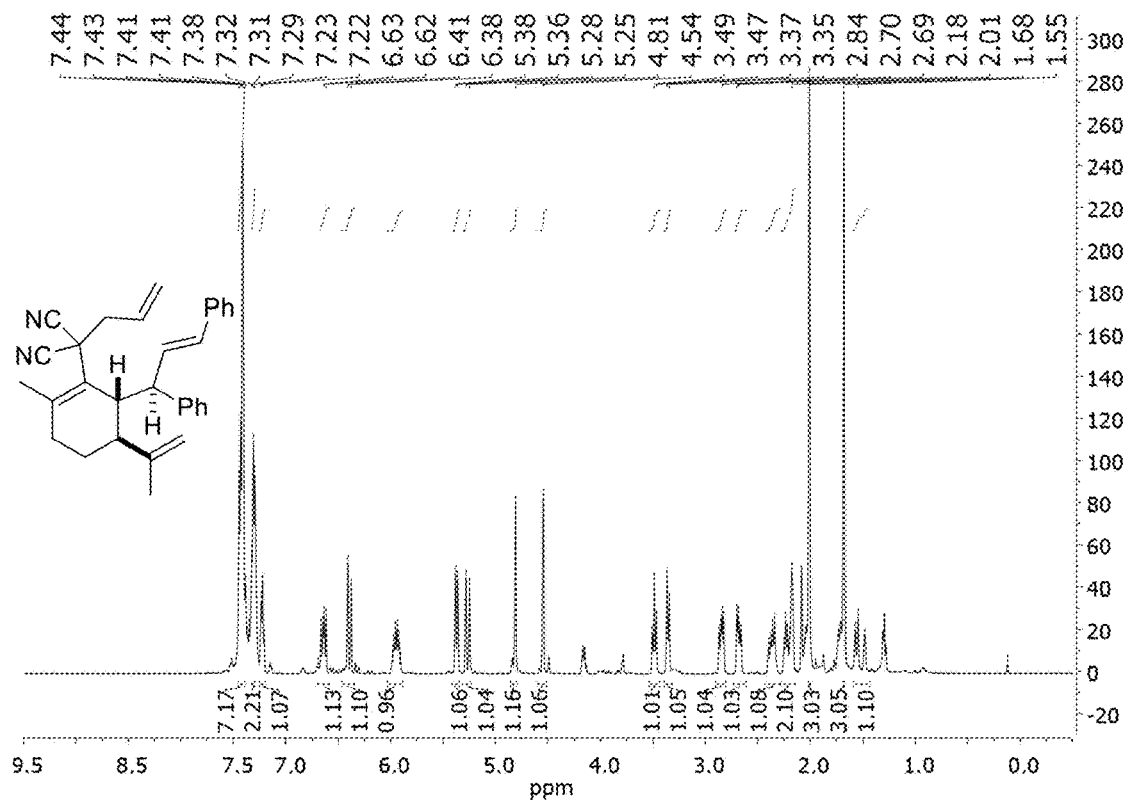
FIG. 16A shows a $^1$H NMR spectrum of 2-allyl-2-((5S)-6-((E)-1,3-diphenylallyl)-2-methyl-5-(prop-1-en-2-yl)cyclohex-1-en-1-yl)malononitrile (compound 5f).
Figure 16B:
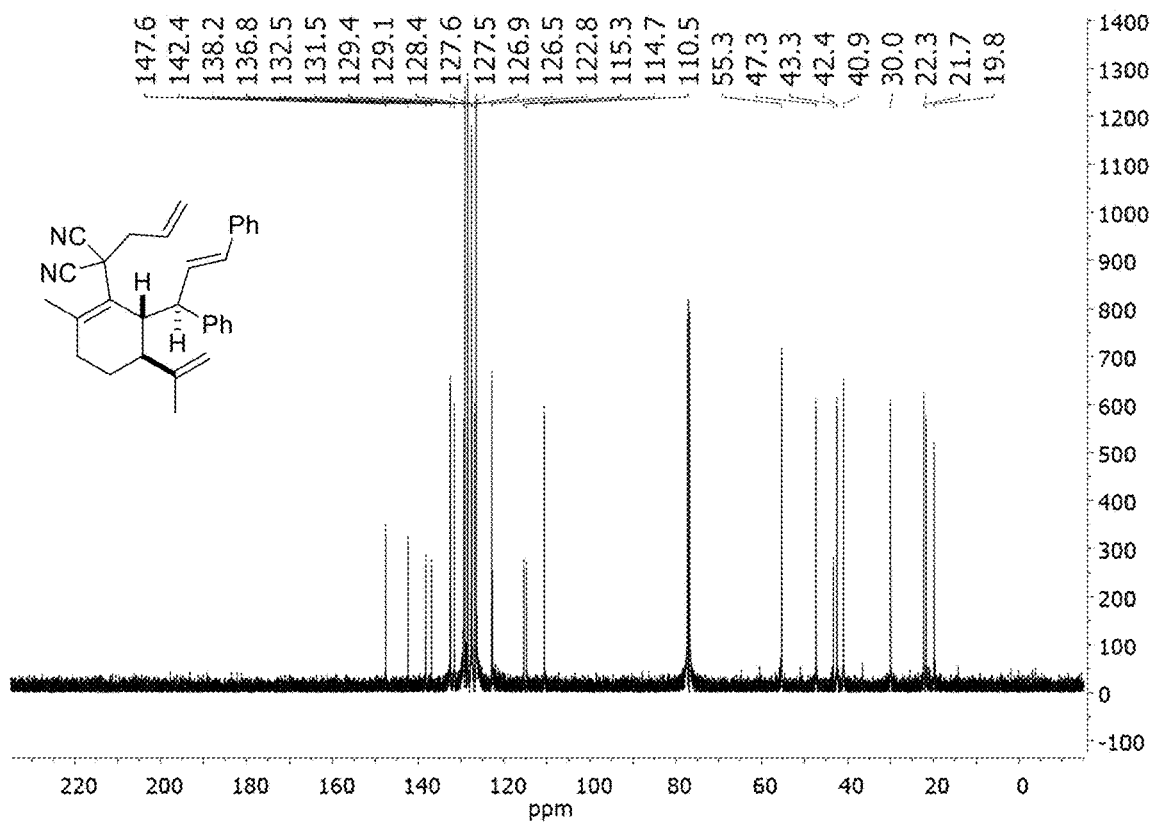
FIG. 16B shows a $^{13}$C NMR spectrum of compound 5f.

Prepared by general procedure A using a reaction time of 30 minutes. Isolated: 60 mg. Yield: 45% (>20:1 dr). Physical state: colorless oil. TLC: $R_f$=0.62 (20% EtOAc in hexanes); Purified using 5% EtOAc in hexane. $^1$H NMR (500 MHz, CDCl$_3$) major diastereomer: δ 7.45-7.38 (m, 7H), 7.30 (d, J=7.2 Hz, 2H), 7.22 (t, J=6.9 Hz, 1H), 6.70-6.59 (m, 1H), 6.39 (d, J=15.8 Hz, 1H), 6.03-5.89 (m, 1H), 5.37 (d, J=10.1 Hz, 1H), 5.26 (d, J=16.9 Hz, 1H), 4.82 (d, J=14.8 Hz, 1H), 4.54 (s, 1H), 3.49 (t, J=9.7 Hz, 1H), 3.36 (d, J=10.2 Hz, 1H), 2.85 (dd, J=13.8, 7.4 Hz, 1H), 2.68 (dd, J=13.9, 6.7 Hz, 1H), 2.37 (dd, J=18.6, 9.9 Hz, 1H), 2.28-2.14 (m, 2H), 2.02 (d, J=15.1 Hz, 4H), 1.68 (s, 4H), 1.52 (dd, J=38.1, 9.2 Hz, 1H). $^{13}$C NMR (126 MHz, CDCl$_3$): δ 147.6, 142.4, 138.2, 136.9, 132.5, 131.5, 129.4, 129.1, 128.7, 128.5, 126.9, 126.5, 122.8, 115.3, 114.7, 110.6, 55.3, 47.3, 43.3, 42.4, 40.9, 30.0, 22.3, 21.7, 19.8. Representative NMR spectra can be seen in FIGS. 16A-16B.

Example 6.7: (E)-2-allyl-2-(6-(1,3-bis(4-methoxyphenyl)allyl)cyclohex-1-en-1-yl)malononitrile (5g)

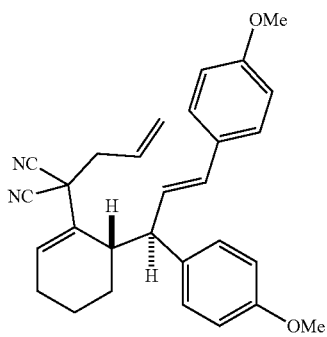 [SMILES: C=CCC(C#N)(C#N)C1=CCCC[C@H]1[C@@H](/C=C/c1ccc(OC)cc1)c1ccc(OC)cc1]

Figure 17A:
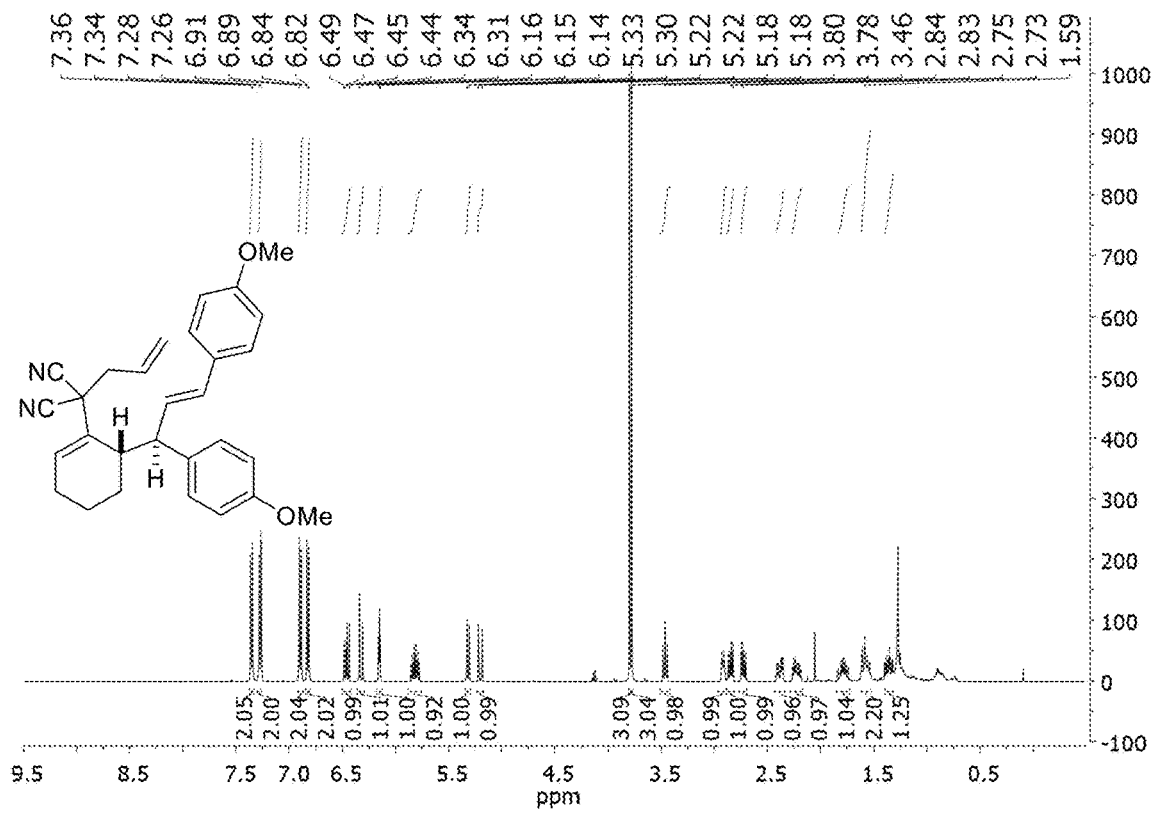
FIG. 17A shows a $^1$H NMR spectrum of (E)-2-allyl-2-(6-(1,3-bis(4-methoxyphenyl)allyl)cyclohex-1-en-1-yl)malononitrile (compound 5g).
Figure 17B:
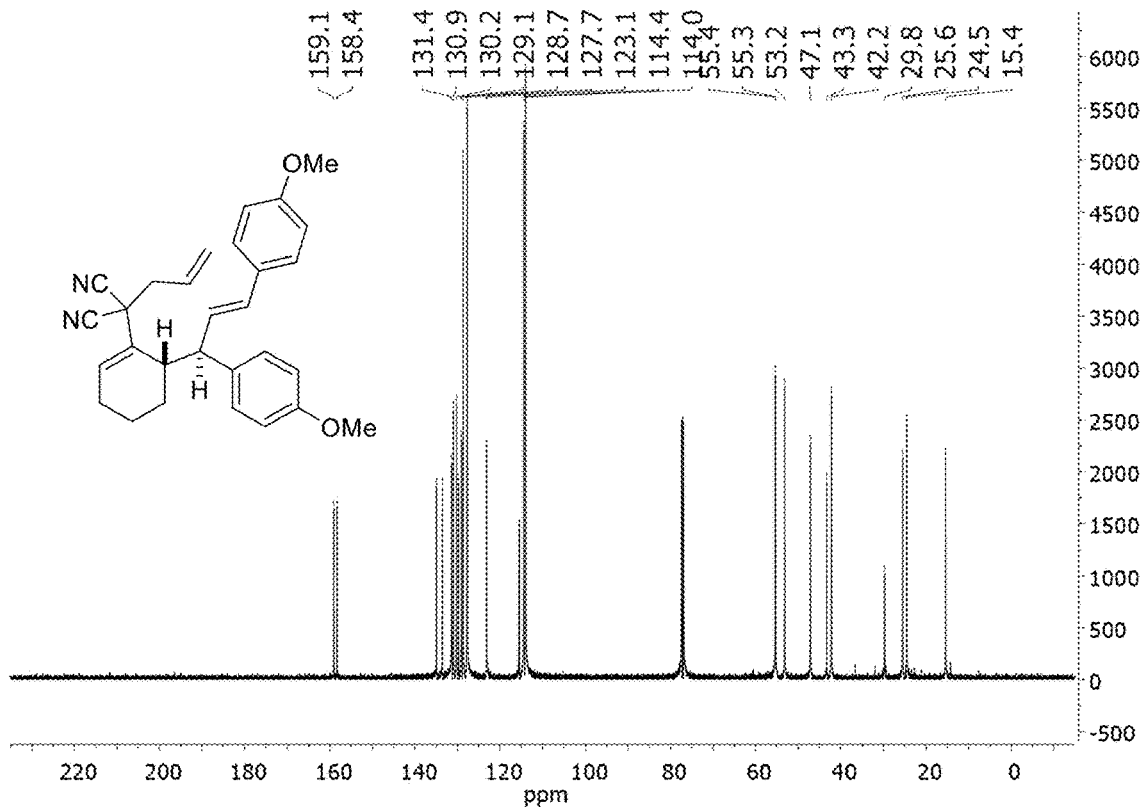
FIG. 17B shows a $^{13}$C NMR spectrum of compound 5g.

Prepared by general procedure A using a reaction time of 3 hours. Isolated: 62 mg. Yield: 45% (>20:1 dr). Physical state: colorless oil. TLC: $R_f$=0.34 (20% EtOAc in hexanes); Purified using 5% EtOAc in hexane. $^1$H NMR (500 MHz, CDCl$_3$) major diastereomer: δ 7.35 (d, J=8.7 Hz, 2H), 7.27 (d, J=8.7 Hz, 2H), 6.90 (d, J=8.7 Hz, 2H), 6.83 (d, J=8.8 Hz, 2H), 6.46 (dd, J=15.7, 9.5 Hz, 1H), 6.32 (d, J=15.7 Hz, 1H), 6.15 (t, J=3.9 Hz, 1H), 5.82 (ddt, J=17.3, 10.1, 7.3 Hz, 1H), 5.32 (d, J=10.2 Hz, 1H), 5.20 (dd, J=16.9, 1.1 Hz, 1H), 3.80 (s, 3H), 3.78 (s, 3H), 3.46 (t, J=9.7 Hz, 1H), 2.92 (d, J=9.8 Hz, 1H), 2.85 (dd, J=13.6, 7.4 Hz, 1H), 2.73 (dd, J=13.6, 7.1 Hz, 1H), 2.38 (ddd, J=19.7, 7.7, 3.1 Hz, 1H), 2.22 (tdd, J=13.3, 8.8, 4.4 Hz, 1H), 1.85-1.72 (m, 1H), 1.64-1.52 (m, 2H), 1.36 (tt, J=13.4, 4.3 Hz, 1H). $^{13}$C NMR (126 MHz, CDCl$_3$): δ 159.1, 158.4, 135.0, 133.6, 131.4, 131.0, 130.2, 129.8, 129.1, 128.7, 127.7, 123.1, 115.5, 115.4, 114.4, 114.0, 55.4, 55.3, 53.2, 47.1, 43.3, 42.2, 29.8, 25.6, 24.5, 15.4. Representative NMR spectra can be seen in FIGS. 17A-17B.

Example 6.8: (E)-2-allyl-2-(6-(1,3-bis(2-methoxyphenyl)allyl)cyclohex-1-en-1-yl)malononitrile (5h)

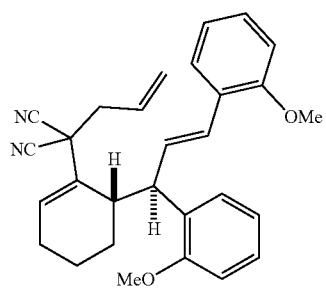 [SMILES: C=CCC(C#N)(C#N)C1=CCCC[C@H]1[C@@H](/C=C/c1ccccc1OC)c1ccccc1OC]

Figure 18A:
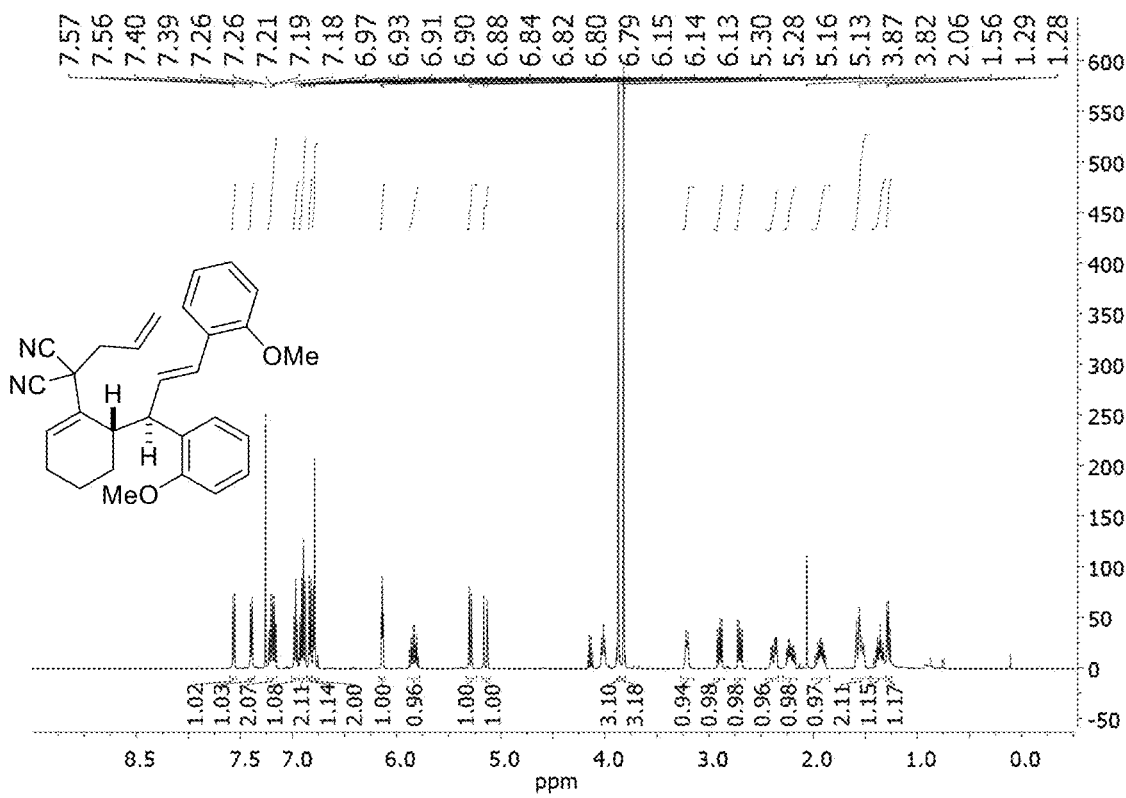
FIG. 18A shows a $^1$H NMR spectrum of (E)-2-allyl-2-(6-(1,3-bis(2-methoxyphenyl)allyl)cyclohex-1-en-1-yl)malononitrile (compound 5h).
Figure 18B:
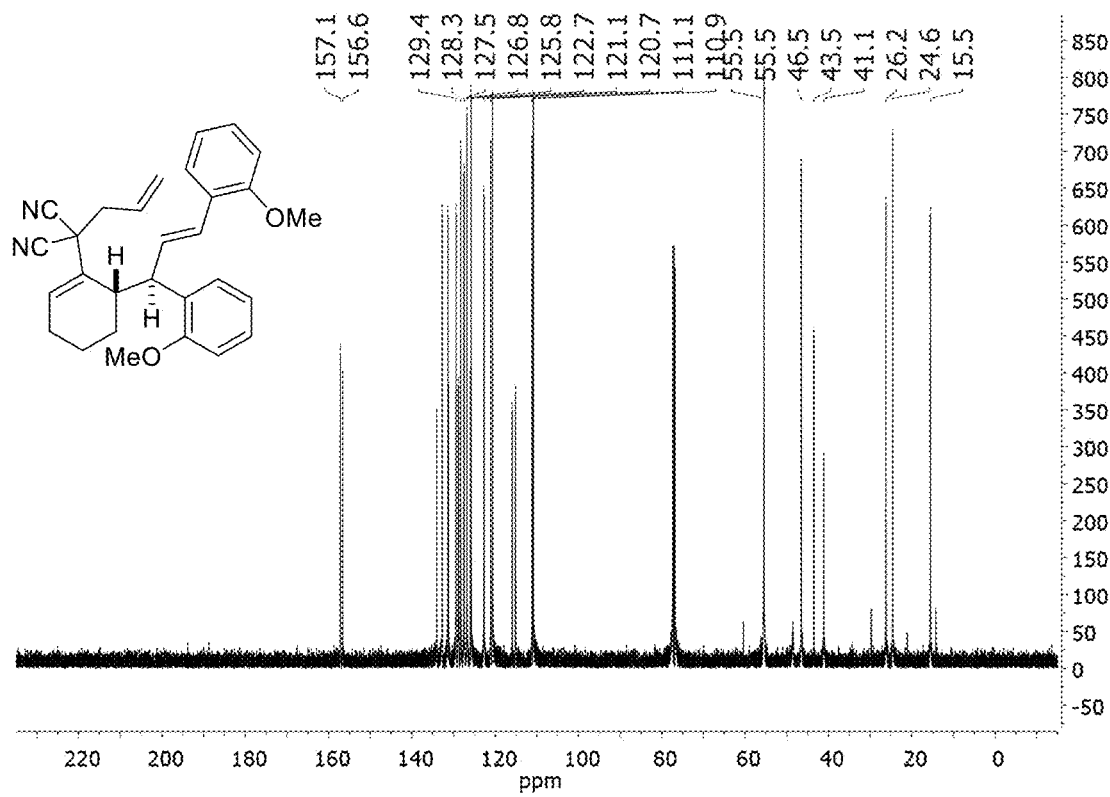
FIG. 18B shows a $^{13}$C NMR spectrum of compound 5h.

Prepared by general procedure A using a reaction time of 1 hour. Isolated: 120 mg. Yield: 85% (>20:1 dr). Physical state: colorless oil. TLC: $R_f$=0.40 (20% EtOAc in hexanes); Purified using 5% EtOAc in hexane. $^1$H NMR (500 MHz, CDCl$_3$) major diastereomer: δ 7.57 (d, J=7.4 Hz, 1H), 7.40 (d, J=7.4 Hz, 1H), 7.19 (dt, J=16.5, 4.1 Hz, 2H), 6.96 (q, J=7.7 Hz, 1H), 6.90 (dd, J=15.7, 7.9 Hz, 2H), 6.86-6.81 (m, 1H), 6.82-6.75 (m, 2H), 6.14 (t, J=3.9 Hz, 1H), 5.89-5.78 (m, 1H), 5.29 (d, J=10.2 Hz, 1H), 5.15 (d, J=16.9 Hz, 1H), 3.87 (s, 3H), 3.82 (s, 3H), 3.21 (d, J=9.7 Hz, 1H), 2.90 (dd, J=13.7, 7.6 Hz, 1H), 2.70 (dd, J=13.7, 7.0 Hz, 1H), 2.45-2.33 (m, 1H), 2.22 (tdd, J=13.5, 8.8, 4.5 Hz, 1H), 2.01-1.84 (m, 1H), 1.63-1.46 (m, 2H), 1.44-1.30 (m, 1H), 1.31-1.24 (m, 1H). $^{13}$C NMR (126 MHz, CDCl$_3$): δ 157.1, 156.6, 134.0, 132.7, 131.3, 129.4, 128.8, 128.3, 127.5, 126.8, 125.9, 125.8, 122.7, 121.1, 120.7, 115.9, 115.2, 111.1, 110.9, 55.5, 55.5, 46.5, 43.5, 41.1, 26.2, 24.6, 15.5. Representative NMR spectra can be seen in FIGS. 18A-18B.

Example 6.9: (E)-2-allyl-2-(6-(1,3-bis(3-methoxyphenyl)allyl)cyclohex-1-en-1-yl)malononitrile (5i)

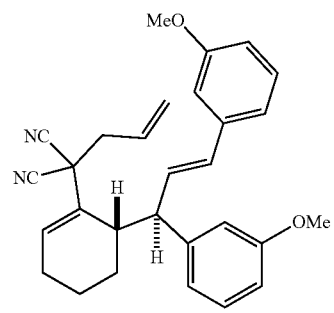 [SMILES: C=CCC(C#N)(C#N)C1=CCCC[C@H]1[C@@H](/C=C/c1cccc(OC)c1)c1cccc(OC)c1]

Figures 19A, 19B:
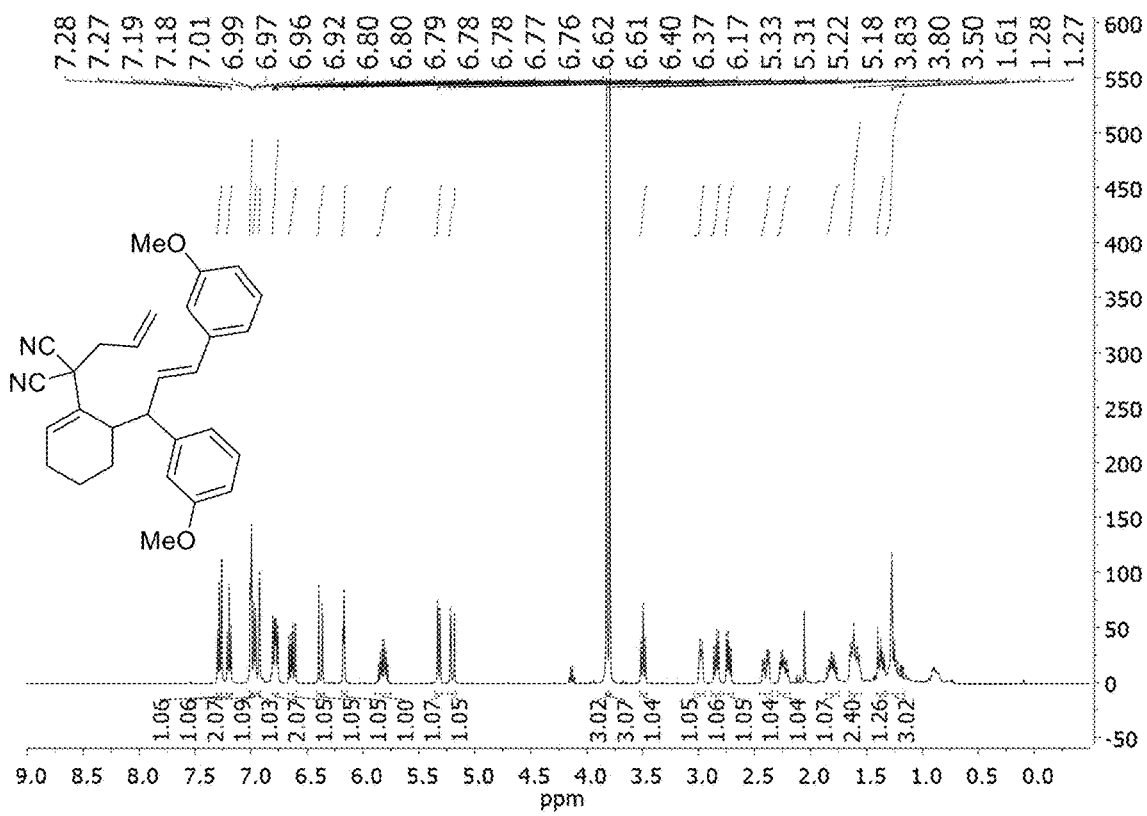
FIG. 19A shows a $^1$H NMR spectrum of (E)-2-allyl-2-(6-(1,3-bis(3-methoxyphenyl)allyl)cyclohex-1-en-1-yl)malononitrile (compound 5i).
FIG. 19B shows a $^{13}$C NMR spectrum of compound 5i.

Prepared by general procedure A using a reaction time of 2 hours. Isolated: 83 mg. Yield: 60% (>20:1 dr). Physical state: colorless oil. TLC: $R_f$=0.43 (20% EtOAc in hexanes); Purified using 5% EtOAc in hexane. $^1$H NMR (500 MHz, CDCl$_3$) major diastereomer: δ 7.28 (t, J=8.0 Hz, 1H), 7.19 (t, J=8.1 Hz, 1H), 7.00 (d, J=6.4 Hz, 2H), 6.96 (d, J=7.6 Hz, 1H), 6.92 (s, 1H), 6.82-6.73 (m, 2H), 6.63 (dd, J=15.7, 9.6 Hz, 1H), 6.38 (d, J=15.7 Hz, 1H), 6.17 (t, J=3.8 Hz, 1H), 5.82 (dq, J=10.0, 7.2 Hz, 1H), 5.32 (d, J=10.2 Hz, 1H), 5.20 (d, J=16.9 Hz, 1H), 3.83 (s, 3H), 3.80 (s, 3H), 3.50 (t, J=9.8 Hz, 1H), 2.40 (ddd, J=19.6, 7.5, 2.4 Hz, 1H), 2.29-2.19 (m, 1H), 1.85-1.75 (m, 1H), 1.66-1.55 (m, 2H), 1.37 (tt, J=12.1, 3.4 Hz, 1H), 1.32-1.16 (m, 3H). $^{13}$C NMR (126 MHz, CDCl$_3$): δ 160.1, 159.8, 144.2, 138.2, 133.4, 133.0, 131.7, 131.1, 130.0, 129.5, 129.0, 123.2, 120.1, 119.4, 115.6, 115.3, 113.9, 113.8, 111.8, 111.3, 55.3, 55.3, 54.1, 47.1, 43.2, 42.0, 29.8, 25.7, 24.5, 15.4. HRMS (ESI) m/z: [M+H]$^+$ Calcd C$_{29}$H$_{31}$NO$_2$ for 439.2380; Found 439.2399. Representative NMR spectra can be seen in FIGS. 19A-19B.

Example 6.10: (E)-2-allyl-2-(6-(1,3-bis(3,4-dimethoxyphenyl)allyl)cyclohex-1-en-1-yl)malononitrile (5j)

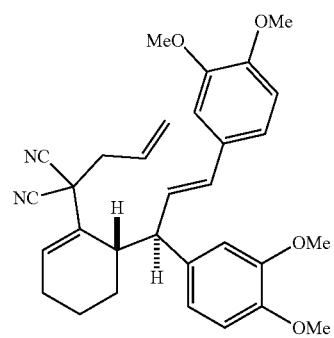 [SMILES: C=CCC(C#N)(C#N)C1=CCCC[C@H]1[C@@H](/C=C/c1ccc(OC)c(OC)c1)c1ccc(OC)c(OC)c1]

Figures 20A, 20B:
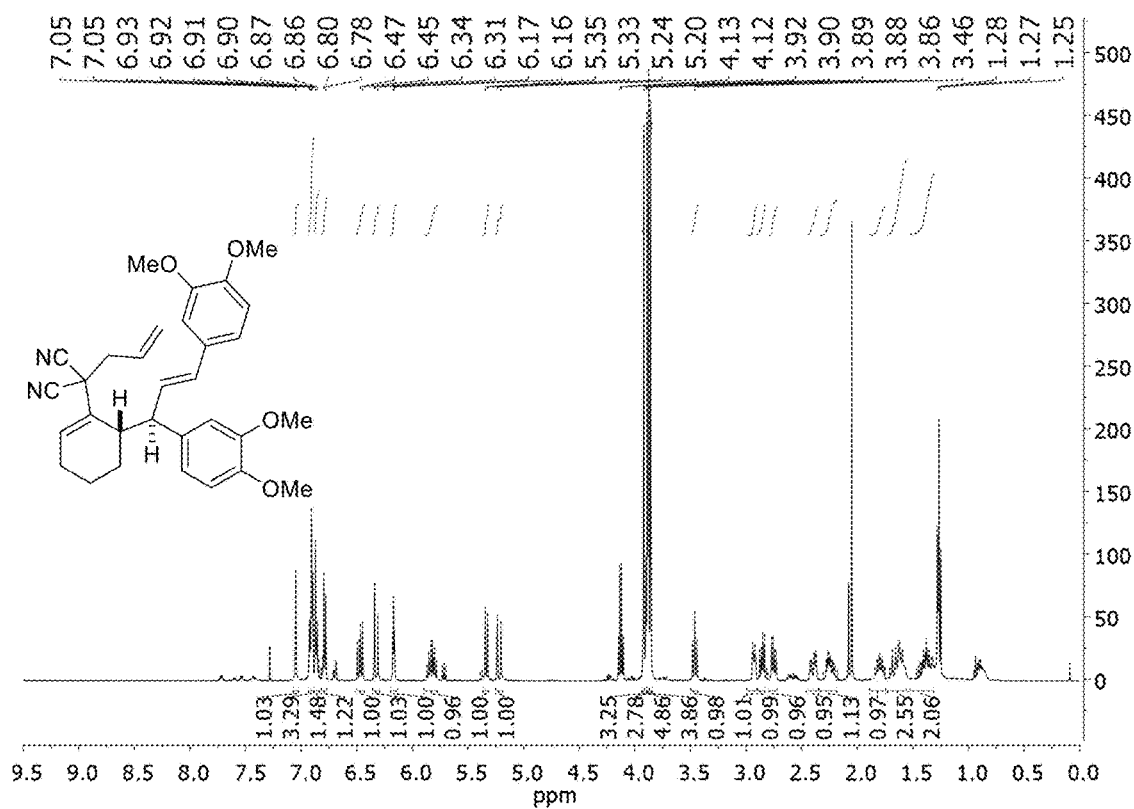
FIG. 20A shows a $^1$H NMR spectrum of (E)-2-allyl-2-(6-(1,3-bis(3,4-dimethoxyphenyl)allyl)cyclohex-1-en-1-yl) malononitrile (compound 5j).
FIG. 20B shows a $^{13}$C NMR spectrum of compound 5j.

Prepared by general procedure A using a reaction time of 2 hours. Isolated: 70 mg. Yield: 50% (>20:1 dr). Physical state: colorless oil. TLC: $R_f$=0.60 (20% EtOAc in hexanes); Purified using 10% EtOAc in hexane. $^1$H NMR (500 MHz, CDCl$_3$) major diastereomer: δ 6.85 (d, J=8.2 Hz, 1H), 6.76 (dd, J=8.2, 1.9 Hz, 1H), 6.71 (d, J=1.8 Hz, 1H), 6.48 (t, J=3.7 Hz, 1H), 5.94 (dd, J=11.3, 4.0 Hz, 1H), 5.76-5.68 (m, 1H), 3.91 (s, 3H), 3.90 (s, 3H), 3.46-3.35 (m, 2H), 2.91-2.76 (m, 2H), 2.33 (dt, J=19.2, 5.0 Hz, 1H), 2.28-2.13 (m, 1H), 1.82-1.68 (m, 1H), 1.69-1.53 (m, 2H), 1.47-1.35 (m, 1H). $^{13}$C NMR (126 MHz, CDCl$_3$): δ 149.3, 148.2, 140.3, 134.8, 133.3, 132.4, 120.5, 119.5, 116.0, 115.9, 111.3, 111.1, 56.0, 55.9, 52.0, 41.7, 37.6, 34.6, 29.7, 25.7, 25.5, 15.8. Representative NMR spectra can be seen in FIGS. 20A-20B.

Example 6.11: (E)-2-allyl-2-(6-(1,3-bis(4-chlorophenyl)allyl)cyclohex-1-en-1-yl)malononitrile (5k)

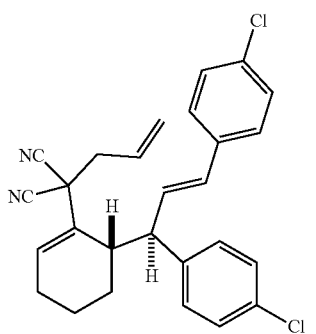 [SMILES: C=CCC(C#N)(C#N)C1=CCCC[C@H]1[C@@H](/C=C/c1ccc(Cl)cc1)c1ccc(Cl)cc1]

Figure 21A:
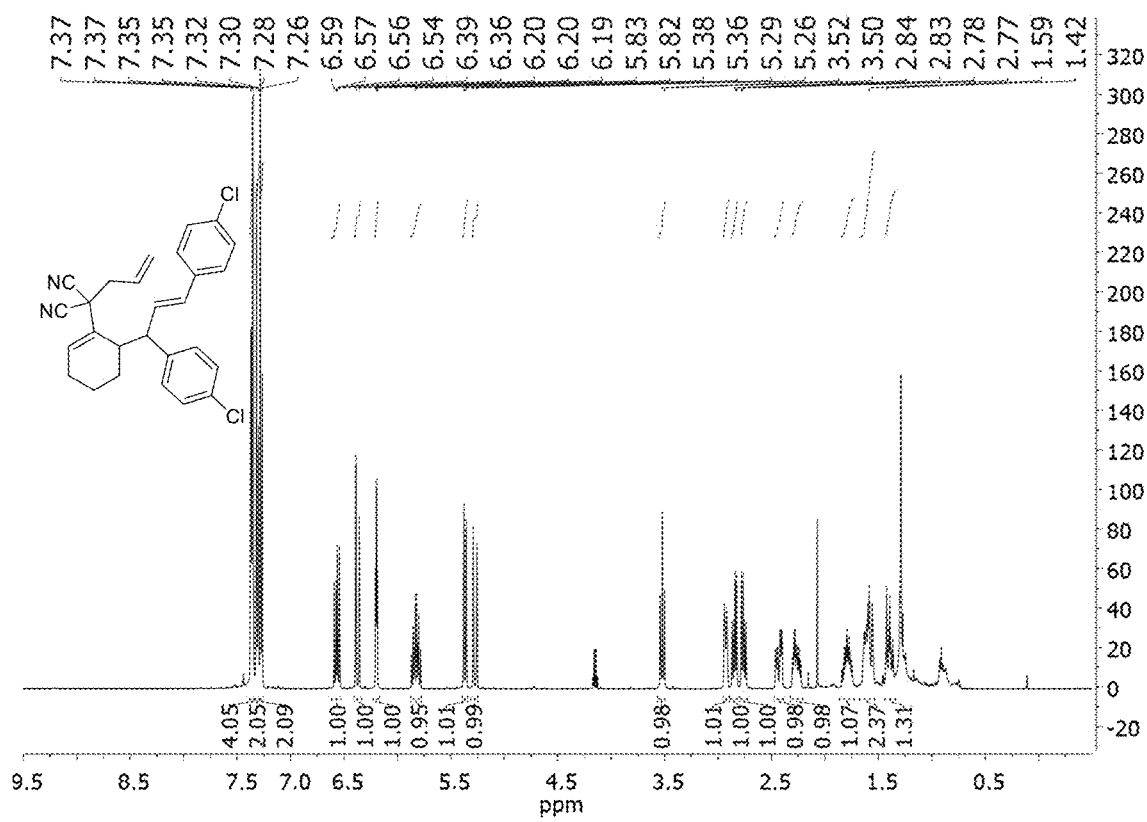
FIG. 21A shows a $^1$H NMR spectrum of (E)-2-allyl-2-(6-(1,3-bis(4-chlorophenyl)allyl)cyclohex-1-en-1-yl)malononitrile (compound 5k).
Figure 21B:
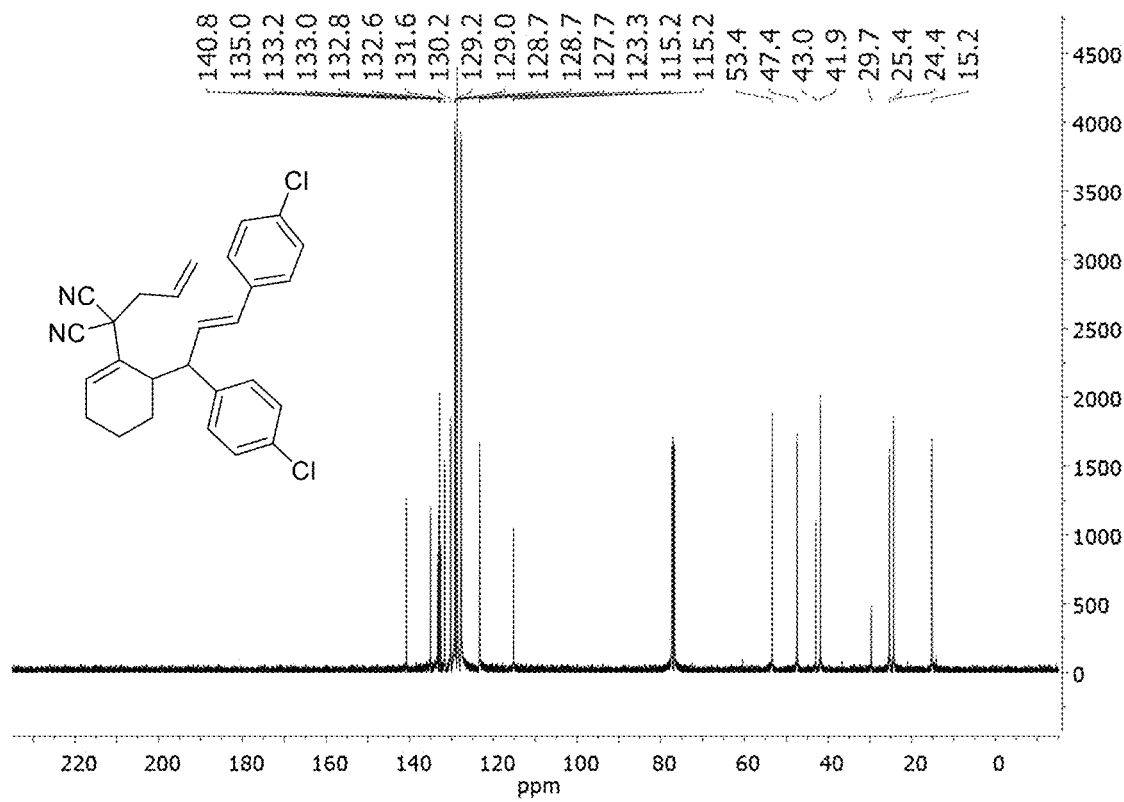
FIG. 21B shows a $^{13}$C NMR spectrum of compound 5k.

Prepared by general procedure A using a reaction time of 2 hours. Isolated: 58 mg. Yield: 42% (>20:1 dr). Physical state: colorless oil. TLC: $R_f$=0.54 (20% EtOAc in hexanes); Purified using 5% EtOAc in hexane. $^1$H NMR (500 MHz, CDCl$_3$) major diastereomer: δ 7.36 (dd, J=8.6, 2.2 Hz, 4H), 7.31 (d, J=8.4 Hz, 2H), 7.27 (d, J=8.7 Hz, 2H), 6.57 (dd, J=15.7, 9.5 Hz, 1H), 6.37 (d, J=15.7 Hz, 1H), 6.20 (t, J=3.9 Hz, 1H), 5.83 (ddt, J=17.2, 10.1, 7.2 Hz, 1H), 5.37 (d, J=10.1 Hz, 1H), 5.27 (d, J=16.9 Hz, 1H), 3.52 (t, J=9.8 Hz, 1H), 2.93 (d, J=10.0 Hz, 1H), 2.85 (dd, J=13.6, 7.3 Hz, 1H), 2.76 (dd, J=13.6, 7.2 Hz, 1H), 2.43 (ddd, J=19.5, 7.8, 2.8 Hz, 1H), 2.26 (tdd, J=13.1, 8.8, 4.4 Hz, 1H), 1.87-1.72 (m, 1H), 1.67-1.53 (m, 2H), 1.44-1.35 (m, 1H). $^{13}$C NMR (126 MHz, CDCl$_3$): δ 140.8, 135.0, 133.2, 133.0, 132.8, 132.6, 131.6, 130.2, 129.2, 129.0, 128.7, 128.7, 127.7, 123.3, 115.2, 115.2, 53.4, 47.4, 43.0, 41.9, 29.7, 25.4, 24.4, 15.2. HRMS (ESI) m/z: [M+NH$_4$]$^+$ Calcd C$_{27}$H$_{28}$Cl$_2$N$_3$ for 464.1655; Found 464.1647. Representative NMR spectra can be seen in FIGS. 21A-21B.

Example 6.12: methyl(1R)-4-(1,1-dicyanobut-3-en-1-yl)-5-((E)-1,3-diphenylallyl)cyclohex-3-ene-1-carboxylate (5l)

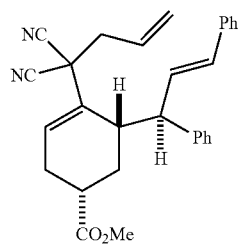

Figure 22A:
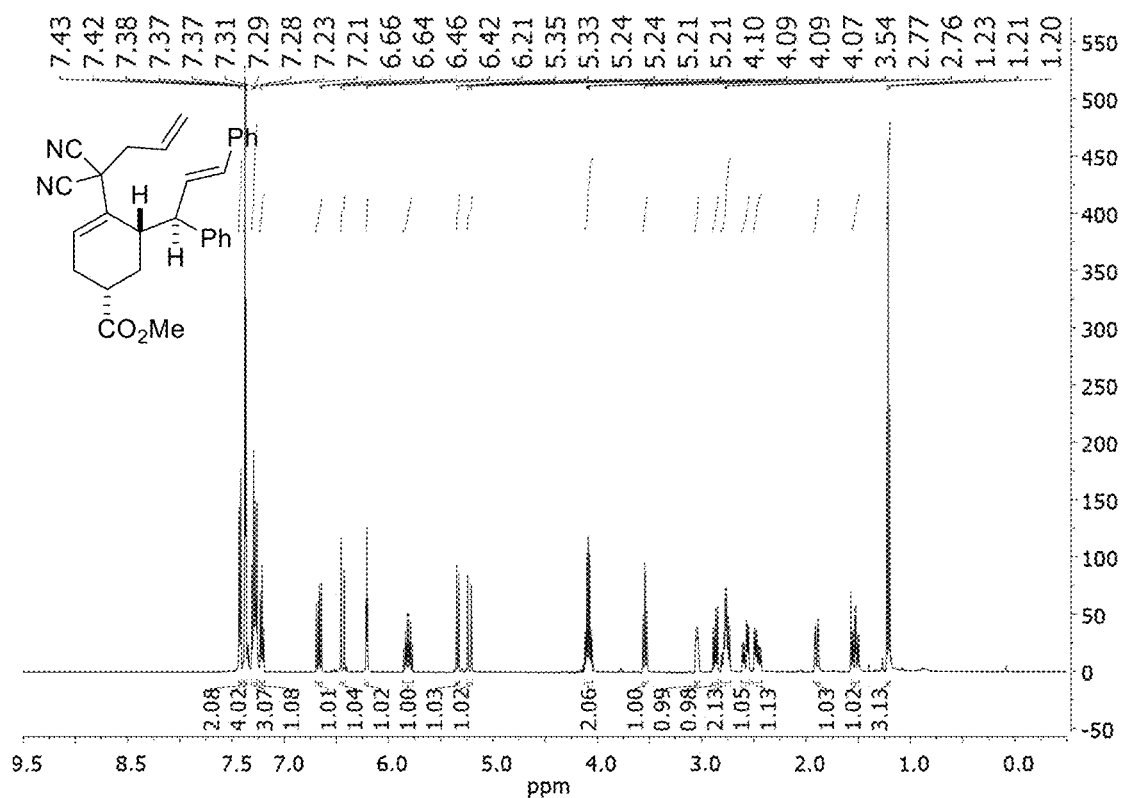
FIG. 22A shows a $^1$H NMR spectrum of methyl(1R)-4-(1,1-dicyanobut-3-en-1-yl)-5-((E)-1,3-diphenylallyl)cyclohex-3-ene-1-carboxylate (compound 5l).
Figure 22B:
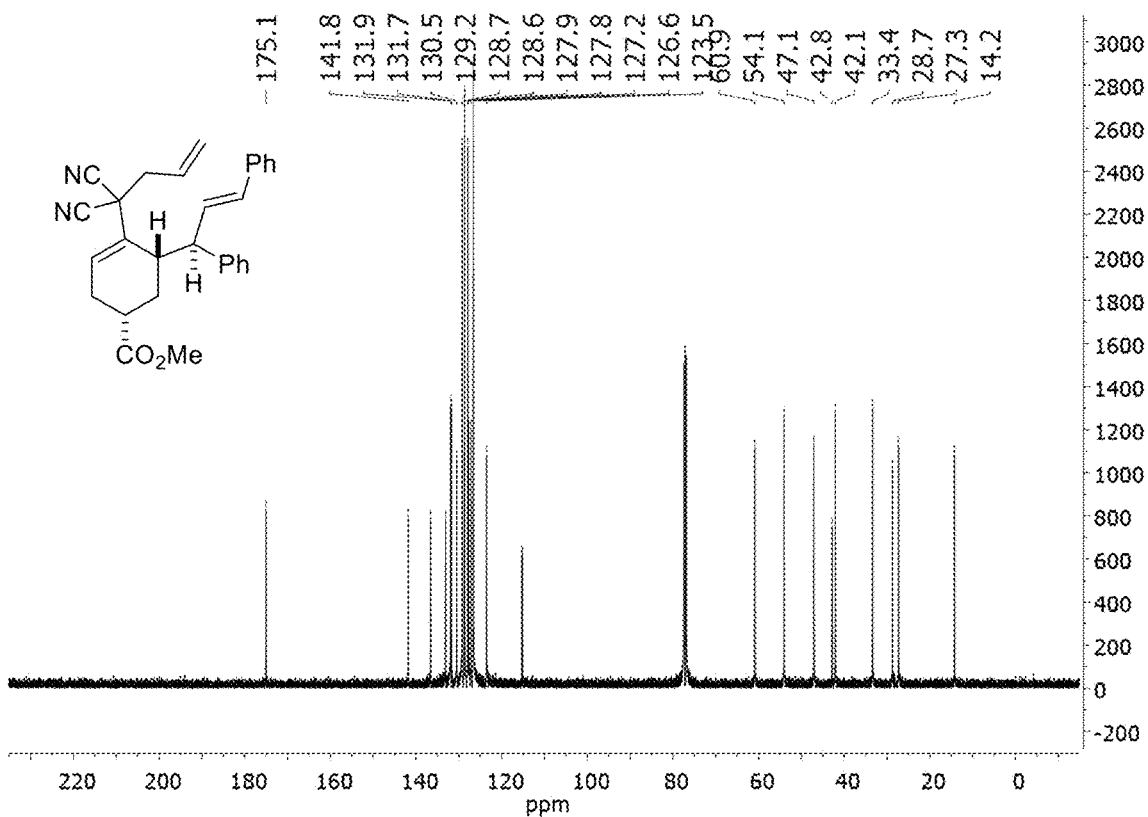
FIG. 22B shows a $^{13}$C NMR spectrum of compound 5l.

Prepared by general procedure A using a reaction time of 1 hour. Isolated: 73 mg. Yield: 41% (2.5:1 dr) (Shown spectra are an isolated diastereomer with >20:1 dr). Physical state: colorless oil. TLC: $R_f$=0.33 (20% EtOAc in hexanes); Purified using 5% EtOAc in hexane. $^1$H NMR (500 MHz, CDCl$_3$) major diastereomer: δ 7.42 (d, J=7.4 Hz, 2H), 7.38-7.36 (m, 4H), 7.32-7.27 (m, 3H), 7.21 (t, J=7.3 Hz, 1H), 6.67 (dd, J=15.7, 9.4 Hz, 1H), 6.44 (d, J=15.7 Hz, 1H), 6.21 (t, J=3.9 Hz, 1H), 5.81 (ddt, J=17.4, 10.1, 7.3 Hz, 1H), 5.34 (d, J=10.1 Hz, 1H), 5.22 (dd, J=16.9, 1.1 Hz, 1H), 4.12-4.05 (m, 2H), 3.54 (t, J=9.3 Hz, 1H), 3.04 (d, J=7.4 Hz, 1H), 2.87 (dd, J=13.6, 7.4 Hz, 1H), 2.82-2.73 (m, 2H), 2.58 (ddd, J=19.4, 7.5, 3.7 Hz, 1H), 2.46 (ddd, J=13.8, 9.3, 3.8 Hz, 1H), 1.90 (ddd, J=13.3, 3.7, 2.3 Hz, 1H), 1.53 (td, J=13.3, 4.5 Hz, 1H), 1.21 (t, J=7.1 Hz, 3H). $^{13}$C NMR (126 MHz, CDCl$_3$): δ 175.1, 141.8, 136.6, 133.1, 131.9, 131.7, 130.5, 129.2, 128.7, 128.6, 127.9, 127.2, 126.6, 123.5, 115.3, 115.2, 60.9, 54.1, 47.1, 42.8, 42.1, 33.4, 28.7, 27.3, 14.2. Representative NMR spectra can be seen in FIGS. 22A-22B.

Example 6.13: (E)-2-allyl-2-(2-(1,3-diphenylallyl)-6,6-dimethyl-5-oxocyclohex-1-en-1-yl)malononitrile (5m)

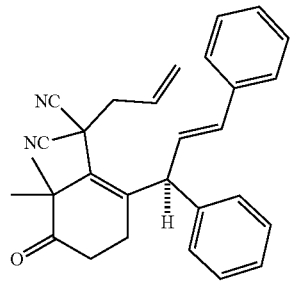 [SMILES: C=CCC(C#N)(C#N)C1=C([C@@H](/C=C/c2ccccc2)c2ccccc2)CCC(=O)C1(C)C]

Figure 23A:
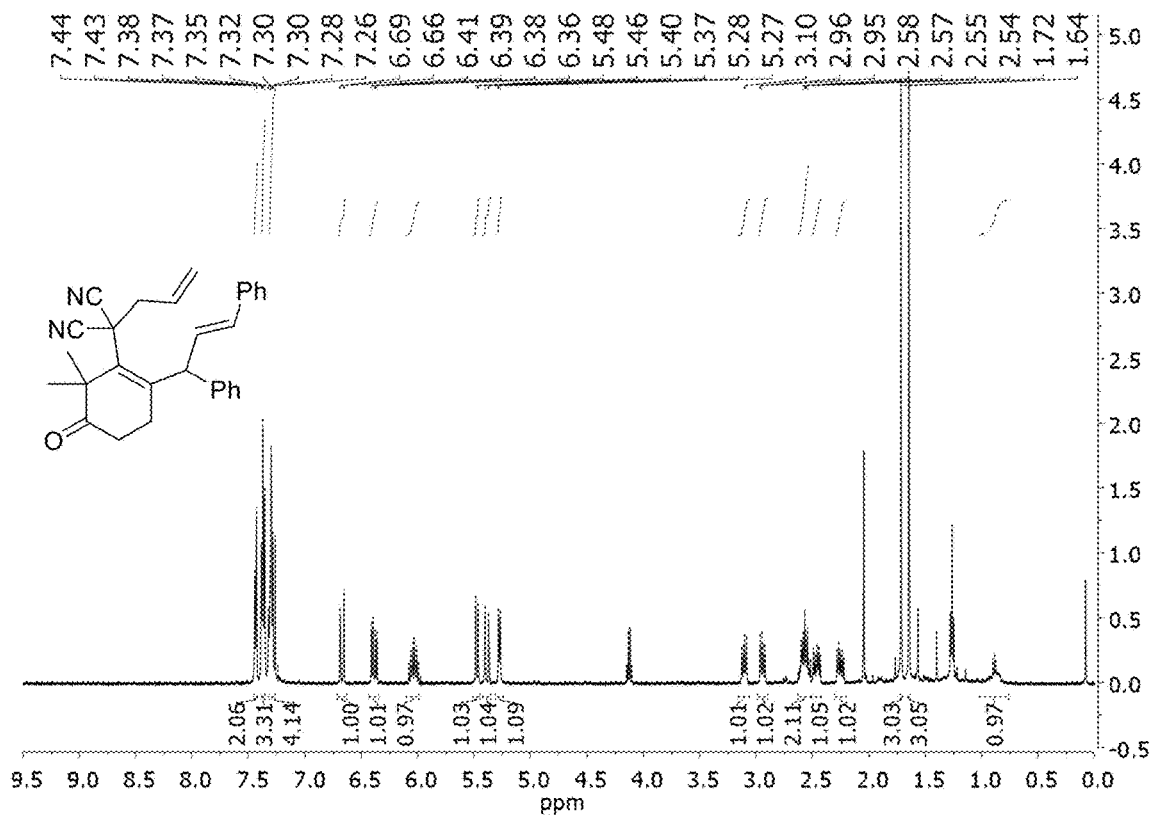
FIG. 23A shows a $^1$H NMR spectrum of (E)-2-allyl-2-(2-(1,3-diphenylallyl)-6,6-dimethyl-5-oxocyclohex-1-en-1-yl)malononitrile (compound 5m).
Figure 23B:
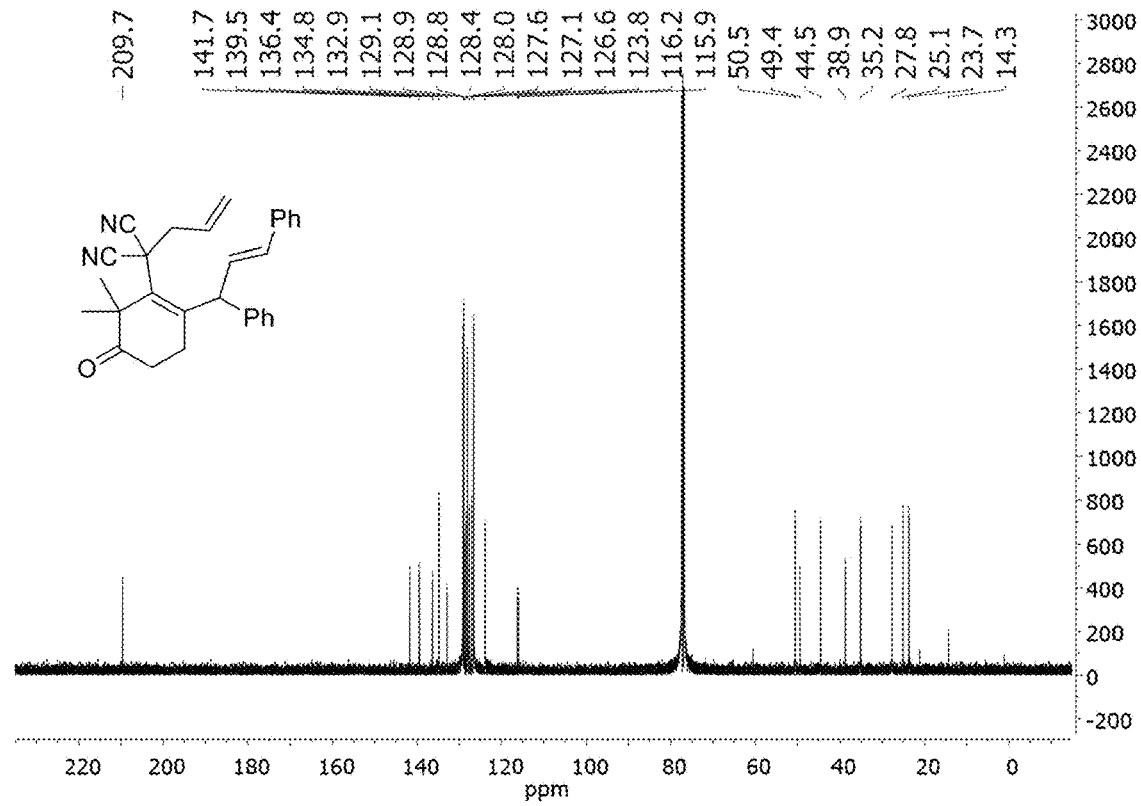
FIG. 23B shows a $^{13}$C NMR spectrum of compound 5m.

Prepared by general procedure A using a reaction time 1 hour. Isolated: 23 mg. Yield: 57% (>20:1 dr). Physical state: colorless oil. TLC: $R_f$=0.27 (20% EtOAc in hexanes); Purified using 5% EtOAc in hexane. $^1$H NMR (500 MHz, CDCl$_3$) major diastereomer: δ 7.43 (d, J=7.4 Hz, 2H), 7.37 (s, 3H), 7.29 (t, J=6.2 Hz, 4H), 6.67 (d, J=16.1 Hz, 1H), 6.39 (dd, J=15.9, 7.4 Hz, 1H), 6.03 (td, J=17.3, 7.3 Hz, 1H), 5.47 (d, J=9.9 Hz, 1H), 5.38 (d, J=16.8 Hz, 1H), 5.27 (d, J=7.4 Hz, 1H), 3.10 (dd, J=14.3, 7.5 Hz, 1H), 2.94 (dd, J=14.3, 7.0 Hz, 1H), 2.63-2.51 (m, 2H), 2.50-2.42 (m, 1H), 2.30-2.20 (m, 1H), 1.72 (s, 3H), 1.64 (s, 3H), 0.89 (t, J=7.3 Hz, 1H). $^{13}$C NMR (126 MHz, CDCl$_3$): δ 209.7, 141.7, 139.5, 136.4, 134.8, 132.9, 129.1, 129.0, 128.8, 128.4, 128.0, 127.6, 127.1, 126.6, 123.8, 116.2, 115.9, 50.5, 49.4, 44.5, 38.9, 35.2, 27.8, 25.1, 23.7, 14.4. Representative NMR spectra can be seen in FIGS. 23A-23B.

Example 6.14: (E)-2-(6-(1,3-diphenylallyl)cyclohex-1-en-1-yl)-2-(2-methylallyl)malononitrile (5n)

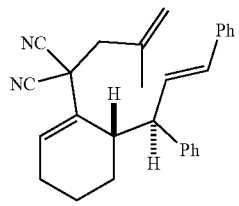 [SMILES: C=C(C)CC(C#N)(C#N)C1=CCCC[C@H]1[C@@H](/C=C/c1ccccc1)c1ccccc1]

Figure 24A:
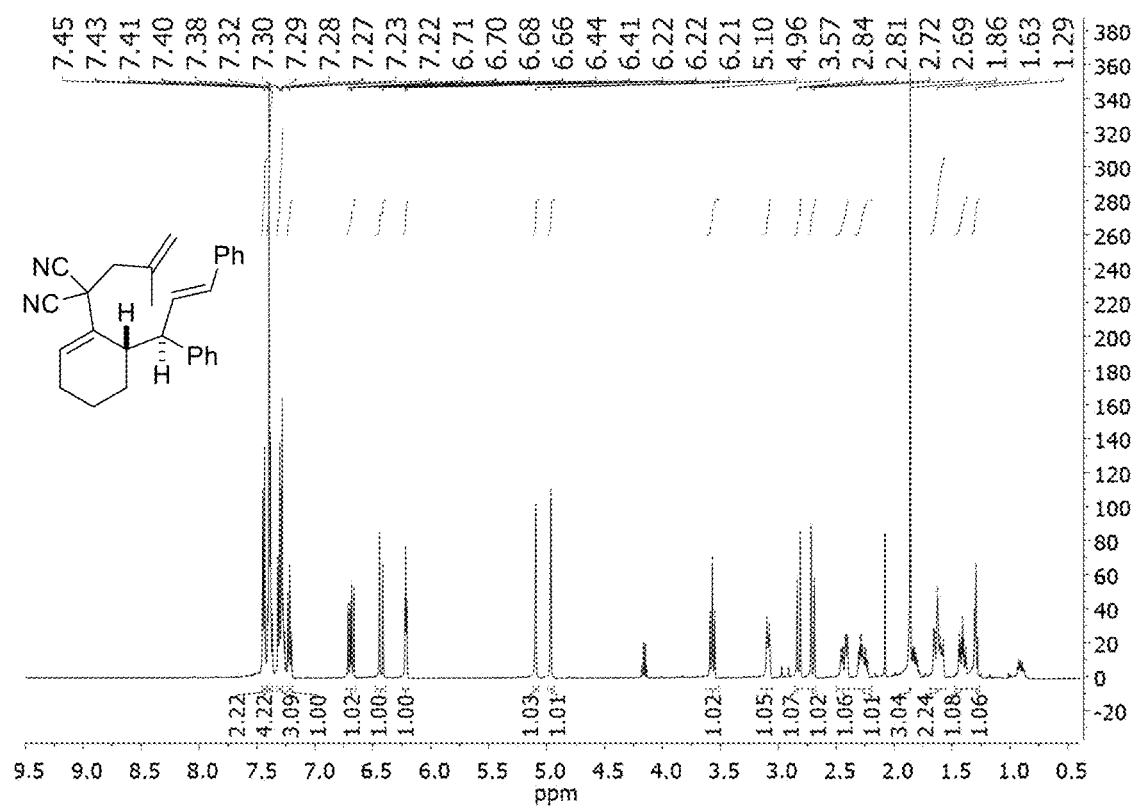
FIG. 24A shows a $^1$H NMR spectrum of (E)-2-(6-(1,3-diphenylallyl)cyclohex-1-en-1-yl)-2-(2-methylallyl)malononitrile (compound 5n).
Figure 24B:
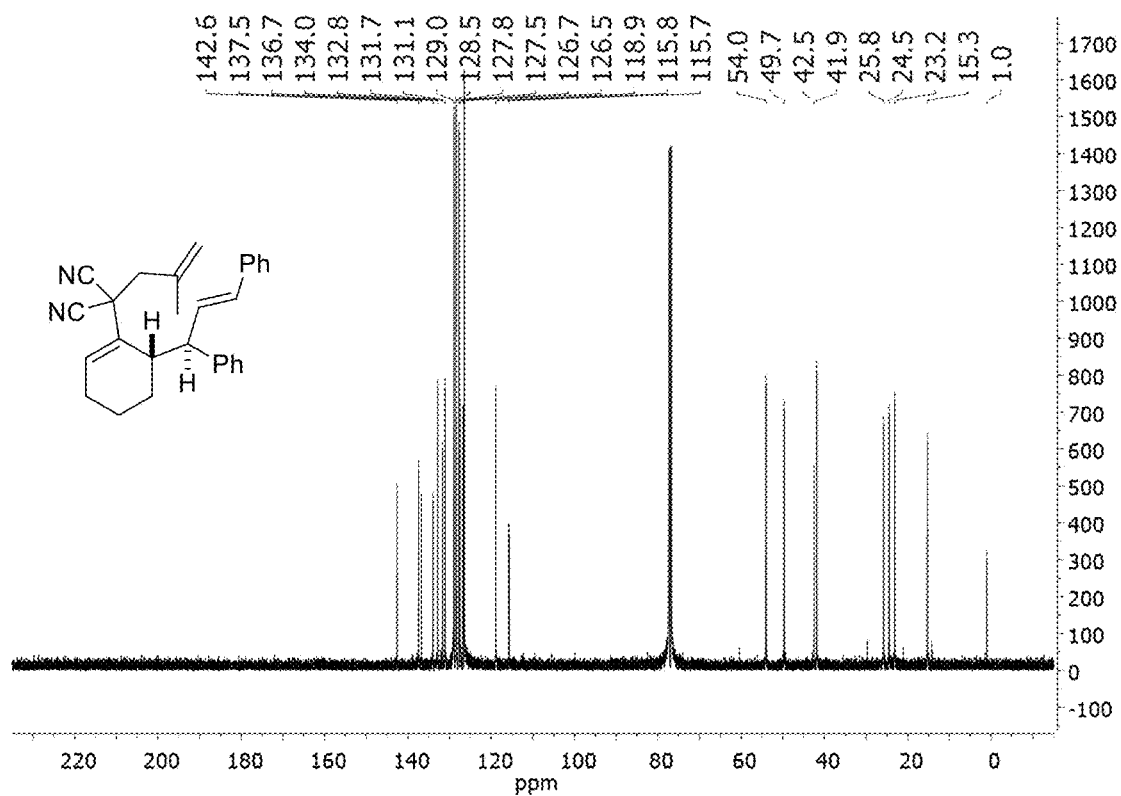
FIG. 24B shows a $^{13}$C NMR spectrum of compound 5n.

Prepared by general procedure A using a reaction time of 2 hours. Isolated: 62 mg. Yield: 55% (>20:1 dr). Physical state: colorless oil. TLC: $R_f$=0.44 (20% EtOAc in hexanes); Purified using 4% EtOAc in hexane. $^1$H NMR (500 MHz, CDCl$_3$) major diastereomer: δ 7.44 (d, J=7.4 Hz, 2H), 7.41-7.36 (m, 4H), 7.30 (dd, J=12.9, 4.8 Hz, 3H), 7.22 (t, J=7.3 Hz, 1H), 6.69 (dd, J=15.7, 9.6 Hz, 1H), 6.43 (d, J=15.7 Hz, 1H), 6.22 (t, J=3.9 Hz, 1H), 5.10 (s, 1H), 4.96 (s, 1H), 3.57 (t, J=9.8 Hz, 1H), 3.09 (d, J=9.9 Hz, 1H), 2.82 (d, J=13.9 Hz, 1H), 2.70 (d, J=13.9 Hz, 1H), 2.43 (ddd, J=19.7, 8.0, 2.5 Hz, 1H), 2.27 (dtd, J=13.1, 8.7, 4.4 Hz, 1H), 1.86 (s, 3H), 1.63 (ddd, J=24.5, 8.4, 3.4 Hz, 2H), 1.41 (ddd, J=18.1, 8.9, 4.3 Hz, 1H), 1.30 (d, J=7.0 Hz, 1H).21. $^{13}$C NMR (126 MHz, CDCl$_3$): δ 142.6, 137.5, 136.7, 134.0, 132.8, 131.7, 131.1, 129.0, 128.5, 127.8, 127.5, 126.8, 126.5, 118.9, 115.8, 115.7, 54.0, 49.7, 42.5, 41.9, 25.8, 24.5, 23.2, 15.3, 1.1. Representative NMR spectra can be seen in FIGS. 24A-24B.

Example 6.15: (E)-2-allyl-2-(6-(1,3-bis(2,5-dimethoxyphenyl)allyl)cyclohex-1-en-1-yl)malononitrile (5o)

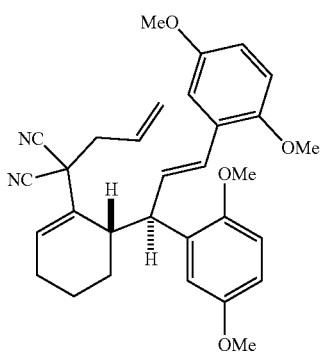 [SMILES: C=CCC(C#N)(C#N)C1=CCCC[C@H]1[C@@H](/C=C/c1cc(OC)ccc1OC)c1cc(OC)ccc1OC]

Figure 25A:
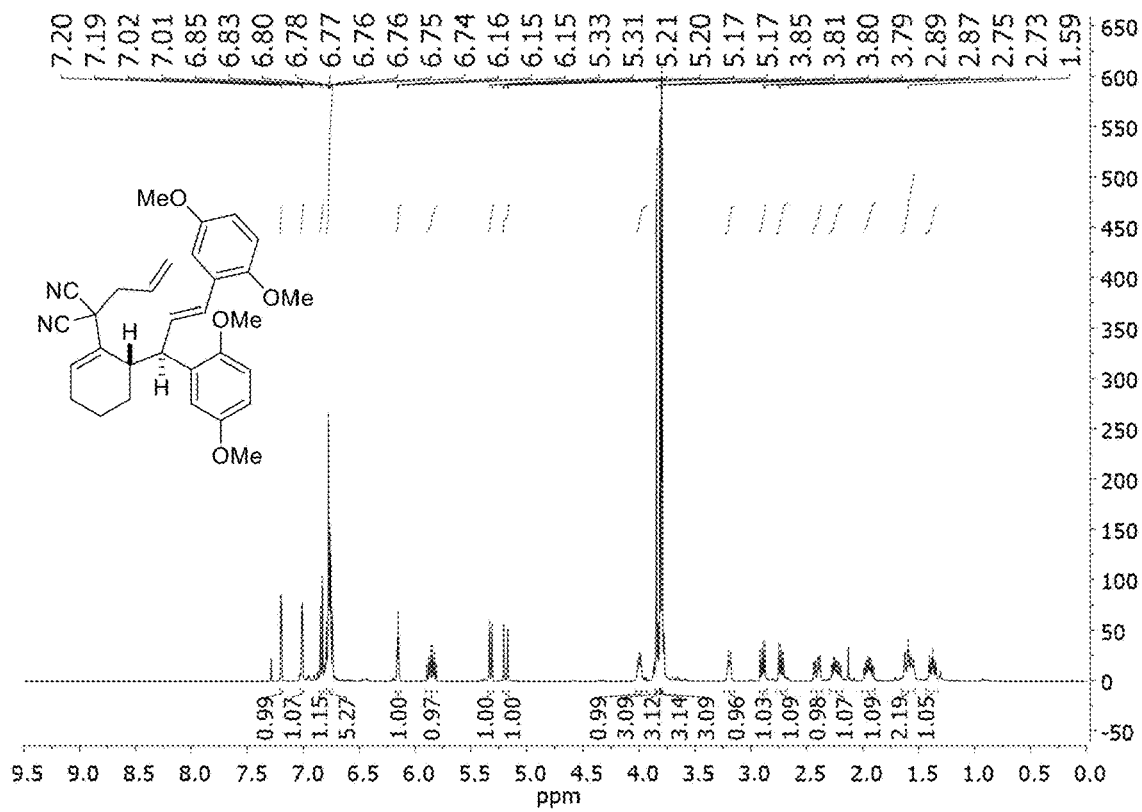
FIG. 25A shows a $^1$H NMR spectrum of (E)-2-allyl-2-(6-(1,3-bis(2,5-dimethoxyphenyl)allyl)cyclohex-1-en-1-yl)malononitrile (compound 5o).
Figure 25B:
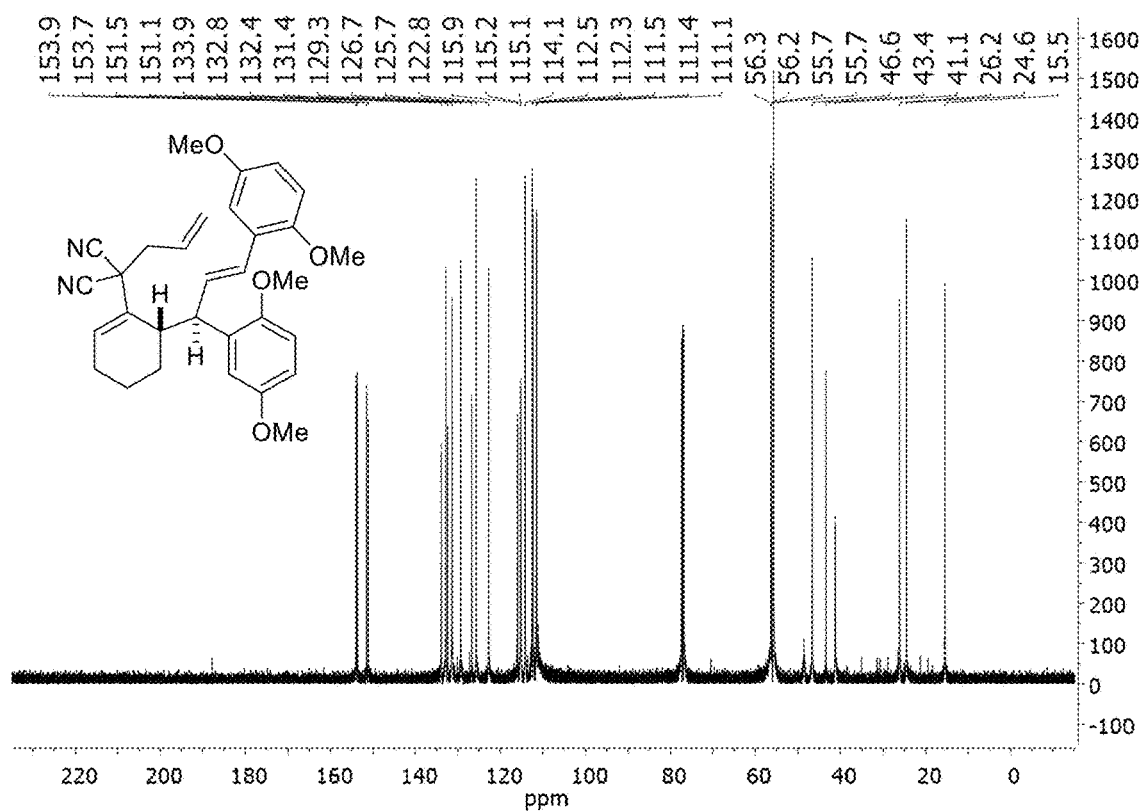
FIG. 25B shows a $^{13}$C NMR spectrum of compound 5o.

Prepared by general procedure A using a reaction time of 2 hours. Isolated: 305 mg. Yield: 86% (>20:1 dr). Physical state: colorless oil. TLC: $R_f$=0.25 (20% EtOAc in hexanes); Purified using 86% EtOAc in hexane. $^1$H NMR (500 MHz, CDCl$_3$) major diastereomer: δ 7.19 (d, J=2.8 Hz, 1H), 7.01 (d, J=2.9 Hz, 1H), 6.84 (d, J=8.9 Hz, 1H), 6.80-6.72 (m, 5H), 6.15 (t, J=3.9 Hz, 1H), 5.85 (ddt, J=17.2, 10.1, 7.3 Hz, 1H), 5.32 (d, J=10.1 Hz, 1H), 5.19 (dd, J=16.9, 0.9 Hz, 1H), 4.03-3.93 (m, 1H), 3.85 (s, 3H), 3.81 (s, 3H), 3.80 (s, 3H), 3.79 (s, 3H), 3.19 (d, J=9.7 Hz, 1H), 2.89 (dd, J=13.7, 7.5 Hz, 1H), 2.73 (dd, J=13.7, 7.0 Hz, 1H), 2.41 (ddd, J=10.4, 8.0, 2.8 Hz, 1H), 2.23 (tdd, J=12.9, 8.6, 4.5 Hz, 1H), 2.01-1.89 (m, 1H), 1.64-1.54 (m, 2H), 1.38 (tt, J=12.5, 3.9 Hz, 1H). $^{13}$C NMR (126 MHz, CDCl$_3$): δ 153.9, 153.7, 151.5, 151.1, 133.9, 132.8, 132.4, 131.4, 129.3, 126.7, 125.7, 122.8, 115.9, 115.2, 115.1, 114.1, 112.5, 112.3, 111.5, 111.4, 56.3, 56.2, 55.7, 55.7, 48.6, 46.6, 43.4, 41.2, 26.2, 24.6, 15.5. Representative NMR spectra can be seen in FIGS. 25A-25B.

Example 7: Preparation of Aryl-cycloheptenes (6a-6k and 6m-6o)

Example 7.1: 9-phenyl-1,2,3,6,9,9a-hexahydro-5H-benzo[7]annulene-5,5-dicarbonitrile (6a)

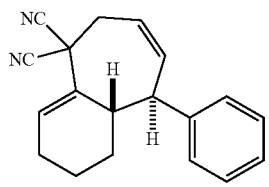

Figure 26A:
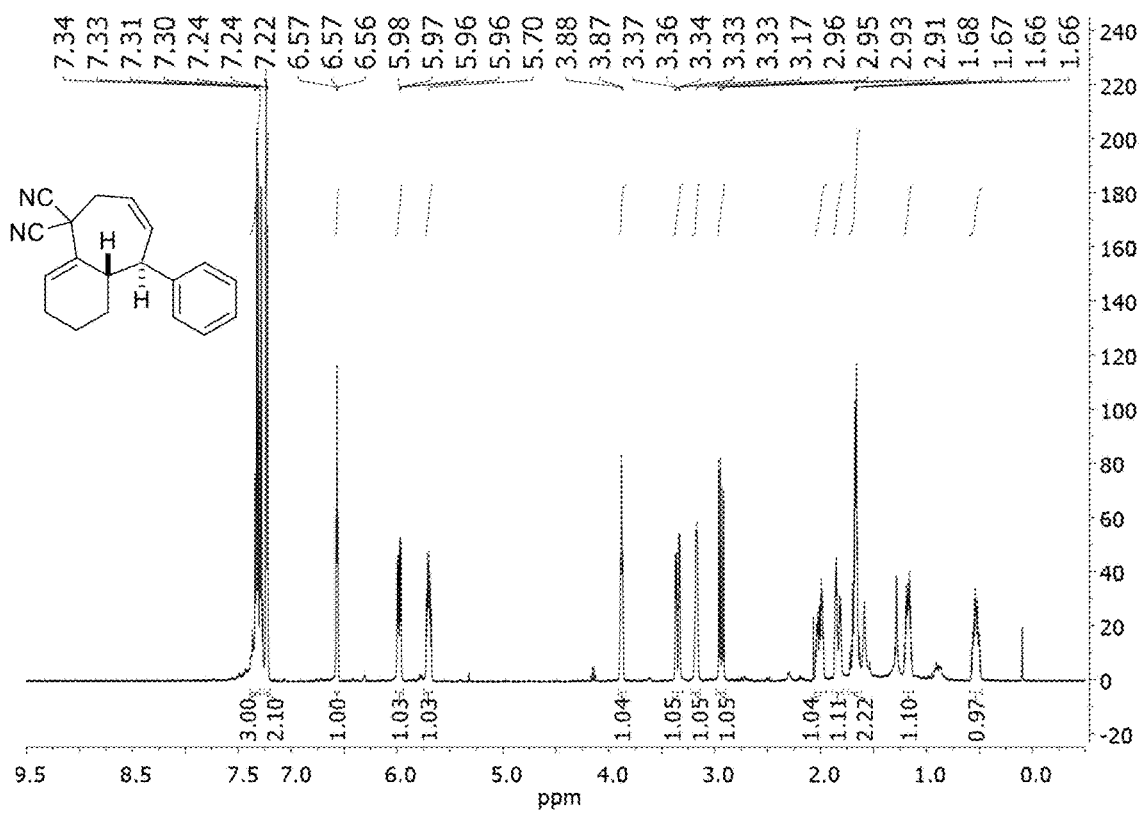
FIG. 26A shows a $^1$H NMR spectrum of 9-phenyl-1,2,3,6,9,9a-hexahydro-5H-benzo[7]annulene-5,5-dicarbonitrile (compound 6a).
Figure 26B:
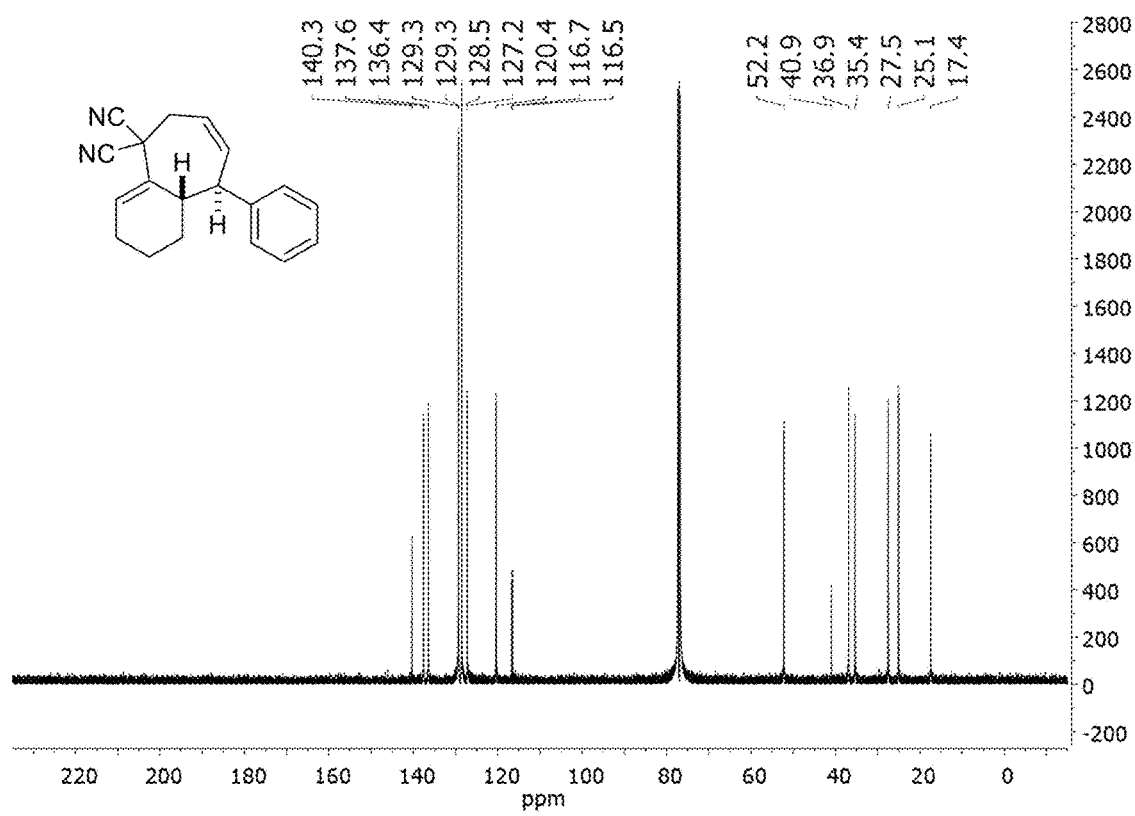

Prepared from 5a by general procedure B using a reaction time of 3 hours. Isolated: 1 g. Yield: 92% (>20:1 dr). Physical state: colorless oil. TLC: $R_f$=0.63 (20% EtOAc in hexanes); Purified using 5% EtOAc in hexane. $^1$H NMR (500 MHz, CDCl$_3$) major diastereomer: δ 7.38-7.29 (m, 3H), 7.25-7.20 (m, 2H), 6.57 (t, J=3.6 Hz, 1H), 5.98 (ddd, J=11.3, 5.5, 2.0 Hz, 1H), 5.74-5.65 (m, 1H), 3.88 (t, J=5.2 Hz, 1H), 3.35 (ddt, J=8.7, 4.3, 2.0 Hz, 1H), 3.17 (s, 1H), 2.94 (dd, J=16.0, 7.6 Hz, 1H), 2.06-1.95 (m, 1H), 1.88-1.79 (m, 1H), 1.75-1.62 (m, 2H), 1.22-1.11 (m, 1H), 0.62-0.46 (m, 1H). $^{13}$C NMR (126 MHz, CDCl$_3$): δ 140.3, 137.6, 136.4, 129.4, 129.3, 128.5, 127.2, 120.4, 116.7, 116.5, 52.2, 40.9, 36.9, 35.4, 27.5, 25.1, 17.4. HRMS (DART) m/z: [M+NH$_4$]$^+$ Calcd for C$_{19}$H$_{22}$N$_3$ 292.1808; Found 292.1812. Representative NMR spectra can be seen in FIGS. 26A-26B.

Example 7.2: 9-phenyl-3,6,9,9a-tetrahydrospirio[benzo[7]annulene-2,2'-[1,3]dioxolane]-5,5(1H)-dicarbonitrile (6b)

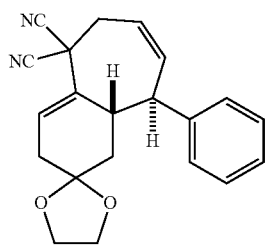

Figure 27A:
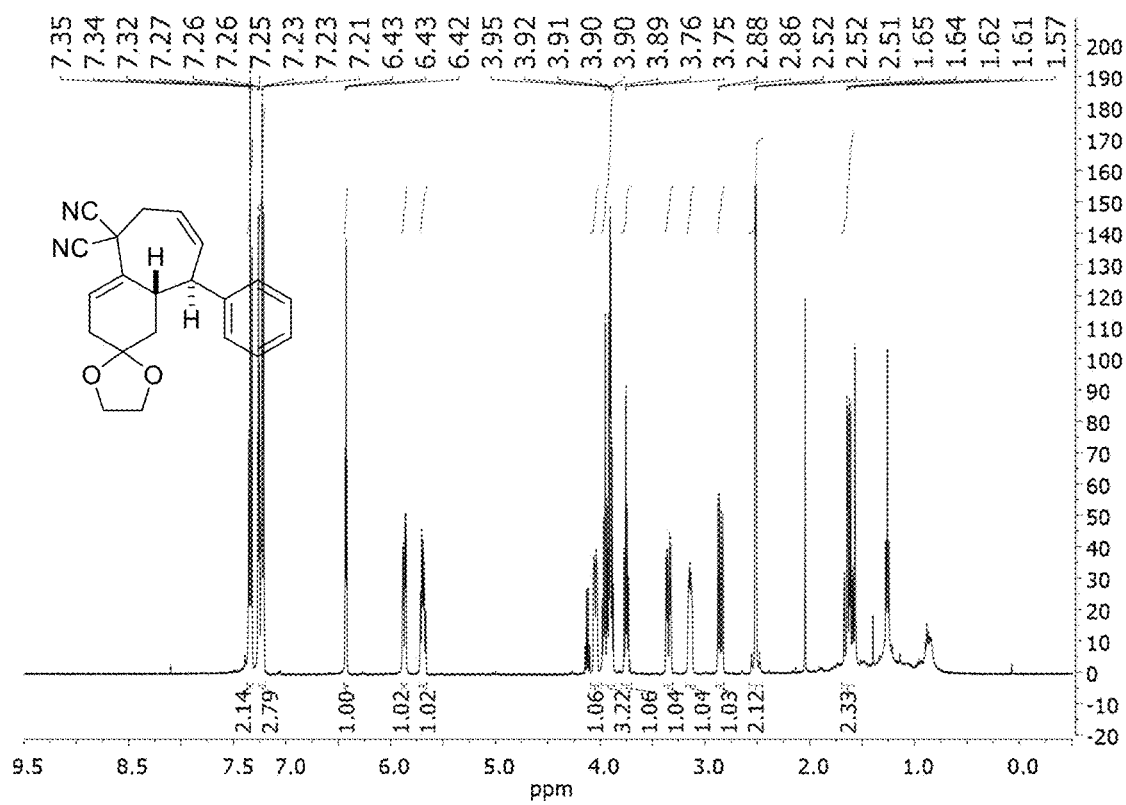
FIG. 27A shows a $^1$H NMR spectrum of 9-phenyl-3,6,9,9a-tetrahydrospiro[benzo[7]annulene-2,2'-[1,3]dioxolane]-5,5(1H)-dicarbonitrile (compound 6b).
Figure 27B:
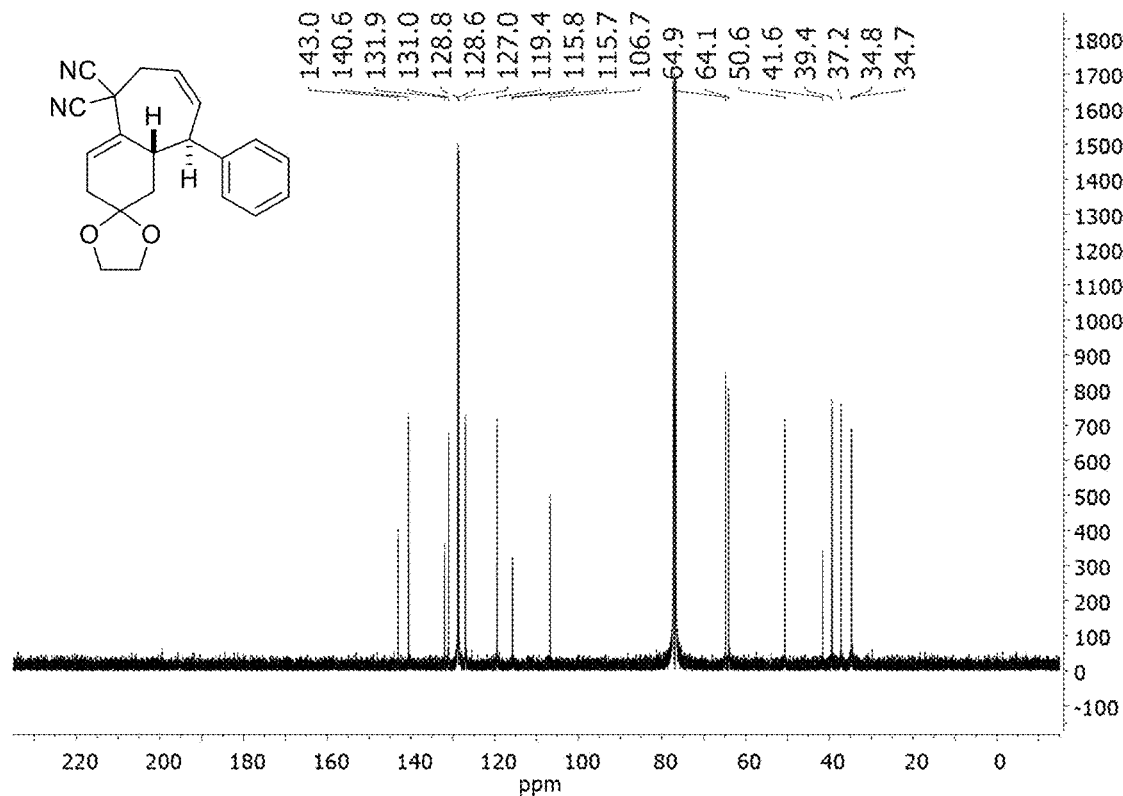
FIG. 27B shows a $^{13}$C NMR spectrum of compound 6b.

Prepared from 5b by general procedure B using a reaction time of 3 hours. Isolated: 20 mg. Yield: 42% (>20:1 dr). Physical state: colorless oil. TLC: $R_f$=0.40 (20% EtOAc in hexanes); Purified using 10% EtOAc in hexane. $^1$H NMR (500 MHz, CDCl$_3$) major diastereomer δ 7.34 (t, J=7.4 Hz, 2H), 7.26-7.19 (m, 3H), 6.43 (t, J=3.9 Hz, 1H), 5.87 (dd, J=11.3, 4.4 Hz, 1H), 5.72-5.65 (m, 1H), 4.05 (dd, J=11.1, 2.1 Hz, 1H), 3.99-3.86 (m, 3H), 3.79-3.70 (m, 1H), 3.35 (dd, J=15.2, 5.9 Hz, 1H), 3.18-3.10 (m, 1H), 2.85 (dd, J=15.2, 7.3 Hz, 1H), 2.58-2.45 (m, 2H), 1.63 (qd, J=13.9, 4.6 Hz, 2H). $^{13}$C NMR (126 MHz, CDCl$_3$): δ 143.0, 140.6, 131.9, 131.0, 128.8, 128.6, 127.0, 119.4, 115.8, 115.7, 106.7, 64.9, 64.1, 50.6, 41.6, 39.4, 37.2, 34.8, 34.7. HRMS (ESI) m/z: [M+Na]⁺ Calcd for $C_{21}H_{20}N_2O_2Na$ 355.1417; Found 355.1425. Representative NMR spectra can be seen in FIGS. 27A-27B.

Example 7.3: 2,2-difluoro-9-phenyl-1,2,3,6,9,9a-hexahydro-5H-benzo[7]annulene-5,5-dicarbonitrile (6c)

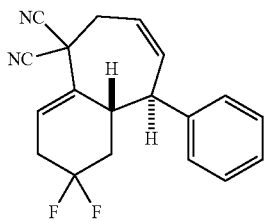

Figures 28A, 28B:
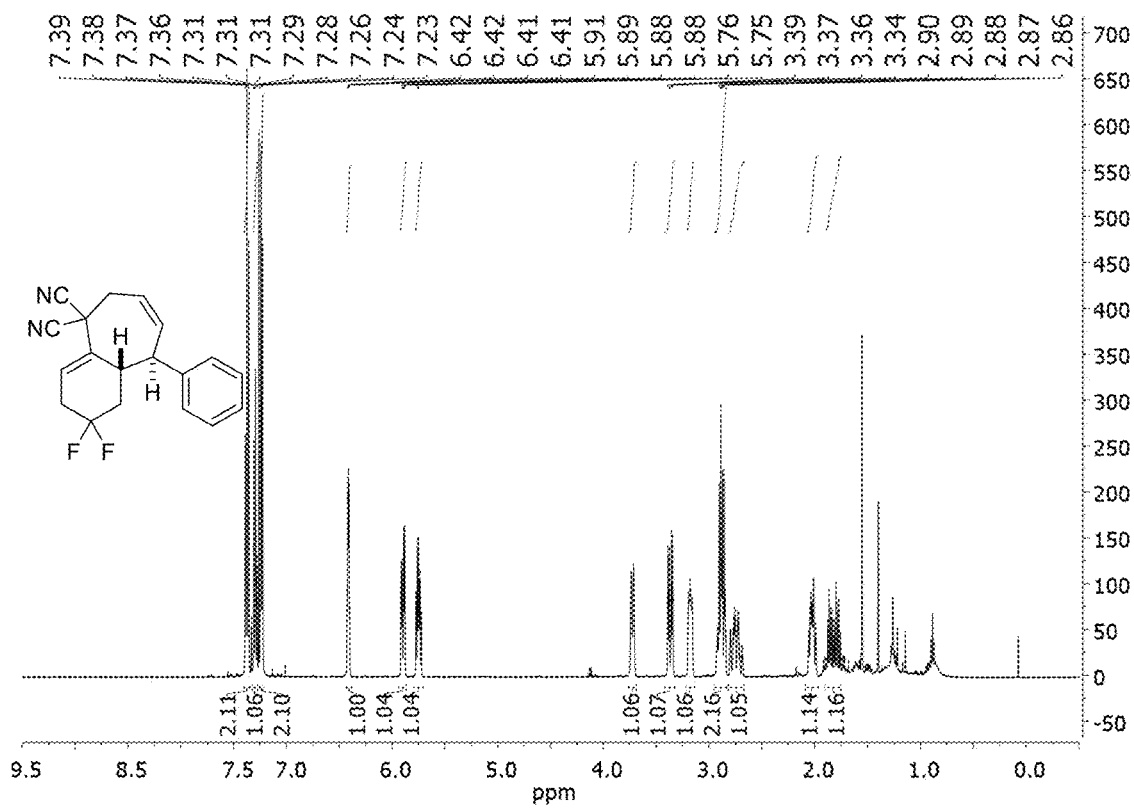
FIG. 28A shows a $^1$H NMR spectrum of 2,2-difluoro-9-phenyl-1,2,3,6,9,9a-hexahydro-5H-benzo[7]annulene-5,5-dicarbonitrile (compound 6c).
FIG. 28B shows a $^{13}$C NMR spectrum of compound 6c.

Prepared from 5c by general procedure B using a reaction time of 3 hours. Isolated: 17 mg. Yield: 76% (>20:1 dr). Physical state: colorless oil. TLC: $R_f$=0.51 (20% EtOAc in hexanes); Purified using 10% EtOAc in hexane. ¹H NMR (500 MHz, CDCl₃) major diastereomer δ 7.38 (dd, J=10.3, 4.6 Hz, 2H), 7.32-7.27 (m, 1H), 7.23 (d, J=7.2 Hz, 2H), 6.43-6.38 (m, 1H), 5.93-5.86 (m, 1H), 5.79-5.71 (m, 1H), 3.76-3.69 (m, 1H), 3.37 (ddt, J=15.2, 5.9, 1.6 Hz, 1H), 3.22-3.14 (m, 1H), 2.95-2.83 (m, 2H), 2.82-2.67 (m, 1H), 2.09-1.96 (m, 1H), 1.91-1.75 (m, 1H). ¹³C NMR (126 MHz, CDCl₃): δ 141.7, 139.8, 132.5, 129.1, 128.6, 128.4, 128.4, 127.5, 123.7, 121.7, 119.8, 115.3, 115.3, 50.8, 50.8, 41.4, 39.1, 39.0, 36.0, 35.8, 35.6, 34.7, 33.8, 33.5. HRMS (DART) m/z: [M+H]⁺ Calcd for $C_{19}H_{16}F_2N_2$ 311.1354; Found 311.1367. Representative NMR spectra can be seen in FIGS. 28A-28B.

Example 7.4: 3,3-dimethyl-9-phenyl-1,2,3,6,9,9a-hexahydro-5H-benzo[7]annulene-5,5-dicarbonitrile (6d)

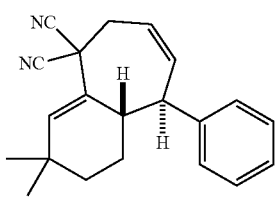

Figure 29A:
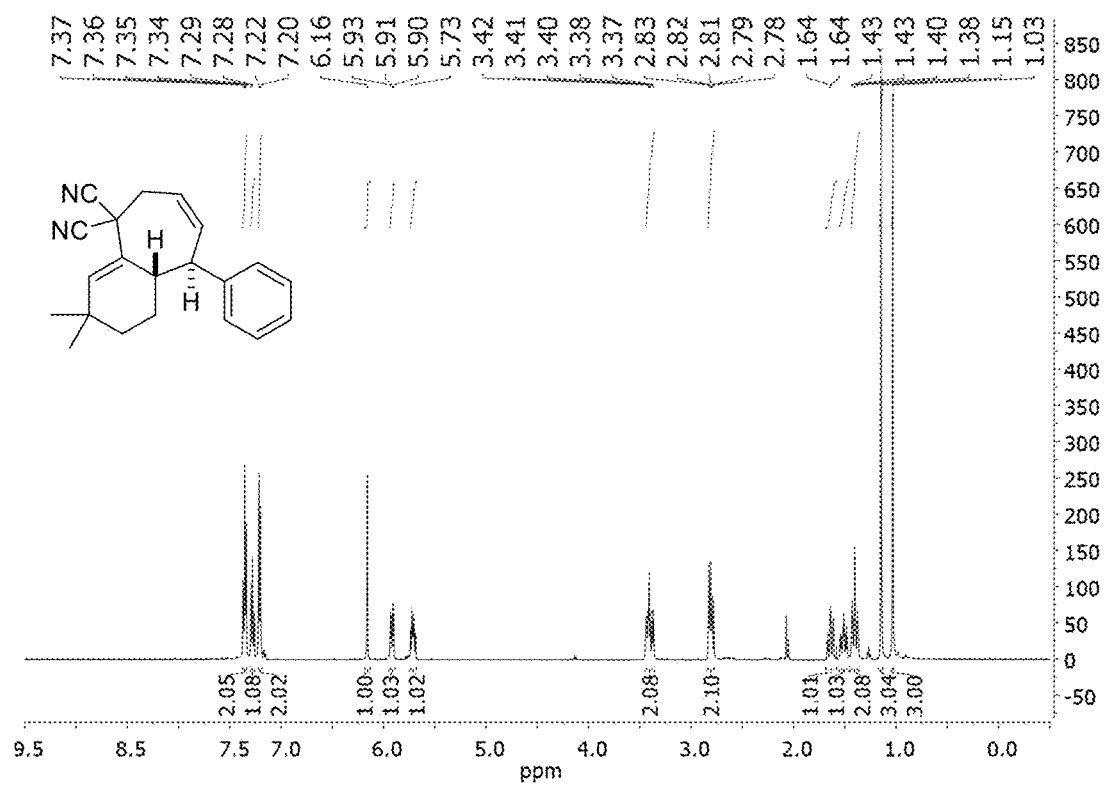
FIG. 29A shows a $^1$H NMR spectrum of 3,3-dimethyl-9-phenyl-1,2,3,6,9,9a-hexahydro-5H-benzo[7]annulene-5,5-dicarbonitrile (compound 6d).
Figure 29B:
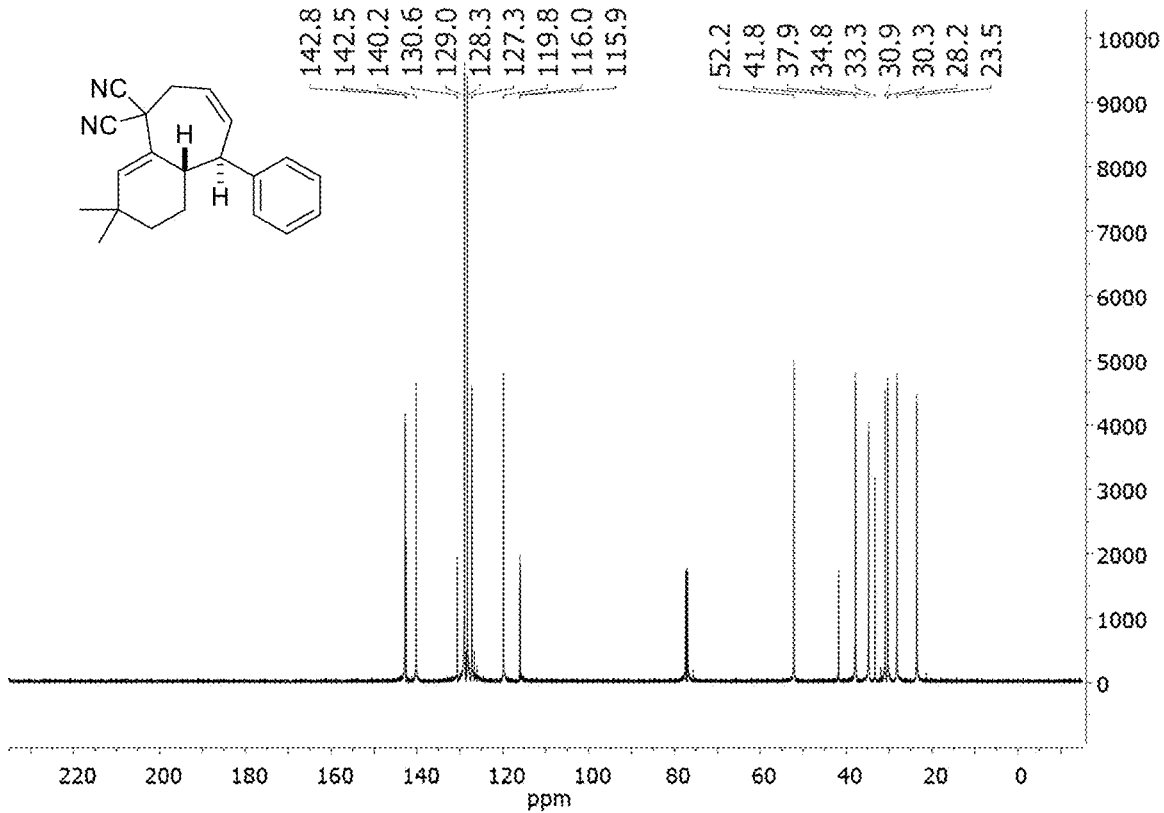
FIG. 29B shows a $^{13}$C NMR spectrum of compound 6d.

Prepared from 5d by general procedure B using a reaction time of 2 hours. Isolated: 73 mg. Yield: 56% (>20:1 dr). Physical state: colorless oil. TLC: $R_f$=0.77 (20% EtOAc in hexanes); Purified using 5% EtOAc in hexane. ¹H NMR (500 MHz, CDCl₃) major diastereomer δ 7.35 (dd, J=9.3, 5.6 Hz, 2H), 7.28 (t, J=7.3 Hz, 1H), 7.21 (d, J=7.1 Hz, 2H), 6.16 (s, 1H), 5.95-5.89 (m, 1H), 5.75-5.68 (m, 1H), 3.45-3.36 (m, 2H), 2.84-2.77 (m, 2H), 1.69-1.58 (m, 1H), 1.56-1.46 (m, 1H), 1.45-1.36 (m, 2H), 1.15 (s, 3H), 1.03 (s, 3H). ¹³C NMR (126 MHz, CDCl₃): δ 142.8, 142.5, 140.2, 130.6, 129.0, 128.3, 127.3, 119.8, 116.1, 115.9, 52.2, 41.8, 37.9, 34.8, 33.3, 30.9, 30.3, 28.2, 23.6. HRMS (DART/ESI) m/z: [M+Na]⁺ Calcd for $C_{21}H_{22}N_2Na$ 325.1675; Found 325.1669. Representative NMR spectra can be seen in FIGS. 29A-29B.

Example 7.5: tert-butyl(1S,4R)-6,6-dicyano-10-phenyl-1,2,3,4,6,7,10,10a-octahydro-1,4-epimino-heptalene-11-carboxylate (6e)

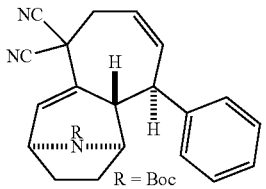

Prepared from 5e by general procedure B using a reaction time of 3 hours. Isolated: 10 mg. Yield: 41% (>20:1 dr). Physical state: colorless oil. TLC: $R_f$=0.64 (20% EtOAc in hexanes); Purified using 10% EtOAc in hexane. All spectroscopic data for this compound was consistent with the reported in the literature.

Example 7.6: 4-methyl-9-phenyl-1-(prop-1-en-2-yl)-1,2,3,6,9,9a-hexahydro-5H-benzo[7]annulene-5,5-dicarbonitrile (6f)

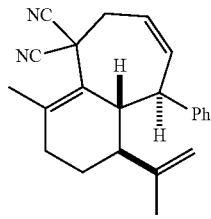

Figure 30A:
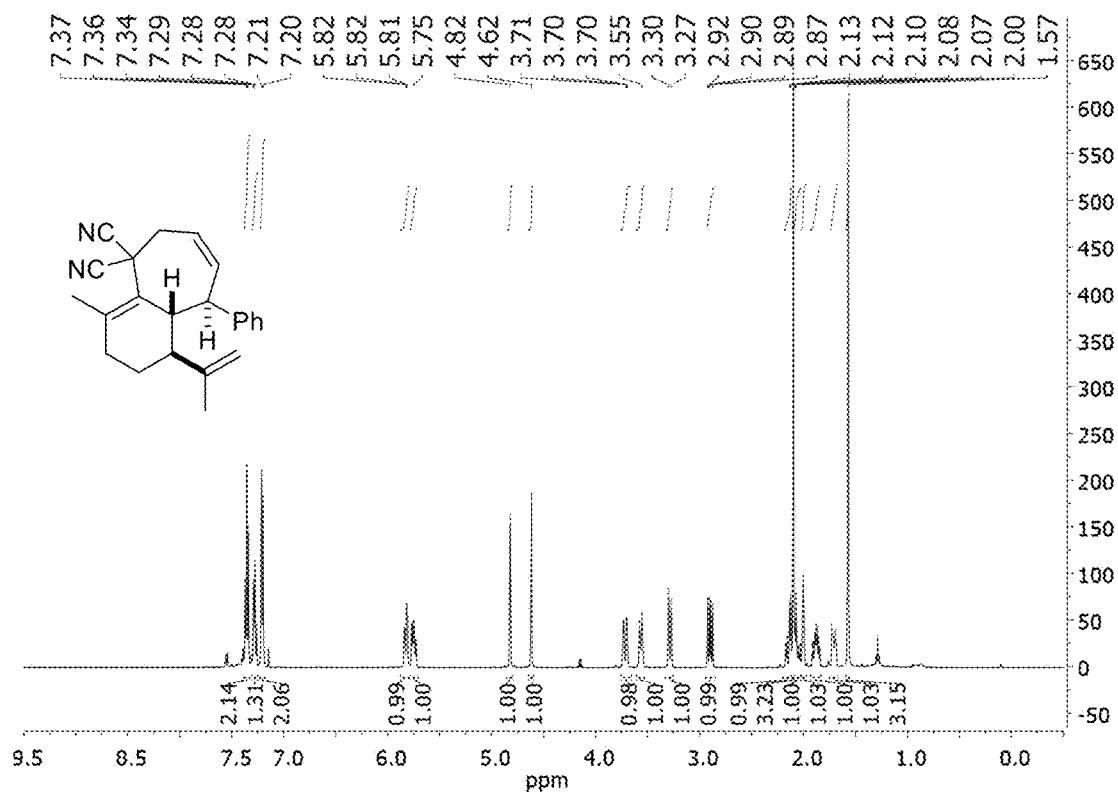
FIG. 30A shows a $^1$H NMR spectrum of 4-methyl-9-phenyl-1-(prop-1-en-2-yl)-1,2,3,6,9,9a-hexahydro-5H-benzo[7]annulene-5,5-dicarbonitrile (compound 6f).
Figure 30B:
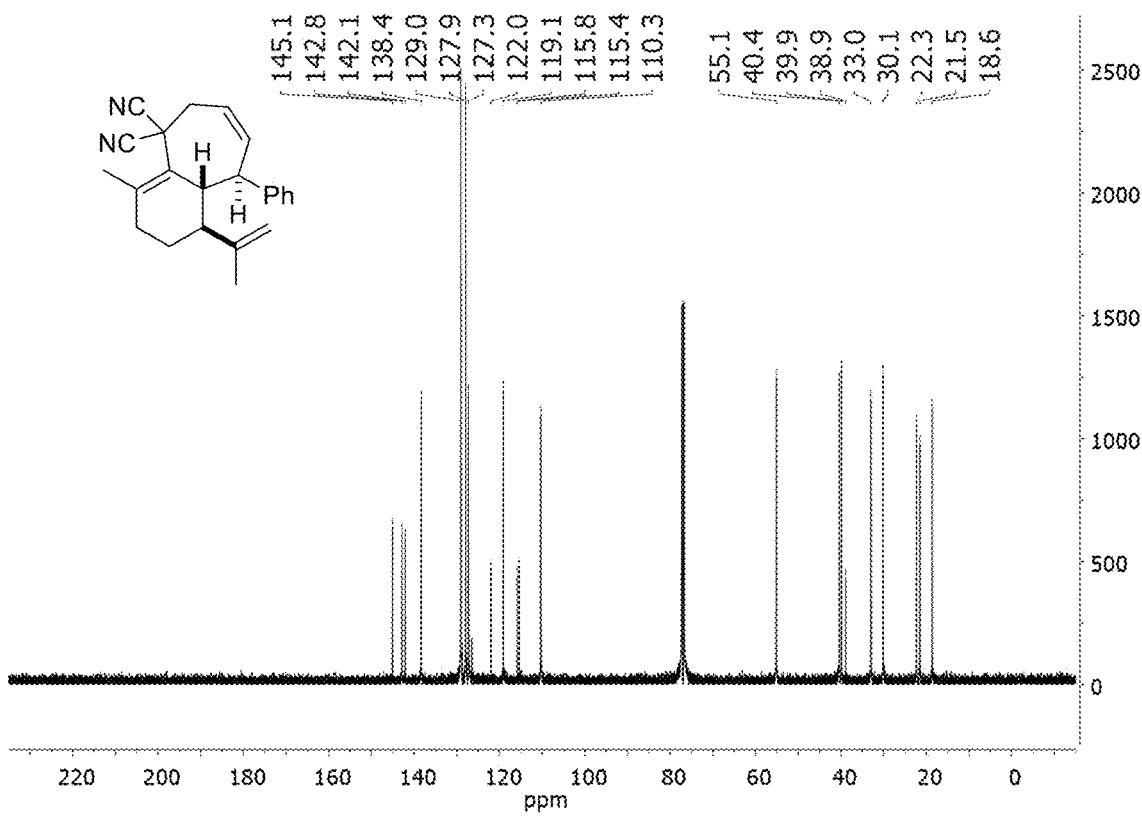
FIG. 30B shows a $^{13}$C NMR spectrum of compound 6f.

Prepared from 5f by general procedure B using a reaction time of 3 hour. Isolated: 32 mg. Yield: 73% (>20:1 dr). Physical state: colorless oil. TLC: $R_f$=0.76 (20% EtOAc in hexanes); Purified using 5% EtOAc in hexane. ¹H NMR (500 MHz, CDCl₃) major diastereomer δ 7.36 (t, J=7.5 Hz, 2H), 7.28 (dd, J=9.4, 5.2 Hz, 1H), 7.21 (d, J=7.3 Hz, 2H), 5.88-5.80 (m, 1H), 5.79-5.71 (m, 1H), 4.82 (s, 1H), 4.62 (s, 1H), 3.76-3.66 (m, 1H), 3.56 (d, J=11.5 Hz, 1H), 3.29 (d, J=11.5 Hz, 1H), 2.90 (dd, J=15.0, 8.8 Hz, 1H), 2.15 (dd, J=18.4, 6.3 Hz, 1H), 2.10 (s, 3H), 2.09-2.02 (m, 1H), 2.00 (s, 1H), 1.93-1.84 (m, 1H), 1.71 (d, J=15.8 Hz, 1H), 1.57 (s, 3H). ¹³C NMR (126 MHz, CDCl₃): δ 145.1, 142.8, 142.1, 138.4, 129.0, 127.9, 127.3, 122.0, 119.1, 115.8, 115.4, 110.3, 55.1, 40.4, 39.9, 38.9, 33.0, 30.1, 22.3, 21.5, 18.6. HRMS (ESI) m/z: [M+Na]⁺ Calcd for $C_{23}H_{24}N_2Na$ 351.1832; Found 351.1820. Representative NMR spectra can be seen in FIGS. 30A-30B.

Example 7.7: 9-(4-methoxyphenyl)-1,2,3,6,9,9a-hexahydro-5H-benzo[7]annulene-5,5-dicarbonitrile (6g)

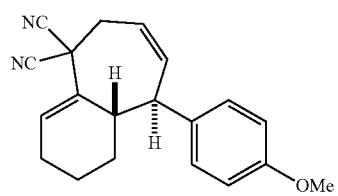

Figure 31A:
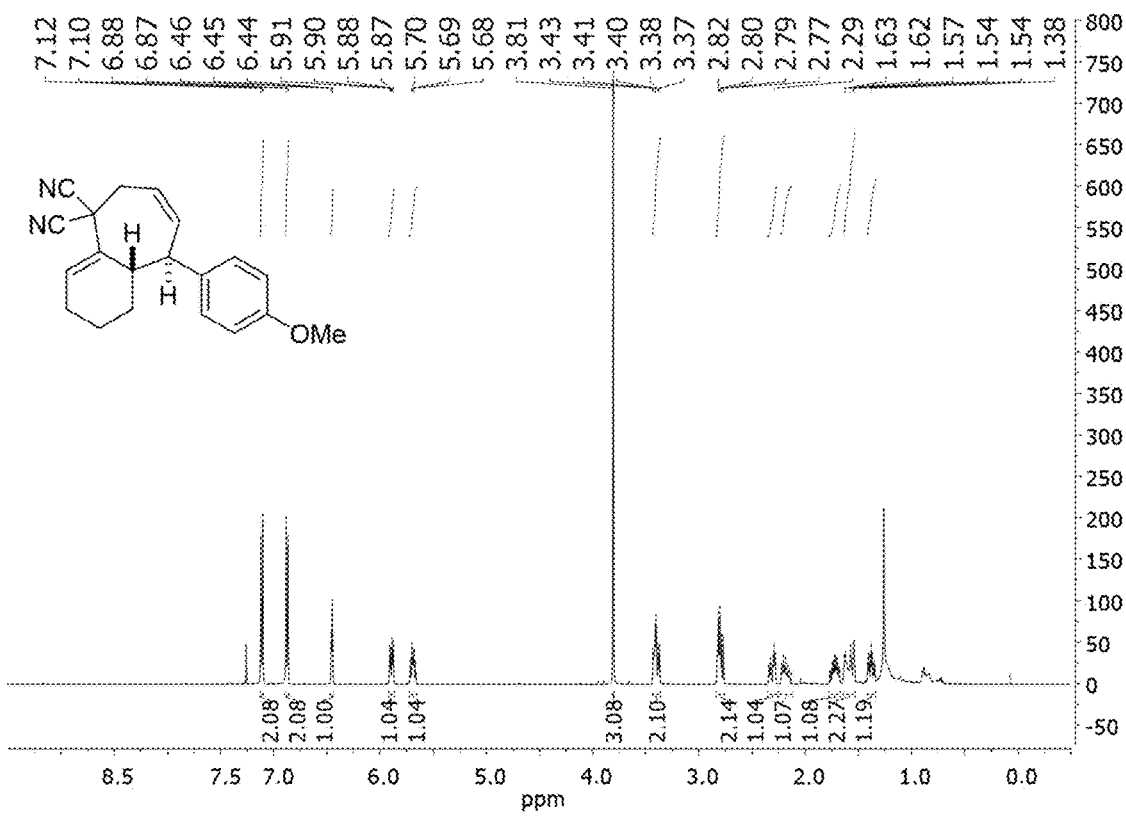
FIG. 31A shows a $^1$H NMR spectrum of 9-(4-methoxyphenyl)-1,2,3,6,9,9a-hexahydro-5H-benzo[7]annulene-5,5-dicarbonitrile (compound 6g).
Figure 31B:
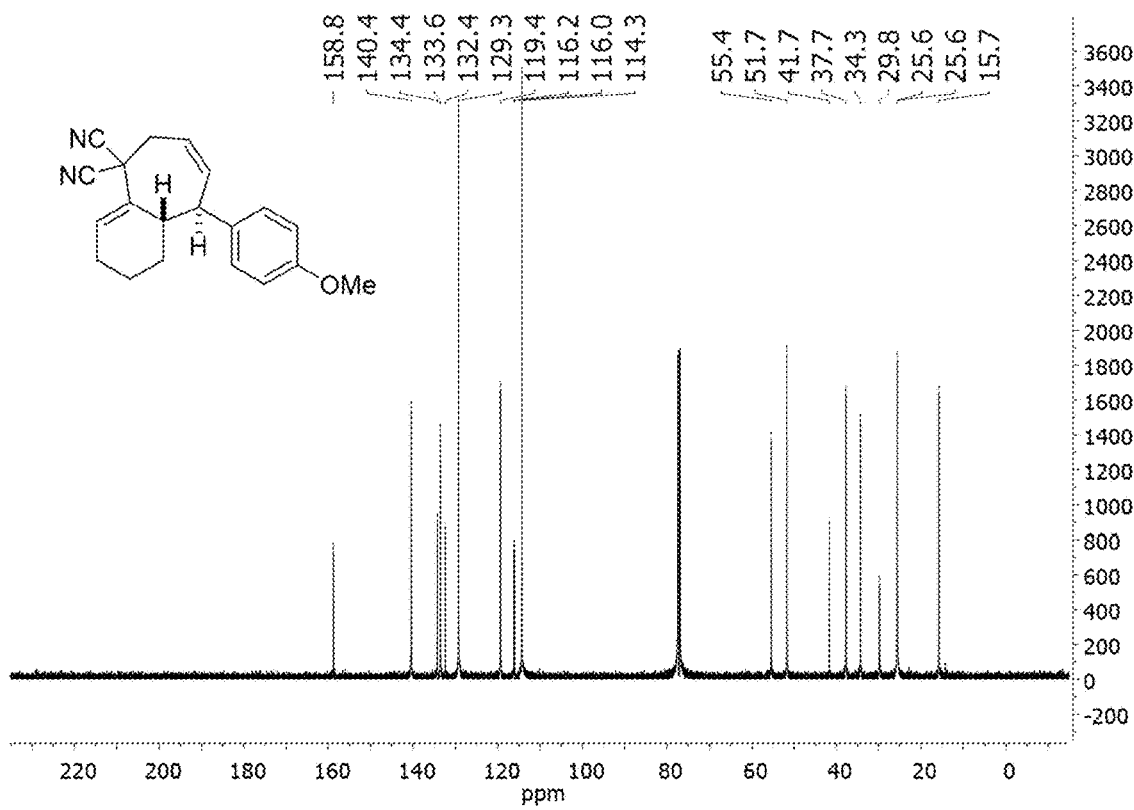
FIG. 31B shows a $^{13}$C NMR spectrum of compound 6g.

Prepared from 5g by general procedure B using a reaction time of 3 hours. Isolated: 27 mg. Yield: 73% (>20:1dr). Physical state: colorless oil. TLC: $R_f$=0.53 (20% EtOAc in hexanes); Purified using 5% EtOAc in hexane. $^1$H NMR (500 MHz, CDCl$_3$) major diastereomer $^1$H NMR (500 MHz, cdcl$_3$) δ 7.11 (d, J=8.5 Hz, 2H), 6.88 (d, J=8.4 Hz, 2H), 6.45 (t, J=3.7 Hz, 1H), 5.89 (dd, J=11.1, 4.3 Hz, 1H), 5.72-5.65 (m, 1H), 3.81 (s, 3H), 3.43-3.36 (m, 2H), 2.80 (dd, J=14.9, 7.6 Hz, 2H), 2.31 (dt, J=19.1, 5.2 Hz, 1H), 2.18 (dt, J=17.5, 9.0 Hz, 1H), 1.78-1.67 (m, 1H), 1.64-1.53 (m, 2H), 1.42-1.34 (m, 1H). $^{13}$C NMR (126 MHz, CDCl$_3$): δ 158.8, 140.4, 134.4, 133.6, 132.4, 129.3, 119.4, 116.2, 116.1, 114.3, 55.4, 51.7, 41.7, 37.8, 34.3, 29.8, 25.6, 25.6, 15.7. HRMS (ESI) m/z: [M+Na]$^+$ Calcd for C$_{20}$H$_{20}$N$_2$ONa 327.1468; Found 327.1464. Representative NMR spectra can be seen in FIGS. 31A-31B.

Example 7.8: 9-(2-methoxyphenyl)-1,2,3,6,9,9a-hexahydro-5H-benzo[7]annulene-5,5-dicarbonitrile (6h)

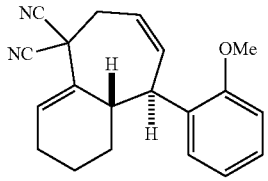

Figure 32A:
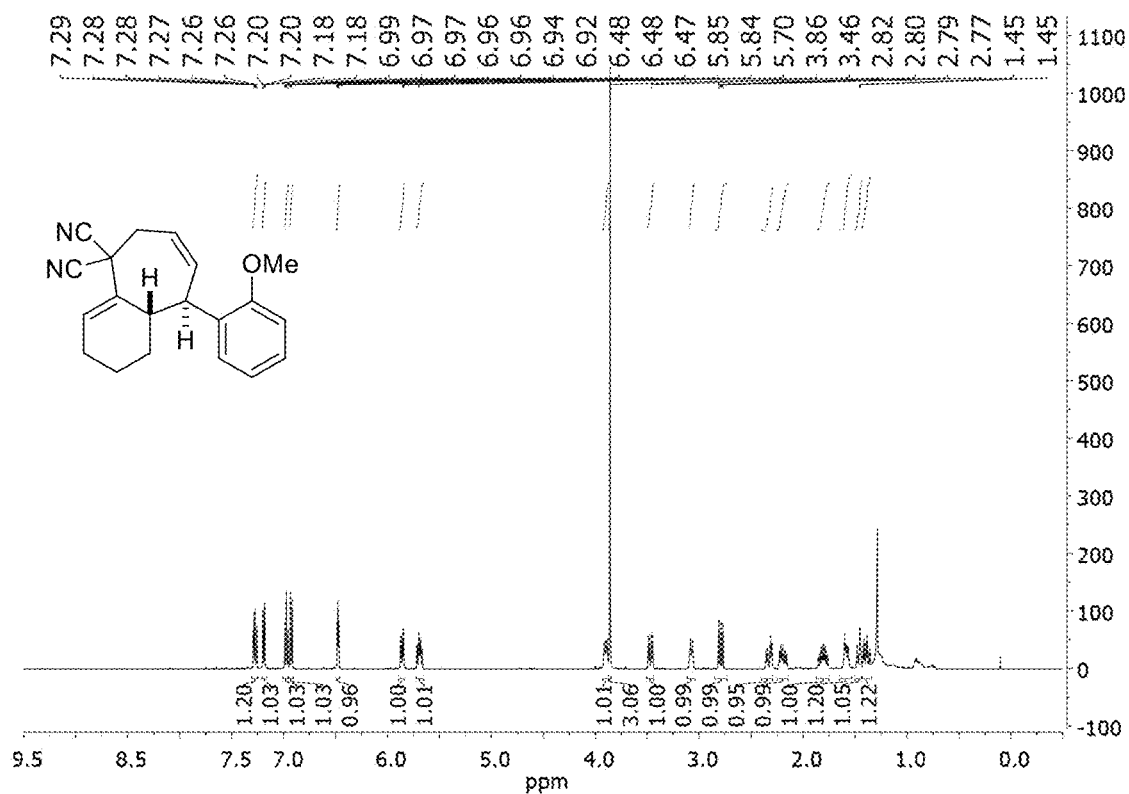
FIG. 32A shows a $^1$H NMR spectrum of 9-(2-methoxyphenyl)-1,2,3,6,9,9a-hexahydro-5H-benzo[7]annulene-5,5-dicarbonitrile (compound 6h).
Figure 32B:
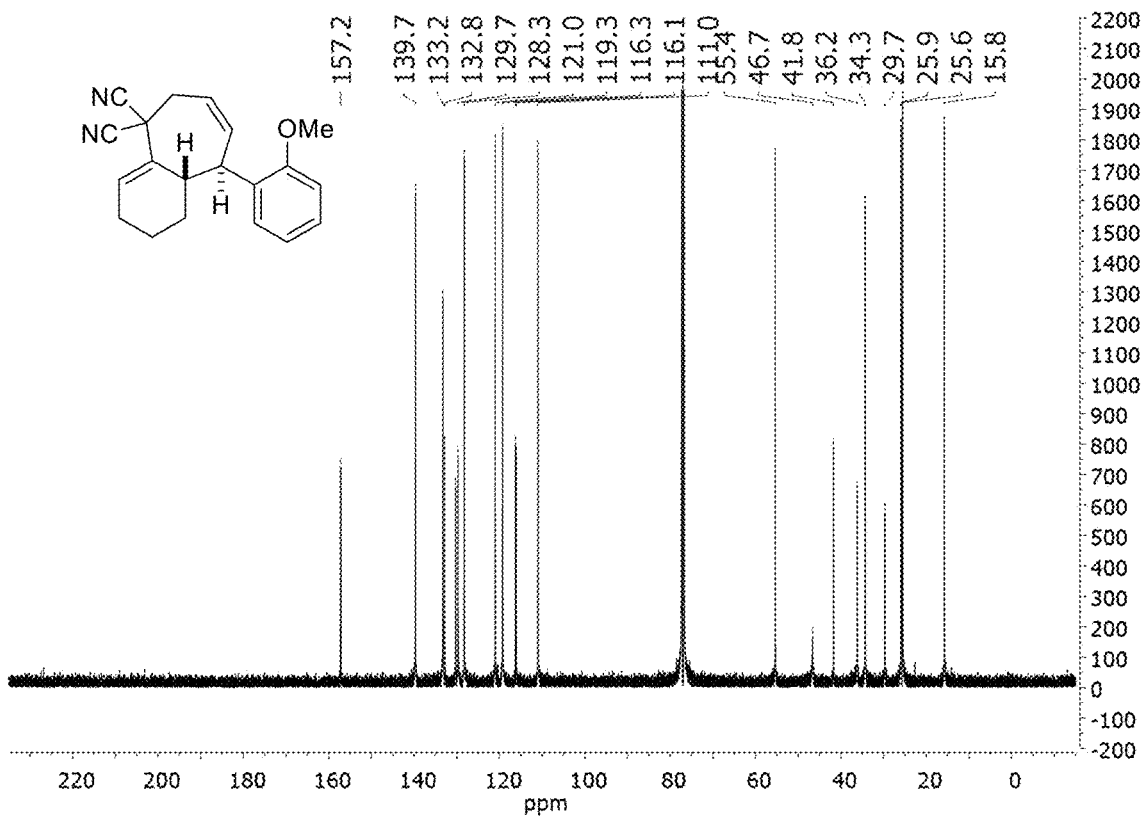
FIG. 32B shows a $^{13}$C NMR spectrum of compound 6h.

Prepared from 5h by general procedure B using a reaction time of 2 hours. Isolated: 53 mg. Yield: 78% (>20:1 dr). Physical state: colorless oil. TLC: $R_f$=0.75 (20% EtOAc in hexanes); Purified using 5% EtOAc in hexane. $^1$H NMR (500 MHz, CDCl$_3$) major diastereomer δ 7.31-7.25 (m, 1H), 7.19 (dd, J=7.5, 1.5 Hz, 1H), 7.01-6.95 (m, 1H), 6.93 (d, J=8.2 Hz, 1H), 6.48 (t, J=3.7 Hz, 1H), 5.86 (dd, J=11.1, 4.9 Hz, 1H), 5.73-5.65 (m, 1H), 3.90 (dd, J=10.6, 4.5 Hz, 1H), 3.86 (s, 3H), 3.47 (dd, J=14.7, 6.1 Hz, 1H), 3.12-3.04 (m, 1H), 2.79 (dd, J=14.7, 7.4 Hz, 1H), 2.33 (dt, J=19.2, 5.3 Hz, 1H), 2.26-2.14 (m, 1H), 1.87-1.75 (m, 1H), 1.65-1.53 (m, 1H), 1.47 (dd, J=13.5, 2.4 Hz, 1H), 1.42-1.35 (m, 1H). $^{13}$C NMR (126 MHz, CDCl$_3$): δ 157.2, 139.7, 133.2, 132.8, 130.2, 129.7, 128.3, 121.0, 119.3, 116.3, 116.1, 111.0, 55.4, 46.7, 41.8, 36.2, 34.3, 29.7, 25.9, 25.6, 15.8. HRMS (DART/ESI) m/z: [M+Na]$^+$ Calcd for C$_{20}$H$_{20}$N$_2$ONa 327.1468; Found 327.1479. Representative NMR spectra can be seen in FIGS. 32A-32B.

Example 7.9: 9-(3-methoxyphenyl)-1,2,3,6,9,9a-hexahydro-5H-benzo[7]annulene-5,5-dicarbonitrile (6i)

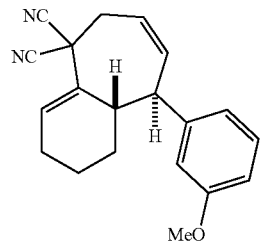

Figure 33A:
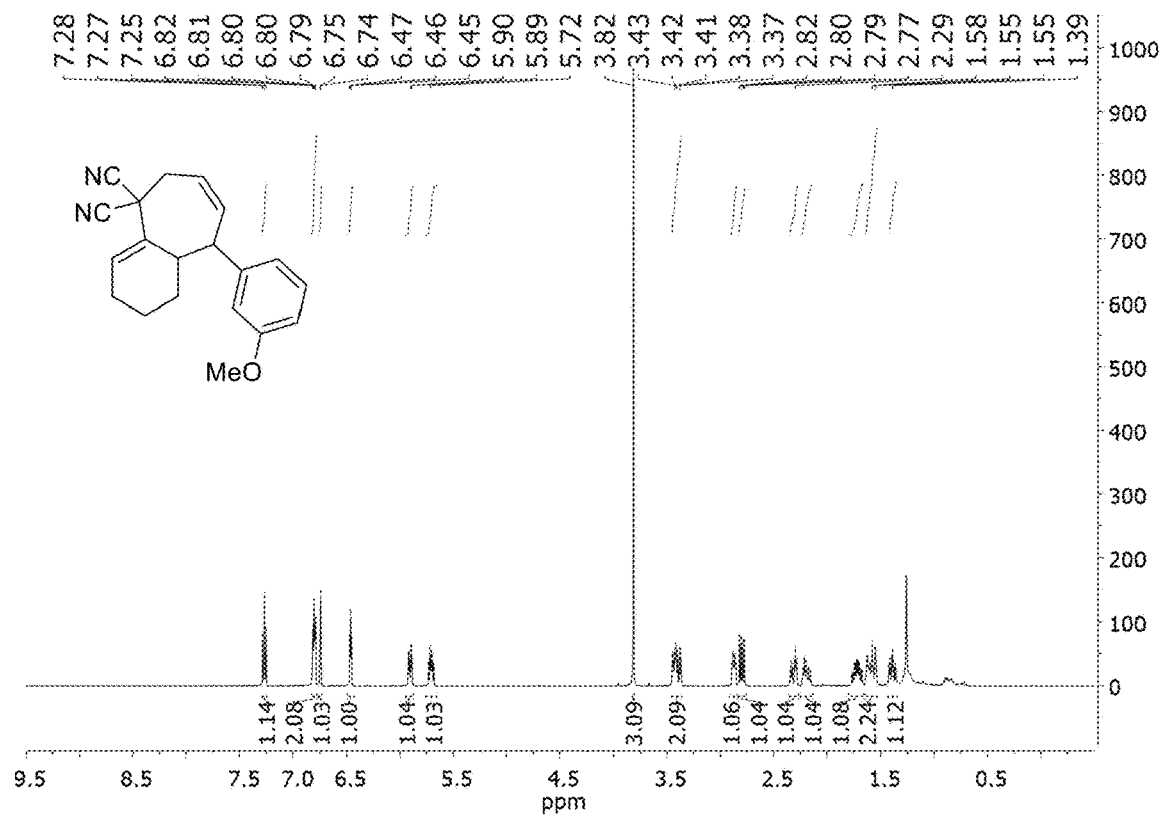
FIG. 33A shows a $^1$H NMR spectrum of 9-(3-methoxyphenyl)-1,2,3,6,9,9a-hexahydro-5H-benzo[7]annulene-5,5-dicarbonitrile (compound 6i).
Figure 33B:
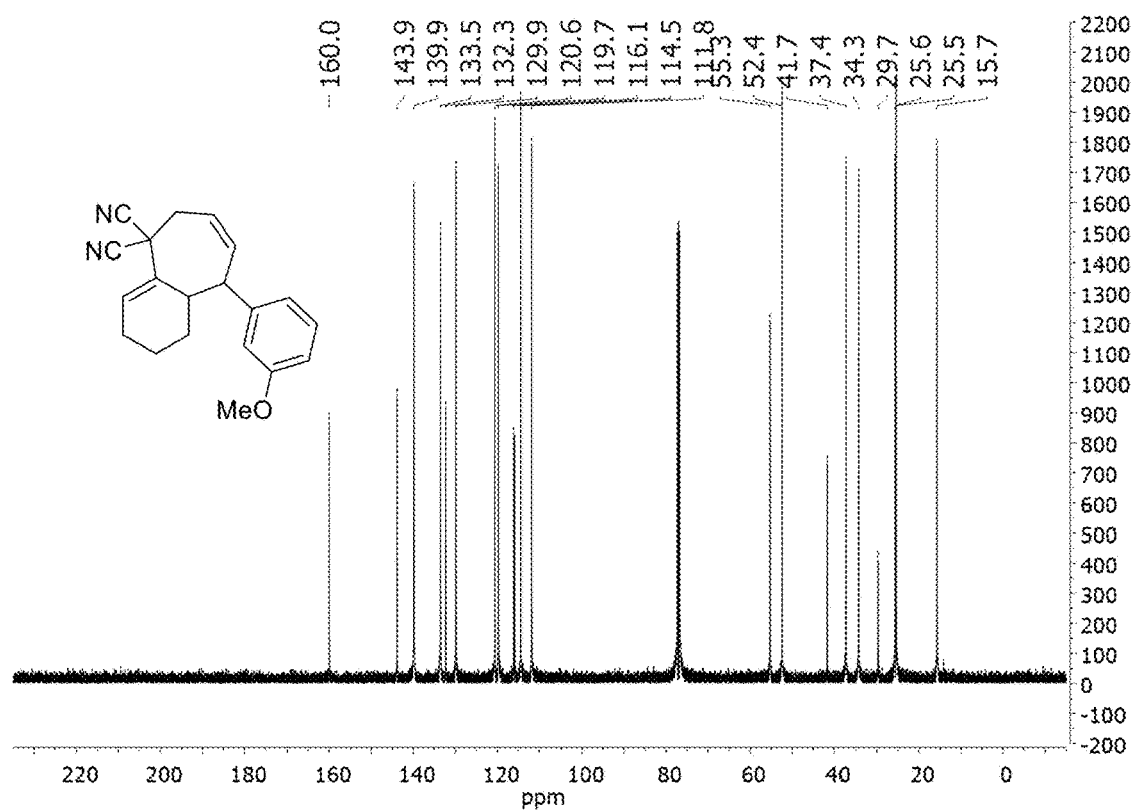
FIG. 33B shows a $^{13}$C NMR spectrum of compound 6i.

Prepared from 5i by general procedure B using a reaction time of 3 hours. Isolated: 38 mg. Yield: 74% (>20:1 dr). Physical state: colorless oil. TLC: $R_f$=0.50 (% EtOAc in hexanes); Purified using 5% EtOAc in hexane. $^1$H NMR (500 MHz, CDCl$_3$) major diastereomer: δ 7.27 (t, J=7.9 Hz, 1H), 6.84-6.78 (m, 2H), 6.75-6.74 (m, 1H), 6.46 (t, J=3.7 Hz, 1H), 5.91 (dd, J=11.2, 4.0 Hz, 1H), 5.74-5.67 (m, 1H), 3.82 (s, 3H), 3.41 (ddd, J=21.1, 12.9, 5.3 Hz, 2H), 2.87 (dd, J=8.6, 2.1 Hz, 1H), 2.80 (dd, J=14.9, 7.5 Hz, 1H), 2.31 (dt, J=19.0, 5.1 Hz, 1H), 2.25-2.14 (m, 1H), 1.78-1.67 (m, 1H), 1.65-1.53 (m, 2H), 1.43-1.35 (m, 1H). $^{13}$C NMR (126 MHz, CDCl$_3$): δ 160.0, 143.9, 139.9, 133.5, 132.3, 129.9, 120.6, 119.7, 116.1, 115.9, 114.5, 111.8, 55.3, 52.4, 41.7, 37.4, 34.3, 25.6, 25.5, 15.7. HRMS (DART) m/z: [M+H]$^+$ Calcd for C$_{20}$H$_{21}$N$_2$O 305.1648; Found 305.1639. Representative NMR spectra can be seen in FIGS. 33A-33B.

Example 7.10: 9-(3,4-dimethoxyphenyl)-1,2,3,6,9,9a-hexahydro-5H-benzo[7]annulene-5,5-dicarbonitrile (6j)

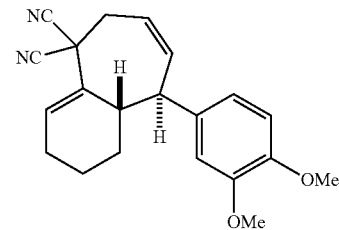

Figure 34A:
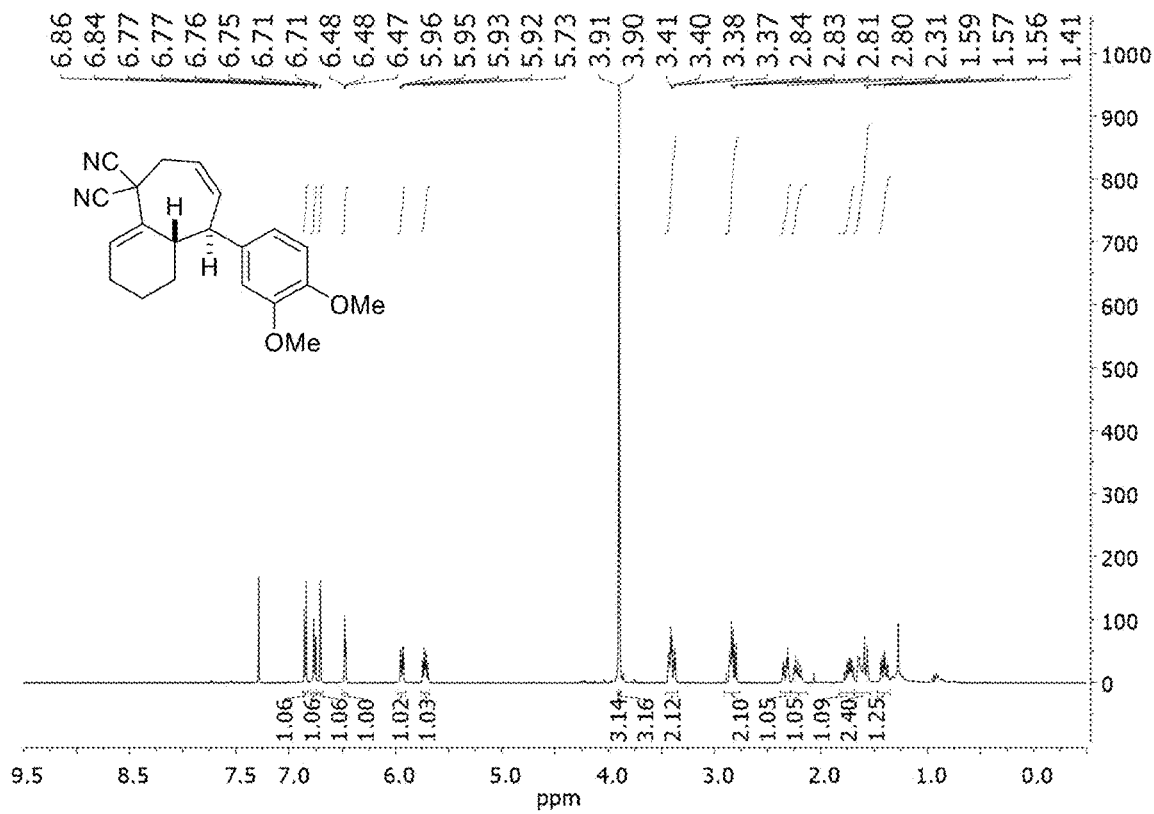
FIG. 34A shows a $^1$H NMR spectrum of 9-(3,4-dimethoxyphenyl)-1,2,3,6,9,9a-hexahydro-5H-benzo[7]annulene-5,5-dicarbonitrile (compound 6j).
Figure 34B:
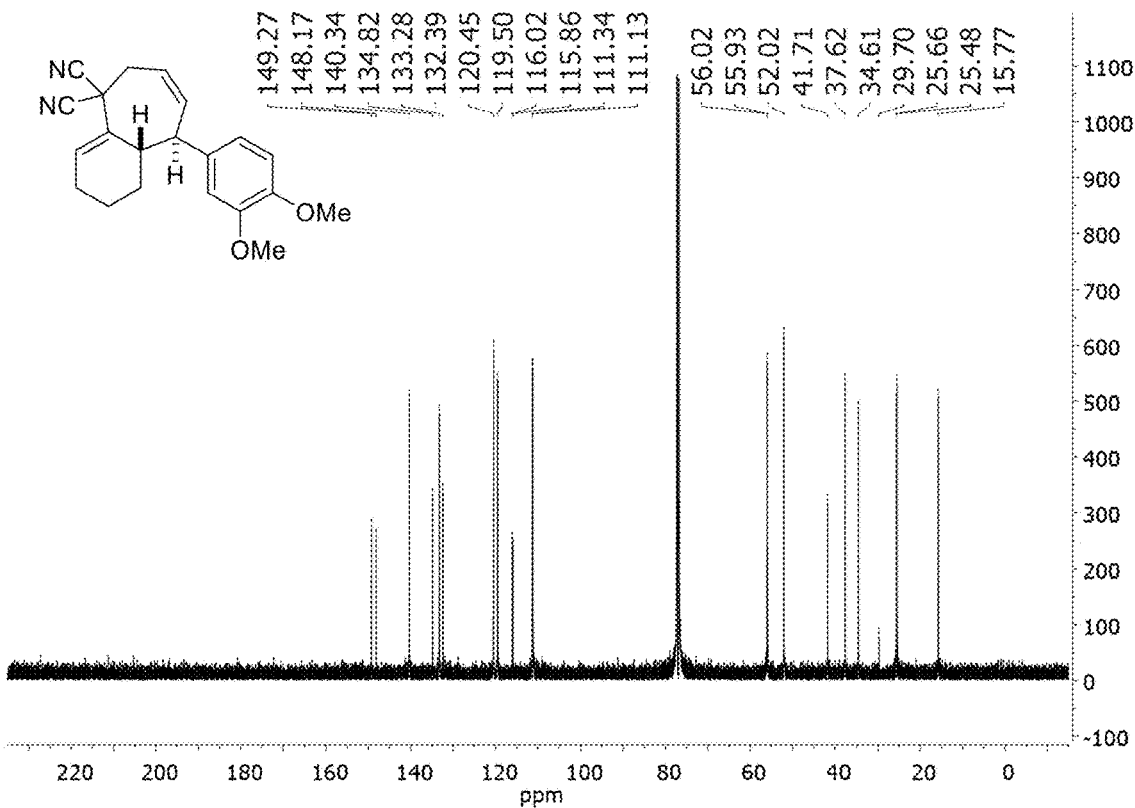
FIG. 34B shows a $^{13}$C NMR spectrum of compound 6j.

Prepared from 5j by general procedure B using a reaction time of 3 hours. Isolated: 26 mg. Yield: 60% (>20:1 dr). Physical state: colorless oil. TLC: $R_f$=0.20 (20% EtOAc in hexanes); Purified using 10% EtOAc in hexane. $^1$H NMR (500 MHz, CDCl$_3$) major diastereomer δ 6.85 (d, J=8.2 Hz, 1H), 6.76 (dd, J=8.2, 1.9 Hz, 1H), 6.71 (d, J=1.8 Hz, 1H), 6.48 (t, J=3.7 Hz, 1H), 5.94 (dd, J=11.3, 4.0 Hz, 1H), 5.76-5.68 (m, 1H), 3.91 (s, 3H), 3.90 (s, 3H), 3.46-3.35 (m, 2H), 2.91-2.76 (m, 2H), 2.33 (dt, J=19.2, 5.0 Hz, 1H), 2.28-2.13 (m, 1H), 1.82-1.68 (m, 1H), 1.69-1.53 (m, 2H), 1.47-1.35 (m, 1H). $^{13}$C NMR (126 MHz, CDCl$_3$): δ 149.3, 148.2, 140.3, 134.8, 133.3, 132.4, 120.5, 119.5, 116.0, 115.9, 111.3, 111.1, 56.0, 55.9, 52.0, 41.7, 37.6, 34.6, 29.7, 25.7, 25.5, 15.8. HRMS (ESI) m/z: [M+Na]$^+$ Calcd for C$_{21}$H$_{22}$N$_2$O$_2$Na 357.1573; Found 357.1575. Representative NMR spectra can be seen in FIGS. 34A-34B.

Example 7.11: 9-(4-chlorophenyl)-1,2,3,6,9,9a-hexahydro-5H-benzo[7]annulene-5,5-dicarbonitrile (6k)

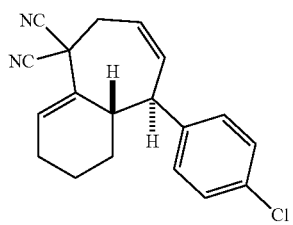

Figure 35A:
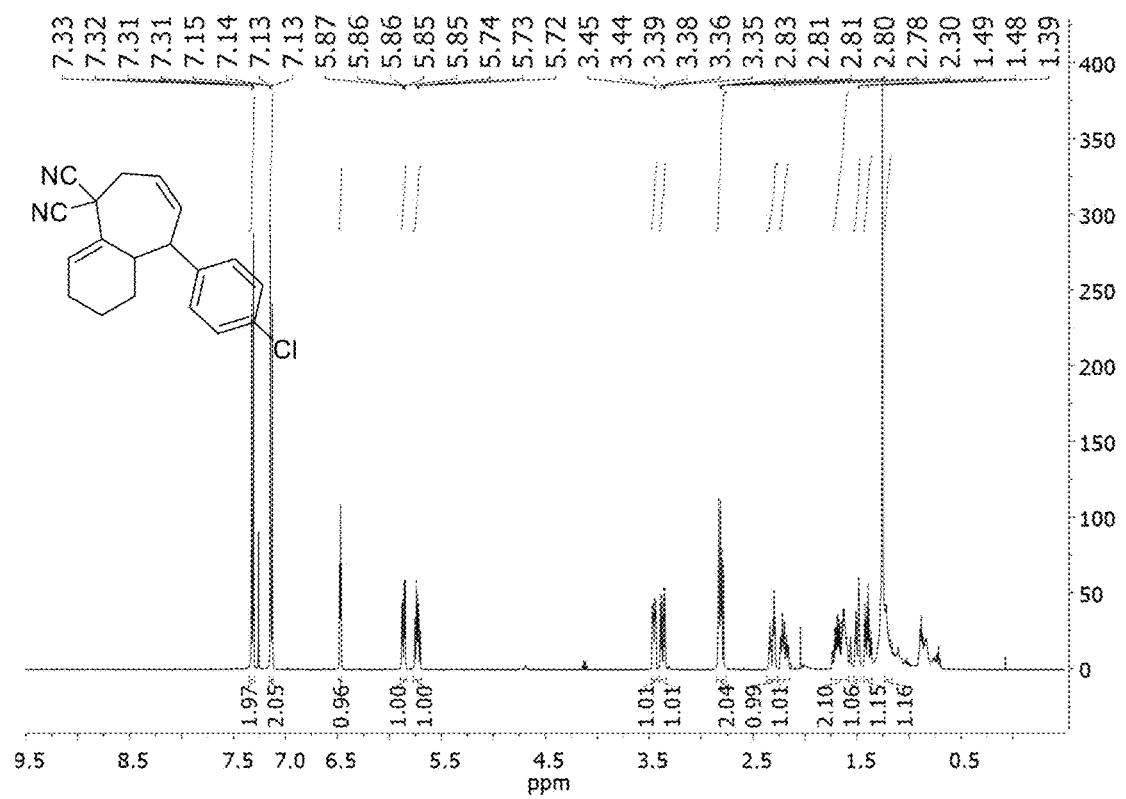
FIG. 35A shows a $^1$H NMR spectrum of 9-(4-chlorophenyl)-1,2,3,6,9,9a-hexahydro-5H-benzo[7]annulene-5,5-dicarbonitrile (compound 6k).
Figure 35B:
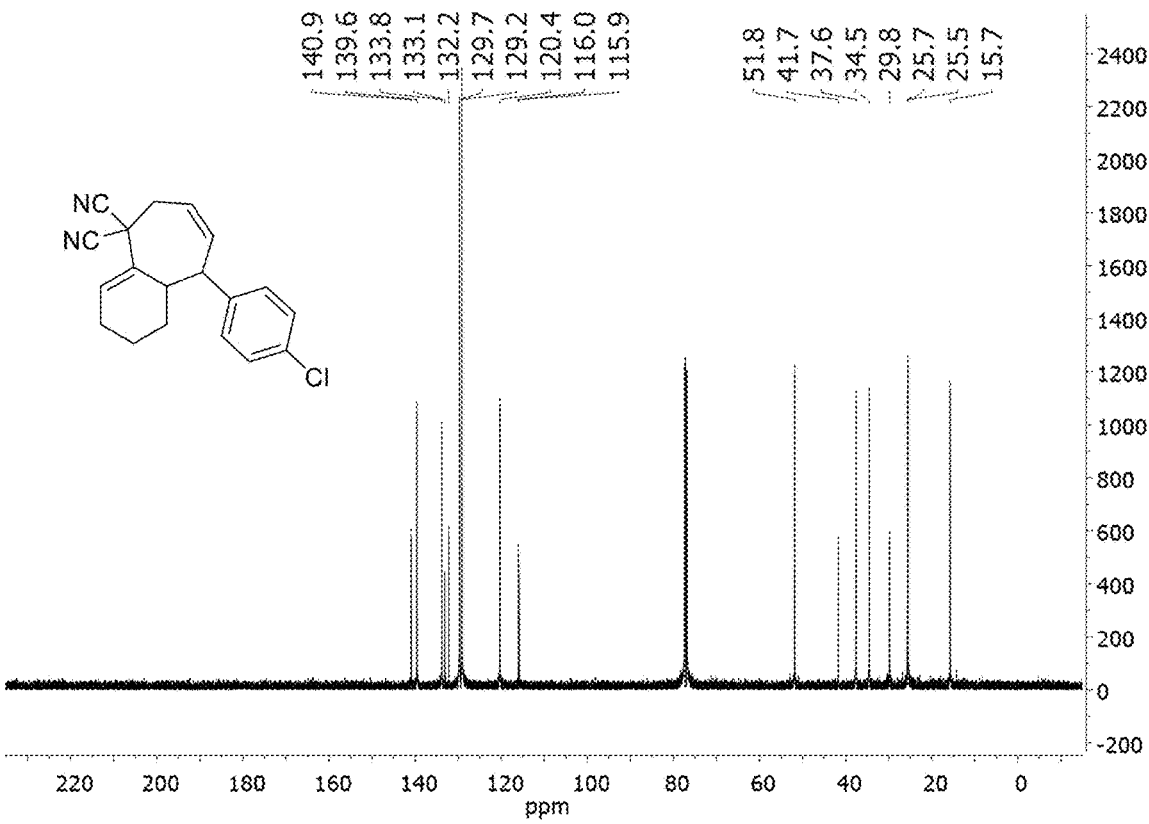
FIG. 35B shows a $^{13}$C NMR spectrum of compound 6k.

Prepared from 5k by general procedure B using a reaction time of 3 hours. Isolated: 28 mg. Yield: 75% (>20:1 dr). Physical state: oil. TLC: $R_f$=0.56 (% EtOAc in hexanes); Purified using 5% EtOAc in hexane. $^1$H NMR (500 MHz, CDCl$_3$) major diastereomer: δ 7.34-7.30 (m, 2H), 7.16-7.12 (m, 2H), 5.86 (ddd, J=11.3, 4.7, 1.1 Hz, 1H), 5.76-5.70 (m, 1H), 3.45 (dd, J=10.8, 4.7 Hz, 1H), 3.40-3.34 (m, 1H), 2.85-2.78 (m, 2H), 2.32 (dt, J=19.1, 4.7 Hz, 1H), 2.25-2.15 (m, 1H), 1.75-1.58 (m, 2H), 1.53-1.47 (m, 1H), 1.39 (tt, J=13.5, 4.0 Hz, 1H), 1.24-1.17 (m, 1H). $^{13}$C NMR (126 MHz, CDCl$_3$): δ 140.9, 139.6, 133.8, 133.1, 132.2, 129.7, 129.2, 120.4, 116.1, 115.9, 51.8, 41.7, 37.6, 34.5, 29.8, 25.7, 25.5, 15.8. HRMS (DART) m/z: [M+H]$^+$ Calcd for $C_{11}H_{18}ClN_2$ 309.1153; Found 309.1157. Representative NMR spectra can be seen in FIGS. 35A-35B.

Example 7.12: 4,4-dimethyl-3-oxo-9-phenyl-1,2,3,4,6,9-hexahydro-5H-benzo[7]annulene-5,5-dicarbonitrile (6m)

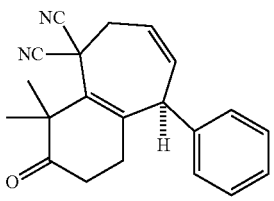 [SMILES: CC1(C)C(=O)CCC2=C1C(C#N)(C#N)CC=C[C@H]2c1ccccc1]

Figure 36A:
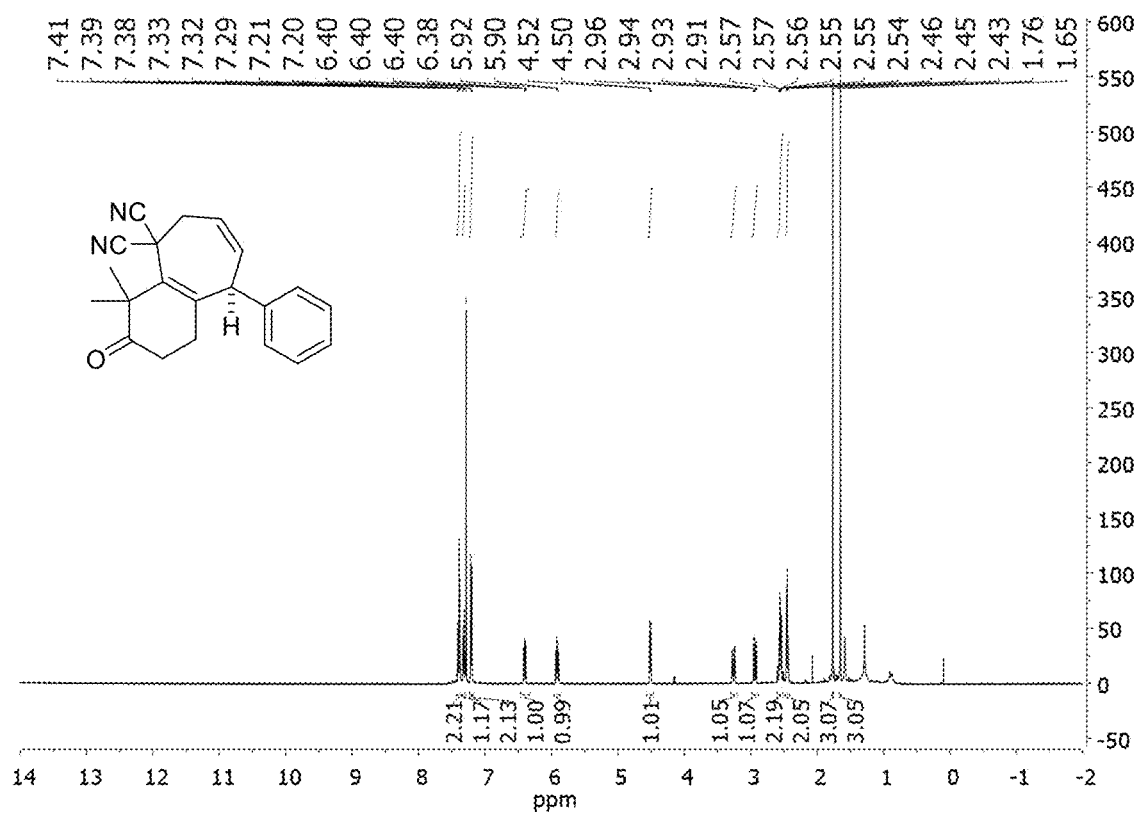
FIG. 36A shows a $^1$H NMR spectrum of 4,4-dimethyl-3-oxo-9-phenyl-1,2,3,4,6,9-hexahydro-5H-benzo[7]annulene-5,5-dicarbonitrile (compound 6m).
Figure 36B:
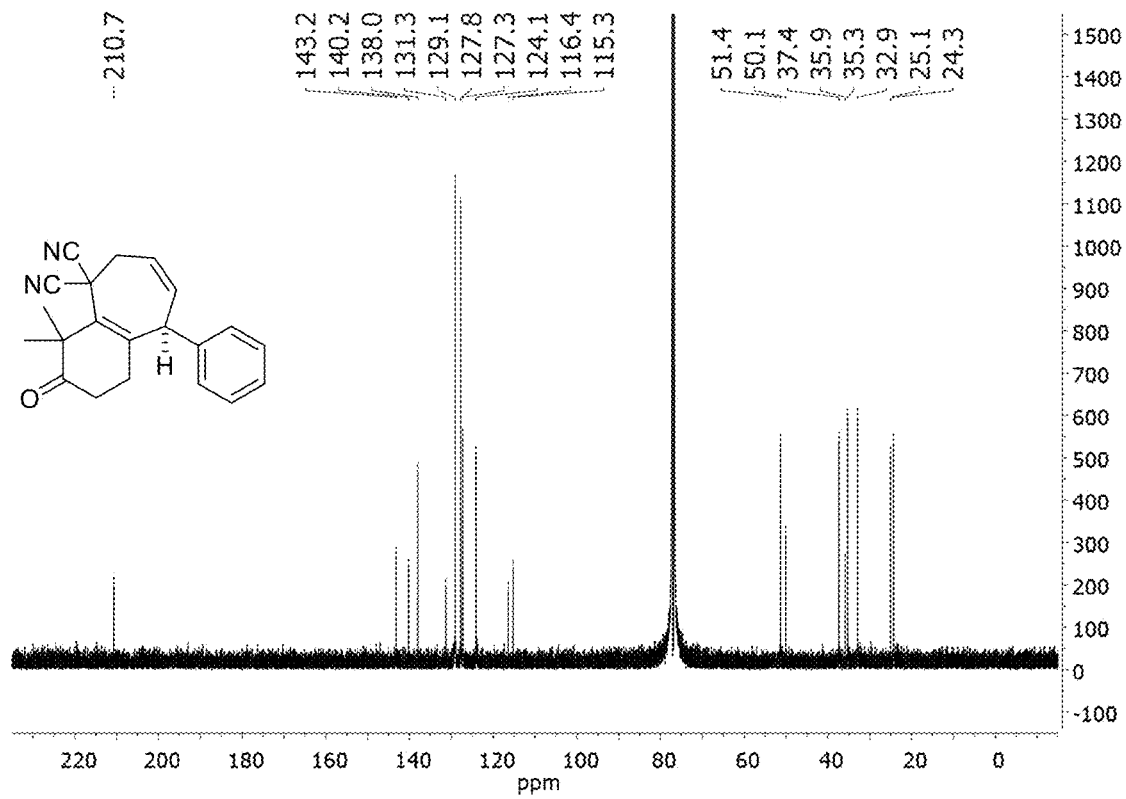
FIG. 36B shows a $^{13}$C NMR spectrum of compound 6m.

Prepared from 3c by general procedure B using a reaction time of 3 hours. Isolated: 13 mg. Yield: 78% (>20:1 dr). Physical state: yellow oil. TLC: $R_f$=0.33 (20% EtOAc in hexanes); Purified using 10% EtOAc in hexane. $^1$H NMR (500 MHz, CDCl$_3$) major diastereomer: δ 7.39 (t, J=7.5 Hz, 2H), 7.31 (dd, J=13.1, 5.9 Hz, 1H), 7.21 (d, J=7.3 Hz, 2H), 6.40 (ddd, J=9.9, 7.1, 1.7 Hz, 1H), 5.96-5.87 (m, 1H), 4.51 (d, J=7.0 Hz, 1H), 3.26 (dd, J=15.4, 5.8 Hz, 1H), 2.93 (dd, J=15.1, 7.0 Hz, 1H), 2.60-2.51 (m, 2H), 2.45 (t, J=7.0 Hz, 2H), 1.76 (s, 3H), 1.65 (s, 3H). $^{13}$C NMR (126 MHz, CDCl$_3$): δ 210.7, 143.2, 140.2, 138.0, 131.3, 129.1, 127.8, 127.3, 124.1, 116.4, 115.3, 51.4, 50.1, 37.4, 35.9, 35.3, 32.9, 25.1, 24.3. HRMS (DART/ESI) m/z: [M+NH4]$^+$ Calcd for $C_{21}H_{24}N_3O$ 334.1914; Found 334.1909. Representative NMR spectra can be seen in FIGS. 36A-36B.

Example 7.13: 7-methyl-9-phenyl-1,2,3,6,9,9a-hexahydro-5H-benzo[7]annulene-5,5-dicarbonitrile (6n)

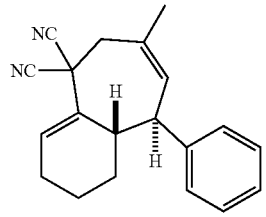

Figure 37A:
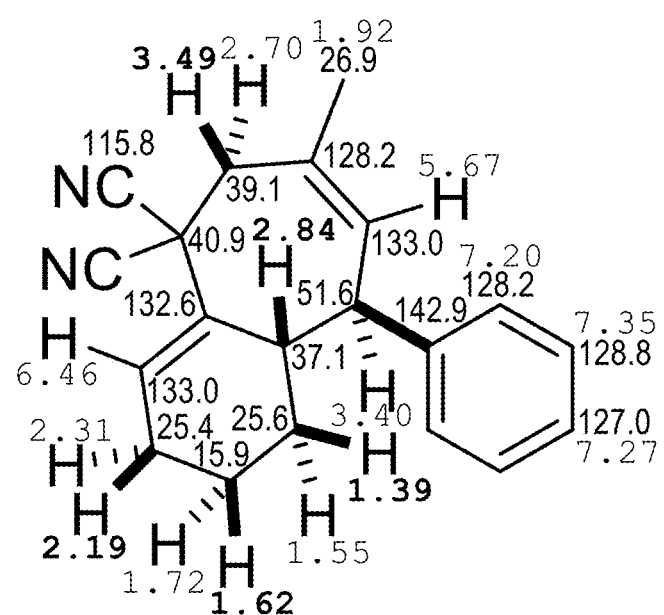
Figure 37B:
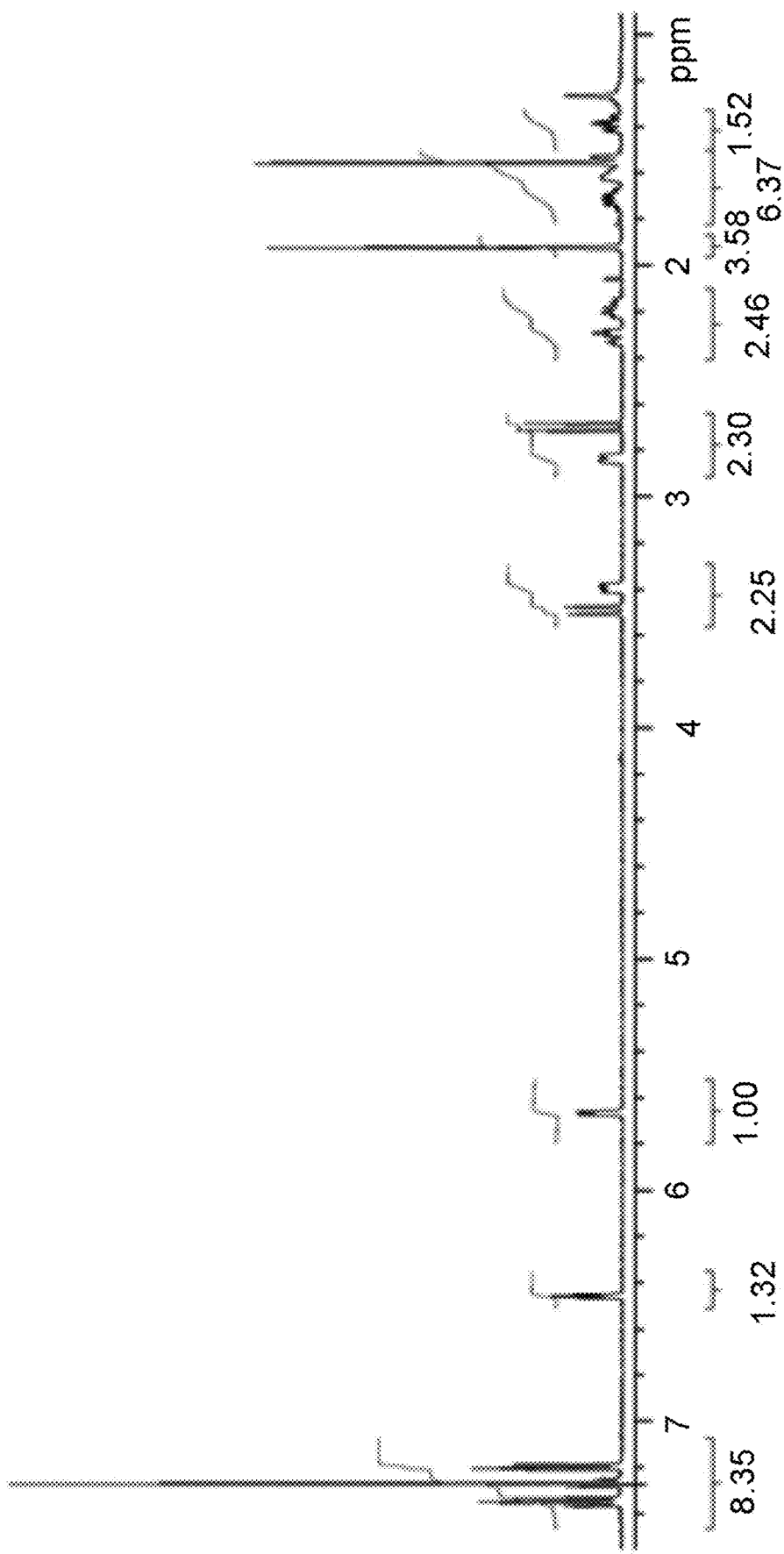
Figure 37D:
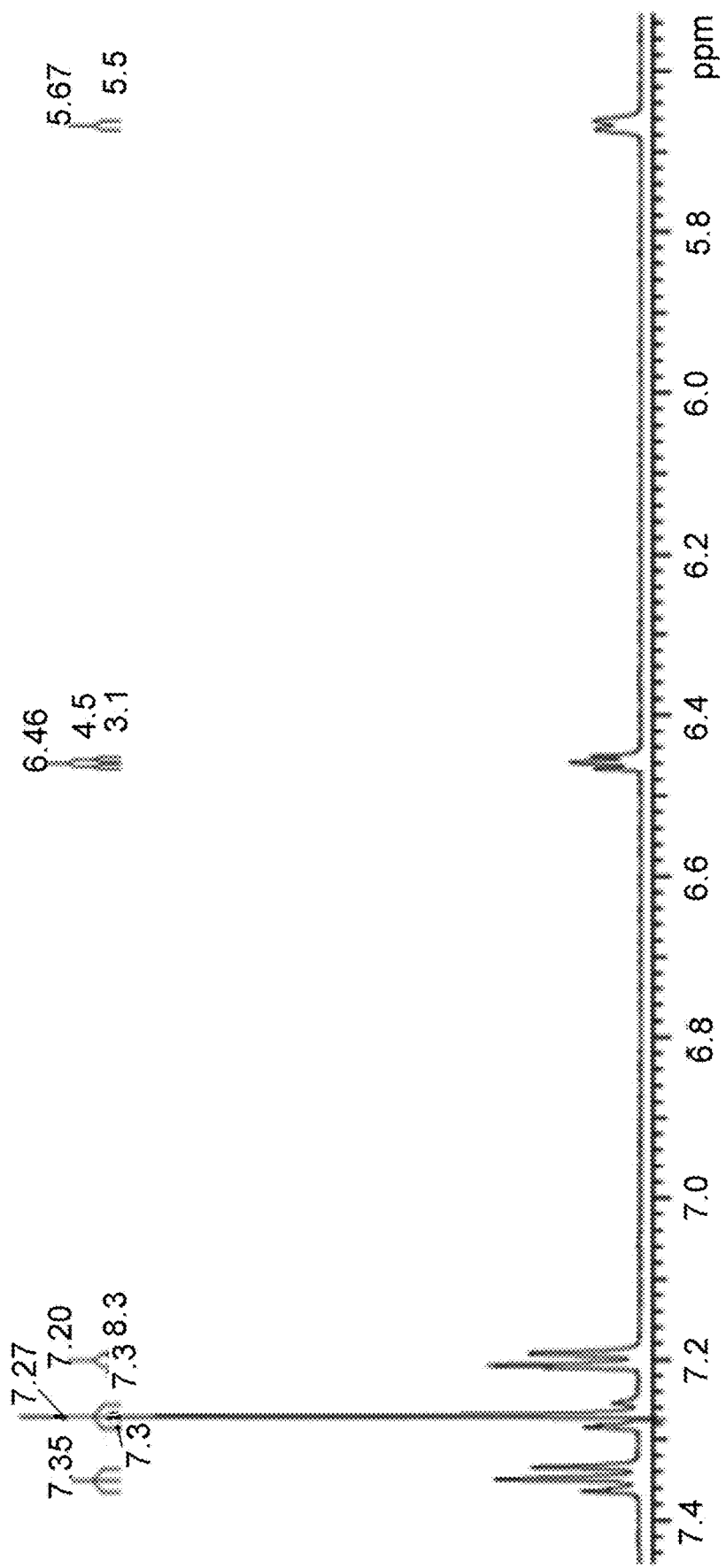
Figure 37E:
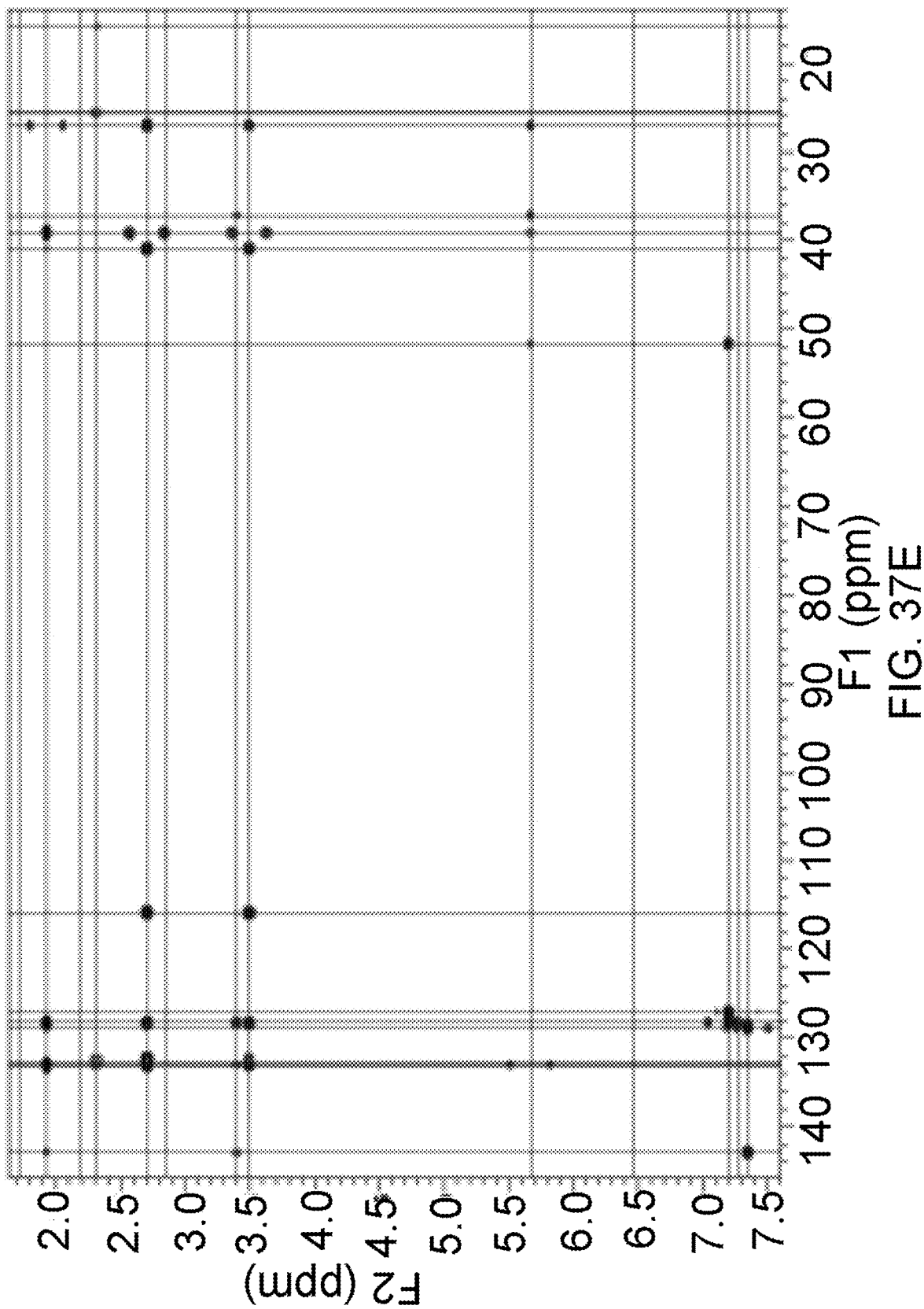
Figure 37F:
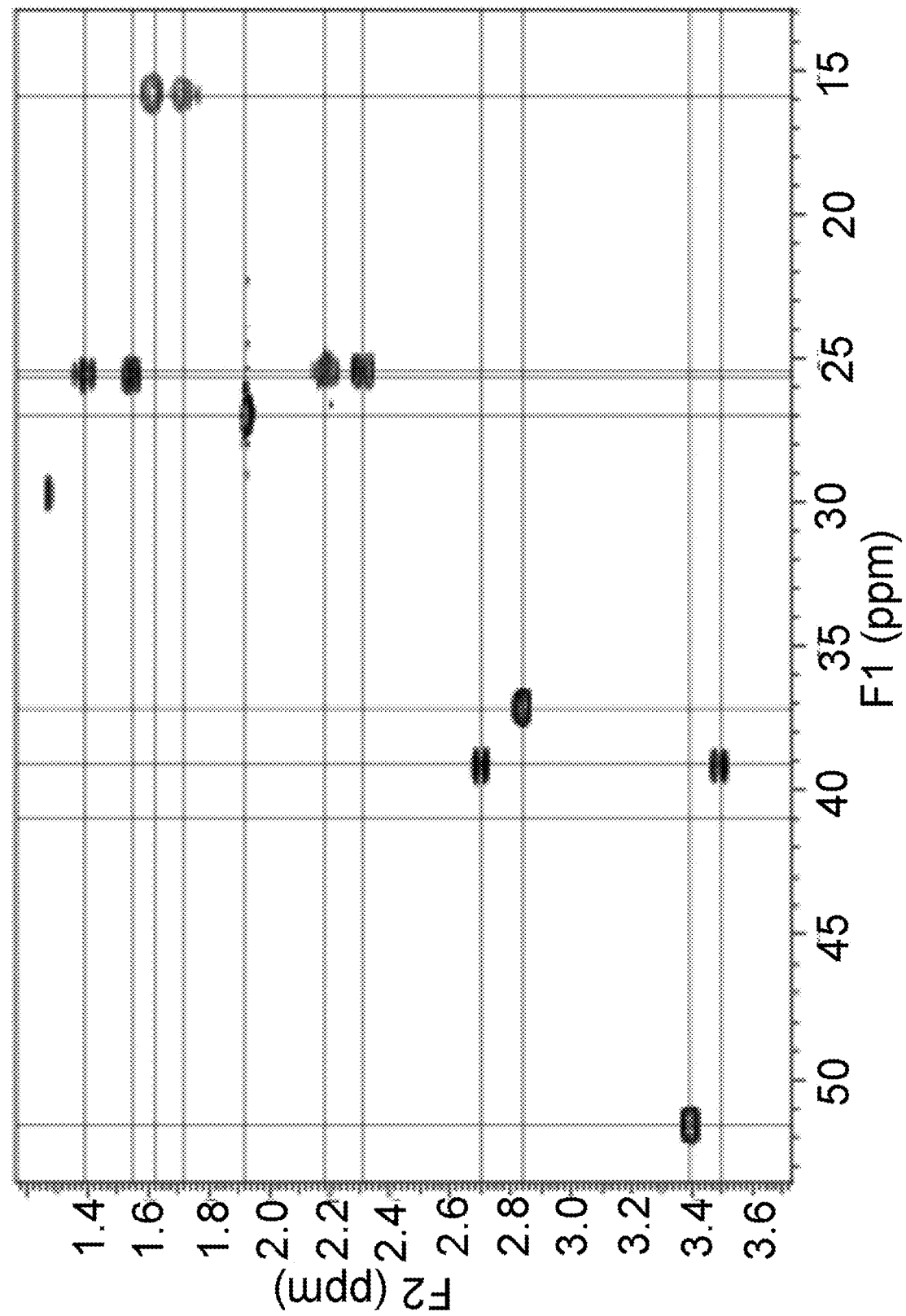
Figure 37G:
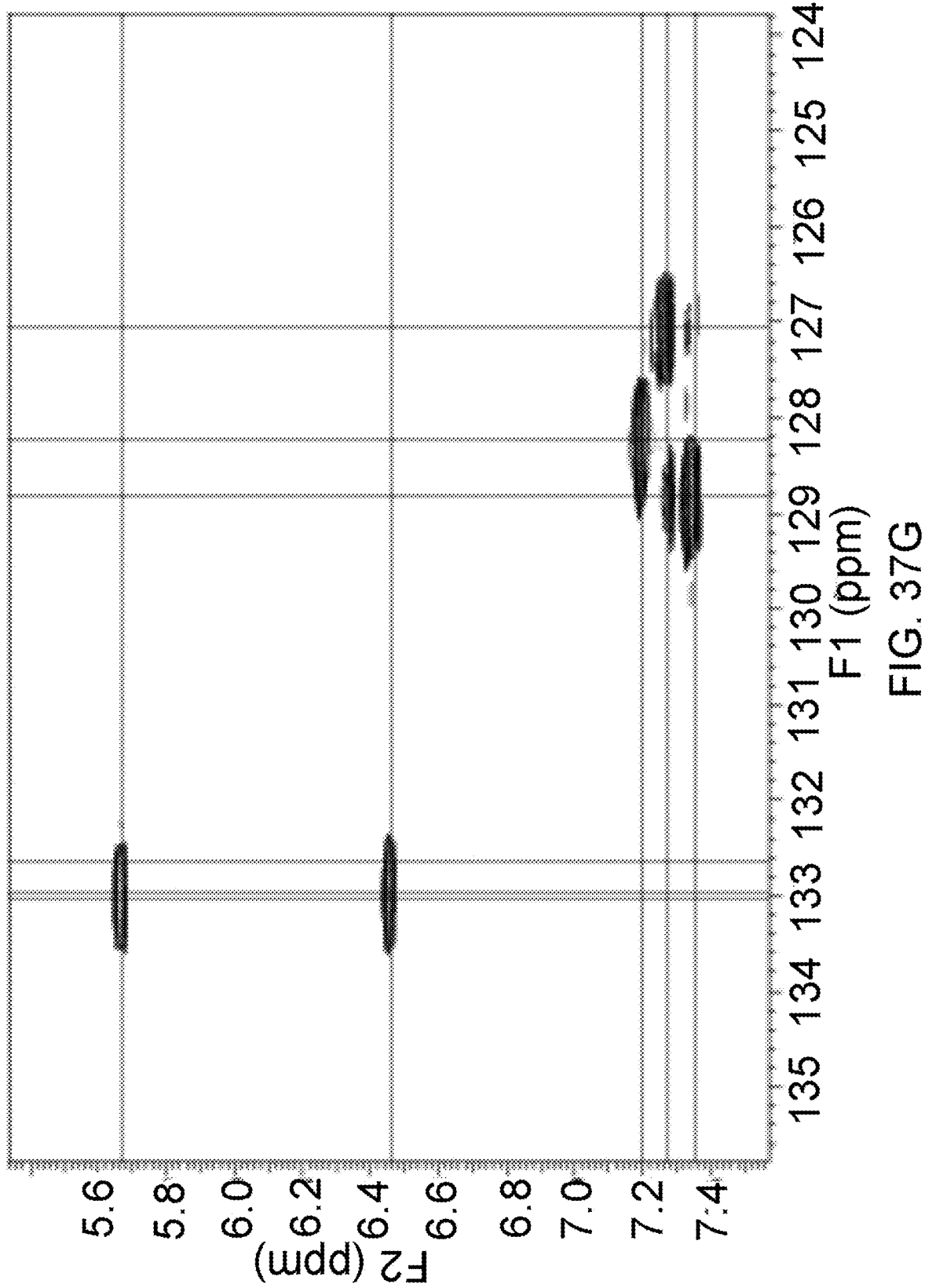
Figure 37H:
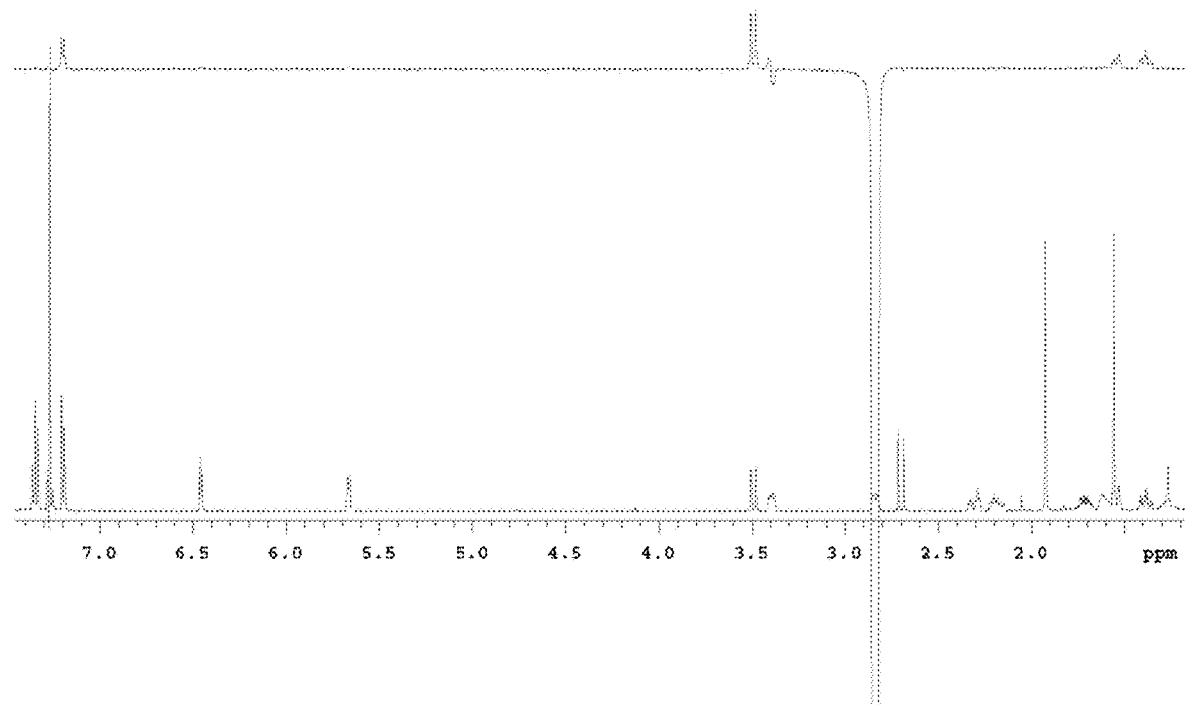
Figure 37I:
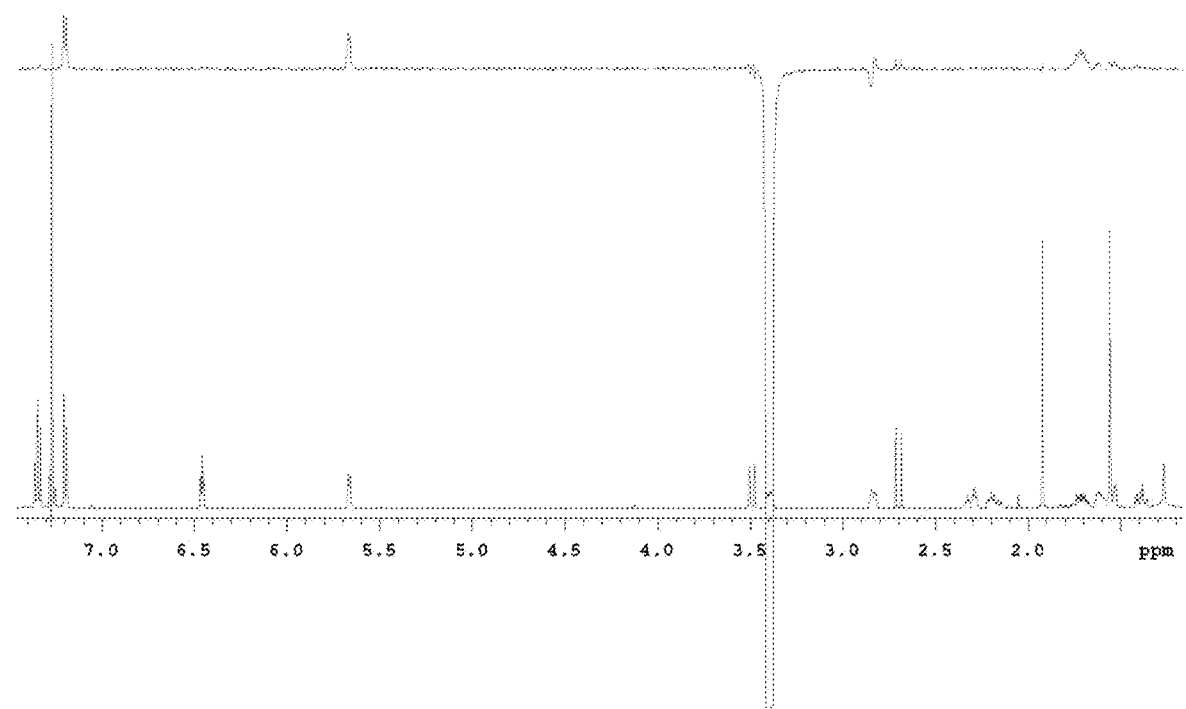

Prepared from 5n by general procedure B by reaction overnight. Isolated: 20 mg. Yield: 54% (>20:1 dr). Physical state: colorless oil. TLC: $R_f$=0.52 (20% EtOAc in hexanes); Purified using 5% EtOAc in hexane. $^1$H NMR (500 MHz, CDCl$_3$) major diastereomer: δ 7.35 (t, J=7.3 Hz, 2H), 7.27 (t, J=7.3 Hz, 1H), 7.20 (d, J=8.3 Hz, 2H), 6.46 (dd, J=4.5, 3.1 Hz, 1H), 5.67 (d, J=5.5 Hz, 1H), 3.49 (d, J=14.6 Hz, 1H), 3.40 (dd, J=10.4, 5.1 Hz, 1H), 2.84 (ddt, J=10.9, 4.5, 2.2 Hz, 1H), 2.70 (d, J=14.8 Hz, 1H), 2.31 (dt, J=19.3, 5.3 Hz, 1H), 2.19 (dtdd, J=18.8, 8.3, 3.1, 2.0 Hz, 1H), 1.92 (s, 3H), 1.72 (qdd, J=12.7, 6.2, 2.8 Hz, 1H), 1.62 (tdd, J=13.7, 4.7, 3.4 Hz, 1H), 1.55 (m, 1H), 1.39 (dq, J=13.4, 3.0 Hz, 1H). $^{13}$C NMR (126 MHz, CDCl$_3$): δ 142.9, 133.0, 133.0, 132.6, 128.8, 128.2, 127.0, 115.8, 51.6, 40.9, 39.1, 37.1, 26.9, 25.6, 25.4, 15.9. HRMS (ESI) m/z: [M+Na]$^+$ Calcd for $C_{22}H_{24}N_2Na$ 339.1832; Found 339.1824. Stereochemistry: Structural assignments were made using additional information from gHMBC, HSQC, and NOESY experiments. Structural assignments based on NMR spectra can be seen in FIG. 37A. Representative 1D and 2D NMR spectra can be seen in FIGS. 37B-37I.

Example 7.14: 9-(2,5-dimethoxyphenyl)-1,2,3,6,9,9a-hexahydro-5H-benzo[7]annulene-5,5-dicarbonitrile (6o)

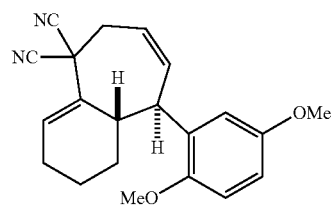

Figure 38A:
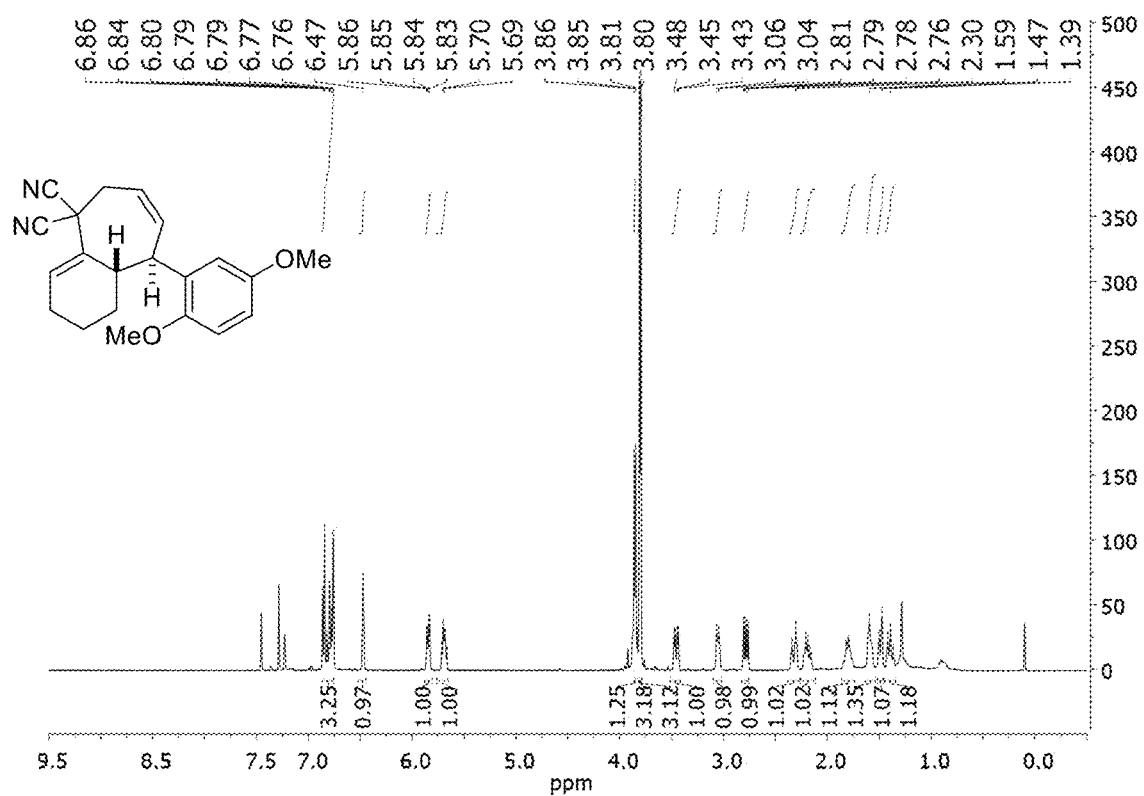
FIG. 38A shows a $^1$H NMR spectrum of 9-(2,5-dimethoxyphenyl)-1,2,3,6,9,9a-hexahydro-5H-benzo[7]annulene-5,5-dicarbonitrile (compound 6o).
Figure 38B:
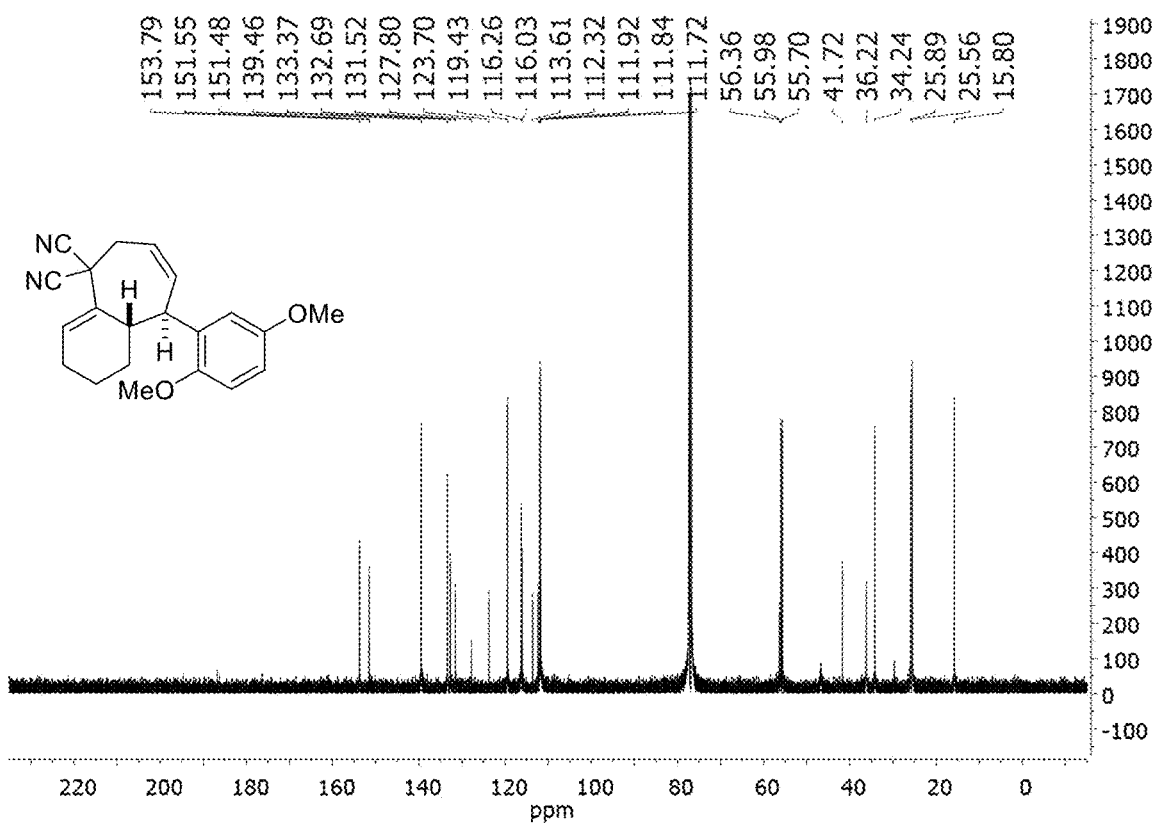
FIG. 38B shows a $^{13}$C NMR spectrum of compound 6o.

Prepared from 5o by general procedure B using a reactor time of 3 hours. Isolated: 45 mg. Yield: 84% (>20:1 dr). Physical state: colorless oil. TLC: $R_f$=0.42 (20% EtOAc in hexanes); Purified using 10% EtOAc in hexane. $^1$H NMR (500 MHz, CDCl$_3$) major diastereomer δ 6.80 (ddd, J=17.4, 16.4, 7.4 Hz, 3H), 6.47 (s, 1H), 5.84 (dd, J=11.0, 4.7 Hz, 1H), 5.76-5.65 (m, 1H), 3.85 (d, J=6.2 Hz, 1H), 3.81 (s, 3H), 3.80 (s, 3H), 3.45 (dd, J=14.7, 6.0 Hz, 1H), 3.05 (d, J=9.9 Hz, 1H), 2.78 (dd, J=14.8, 7.5 Hz, 1H), 2.32 (d, J=19.2 Hz, 1H), 2.18 (dd, J=19.1, 8.9 Hz, 1H), 1.81 (dd, J=10.2, 3.4 Hz, 1H), 1.59 (s, 1H), 1.49 (d, J=13.5 Hz, 1H), 1.39 (t, J=13.7 Hz, 1H). $^{13}$C NMR (126 MHz, CDCl$_3$): δ 153.8, 151.6, 139.5, 133.4, 132.7, 131.5, 127.8, 123.7, 119.4, 116.3, 116.0, 113.6, 112.3, 111.9, 111.8, 56.4, 56.0, 55.7, 41.7, 36.2, 34.2, 25.9, 25.6, 15.8. HRMS (ESI) m/z: [M+NH4]$^+$ Calcd for $C_{21}H_{26}N_3O_2$ 352.2020; Found 352.2016. Representative NMR spectra can be seen in FIGS. 38A-38B.

Example 8: Preparation of Non-Symmetric Chalcone Derivatives (9a-9d)

Example 8.1: (E)-2-allyl-2-(6-(3-(4-methoxyphenyl)-1-(4-nitrophenyl)allyl)cyclohex-1-en-1-yl)malononitrile (9a)

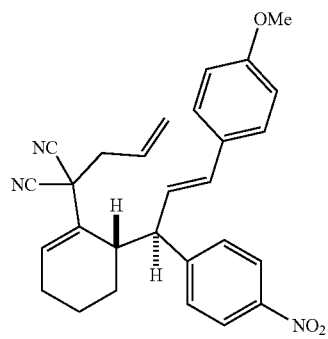 [SMILES: C=CCC(C#N)(C#N)C1=CCCC[C@H]1[C@@H](/C=C/c1ccc(OC)cc1)c1ccc([N+](=O)[O-])cc1]

Figure 39A:
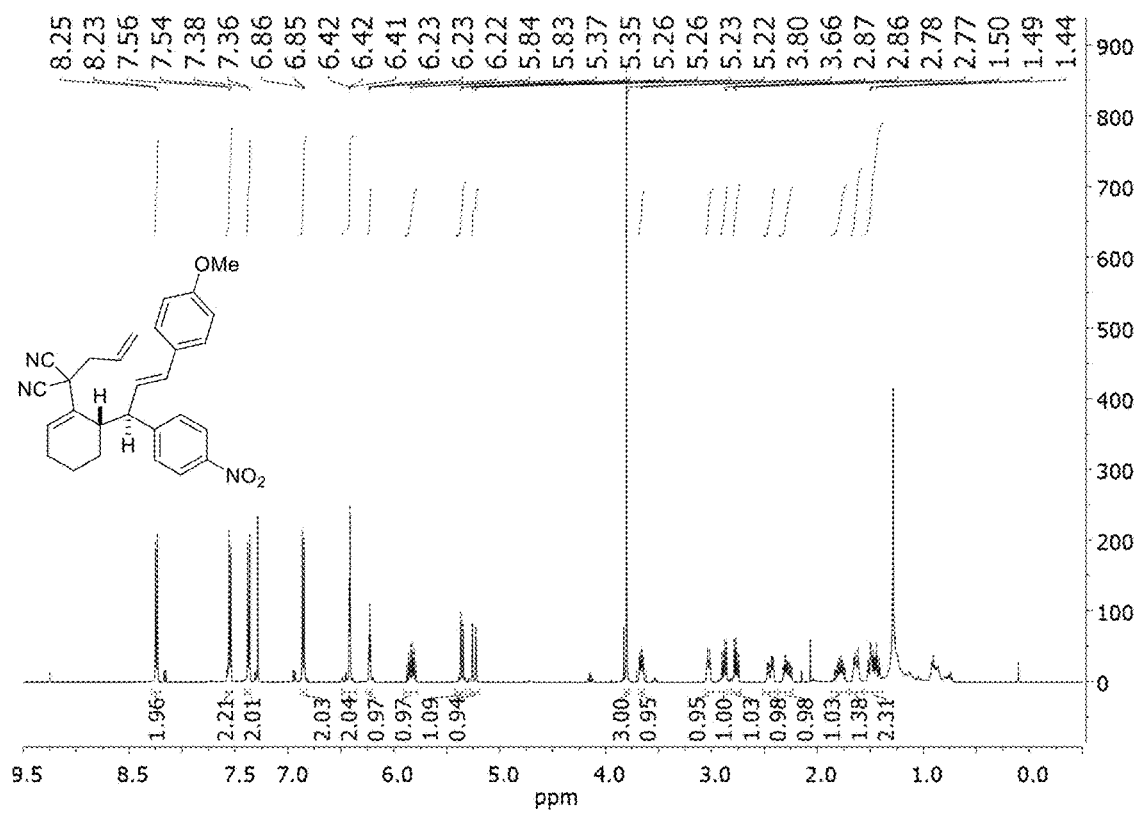
FIG. 39A shows a $^1$H NMR spectrum of (E)-2-allyl-2-(6-(3-(4-methoxyphenyl)-1-(4-nitrophenyl)allyl)cyclohex-1-en-1-yl)malononitrile (compound 9a).
Figure 39B:
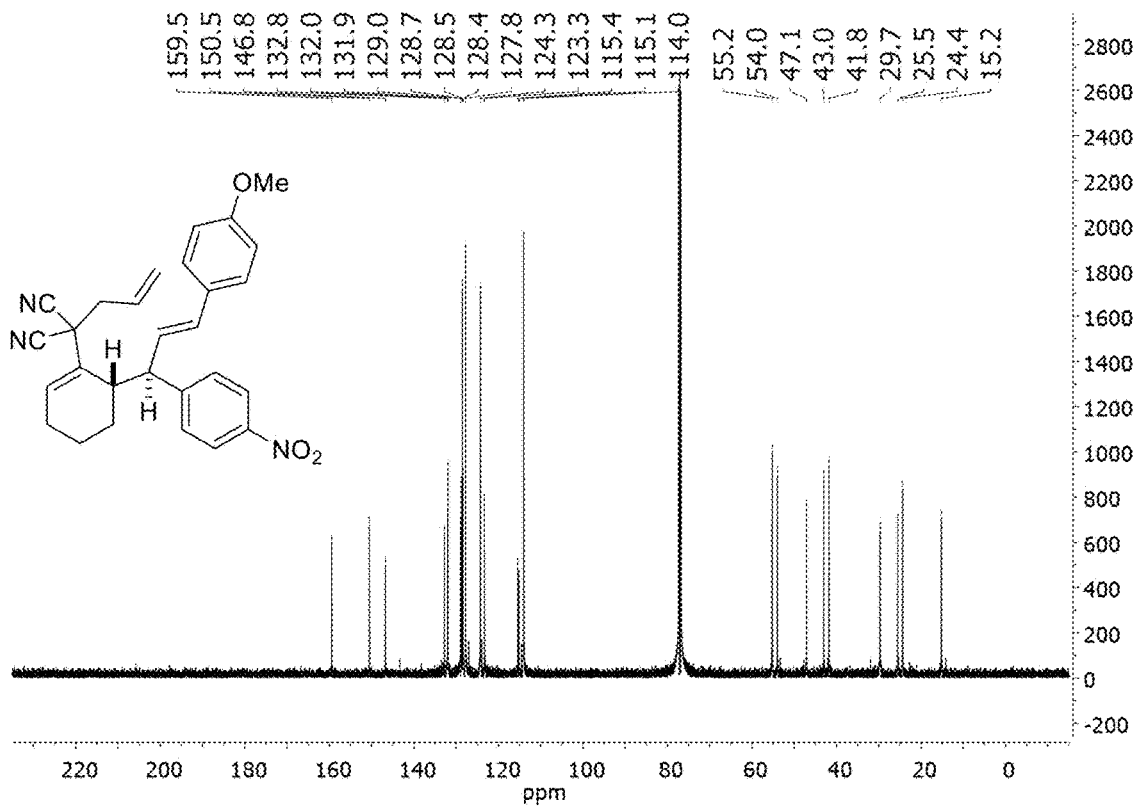

Prepared by general procedure A using a reaction time of 1 hour. Isolated: 71 mg. Yield: 51% (>20:1 dr). Physical state: colorless oil. TLC: $R_f$=0.19 (20% EtOAc in hexanes); Purified using 10% EtOAc in hexane. $^1$H NMR (500 MHz, CDCl$_3$) major diastereomer: δ 8.24 (d, J=8.7 Hz, 2H), 7.55 (d, J=8.7 Hz, 2H), 7.37 (d, J=8.8 Hz, 2H), 6.85 (d, J=8.8 Hz, 2H), 6.49-6.36 (m, 2H), 6.23 (t, J=3.9 Hz, 1H), 5.83 (ddt, J=17.3, 10.1, 7.2 Hz, 1H), 5.36 (d, J=10.1 Hz, 1H), 5.24 (dd, J=16.9, 1.0 Hz, 1H), 3.80 (s, 3H), 3.69-3.64 (m, 1H), 3.03 (d, J=10.0 Hz, 1H), 2.88 (dd, J=13.6, 7.4 Hz, 1H), 2.76 (dd, J=13.6, 7.1 Hz, 1H), 2.44 (ddd, J=19.8, 7.0, 3.3 Hz, 1H), 2.28 (tdd, J=13.2, 8.8, 4.3 Hz, 1H), 1.86-1.73 (m, 1H), 1.70-1.58 (m, 1H), 1.56-1.39 (m, 1H). $^{13}$C NMR (126 MHz, CDCl$_3$): δ 159.5, 150.5, 146.8, 132.8, 132.0, 131.9, 129.0, 128.7, 128.5, 128.4, 127.8, 124.3, 123.3, 115.4, 115.2, 114.0, 55.2, 54.0, 47.1, 43.0, 41.8, 29.7, 25.5, 24.4, 15.2. Representative NMR spectra can be seen in FIGS. 39A-39B.

Example 8.2: (E)-2-allyl-2-(6-(1-(2,6-dichlorophenyl)-3-(4-methoxyphenyl)allyl)cyclohex-1-en-1-yl)malononitrile (9b)

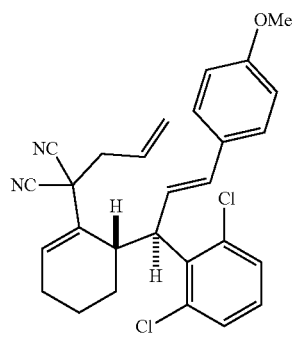 [SMILES: C=CCC(C#N)(C#N)C1=CCCC[C@H]1[C@@H](/C=C/c1ccc(OC)cc1)c1c(Cl)cccc1Cl]

Figure 40A:
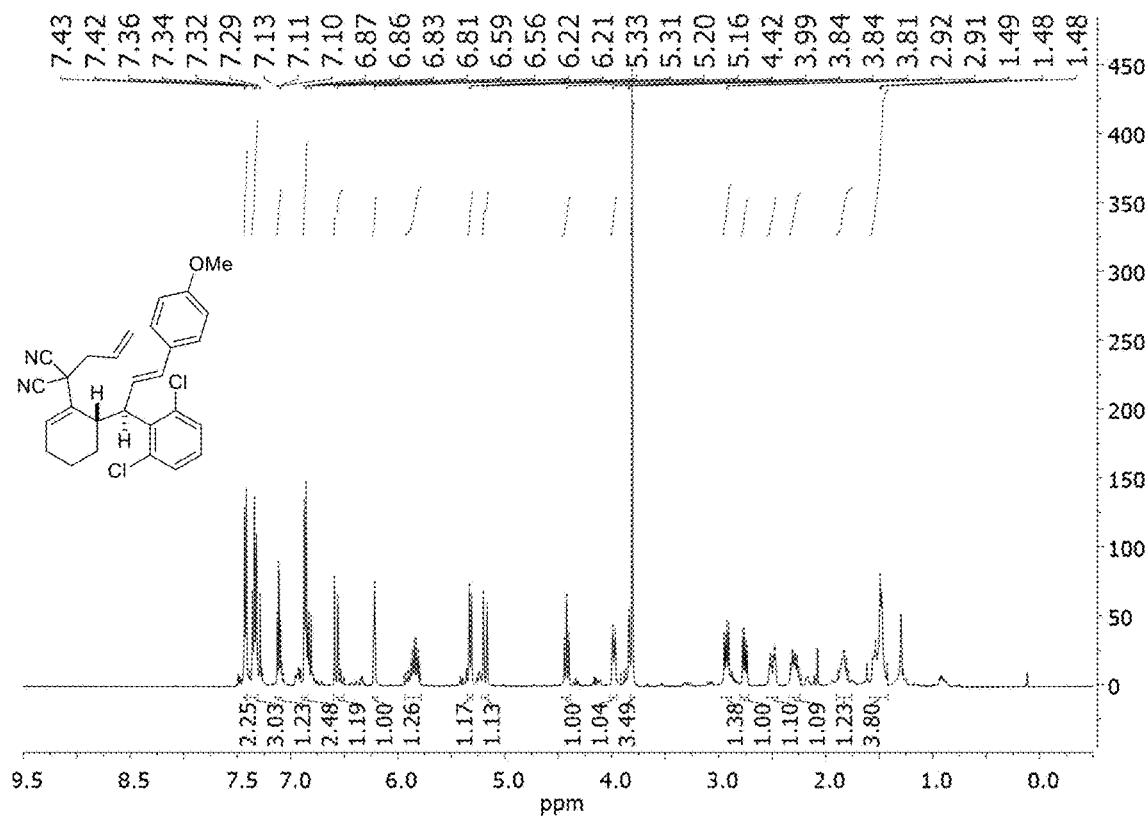
FIG. 40A shows a $^1$H NMR spectrum of (E)-2-allyl-2-(6-(1-(2,6-dichlorophenyl)-3-(4-methoxyphenyl)allyl)cyclohex-1-en-1-yl)malononitrile (compound 9b).
Figure 40B:
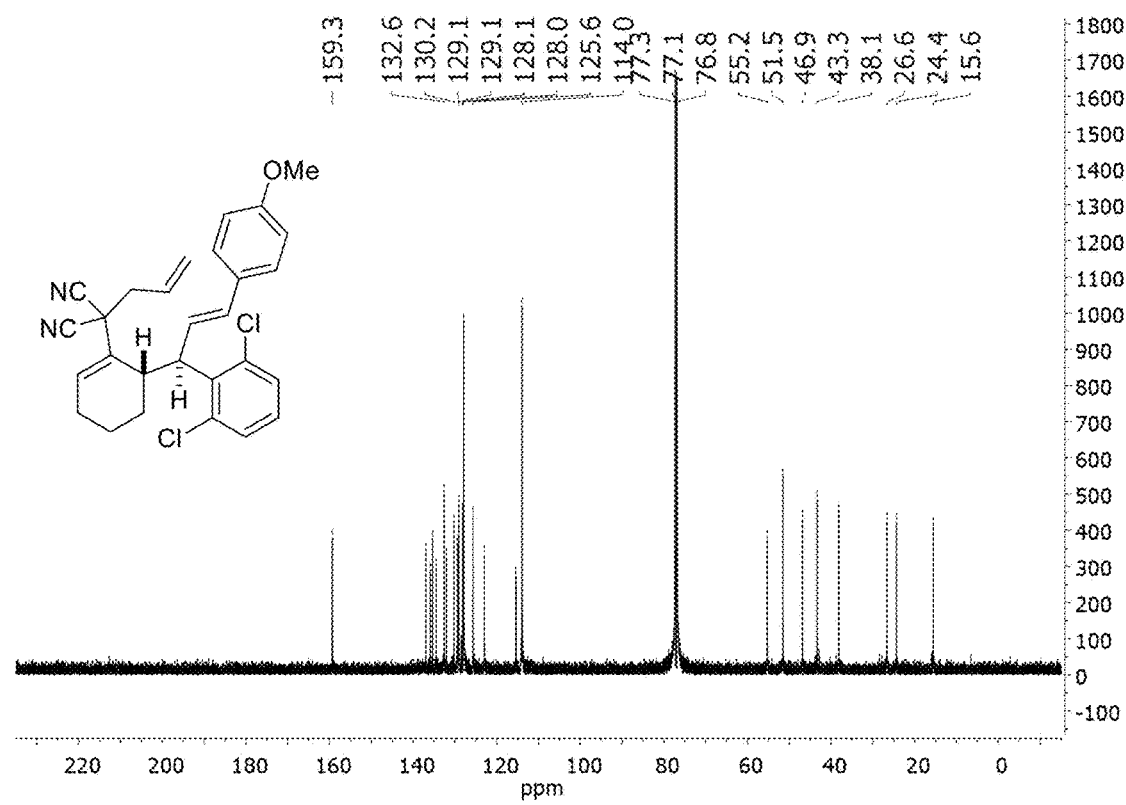
FIG. 40B shows a $^{13}$C NMR spectrum of compound 9b.

Prepared by general procedure A using a reaction time of 2 hours. Isolated: 90 mg. Yield: 66% (>20:1 dr). Physical state: colorless oil. TLC: $R_f$=0.55 (20% EtOAc in hexanes); Purified using 5% EtOAc in hexane. $^1$H NMR (500 MHz, CDCl$_3$) major diastereomer: δ 7.42 (d, J=8.3 Hz, 2H), 7.37-7.30 (m, 3H), 7.11 (t, J=8.0 Hz, 1H), 6.86 (d, J=7.7 Hz, 2H), 6.55 (dd, J=27.6, 15.0 Hz, 1H), 6.21 (d, J=3.4 Hz, 1H), 5.93-5.78 (m, 1H), 5.32 (d, J=10.2 Hz, 1H), 5.18 (d, J=16.9 Hz, 1H), 4.42 (t, J=10.3 Hz, 1H), 3.98 (d, J=10.6 Hz, 1H), 3.81 (s, 3H), 2.92 (dt, J=18.5, 9.2 Hz, 1H), 2.75 (dd, J=13.6, 7.0 Hz, 1H), 2.50 (dd, J=19.4, 5.2 Hz, 1H), 2.29 (ddd, J=18.9, 13.3, 8.6 Hz, 1H), 1.90-1.76 (m, 1H), 1.59-1.42 (m, 3H). $^{13}$C NMR (126 MHz, CDCl$_3$): δ 159.3, 137.0, 135.9, 135.3, 134.5, 132.6, 132.0, 130.2, 129.3, 129.1, 129.1, 128.2, 128.0, 125.7, 123.0, 115.4, 115.3, 114.0, 55.2, 51.5, 46.9, 43.3, 38.1, 26.7, 24.4, 15.6. Representative NMR spectra can be seen in FIGS. 40A-40B.

Example 8.3: (E)-2-allyl-2-(6-(1-(2-bromo-3,6-dimethoxyphenyl)-3-(4-methoxyphenyl)allyl)cyclohex-1-en-1-yl)malononitrile (9c)

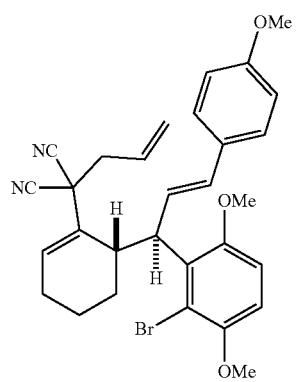 [SMILES: C=CCC(C#N)(C#N)C1=CCCC[C@H]1[C@@H](/C=C/c1ccc(OC)cc1)c1c(OC)ccc(OC)c1Br]

Figure 41A:
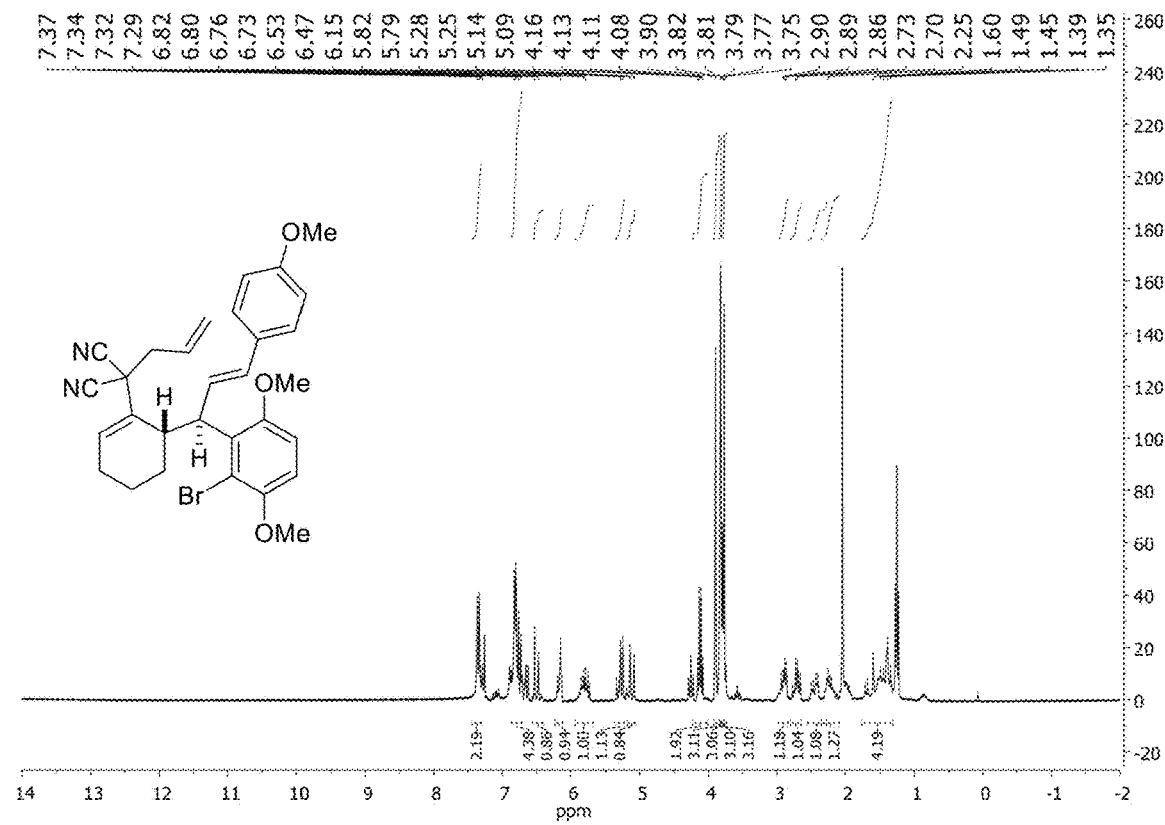
FIG. 41A shows a $^1$H NMR spectrum of (E)-2-allyl-2-(6-(1-(2-bromo-3,6-dimethoxyphenyl)-3-(4-methoxyphenyl)allyl) cyclohex-1-en-1-yl)malononitrile (compound 9c).
Figure 41B:
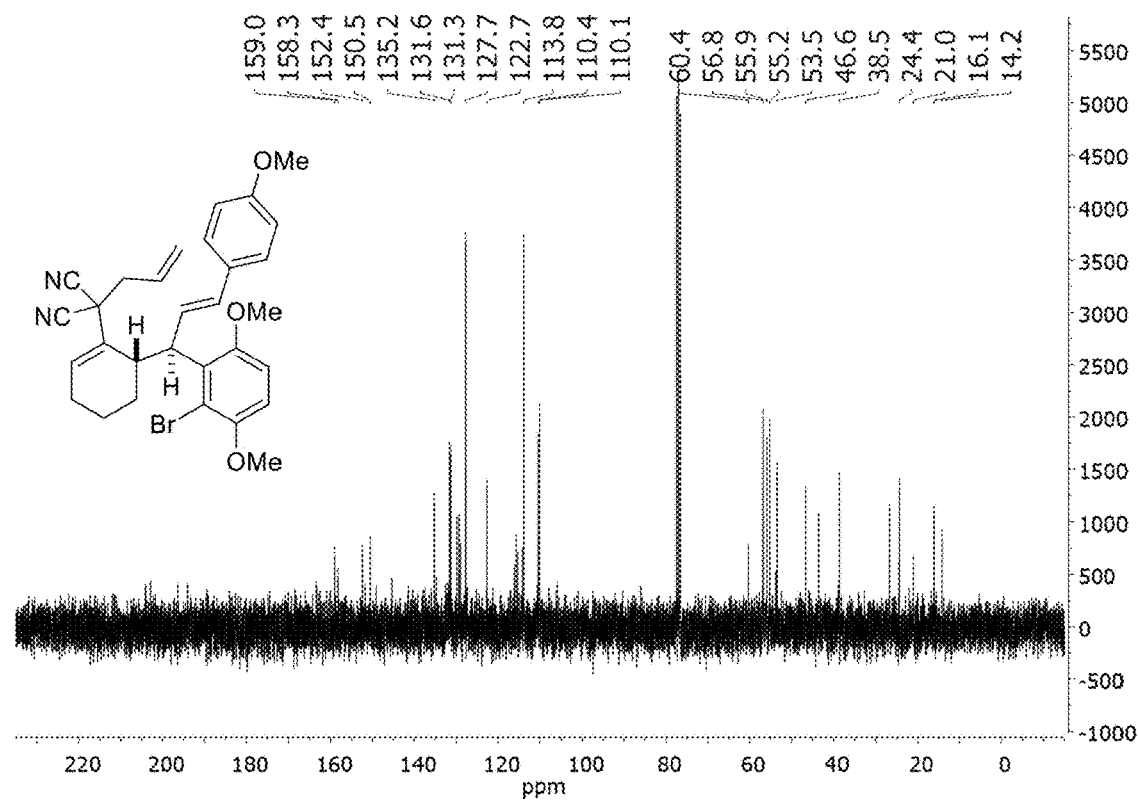
FIG. 41B shows a $^{13}$C NMR spectrum of compound 9c.

Prepared by general procedure A using a reaction time of 2 hours. Isolated: 40 mg. Yield: 62% (>4.4:1 dr). Physical state: colorless oil. TLC: $R_f$=0.27 (20% EtOAc in hexanes); Purified using 20% EtOAc in hexane. $^1$H NMR (300 MHz, CDCl$_3$) major diastereomer: δ 7.33 (dd, J=14.5, 8.5 Hz, 2H), 6.86-6.72 (m, 4H), 6.50 (d, J=16.0 Hz, 1H), 6.22-6.10 (m, 1H), 5.29 (dd, J=16.6, 10.5 Hz, 1H), 5.11 (d, J=17.3 Hz, 1H), 4.12 (q, J=7.1 Hz, 1H), 3.90 (s, 3H), 3.82 (s, 3H), 3.81 (s, 3H), 3.77 (s, 3H), 2.90 (dd, J=13.5, 8.0 Hz, 1H), 2.79-2.63 (m, 1H), 2.45 (dd, J=20.0, 8.4 Hz, 1H), 2.32-2.10 (m, 1H), 1.73-1.34 (m, 4H). $^{13}$C NMR (75 MHz, CDCl$_3$): δ 159.0, 152.4, 150.5, 135.2, 131.6, 131.3, 127.7, 122.7, 113.8, 110.4, 110.1, 60.4, 56.8, 55.9, 55.2, 53.5, 46.6, 38.5, 24.4, 16.1, 14.2. Representative NMR spectra can be seen in FIGS. 41A-41B.

Example 8.4: (E)-2-allyl-2-(6-(1-mesityl-3-(4-methoxyphenyl)allyl)cyclohex-1-en-1-yl)malononitrile (9d)

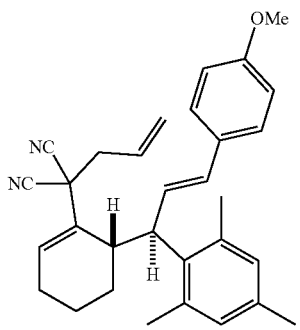 [SMILES: C=CCC(C#N)(C#N)C1=CCCC[C@H]1[C@@H](/C=C/c1ccc(OC)cc1)c1c(C)cc(C)cc1C]

Figure 42A:
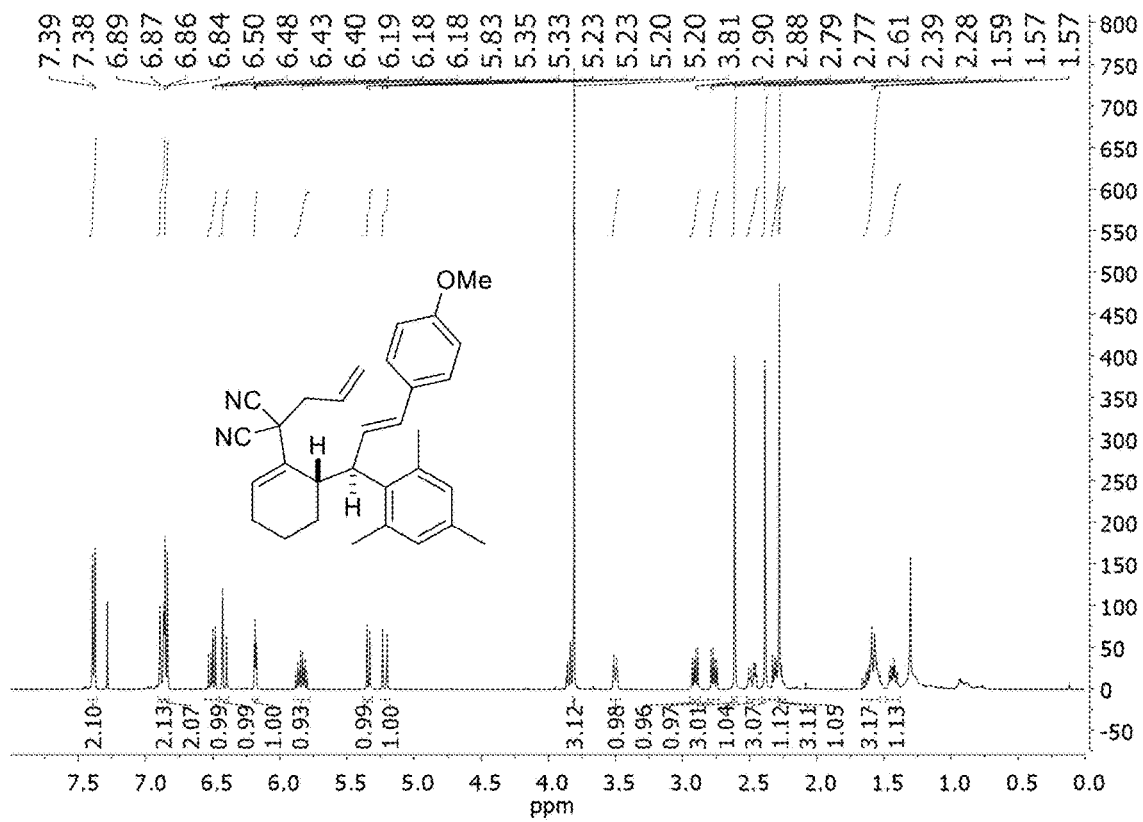
FIG. 42A shows a $^1$H NMR spectrum of (E)-2-allyl-2-(6-(1-mesityl-3-(4-methoxyphenyl)allyl)cyclohex-1-en-1-yl)malononitrile (compound 9d).
Figure 42B:
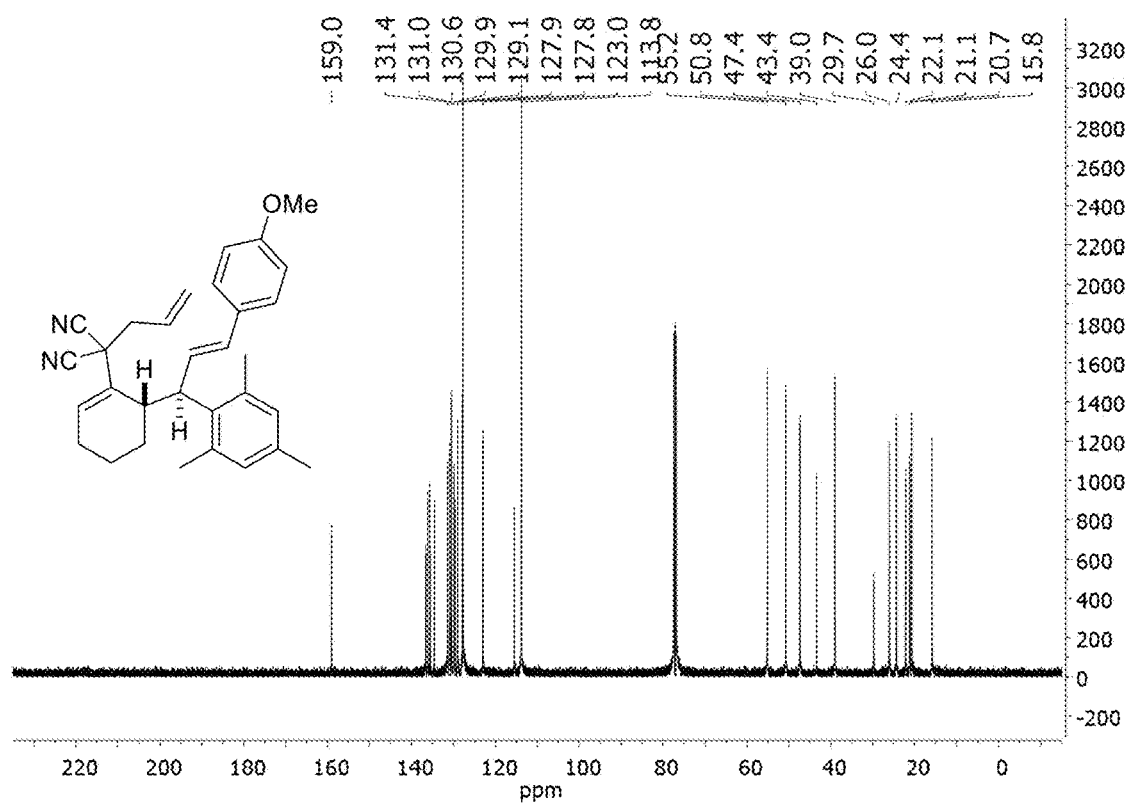
FIG. 42B shows a $^{13}$C NMR spectrum of compound 9d.

Prepared by general procedure A using a reaction time of 2 hours. Isolated: 78 mg. Yield: 60% (>20:1 dr). Physical state: colorless oil. TLC: $R_f$=0.68 (20% EtOAc in hexanes); Purified using 5% EtOAc in hexane. $^1$H NMR (500 MHz, CDCl$_3$) major diastereomer: δ 7.39 (d, J=8.7 Hz, 2H), 6.88 (d, J=13.8 Hz, 2H), 6.85 (d, J=8.8 Hz, 2H), 6.51 (dd, J=15.6, 9.7 Hz, 1H), 6.41 (d, J=15.6 Hz, 1H), 6.18 (t, J=4.0 Hz, 1H), 5.84 (ddt, J=17.3, 10.1, 7.3 Hz, 1H), 5.34 (d, J=10.1 Hz, 1H), 5.22 (dd, J=16.9, 1.1 Hz, 1H), 3.81 (s, 3H), 3.50 (d, J=11.1 Hz, 1H), 2.91 (dd, J=13.6, 7.4 Hz, 1H), 2.77 (dd, J=13.6, 7.1 Hz, 1H), 2.61 (s, 3H), 2.52-2.44 (m, 1H), 2.39 (s, 3H), 2.35-2.29 (m, 1H), 2.28 (s, 3H), 2.26 (d, J=9.0 Hz, 1H), 1.66-1.52 (m, 3H), 1.48-1.38 (m, 1H). $^{13}$C NMR (126 MHz, CDCl$_3$): δ 159.0, 136.7, 136.2, 135.7, 135.6, 134.6, 131.4, 131.0, 130.6, 129.9, 129.6, 129.1, 127.9, 127.8, 123.0, 115.5, 115.5, 113.8, 55.2, 50.8, 47.4, 43.4, 39.0, 29.7, 26.0, 24.4, 22.1, 21.1, 20.7, 15.8. Representative NMR spectra can be seen in FIGS. 42A-42B.

Example 9: Preparation of Aryl 6-7 Scaffolds (10a-10d)

Example 9.1: 9-(4-nitrophenyl)-1,2,3,6,9,9a-hexahydro-5H-benzo[7]annulene-5,5-dicarbonitrile (10a)

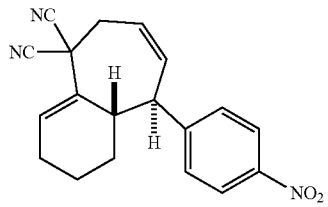

Figure 43A:
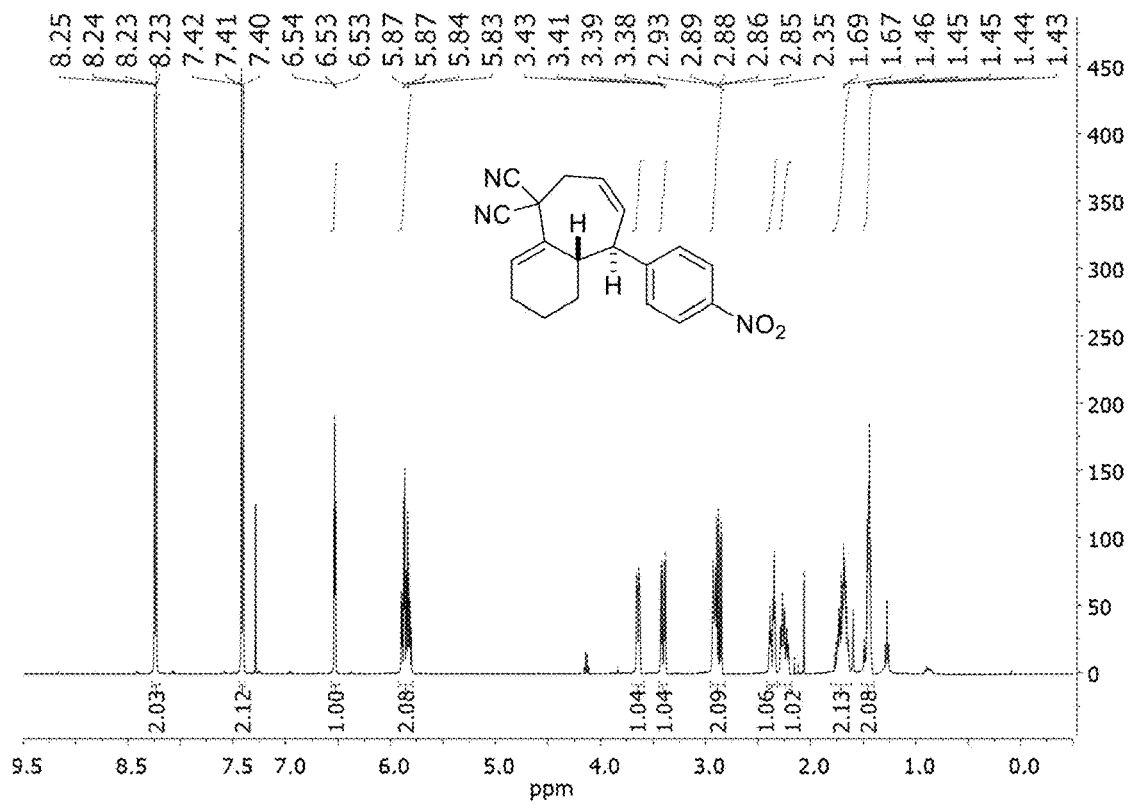
FIG. 43A shows a $^1$H NMR spectrum of 9-(4-nitrophenyl)-1,2,3,6,9,9a-hexahydro-5H-benzo[7]annulene-5,5-dicarbonitrile (compound 10a).
Figure 43B:
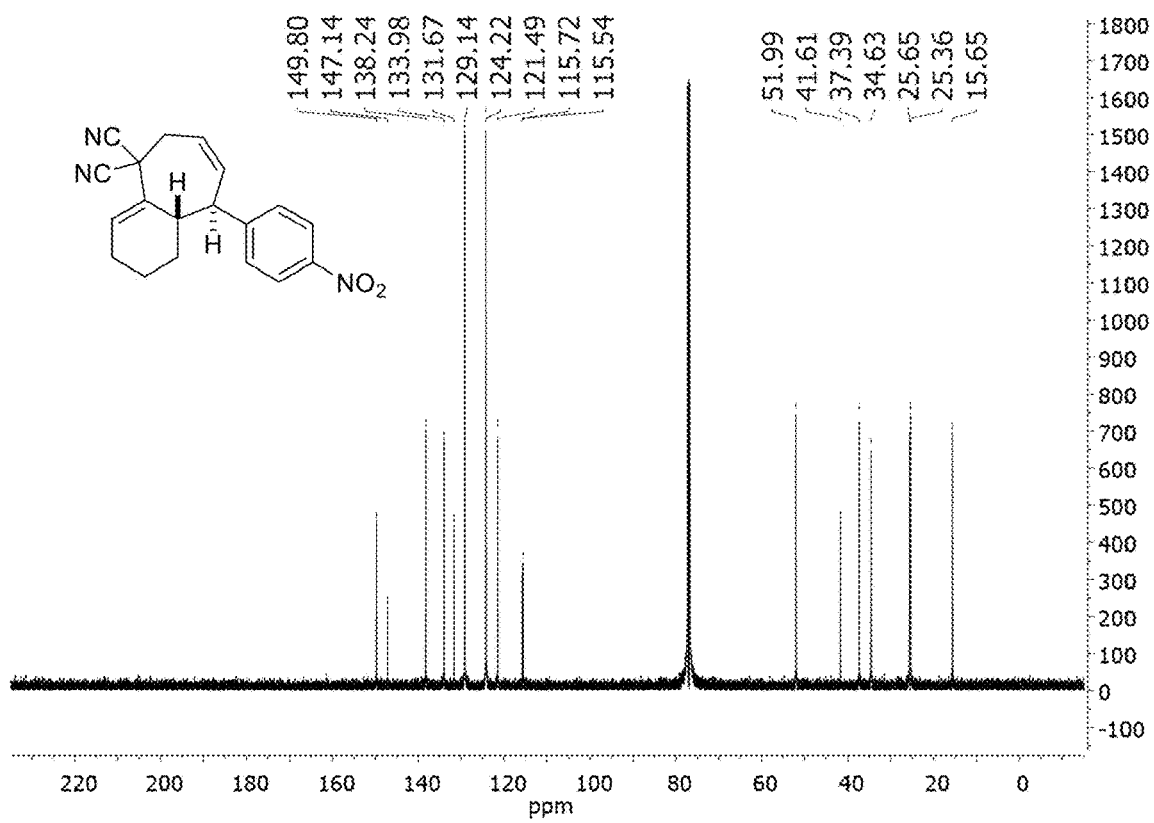

Prepared from 9a by general procedure B using a reaction time of 3 hours. Isolated: 27 mg. Yield: 59% (>20:1 dr). Physical state: colorless oil. TLC: $R_f$=0.30 (20% EtOAc in hexanes); Purified using 10% EtOAc in hexane. $^1$H NMR (500 MHz, CDCl$_3$) major diastereomer δ 8.27-8.19 (m, 2H), 7.43-7.38 (m, 2H), 6.53 (t, J=3.7 Hz, 1H), 5.84 (tdd, J=11.3, 9.6, 3.0 Hz, 2H), 3.64 (dd, J=10.9, 3.9 Hz, 1H), 3.40 (dd, J=15.2, 5.8 Hz, 1H), 2.96-2.82 (m, 2H), 2.41-2.32 (m, 1H), 2.30-2.18 (m, 1H), 1.80-1.62 (m, 2H), 1.52-1.40 (m, 2H). $^{13}$C NMR (126 MHz, CDCl$_3$): δ 149.8, 147.1, 138.2, 134.0, 131.7, 129.1, 124.2, 121.5, 115.7, 115.5, 52.0, 41.6, 37.4, 34.6, 25.7, 25.4, 15.7. HRMS (DART) m/z: [M+H]$^+$ Calcd for $C_{19}H_{18}N_3O_2$ 320.1394; Found 320.1406. Representative NMR spectra can be seen in FIGS. 43A-43B.

Example 9.2: 9-(2,6-dichlorophenyl)-1,2,3,6,9,9a-hexahydro-5H-benzo[7]annulene-5,5-dicarbonitrile (10b)

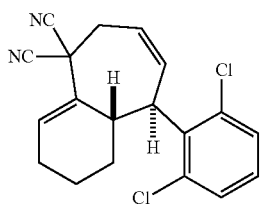

Figure 44A:
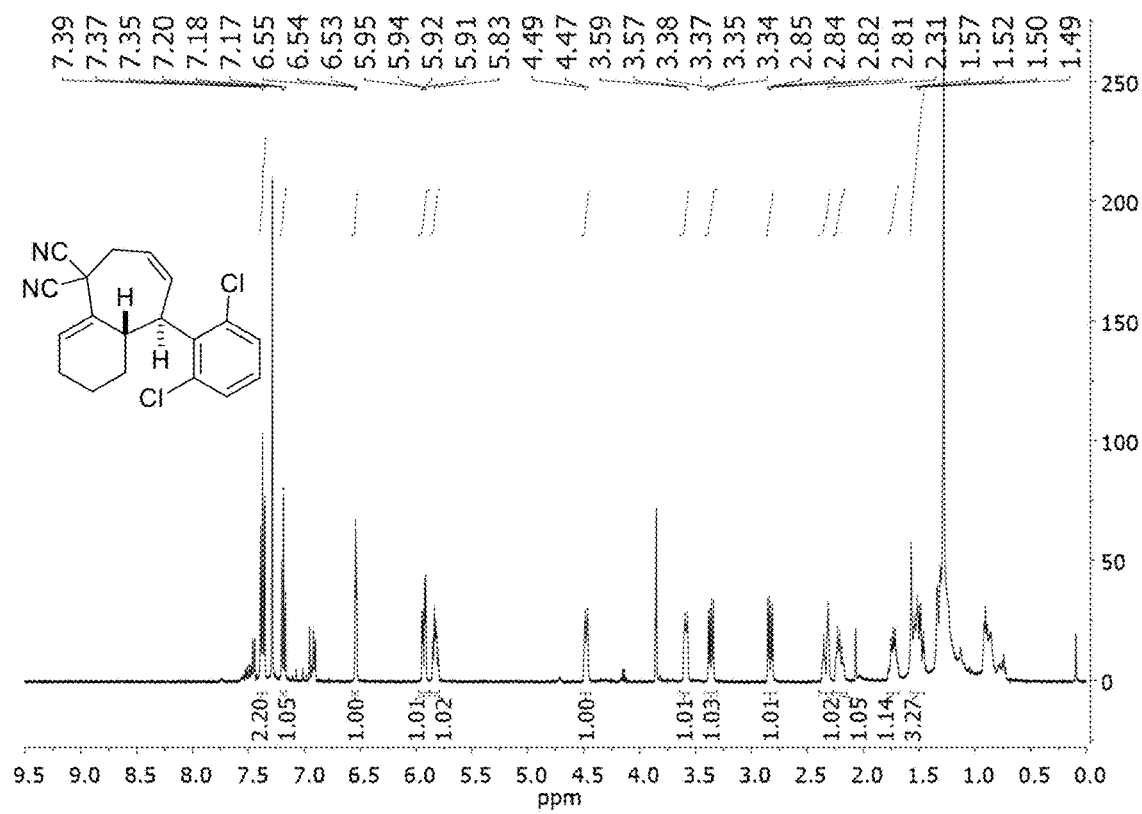
FIG. 44A shows a $^1$H NMR spectrum of 9-(2,6-dichlorophenyl)-1,2,3,6,9,9a-hexahydro-5H-benzo[7]annulene-5,5-dicarbonitrile (compound 10b).
Figure 44B:
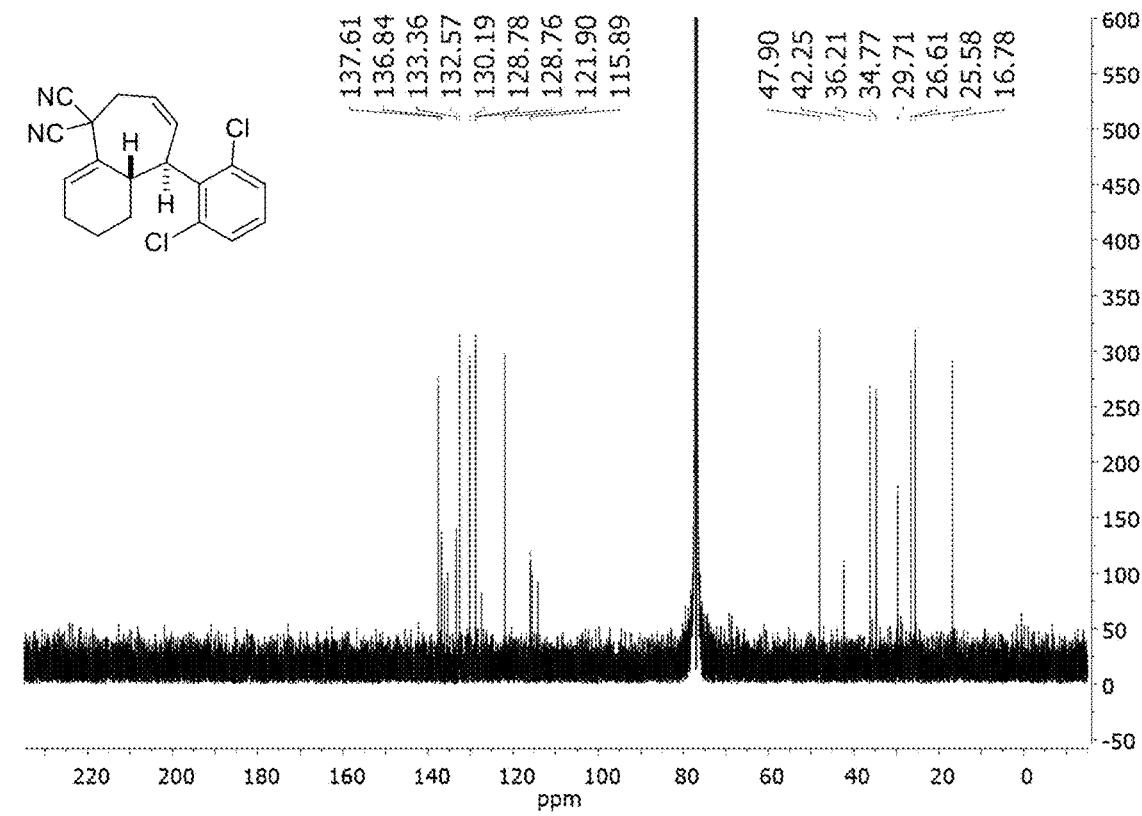
FIG. 44B shows a $^{13}$C NMR spectrum of compound 10b.

Prepared from 9b by general procedure B using a reaction time of 4 hours. Isolated: 10 mg. Yield: 50% (>20:1 dr). Physical state: colorless oil. TLC: $R_f$=0.62 (20% EtOAc in hexanes); Purified using 5% EtOAc in hexane. $^1$H NMR (500 MHz, CDCl$_3$) major diastereomer δ 7.42-7.33 (m, 2H), 7.18 (t, J=8.0 Hz, 1H), 6.54 (t, J=3.6 Hz, 1H), 5.93 (dd, J=11.2, 4.2 Hz, 1H), 5.83 (dd, J=13.6, 9.0 Hz, 1H), 4.48 (d, J=10.6 Hz, 1H), 3.58 (d, J=10.1 Hz, 1H), 3.36 (dd, J=15.0, 6.9 Hz, 1H), 2.83 (dd, J=14.8, 6.4 Hz, 1H), 2.33 (d, J=18.8 Hz, 1H), 2.27-2.14 (m, 1H), 1.79-1.68 (m, 1H), 1.58-1.45 (m, 3H). $^{13}$C NMR (126 MHz, CDCl$_3$): δ 137.6, 136.8, 133.4, 132.6, 130.2, 128.8, 128.8, 121.9, 115.9, 47.9, 42.3, 36.2, 34.8, 29.7, 26.6, 25.6, 16.8. HRMS (DART) m/z: [M+H]$^+$ Calcd for $C_{19}H_{16}Cl_2N_2$ 343.0763; Found 343.0774. Representative NMR spectra can be seen in FIGS. 44A-44B.

Example 9.3: 9-(2-bromo-3,6-dimethoxyphenyl)-1,2,3,6,9,9a-hexahydro-5H-benzo[7]annulene-5,5-dicarbonitrile (10c)

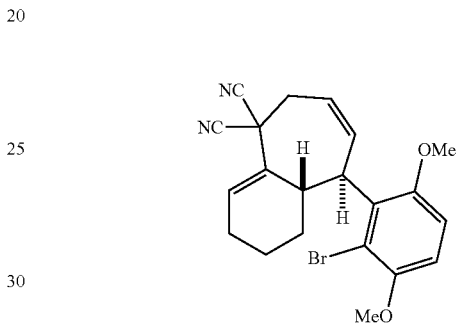

Figure 45A:
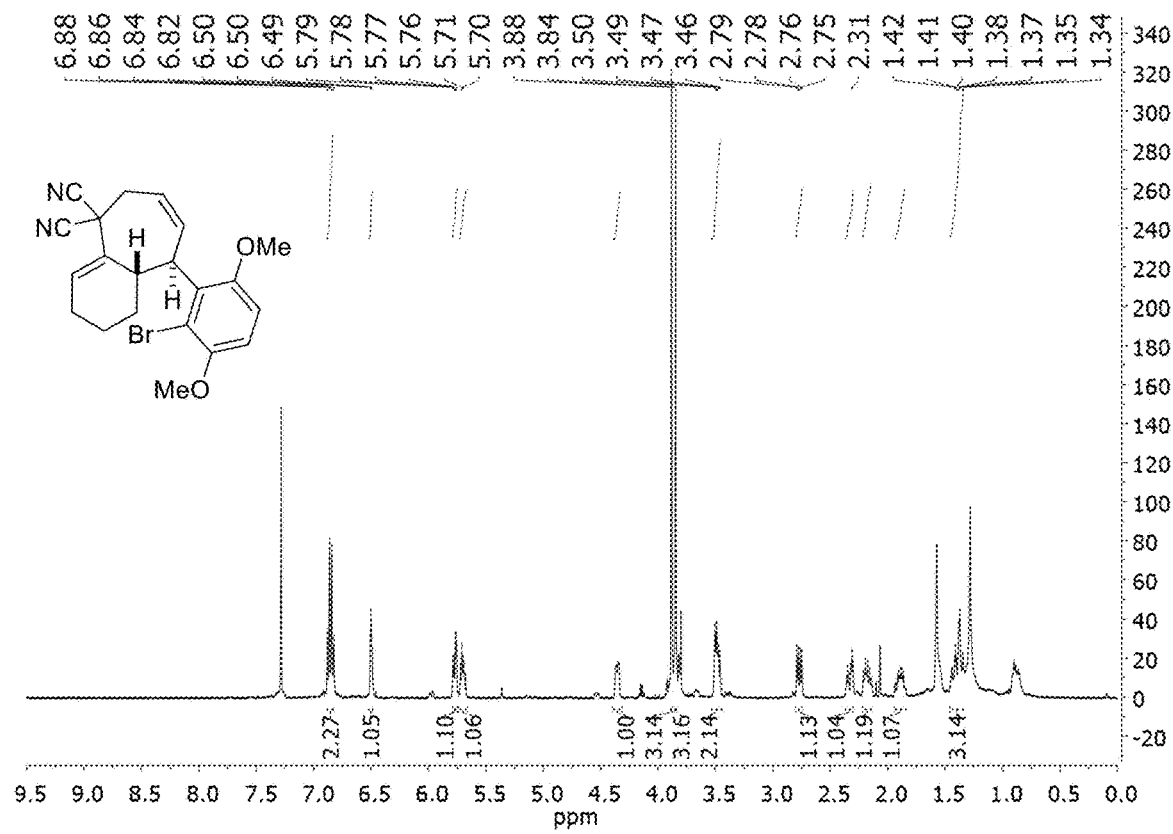
FIG. 45A shows a $^1$H NMR spectrum of 9-(2-bromo-3,6-dimethoxyphenyl)-1,2,3,6,9,9a-hexahydro-5H-benzo[7]annulene-5,5-dicarbonitrile (compound 10c).
Figure 45B:
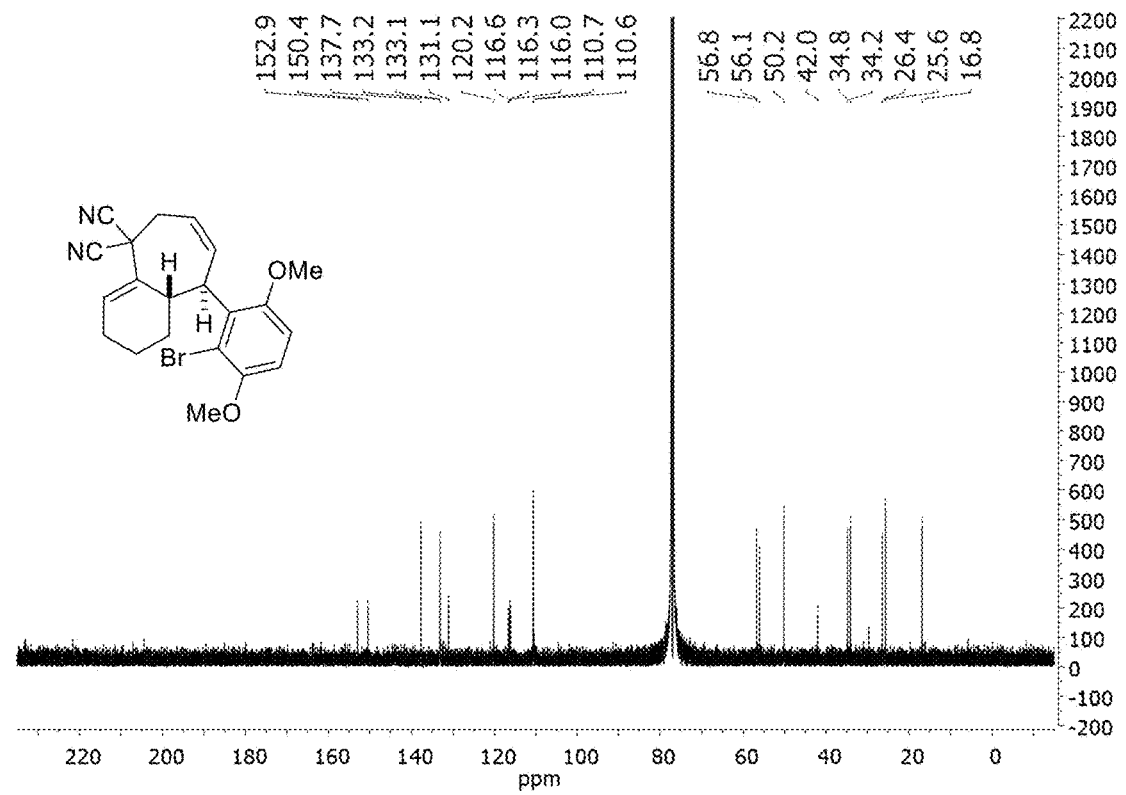
FIG. 45B shows a $^{13}$C NMR spectrum of compound 10b.

Prepared from 9c by general procedure B using a reaction time of 3 hours. Isolated: 17 mg. Yield: 61% (>4.4:1 dr) [one of the diastereomers was isolated and the dr was >11:1 dr]. Physical state: colorless oil. TLC: $R_f$=0.32 (20% EtOAc in hexanes); Purified using 10% EtOAc in hexane. $^1$H NMR (500 MHz, CDCl$_3$) major diastereomer δ 6.85 (q, J=8.9 Hz, 2H), 6.51-6.49 (m, 1H), 5.77 (dd, J=11.0, 4.6 Hz, 1H), 5.73-5.67 (m, 1H), 4.35 (d, J=6.1 Hz, 1H), 3.88 (s, 3H), 3.84 (s, 3H), 3.48 (dd, J=13.8, 6.8 Hz, 2H), 2.77 (dd, J=14.5, 6.9 Hz, 1H), 2.36-2.29 (m, 1H), 2.24-2.11 (m, 1H), 1.94-1.84 (m, 1H), 1.46-1.33 (m, 3H). $^{13}$C NMR (126 MHz, CDCl$_3$): δ 152.9, 150.4, 137.8, 133.2, 133.1, 131.1, 120.2, 116.6, 116.3, 116.1, 110.7, 110.6, 56.8, 56.1, 50.2, 42.0, 34.8, 34.2, 26.4, 25.6, 16.9. HRMS (DART) m/z: [M+H]$^+$ Calcd for $C_{21}H_{22}BrN_2O_2$ 413.0859; Found 413.0875. Representative NMR spectra can be seen in FIGS. 45A-45B.

Example 9.4: 9-mesityl-1,2,3,6,9,9a-hexahydro-5H-benzo[7]annulene-5,5-dicarbonitrile (10d)

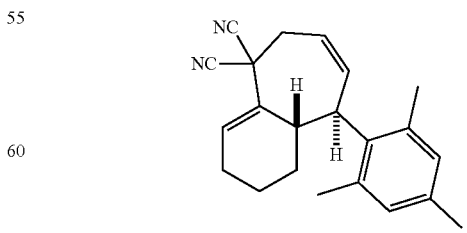

Figure 46A:
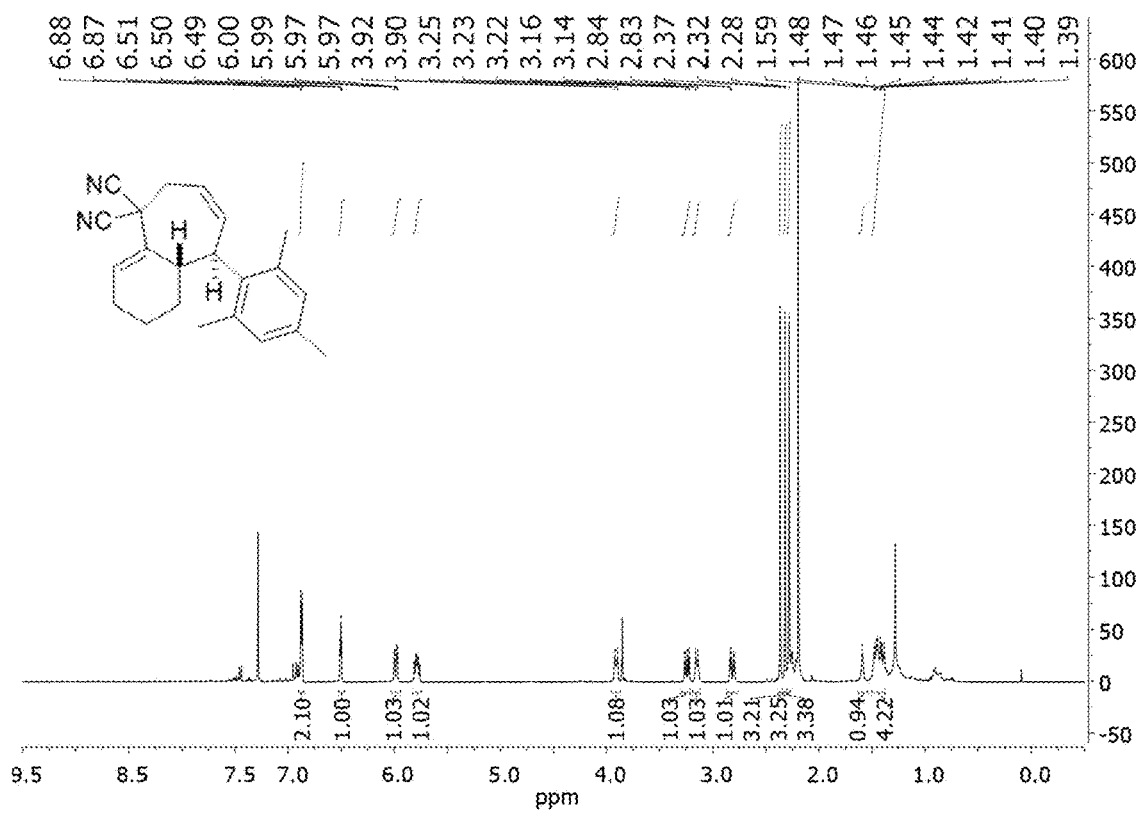
FIG. 46A shows a $^1$H NMR spectrum of 9-mesityl-1,2,3,6,9,9a-hexahydro-5H-benzo[7]annulene-5,5-dicarbonitrile (compound 10d).
Figure 46B:
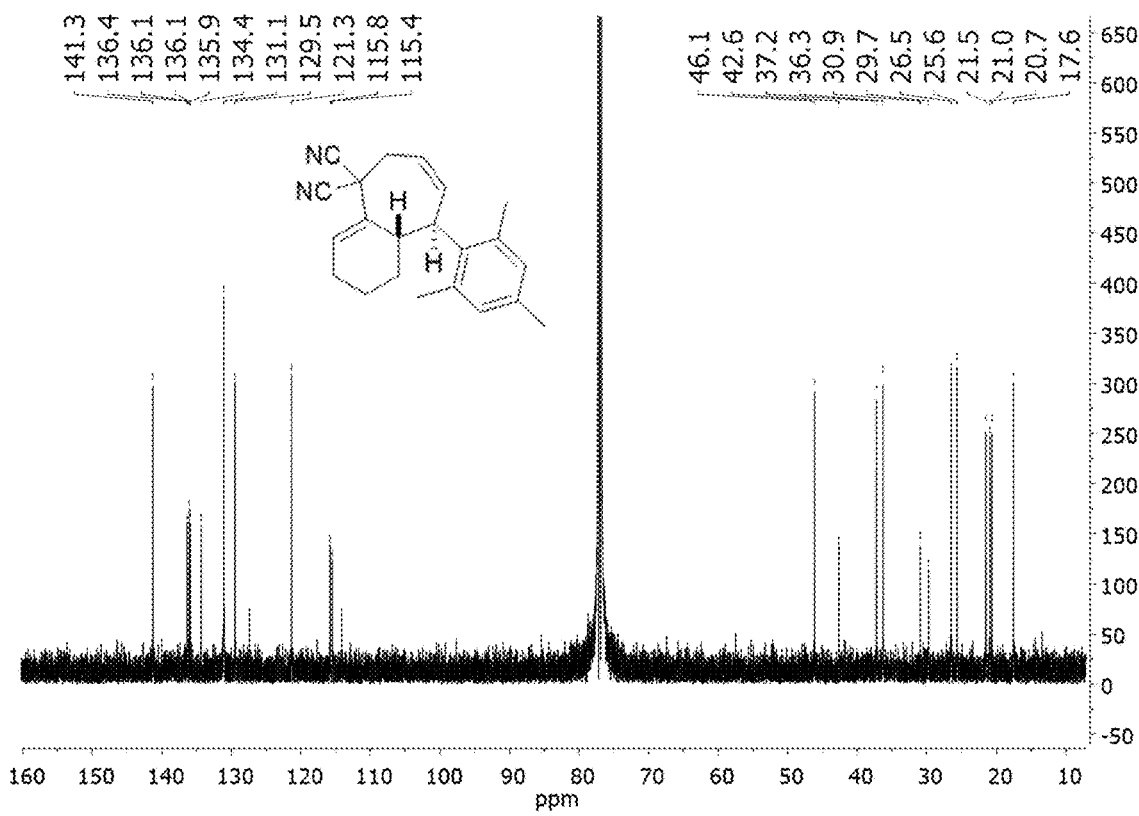
FIG. 46B shows a $^{13}$C NMR spectrum of compound 10d.

Prepared from 9d by general procedure B using a reaction time of 3 hours. Isolated: 20 mg. Yield: 77% (>20:1 dr). Physical state: colorless oil. TLC: $R_f$=0.74 (20% EtOAc in hexanes); Purified using 2% EtOAc in hexane. $^1$H NMR (500 MHz, CDCl$_3$) major diastereomer δ 6.87 (d, J=6.0 Hz, 2H), 6.50 (t, J=3.8 Hz, 1H), 5.98 (dd, J=11.2, 3.1 Hz, 1H), 5.83-5.74 (m, 1H), 3.91 (d, J=11.0 Hz, 1H), 3.24 (dd, J=15.1, 6.9 Hz, 1H), 3.15 (d, J=10.5 Hz, 1H), 2.82 (dd, J=15.0, 5.9 Hz, 1H), 2.37 (s, 3H), 2.32 (s, 3H), 2.27 (d, J=10.2 Hz, 3H), 1.59 (s, 1H), 1.51-1.36 (m, 4H). $^{13}$C NMR (126 MHz, CDCl$_3$): 141.3, 136.4, 136.1, 136.1, 135.9, 134.4, 131.1, 129.5, 121.3, 115.8, 115.5, 46.2, 42.6, 37.2, 36.3, 30.9, 29.7, 26.5, 25.6, 21.5, 21.0, 20.7, 17.6. HRMS (ESI) m/z: [M+Na]$^+$ Calcd for C$_{22}$H$_{24}$N$_2$Na 339.1832; Found 339.1824. Representative NMR spectra can be seen in FIGS. 46A-46B.

Example 10: γ-Allylation Occurs by Transient Cope Rearrangement; Synthesis of (E)-2-allyl-2-(1-(4-methoxyphenyl)-3-(4-nitrophenyl)allyl)malononitrile (11b)

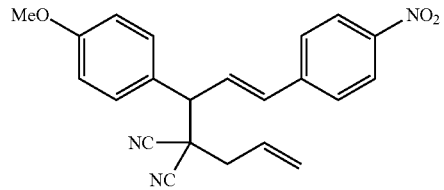 [SMILES: C=CCC(C#N)(C#N)C(/C=C/c1ccc([N+](=O)[O-])cc1)c1ccc(OC)cc1]

Figure 47A:
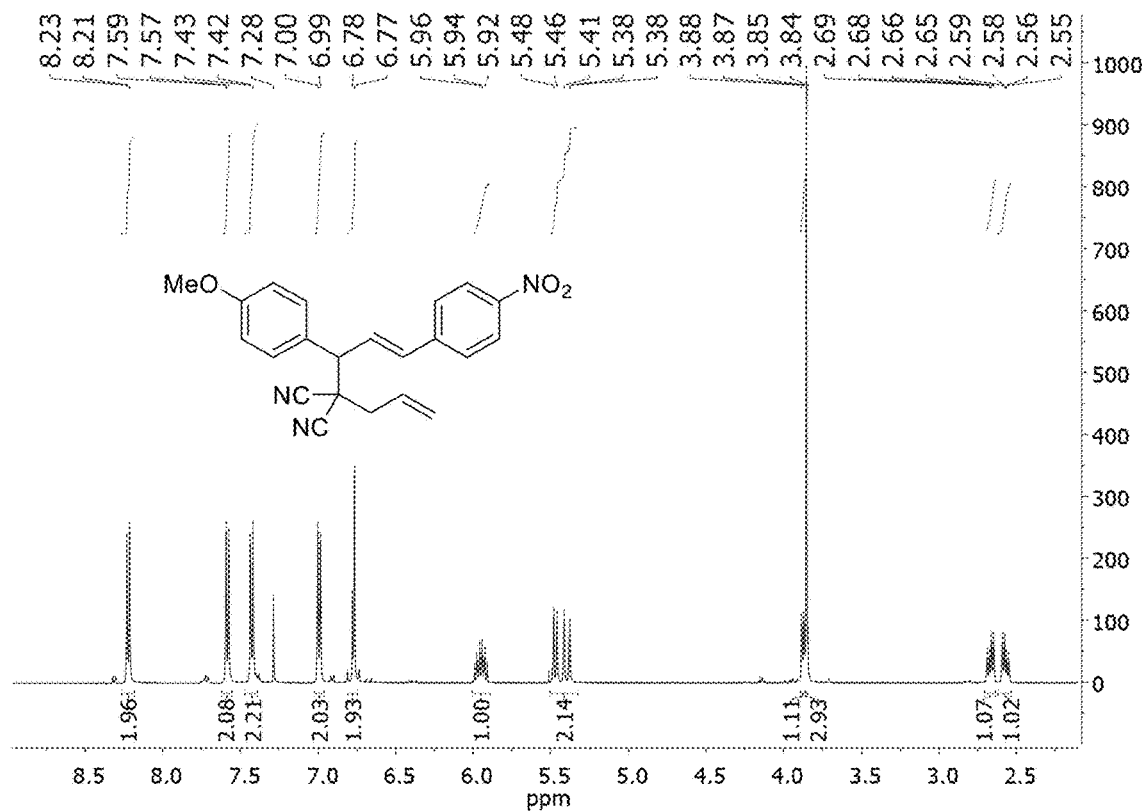
FIG. 47A shows a $^1$H NMR spectrum of (E)-2-allyl-2-(1-(4-methoxyphenyl)-3-(4-nitrophenyl)allyl)malononitrile (compound 11b).
Figure 47B:
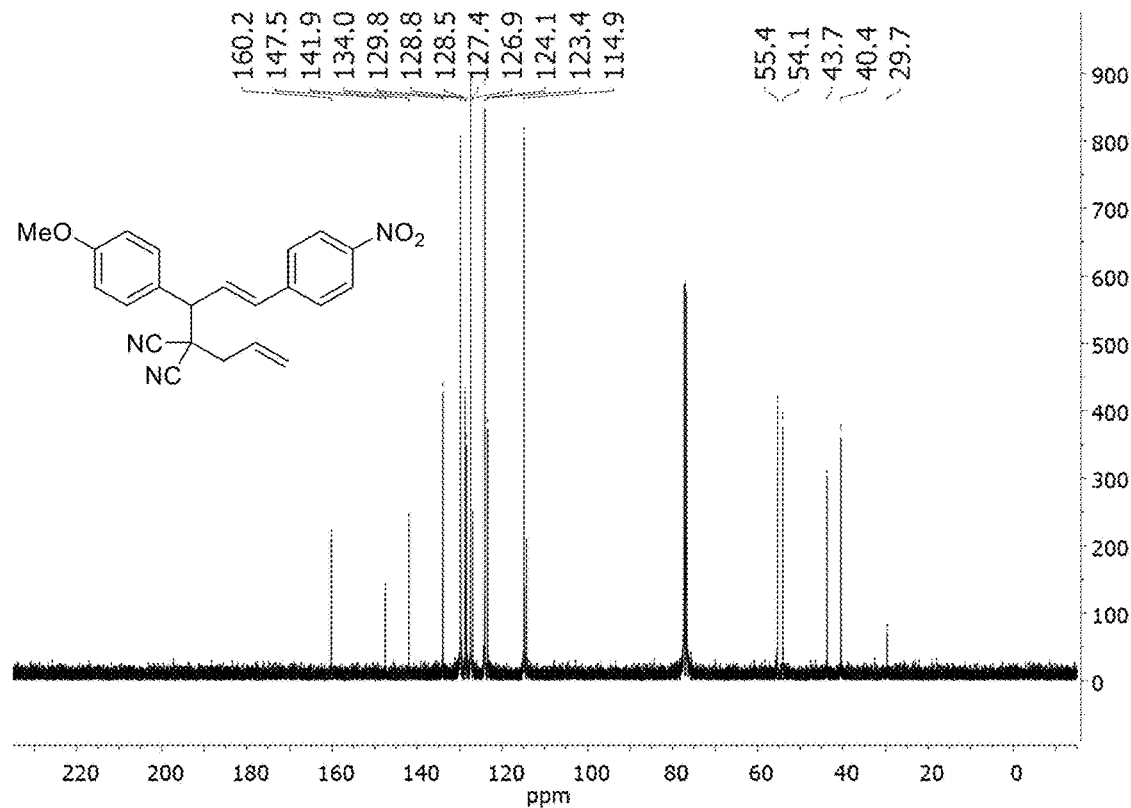
FIG. 47B shows a $^{13}$C NMR spectrum of compound 11b.
Figure 48A:
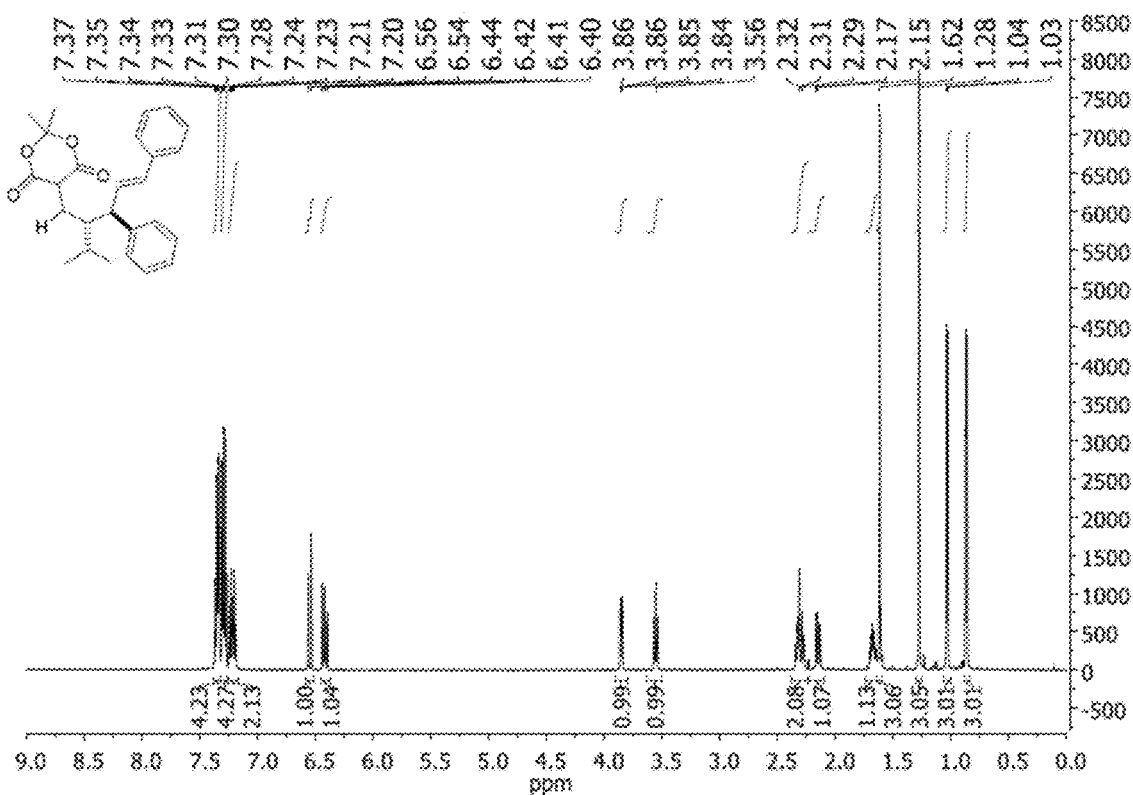
FIG. 48A shows a $^1$H NMR spectrum of (E)-5-(2-isopropyl-3,5-diphenylpent-4-en-1-yl)-2,2-dimethyl-1,3-dioxane-4,6-dione (compound 12b).
Figure 48B:
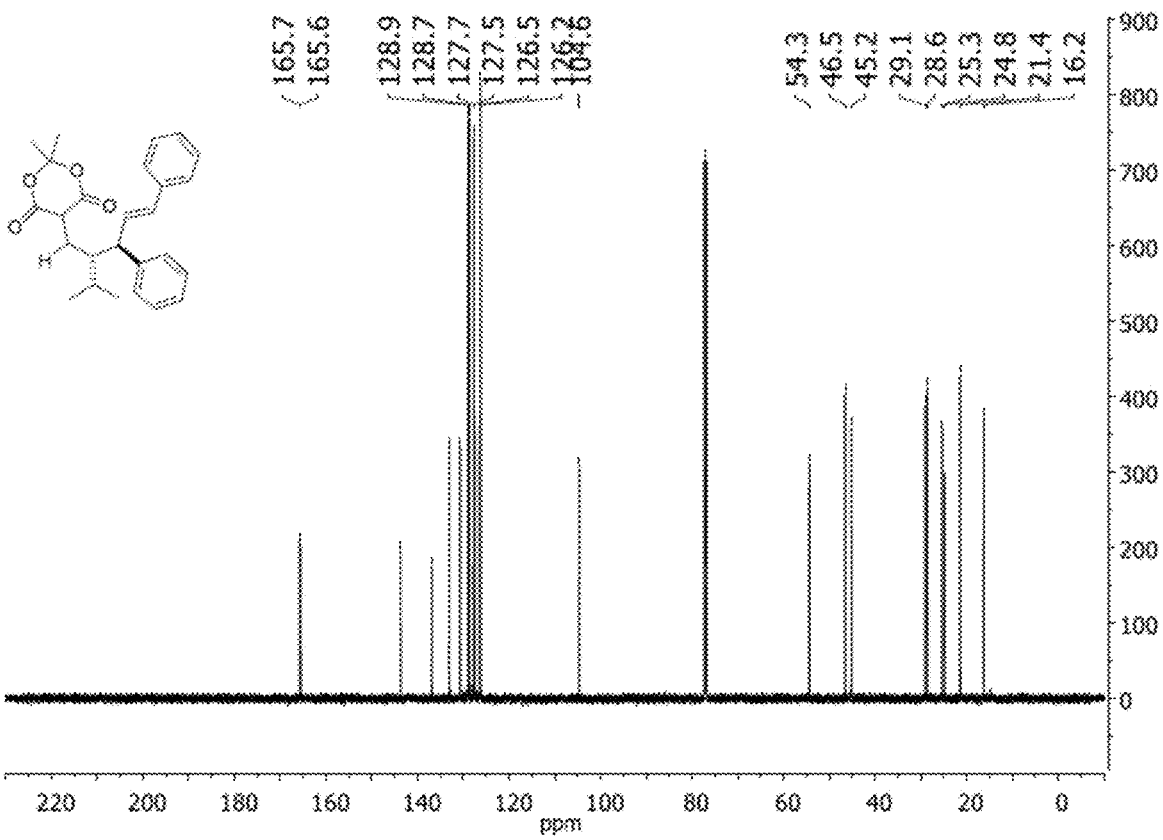
FIG. 48B shows a $^{13}$C NMR spectrum of compound 12b.
Figure 49A:
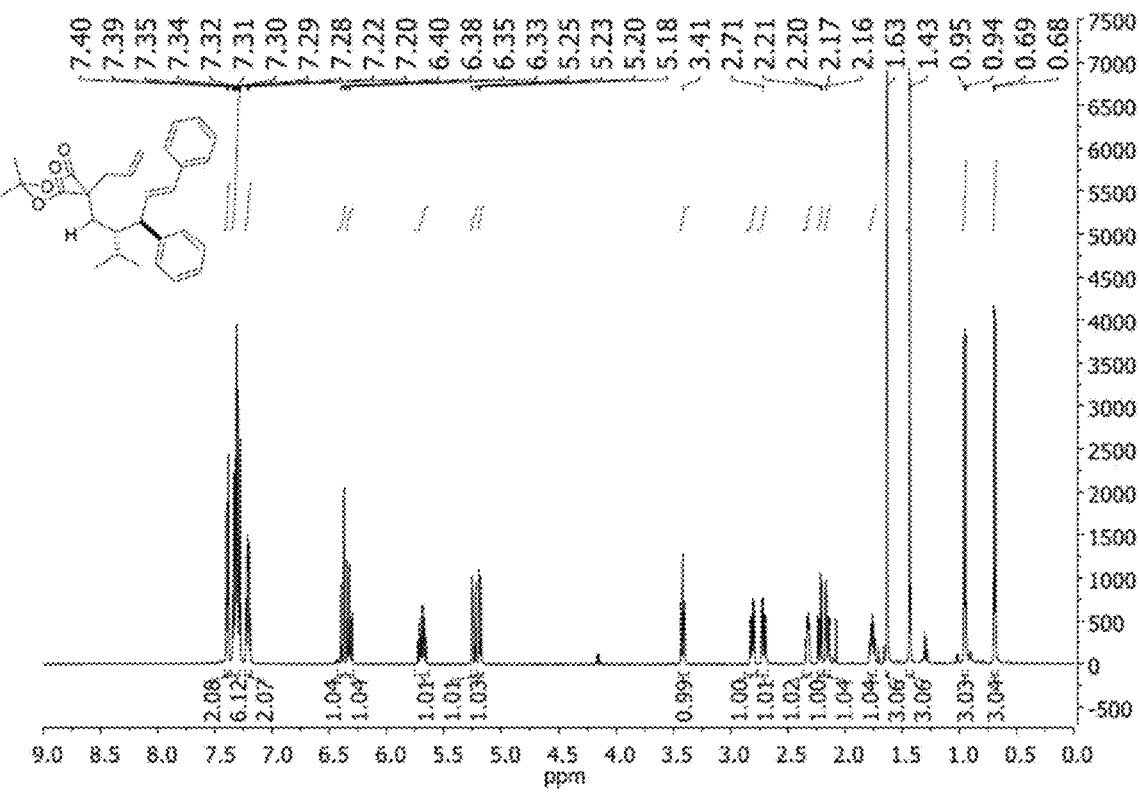
FIG. 49A shows a $^1$H NMR spectrum of (E)-5-allyl-5-(2-isopropyl-3,5-diphenylpent-4-en-1-yl)-2,2-dimethyl-1,3-dioxane-4,6-dione (compound 12b-2).
Figure 49B:
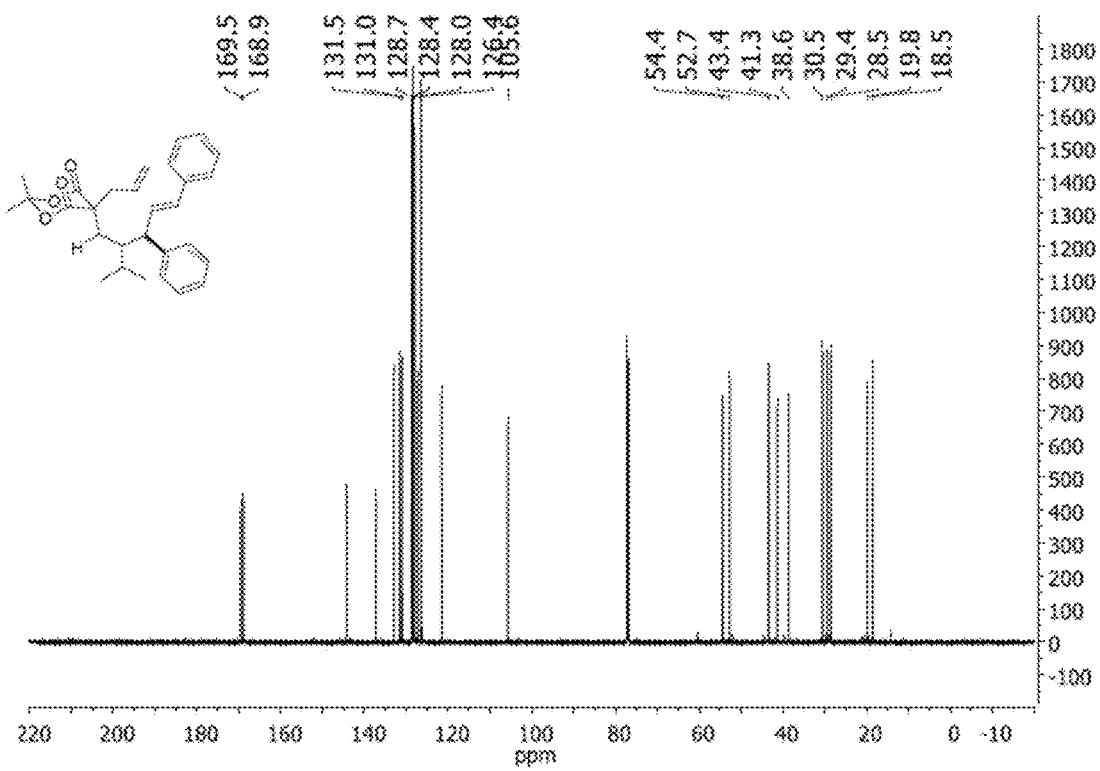
FIG. 49B shows a $^{13}$C NMR spectrum of compound 12b-2.
Figure 50A:
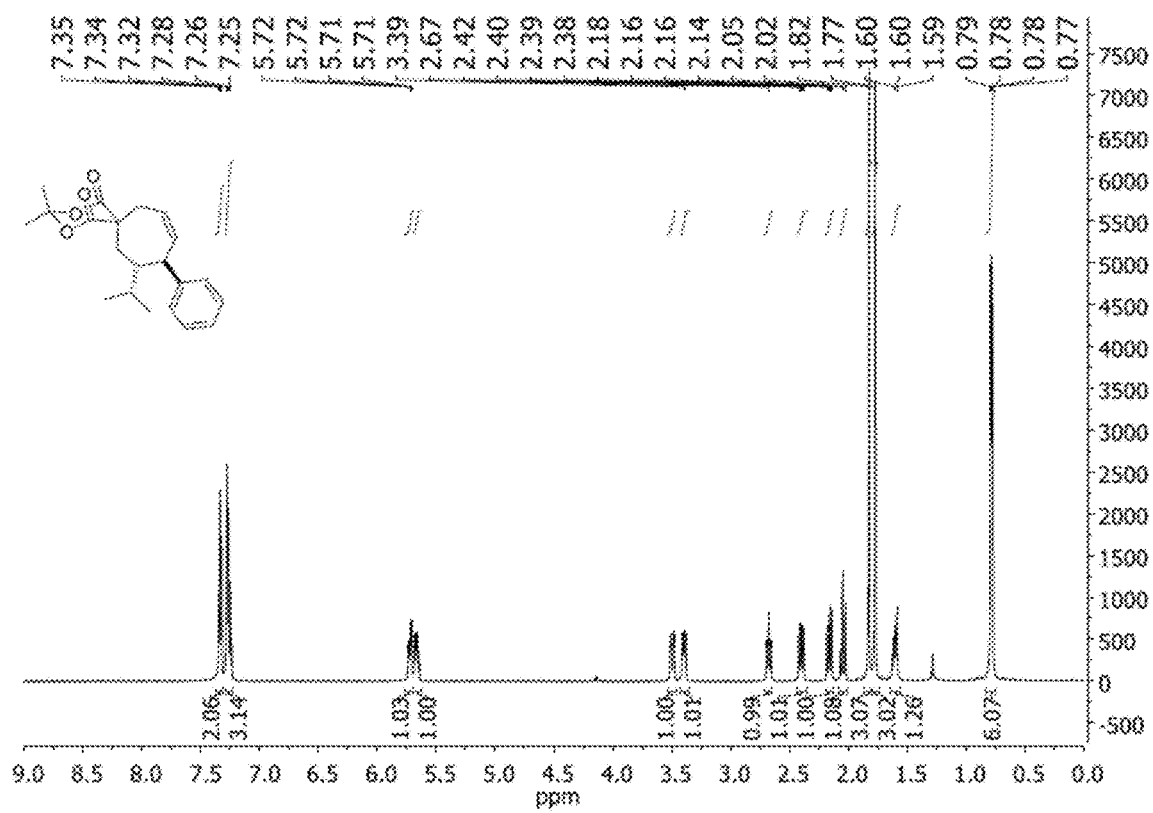
FIG. 50A shows a $^1$H NMR spectrum of (E)-5-(2-isopropyl-3,5-diphenylpent-4-en-1-yl)-2,2-dimethyl-1,3-dioxane-4,6-dione (compound 12c).
Figure 50B:
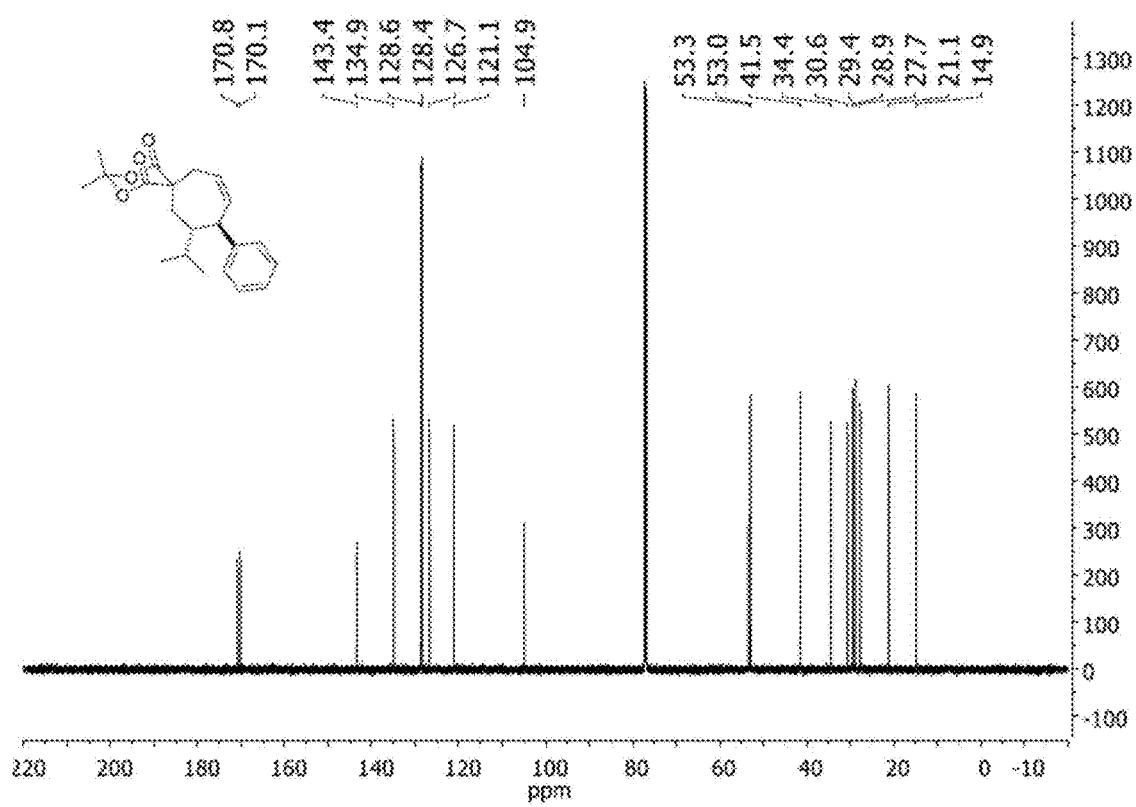
FIG. 50B shows a $^{13}$C NMR spectrum of compound 12c.

Prepared by general procedure A1 using a reaction time of 2 hours. Isolated: 50 mg. Yield: 60% (>20:1 rr). Physical state: colorless oil. TLC: R$_f$=0.20 (20% EtOAc in hexanes); Purified using 20% EtOAc in hexane. $^1$H NMR (500 MHz, CDCl$_3$) major diastereomer: δ 8.22 (d, J=8.8 Hz, 2H), 7.58 (d, J=8.8 Hz, 2H), 7.42 (t, J=9.2 Hz, 2H), 6.99 (d, J=8.7 Hz, 2H), 6.77 (d, J=6.7 Hz, 2H), 6.01-5.89 (m, 1H), 5.43 (dt, J=17.8, 3.5 Hz, 2H), 3.89-3.86 (m, 1H), 3.85 (s, 3H), 2.67 (dd, J=14.0, 7.2 Hz, 1H), 2.57 (dd, J=14.0, 7.3 Hz, 1H). $^{13}$C NMR (126 MHz, CDCl$_3$): δ 160.2, 147.5, 141.9, 134.0, 129.8, 128.8, 128.5, 127.4, 126.9, 124.1, 123.5, 114.9, 55.4, 54.1, 43.7, 40.4, 29.7. Representative NMR spectra can be seen in FIGS. 47A-47B.

Example 11: Meldrum's Acid-Derived Knoevenagel Adducts

Example 11.1: 2,2-dimethyl-5-(3-methylbutyl-idene)-1,3-dioxane-4,6-dione (12a)

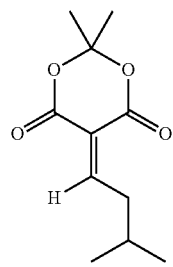

Compound 12a was prepared by a previously published procedure and the NMR spectra were consistent with those reported in the literature. Isolated: 33 g. Yield: 67%. Physical state: colorless oil. TLC: R$_f$=0.44 (20% EtOAc in hexanes).

Example 11.2: (E)-5-(2-isopropyl-3,5-diphenylpent-4-en-1-yl)-2,2-dimethyl-1,3-dioxane-4,6-dione (12b)

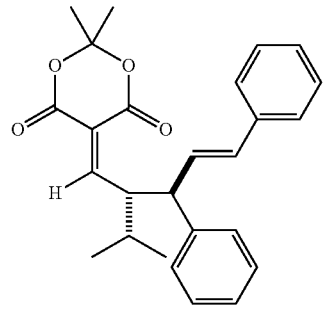 [SMILES: CC(C)[C@H](C=C1C(=O)OC(C)(C)OC1=O)[C@@H](/C=C/c1ccccc1)c1ccccc1]

Compound 12b was prepared according to the following procedure:

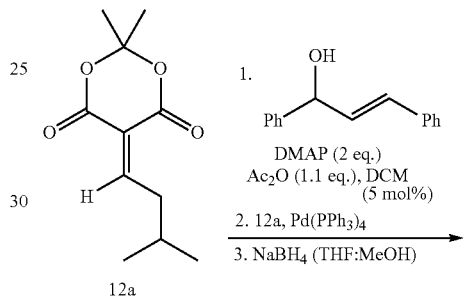

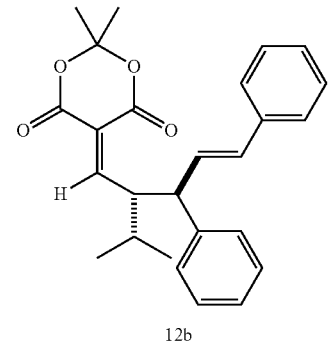

Reaction time 1: 5 min; reaction time 2: 30 min; reaction time 3: 10 min. Isolated: 100 mg. Yield: 52% (>20:1). Physical state: colorless oil. TLC: R$_f$=0.45 (20% EtOAc in hexanes); purified using 10% EtOAc in hexane. $^1$H NMR (500 MHz, CDCl$_3$) major diastereomer: δ 7.35 (dd, J=14.0, 7.0 Hz, 4H), 7.32-.27 (m, 4H), 7.22 (dt, J=18.8, 7.3 Hz, 2H), 6.55 (d, J=15.8 Hz, 1H), 6.42 (dd, J=15.8, 9.7 Hz, 1H), 3.85 (dd, J=8.9, 2.7 Hz, 1H), 3.56 (t, J=9.2 Hz, 1H), 2.37-2.25 (m, 2H), 2.15 (dd, J=12.6, 9. Hz, 1H), 1.68 (dtd, J=13.8, 6.9, 3.1 Hz, 1H), 1.62 (s, 3H), 1.28 (s, 3H), 1.04 (d, J=6.9 Hz, 3H), 0.87 (d, J=6.9 Hz, 3H). $^{13}$C NMR (126 MHz, CDCl$_3$): δ 165.7, 165.6, 143.7, 136.9, 133.1, 130.7, 128.9, 128.7, 127.7, 127.5, 126.5, 126.2, 104.6, 54.4, 46.5, 45.2, 29.1, 28.6, 25.3, 24.8, 21.4, 16.3.

Example 11.3: (E)-5-(2-isopropyl-3,5-diphenylpent-4-en-1-yl)-2,2-dimethyl-1,3-dioxane-4,6-dione (12c)

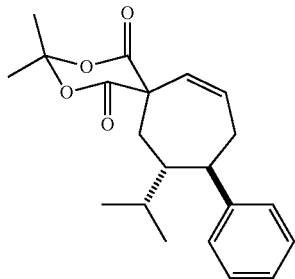 [SMILES: CC(C)[C@@H]1CC2(C=CC[C@H]1c1ccccc1)C(=O)OC(C)(C)OC2=O]

Compound 12c was prepared according to the following procedure:

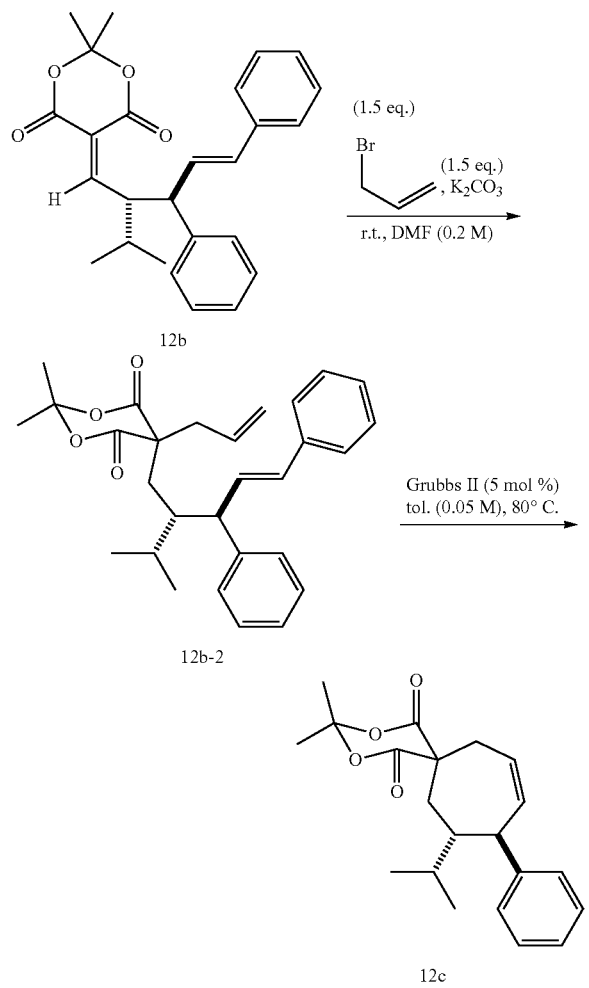

Reaction time 1: 1 hour; reaction time 2: 3 hours. Isolated: First step, 100 mg; second step: 28 mg. Yield: First step: 93% (>20:1 dr); second step: 80% (>20:1 dr). Physical state: First step: colorless oil; second step: colorless oil. TLC: First step: $R_f$=0.48 (20% EtOAc in hexanes); purified using 10% EtOAc in hexane. Second step: $R_f$=0.41 (20% EtOAc in hexanes); purified using 10% EtOAc in hexane.

$^1$HNMR (600 MHz, CDCl$_3$) 12b-2 major diastereomer: δ 7.39 (d, J=7.5 Hz, 2H), 7.31 (ddd, J=18.8, 13.0, 5.5 Hz, 6H), 7.21 (dd, J=16.1, 7.4 Hz, 2H), 6.39 (d, J=15.7 Hz, 1H), 6.32 (dd, J=15.7, 9.3 Hz, 1H), 5.74-5.64 (m, 1H), 5.24 (d, J=16.8 Hz, 1H), 5.19 (d, J=10.2 Hz, 1H), 3.41 (t, J=9.0 Hz, 1H), 2.81 (dd, J=13.0, 7.4 Hz, 1H), 2.71 (dd, J=13.0, 7.6 Hz, 1H, 2.36-2.30 (m, 1H), 2.22 (dd, J=14.6, 3.6 Hz, 1H), 2.15 (dd, J=14.6, 5.3 Hz, 1H), 1.76 (dtd, J=13.9, 7.0, 2.2 Hz, 1H), 1.63 (s, 3H), 1.43 (s, 3H), 0.95 (d, J=7.0 Hz, 3H), 0.69 (d, J=6.9 Hz, 3H). $^{13}$C NMR (151 MHz, CDCl$_3$) 12b-2: δ 169.45 (s), 168.94 (s), 144.16 (s), 1237.23 (s), 132.98 (s), 131.51 (s), 131.02 (s), 128.71 (s), 128.43 (s), 127.97 (s), 127.25 (s), 126.42 (s), 126.38 (s), 121.48 (s), 105.65 (s), 54.39 (s), 52.75 (s), 43.39 (s), 41.30 (s), 38.61 (s), 30.53 (s), 29.38 (s), 28.54 (s), 19.85 (s), 18.54 (s).

$^1$HNMR (600 MHz, CDCl$_3$) 12c major diastereomer: δ 7.34 (t, J=7.5 Hz, 2H), 7.26 (dd, J=16.6, 7.5 Hz, 3H), 5.72 (ddd, J=10.8, 5.3, 1.7 Hz, 1H), 5.69-5.64 (m, 1H), 3.54-3.46 (m, 1H), 3.39 (dd, J=11.5, 5.2 Hz, 1H), 2.70-2.64 (m, 1H), 2.40 (dd, J=14.9, 8.6 Hz, 1H), 2.15 (dd, J=14.2, 8.9 Hz, 1H), 2.04 (d, J=14.2 Hz, 1H), 1.82 (s, 3H), 1.77 (s, 3H), 1.65-1.56 (m, 1H), 0.78 (dd, J=6.8, 3.3 Hz, 6H). $^{13}$C NMR (151 MHz, CDCl$_3$) 12c: δ 170.8, 170.1, 143.4, 135.0, 128.6, 128.4, 126.7, 121.1, 104.9, 53.3, 53.0, 41.5, 34.4, 30.6, 29.4, 28.9, 27.7, 21.1, 14.9. m/z (ESI-MS) 12c: 365.1 [M+Na]$^+$.

Example 12: Computational Methods

Example 12.1: Software Packages and Models

Conformational searches of the starting material and product were performed using the Schrodinger MacroModel software package to identify low-energy conformers for quantum mechanical calculations; reported quantum mechanical energies and geometries are for the lowest energy conformer. All quantum mechanical calculations were performed using the Gaussian 09 software package.

Figure 8:
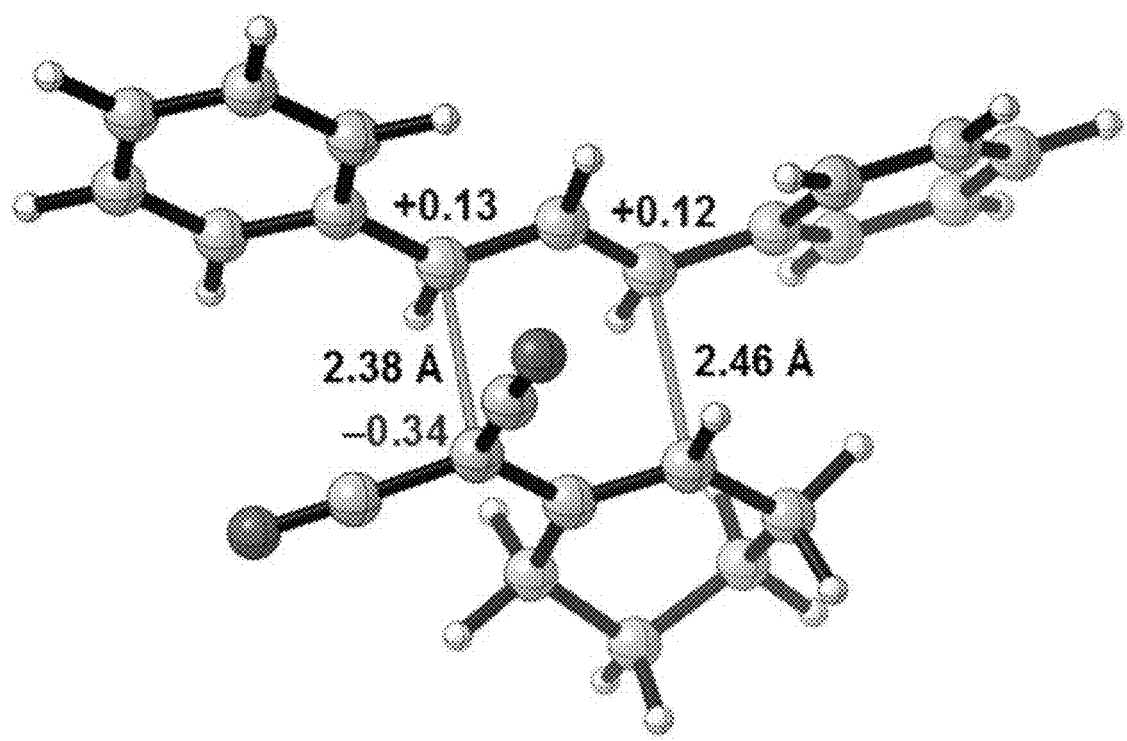
FIG. 8 shows a representative computational model for the transition state for the Cope rearrangement leading to the formation of (E)-2-(2-(1,3-diphenylallyl)cyclohexylidene) malononitrile (compound 3a) computed via density functional theory.

To probe whether a room-temperature Cope rearrangement of 4,6-diaryl-3,3-dicyano-1,5-dienes was reasonable, computational studies were carried out for the synthesis of 3a. Density functional theory calculations showed that the Cope rearrangement was exergonic by 8.6 kcal/mol and had an unusually low free energy barrier of 19.5 kcal/mol, corresponding to a half-life of 23 seconds at room temperature. To explain the facility of this Cope rearrangement at room temperature, bond lengths and atomic charges in the transition state were investigated (FIG. 8). The transition state revealed substantial dissociative character (2.38 Å and 2.46 Å for the breaking and forming bonds respectively) and significant charge separation, with a stabilized negative charge (−0.34e) alpha to the two nitrile groups and stabilized positive charges (+0.13e and +0.12e) at the two benzylic positions. The ability of the nitrile groups and phenyl groups to stabilize each transition state fragment via conjugation accounts for the low barrier of this Cope rearrangement. All structures were optimized at the M06-2X/6-31+G(d) level of theory with single-point energy corrections computed at the M06-2X-D3/6-311++G(2d,2p) level of theory with dichloromethane CPCM solvent; partial charges were computed via NBO analysis and hydrogen atom charges were summed into the neighboring heavy atom.

Example 12.2: Optimized Quantum Mechanical Energies and Geometries

Optimized quantum mechanical energies and geometries are provided in Table 3 below:

TABLE 3

Optimized Quantum Mechanical Energies and Geometries

| Structure | Single-Point Energy (Hartree) M06-2X/6-311++G(2d,2p) CPCM dichloromethane solvent D3 dispersion correction | Enthalpy Correction (Hartree) M06-2X/6-31+G(d) CPCM dichloromethane solvent | Gibbs Free Energy Correction (Hartree) M06-2X/6-31+G(d) CPCM dichloromethane solvent |
|---|---|---|---|
| Starting Material | −1037.13337591 | 0.423517 | 0.343704 |
| Transition State | −1037.10414202 | 0.421206 | 0.345621 |
| Product | −1037.14820643 | 0.424433 | 0.344843 |

Starting material geometries are provided in Table 4 below:

TABLE 4

Starting Material Geometries

| | | | |
|---|---|---|---|
| 0 | 1 | | |
| C | −0.420056 | 2.664409 | 1.250945 |
| C | 0.236517 | 2.171056 | 0.196394 |
| C | −0.096867 | 2.550167 | −1.229027 |
| C | −0.952715 | 3.8169 | −1.284209 |
| C | −2.113137 | 3.70961 | −0.296446 |
| C | −1.580257 | 3.616611 | 1.133479 |
| C | 1.375555 | 1.151907 | 0.35409 |
| C | 2.621717 | 1.730212 | −0.198728 |
| C | 1.631812 | 0.834208 | 1.772994 |
| C | 1.04161 | −0.191205 | −0.425163 |
| C | −0.280242 | −0.722637 | 0.058744 |
| C | −1.296838 | −0.987305 | −0.769059 |
| C | −2.621433 | −1.513298 | −0.392117 |
| C | −3.644684 | −1.505261 | −1.350105 |
| C | −4.920508 | −1.97424 | −1.041118 |
| C | −5.191985 | −2.466122 | 0.234511 |
| C | −4.177705 | −2.489141 | 1.195324 |
| C | −2.905006 | −2.020164 | 0.885848 |
| C | 2.181144 | −1.194179 | −0.341792 |
| C | 2.308546 | −2.082804 | 0.731997 |
| C | 3.373755 | −2.980696 | 0.782918 |
| C | 4.322229 | −3.004943 | −0.239539 |
| C | 4.198656 | −2.12824 | −1.316664 |
| C | 3.133303 | −1.230615 | −1.365953 |
| N | 1.808372 | 0.563332 | 2.881942 |
| N | 3.569622 | 2.196096 | −0.667506 |
| H | −0.125024 | 2.380862 | 2.259388 |
| H | −0.641245 | 1.723203 | −1.707166 |
| H | 0.825867 | 2.689868 | −1.807017 |
| H | −1.318537 | 3.965958 | −2.304855 |
| H | −0.334205 | 4.687245 | −1.028419 |
| H | −2.698276 | 2.808861 | −0.527417 |
| H | −2.7874 | 4.566643 | −0.390783 |
| H | −2.370605 | 3.299533 | 1.823596 |
| H | −1.25414 | 4.606657 | 1.483051 |
| H | 0.9385 | 0.108134 | −1.47383 |
| H | −0.383889 | −0.879694 | 1.13267 |
| H | −1.163264 | −0.791586 | −1.834385 |
| H | −3.436249 | −1.122675 | −2.346568 |
| H | −5.699894 | −1.956203 | −1.797183 |
| H | −6.183528 | −2.835115 | 0.479118 |
| H | −4.378755 | −2.880365 | 2.188343 |
| H | −2.126192 | −2.061284 | 1.642071 |
| H | 1.575759 | −2.083265 | 1.534114 |
| H | 3.458793 | −3.66474 | 1.621995 |
| H | 5.149495 | −3.707209 | −0.199366 |
| H | 4.927557 | −2.143998 | −2.121408 |
| H | 3.038812 | −0.552205 | −2.210952 |

TABLE 4-continued

Starting Material Geometries

Transition state geometries are provided in Table 5 below:

TABLE 5

Transition State Geometries

| | | | |
|---|---|---|---|
| 0 | 1 | | |
| C | −2.824717 | 2.634666 | −0.491721 |
| C | −2.748596 | 1.705463 | 0.718872 |
| C | −1.358747 | 1.181845 | 0.954005 |
| C | −0.230753 | 1.838351 | 0.519414 |
| C | −0.327517 | 2.978508 | −0.470072 |
| C | −1.695764 | 3.663087 | −0.439974 |
| C | 1.06368 | 1.326158 | 0.837774 |
| C | 1.220683 | 0.409447 | 1.925332 |
| C | 2.240542 | 2.053139 | 0.47697 |
| N | 3.195586 | 2.625901 | 0.148969 |
| N | 1.317662 | −0.359287 | 2.789472 |
| C | −1.154522 | −0.557744 | −0.776582 |
| C | −2.416571 | −1.245153 | −0.483031 |
| C | 0.098258 | −1.0574 | −0.46179 |
| C | 1.257655 | −0.369537 | −0.824235 |
| C | 2.621425 | −0.871143 | −0.642439 |
| C | 3.661194 | −0.285219 | −1.383496 |
| C | 4.972718 | −0.731099 | −1.246685 |
| C | 5.267391 | −1.766189 | −0.359441 |
| C | 4.243535 | −2.352958 | 0.388714 |
| C | 2.932024 | −1.911975 | 0.250753 |
| C | −2.5629 | −2.095166 | 0.625319 |
| C | −3.777681 | −2.724498 | 0.874864 |
| C | −4.867917 | −2.513268 | 0.025976 |
| C | −4.736626 | −1.664167 | −1.072279 |
| C | −3.521123 | −1.030006 | −1.320461 |
| H | −1.252827 | 0.409787 | 1.714511 |
| H | −1.208529 | 0.220959 | −1.536565 |
| H | −3.79959 | 3.131942 | −0.518821 |
| H | −2.741044 | 2.048091 | −1.417377 |
| H | −3.449442 | 0.868077 | 0.620741 |
| H | −3.059698 | 2.250003 | 1.623231 |
| H | −0.134221 | 2.581789 | −1.480493 |
| H | 0.46639 | 3.707609 | −0.276419 |
| H | −1.76849 | 4.364275 | −1.277195 |
| H | −1.785346 | 4.251018 | 0.482862 |
| H | 0.174362 | −1.946763 | 0.159675 |
| H | 1.151962 | 0.425848 | −1.561887 |
| H | 3.432008 | 0.524256 | −2.07185 |
| H | 5.763493 | −0.269721 | −1.830353 |
| H | 6.289743 | −2.115355 | −0.249432 |
| H | 4.469595 | −3.156367 | 1.083301 |
| H | 2.151324 | −2.372077 | 0.848413 |

TABLE 5-continued

Transition State Geometries

| | | | |
|---|---|---|---|
| H | −1.730045 | −2.245575 | 1.307977 |
| H | −3.879479 | −3.374427 | 1.738752 |
| H | −5.815906 | −3.003368 | 0.226186 |
| H | −5.580489 | −1.491506 | −1.733406 |
| H | −3.420517 | −0.365631 | −2.175669 |

Product geometries are provided in Table 6 below:

TABLE 6

Product Geometries

| | | | |
|---|---|---|---|
| 0 1 | | | |
| C | −2.948449 | 2.105163 | −1.396539 |
| C | −2.840815 | 1.573936 | 0.032905 |
| C | −1.437876 | 1.022154 | 0.359379 |
| C | −0.396384 | 2.055469 | 0.014895 |
| C | −0.478984 | 2.662026 | −1.354013 |
| C | −1.89681 | 3.185408 | −1.646351 |
| C | 0.575936 | 2.404577 | 0.89555 |
| C | 0.695399 | 1.782265 | 2.187098 |
| C | 1.584609 | 3.381255 | 0.583065 |
| N | 2.398811 | 4.167109 | 0.33802 |
| N | 0.799985 | 1.266027 | 3.218545 |
| C | −1.121494 | −0.318277 | −0.385292 |
| C | −2.154893 | −1.373746 | −0.031325 |
| C | 0.274651 | −0.77505 | −0.049979 |
| C | 1.262777 | −0.880807 | −0.945507 |
| C | 2.655863 | −1.265727 | −0.648761 |
| C | 3.473156 | −1.731413 | −1.688044 |
| C | 4.790233 | −2.117824 | −1.445607 |
| C | 5.316237 | −2.034434 | −0.156865 |
| C | 4.517534 | −1.554929 | 0.884018 |
| C | 3.202314 | −1.169687 | 0.640693 |
| C | −2.301175 | −1.827765 | 1.28528 |
| C | −3.256496 | −2.791529 | 1.601687 |
| C | −4.081509 | −3.316282 | 0.605037 |
| C | −3.94209 | −2.871556 | −0.708501 |
| C | −2.983681 | −1.906434 | −1.022047 |
| H | −1.39164 | 0.80856 | 1.433297 |
| H | −1.175004 | −0.144575 | −1.466505 |
| H | −3.950805 | 2.514707 | −1.559029 |
| H | −2.822486 | 1.288682 | −2.120045 |
| H | −3.578775 | 0.786539 | 0.218547 |
| H | −3.059783 | 2.388947 | 0.734607 |
| H | −0.234648 | 1.871039 | −2.078811 |
| H | 0.265259 | 3.451944 | −1.481464 |
| H | −1.933715 | 3.539034 | −2.681004 |
| H | −2.09766 | 4.049428 | −1.000253 |
| H | 0.462015 | −1.005607 | 1.000511 |
| H | 1.042211 | −0.681526 | −1.995744 |
| H | 3.066752 | −1.796787 | −2.694686 |
| H | 5.405124 | −2.481529 | −2.263708 |
| H | 6.343229 | −2.330393 | 0.035202 |
| H | 4.924881 | −1.470641 | 1.887348 |
| H | 2.602537 | −0.774495 | 1.456809 |
| H | −1.6669 | −1.42924 | 2.074887 |
| H | −3.356689 | −3.133653 | 2.627658 |
| H | −4.826325 | −4.066812 | 0.852319 |
| H | −4.578307 | −3.273675 | −1.491622 |
| H | −2.879174 | −1.562665 | −2.048933 |

The present disclosure surprisingly provides a two-step route to core scaffolds, such as those inspired by arylcycloheptane architectures (FIG. 1), that is amenable to structural change due to the concise synthetic sequence from abundant starting material classes. The route is made possible by a surprisingly low-barrier Cope rearrangement, occurring transiently with a calculated barrier of 19.5 kcal/mol, enabling a one-pot bis-allylation protocol to be developed for Knoevenagel adducts.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A method of synthesizing a bis-allylated compound, the method comprising:

reacting a Knoevenagel adduct and chalcone-derived electrophile in the presence of a palladium catalyst and base at a first reaction temperature for a first reaction time;

wherein the Knoevenagel adduct has a formula represented by a structure:

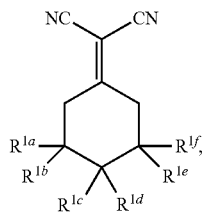

wherein each of $R^{1a}$, $R^{1b}$, $R^{1c}$, $R^{1d}$, $R^{1e}$ and $K^{1f}$ is independently selected from hydrogen, halogens, and C1-C8 alkyl; or wherein each of $R^{1a}$, $R^{1b}$, $R^{1e}$ and $R^{1f}$ is independently selected from hydrogen and C1-C8 alkyl, and wherein $R^{1c}$ and $R^{1d}$ are optionally combined and form a $C_3$ to $C_8$ cycloalkyl, $C_3$ to $C_8$ cycloalkenyl, or 5-atom or 6-atom heterocycle containing one or more oxygens;

wherein the chalcone-derived electrophile has a formula represented by a structure:

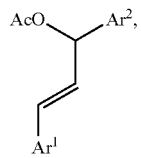

wherein $Ar^1$ is a phenyl group optionally substituted with 1, 2, or 3 groups that are electron-withdrawing or electron-donating; and wherein $Ar^2$ is a phenyl group optionally substituted with 1, 2, or 3 groups that are electron-withdrawing or electron-donating; and wherein at least one of $Ar^1$ and $Ar^2$ is substituted with 1, 2, or 3 groups that are electron-withdrawing or electron-donating;

after completion of the first reaction time, adding to the reaction an allylic electrophile and continuing the reaction at second reaction temperature for a second reaction time, wherein the allylic electrophile has a formula represented by a structure:

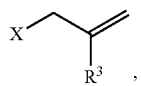

wherein X is a halogen; and wherein $R^3$ is selected from hydrogen and C1-C8 alkyl;

thereby synthesizing the bis-allylated compound, wherein the bis-allylated compound has a formula represented by a structure:

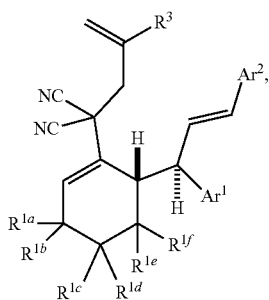

2. The method of claim 1, wherein the first reaction temperature is from 0° C. to 50° C.

3. The method of claim 1, wherein the first reaction temperature is from 20 to 30° C.

4. The method of claim 1, wherein the second reaction temperature is from 0° C. to 50° C.

5. The method of claim 1, wherein $Ar^1$ and $Ar^2$ are, independently, selected from 2-methoxyphenyl, 3-methoxyphenyl, 4-methoxyphenyl, 3,4-dimethoxyphenyl, 2,5-dimethoxyphenyl, and 4-chlorophenyl.

6. The method of claim 1, wherein $R^{1c}$ and $R^{1d}$ are fluoro, chloro, bromo, or iodo groups.

7. The method of claim 1, wherein $R^{1c}$ and $R^{1d}$ are combined to form a 5-atom heterocycle with two oxygen atoms.

8. The method of claim 1, wherein $Ar^1$ and $Ar^2$ are phenyl and $R^{1c}$ and $R^{1d}$ are combined to form a 5-atom heterocycle with two oxygen atoms.

9. A method of synthesizing an aryl-cycloheptene compound, the method comprising:

reacting a bis-allylated compound in the presence of a Grubbs catalyst, and wherein the bis-allylated compound has a formula represented by a structure:

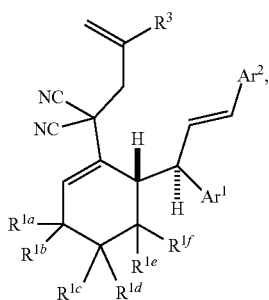

wherein each of $R^{1a}$, $R^{1b}$, $R^{1c}$, $R^{1d}$, $R^{1e}$, $R^{1f}$ and $R^3$ is independently selected from hydrogen, halogen, and C1-C8 alkyl; or wherein each of $R^{1a}$, $R^{1b}$, $R^{1e}$, $R^{1f}$ and $R^3$ is independently selected from hydrogen and C1-C8 alkyl, and wherein $R^{1c}$ and $R^{1d}$ are optionally combined to form a $C_3$ to $C_8$ cycloalkyl, $C_3$ to $C_8$ cycloalkenyl, or 5-atom or 6-atom heterocycle containing one or more oxygens;

wherein $Ar^1$ is a phenyl group optionally substituted with 1, 2, or 3 groups that are electron-withdrawing or electron-donating; and wherein $Ar^2$ is a phenyl group optionally substituted with 1, 2, or 3 groups that are electron-withdrawing or electron-donating; and wherein at least one of $Ar^1$ and $Ar^2$ is substituted with 1, 2, or 3 groups that are electron-withdrawing or electron-donating;

thereby synthesizing an aryl-cycloheptene compound having a formula represented by a structure:

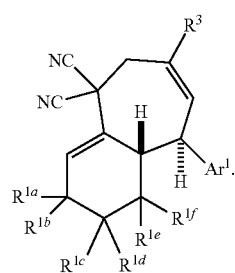

10. The method of claim 9, wherein $Ar^1$ and $Ar^2$ are, independently, selected from 2-methoxyphenyl, 3-methoxyphenyl, 4-methoxyphenyl, 3,4-dimethoxyphenyl, 2,5-dimethoxyphenyl, and 4-chlorophenyl.

11. The method of claim 9, wherein $R^{1c}$ and $R^{1d}$ are fluoro, chloro, bromo, or iodo groups.

12. The method of claim 9, wherein $R^{1c}$ and $R^{1d}$ are combined to form a C3 cycloalkyl group with two oxygen atoms.

13. The method of claim 9, wherein $Ar^1$ and $Ar^2$ are phenyl and $R^{1c}$ and $R^{1d}$ are combined to form a C3 cycloalkyl group with two oxygen atoms.

14. A compound having a formula represented by a structure:

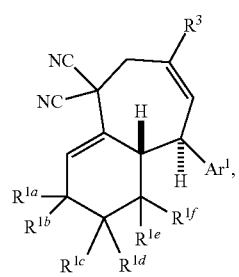

wherein each of $R^{1a}$, $R^{1b}$, $R^{1c}$, $R^{1d}$, $R^{1e}$, $R^{1f}$ and $R^3$ is independently selected from hydrogen and C1-C8 alkyl; or wherein each of $R^{1a}$, $R^{1b}$, $R^{1e}$, $R^{1f}$ and $R^3$ is independently selected from hydrogen, halogen, and C1-C8 alkyl, and wherein $R^{1c}$ and $R^{1d}$ are optionally combined and form a $C_3$ to $C_8$ cycloalkyl, $C_3$ to $C_8$ cycloalkenyl, or 5-atom or 6-atom heterocycle containing one or more oxygens; and wherein $Ar^1$ is a phenyl group substituted with 1, 2, or 3 groups that are electron-withdrawing or electron-donating.

15. The compound of claim 14, wherein $Ar^1$ is selected from 2-methoxyphenyl, 3-methoxyphenyl, 4-methoxyphenyl, 3,4-dimethoxyphenyl, 2,5-dimethoxyphenyl, and 4-chlorophenyl.

16. The compound of claim 14, wherein $R^{1c}$ and $R^{1d}$ are selected from fluoro, chloro, bromo, and iodo groups.

17. The compound of claim 14, wherein $Ar^1$ is phenyl and $R^{1c}$ and $R^{1d}$ are combined to form a C3 cycloalkyl group with two oxygen atoms.

18. A pharmaceutical composition comprising the compound of claim 14 and a pharmaceutically acceptable carrier.

* * * * *